US008227661B2

(12) United States Patent
Edwards et al.

(10) Patent No.: US 8,227,661 B2
(45) Date of Patent: Jul. 24, 2012

(54) METHODS OF IDENTIFYING AGENTS THAT AMELIORATE OR MODULATE EFFECTS OF PRO1328 GENE DISRUPTIONS

(75) Inventors: Joel A. Edwards, Las Flores, CA (US); Wenhu Huang, San Digeo, CA (US); Charles Montgomery, Jay, OK (US); Ni Nancy Qian, San Diego, CA (US); Zheng-Zheng Shi, The Woodlands, TX (US); Mary Jean Sparks, Magnolia, TX (US); Peter Vogel, The Woodlands, TX (US); Mindy Oox, Houston, TX (US)

(73) Assignee: Lexicon Genetics, Inc., The Woodlands, TX (US)

( * ) Notice: Subject to any disclaimer, the term of this patent is extended or adjusted under 35 U.S.C. 154(b) by 0 days.

(21) Appl. No.: 12/907,655

(22) Filed: Oct. 19, 2010

(65) Prior Publication Data

US 2011/0093960 A1      Apr. 21, 2011

Related U.S. Application Data

(60) Division of application No. 12/221,669, filed on Aug. 4, 2008, now abandoned, which is a continuation of application No. 11/457,708, filed on Jun. 3, 2009, which is a continuation of application No. PCT/US2005/02723, filed on Jan. 27, 2005.

(60) Provisional application No. 60/544,195, filed on Feb. 12, 2004.

(51) Int. Cl.
*G01N 33/00* (2006.01)
*A01K 67/00* (2006.01)
*A01K 67/027* (2006.01)

(52) U.S. Cl. .................. 800/3; 800/8; 800/9; 800/18

(58) Field of Classification Search .................. 800/3, 8, 800/9, 18
See application file for complete search history.

(56) References Cited

U.S. PATENT DOCUMENTS

| 2003/0180837 A1 | 9/2003 | Eaton et al. |
| 2008/0120731 A1 | 5/2008 | De Strooper et al. |

FOREIGN PATENT DOCUMENTS

| WO | WO 99/14328 | 3/1999 |
| WO | WO 00/08045 | 2/2000 |
| WO | WO 00/39297 | 7/2000 |
| WO | WO 00/70049 | 11/2000 |
| WO | WO 01/05974 | 1/2001 |
| WO | WO 01/16318 | 2/2001 |
| WO | WO 02/00690 | 1/2002 |
| WO | WO 02/08284 | 1/2002 |
| WO | WO 02/08288 | 1/2002 |
| WO | WO 02/40662 | 5/2002 |
| WO | WO 02/45495 | 6/2002 |
| WO | WO 02/070655 | 9/2002 |
| WO | WO 2004/080148 | 9/2004 |

OTHER PUBLICATIONS

Wood. Comp. Med. 50(1): 12-15, 2000.*
Marlow et al, Biochem. Biophys. Res. Comm 305(3)502-509, 2003.*
Abu-Elheiga, et al., "Continuous fatty acid oxidation and reduced fat storage in mice lacking acetyl-CoA carboxylase 2", Science, 291: 2613-2616, (2001).
Barton, et al., "A tissue specific IL-1 receptor antagonist homolog from the IL-1 cluster lacks IL-1, IL-1ra, IL-18 antagonist activities", European Journal of Immunology, 30: 3299-3308, (2000).
Brereton, et al., "Pan1b (17βHSD11)—enzymatic activity and distribution in the lung", Molecular and cellular endocrinology, 171: 111-117, (2001).
Capecchi, et al., "Targeted gene replacement", Scientific American, pp. 52-59, (1994).
Carim-told, et al., "LRRN6A/LERN1 (leucine-rich repeat neuronal protein 1), a novel gene with enriched expression in limbic system and neocortex", European journal ofNeuroscience, 18: 3167-3182, (2003).
Chai, et al., "17β-Hydroxysteroid dehydrogenase type XI localizes to human steroidogenic cells", Endocrinology, 144(5): 2084-2091, (2003).
Clark, et al., "The secreted protein discovery initiative (SPDI), a large scale efforts to identify novel human secreted and transmembrane proteins: A bioinformatics assessment", Genome Research, 13: 2265-2270, (2003).
Conti, et al., "IL-10 subfamily members: IL-19, IL-20, IL-22, IL-24 and IL-26", Immunology Letters, 88: 171-174, (2003).
Debets, et al., "Two novel IL-1 family members, IL-1γ and IL-ε, function as an antagonist and agonist of NF-kB activation through the orphan IL-1 receptor-related protein 2[h]" The Journal of Immunology, 167(3): 1440-1446, (2001).
DeLorey, et al., "Mice lacking the β$_3$ subunit of the GABAA receptor have the epilepsy phenotype and many of the behavioral characteristics of Angelman syndrome", Neuroscience, 18(20): 8505-8514, (1988).
EBI Accession No. EM PRO: AKO27262, "Mus musculus adult male testis cDNA, RIKEN full-length enriched library, clone: 4930471K13 product: hypothetical RNI-like structure containing protein, full insert sequence", (Feb. 9, 2001).
EBI Accession No. UNIPROT: Q9DITO, "Mus musculus adult male testis cDNA, RIKEN full-length enriched library, clone: 4930471K13 product: hypothetical RNI-like structure containing protein, full insert sequence, (Leucine-rich repeat neuronal 6A)", (Jun. 1, 2001).

(Continued)

*Primary Examiner* — Sumesh Kaushal
(74) *Attorney, Agent, or Firm* — Bonny Yeung; Jeffery P. Bernhardt; Arnold & Porter LLP

(57) ABSTRACT

The present invention relates to transgenic animals, as well as compositions and methods relating to the characterization of gene function. Specifically, the present invention provides transgenic mice comprising disruptions in PRO227, PRO233, PRO238, PRO1328, PRO4342, PRO7423, PRO10096, PRO21384, PRO353 or PRO1885 genes. Such in vivo studies and characterizations may provide valuable identification and discovery of therapeutics and/or treatments useful in the prevention, amelioration or correction of diseases or dysfunctions associated with gene disruptions such as neurological disorders; cardiovascular, endothelial or angiogenic disorders; eye abnormalities; immunological disorders; oncological disorders; bone metabolic abnormalities or disorders; lipid metabolic disorders; or developmental abnormalities.

3 Claims, 20 Drawing Sheets

OTHER PUBLICATIONS

EBI Accession No. EM_PRO: AY358284, "*Homo sapiens* clone DNA33786 QVSK201 (UNQ201) mRNA, complete cds", (Oct. 9, 2003).

Ester, et al., "Mice lacking angiotensin-converting enzyme have low blood pressure, renal pathology, and reduced male fertility", Laboratory Investigation, 74(5): 953-965, (1996).

Ivanov, et al., "Expression of Hypoxia-inductible cell-surface transmembrane carbonic anhydrases in human cancer", American Journal of Pathology, 158(3): 905-919, (2001).

Kotenko, et al., "The family of IL-10-related cytokines and their receptors: related but to what extent?", Cytokine & Growth factor reviews, 13: 223-240, (2002).

Kumar, et al., "Identification and initial characterization of four novel members of the interleukin-1 family", The journal of Biological Chemistry, vol. 275, No. 14, pp. 10308-10314, (2000).

Langebach, et al., "Prostaglandin synthase 1 gene disruption in mice reduces arachidonic acid-induced inflammation and indomethancin-induced gastric ulceration", Cell, 83: 483-492, (1995).

LeJeune, et al., "Interleukin-22 (IL-22) activates the JAK/STAT, ERK, JNK and p38 MAP kinase pathways in a RAT Hepatoma cell line", The journal of biological chemistry, 277(37) 33676-33682, (2002).

Li, et al., "Cloning and expression of a novel tissue specific 17β-Hydroxysteroid dehydrogenase", Endrocrine Research, 24(3 & 4): 663-667, (1998).

Nagem, et al., "Crystal structure of recombinant human interleukin-22", Structure, 10: 1051-1062, (2002).

Olive, et al., "Carbonic anhydrase 9 as an endogenous marker for hypoxic cells in cervical cancer", Cancer Research, 61: 9824-8929, (2001).

Pasterok, et al., "Cloning and characterization of MN, a human tumor-associated protein with a domain hommologous to carbonic anhydrase and a putative heliz-loop-helix DNA binding segment", Oncogene, 9: 2877-2888, (1994).

Potter, et al., "Diagnostic, prognostic and therapeutic implications of carbonic anhydrases in cancer", British Journal of Cancer, 89: 2-7, (2003).

Smith, et al., "four new members expand the interleukin-1 superfamily", The Journal of Biological Chemistry, vol. 275, No. 2, pp. 1169-1175, (2000).

Tazi, et al., "Genetic analysis of the interleukin-1 receptor antagonist and its homologuc IL-1IL in alopecia areata: stroll severity association and possible gene interaction", European journal of immunogenetics, 29: 25-30, (2002).

Verdile, et al., "The role of presenilin and its interacting proteins in the biogenesis of alzheimer's beta amyloid", Neurochem. Res., 32: 609-623, (2007).

Wolk, et al., "Cutting edge: Immune cells as sources and targets of the Il-10 family member?", The Journal of Immunology, 168(11): 5397-5402, (2002).

Wu, et al., "Generation of committed erythroid BRU-E and CFU-E progenitors does not require erythropoietin or the erythropoietin receptor", Cell, 83: 59-67, (1995).

Xie, et al., "Interleukin (IL)-22, A novel human cytokine that signals through the interferon receptor-related proteins CRF2-4 and IL-22R", J. Bio. Chem., 275(40): 31335-31339, (2000).

Xu, et al., "A soluble class II cytokine receptor, IL-22RA2, is a naturally occurring IL-22 antagonist", P.N.A.S., 98: 9511-9516, (2001).

Zavada, et al., "Soluble form of carbonic anhydrase IX (CA IX) in the serum and urine of renal carcinoma patients", British Journal of Cancer, 89(6): 1067-1071, (2003).

Clark, et al., "A future for transgenic livestock", Nature Reviews: Genetics: 825-833, (2003).

Holschneider, et al., "Genotype to phenotype: challenges and opportunities", Int J Devl Neuroscience 18: 615-618, (2000).

Niemann, et al., "Transgenic farm animals: present and future", Rev. Sci, Tech. Off. Int. Epiz. 24: 285-298, (2005).

Rex, et al., "Strain Differences in Fear-Motivated Behavior of Rats", Pharmacology Biochemistry and Behavior, 54 (1): 107-111, (1996).

Rodgers, et al., "Contrasting phenotypes of C57BL/6J)laHsd, 12952/SVHsd and 129/SvEv mice in two exploration-based tests of anxiety-related behaviour", Physiol Behav., 77 (2-3): 301-310 (2002).

Schalkwyk, et al., "Interpretation of knockout experiments: the congenic footprint" Genes, Brain and Behavior, 6: 299-303, (2007).

Schoonjans, et al., "Improved Generation of Germline-Competent Embryonic Stem Cell Lines from Inbred Mouse Strains", Stem Cells, 21: 90-97, (2003).

Tecott, et al., "The Genes and Brains of Mice and Men", Am. J. Psychiatry 160: 646-656, (2003).

Tsuda, et al., "Strain-dependent behavioral alterations induced by peripheral interleukin-1 challenge in neonatal mice", Behav Brain Res., 166(1): 19-31, (2006).

Wolfer, et al., "Knockout mice: simple solutions to the problems of genetic background and flanking genes", 25 (7): 336-340 (2002).

* cited by examiner

FIG. 1

ACCGAGCCGAGCGGACCGAAGGCGCGCCCGAGATGCAGGTGAGCAAGAGGATGCTGGCGGGGGGCGTGAGGAGC
ATGCCCAGCCCCCTCCTGGCCTGCTGGCAGCCCATCCTCCTGCTGGTGCTGGGCTCAGTGCTGTCAGGCTCGGC
CACGGGCTGCCCGCCCCGCTGCGAGTGCTCCGCCAGGACCGCGCTGTGCTGTGCCACCGCAAGTGCTTTGTCC
CAGTCCCCGAGGGCATCCCCACCGAGACGCGCCTGCTGGACCTAGGCAAGAACCGCATCAAAACGCTCAACCAG
GACGAGTTCGCCAGCTTCCCGCACCTGGAGGAGCTGGAGCTCAACGAGAACATCGTGAGCGCCGTGGAGCCCGG
CGCCTTCAACAACCTCTTCAACCTCCGGACGCTGGGTCTCCGCAGCAACCGCCTGAAGCTCATCCCGCTAGGCG
TCTTCACTGGCCTCAGCAACCTGACCAAGCAGGACATCAGCGAGAACAAGATCGTTATCCTACTGGACTACATG
TTTCAGGACCTGTACAACCTCAAGTCACTGGAGGTTGGCGACAATGACCTCGTCTACATCTCTCACCGCGCCTT
CAGCGGCCTCAACAGCCTGGAGCAGCTGACGCTGGAGAAATGCAACCTGACCTCCATCCCCACCGAGGCGCTGT
CCCACCTGCACGGCCTCATCGTCCTGAGGCTCCGGCACCTCAACATCAATGCCATCCGGGACTACTCCTTCAAG
AGGCTGTACCGACTCAAGGTCTTGGAGATCTCCCACTGGCCCTACTTGGACACCATGACACCCAACTGCCTCTA
CGGCCTCAACCTGACGTCCCTGTCCATCACACACTGCAATCTGACCGCTGTGCCCTACCTGGCCGTCCGCCACC
TAGTCTATCTCCGCTTCCTCAACCTCTCCTACAACCCCATCAGCACCATTGAGGGCTCCATGTTGCATGAGCTG
CTCCGGCTGCAGGAGATCCAGCTGGTGGGCGGGCAGCTGGCCGTGGTGGAGCCCTATGCCTTCCGCGGCCTCAA
CTACCTGCGCGTGCTCAATGTCTCTGGCAACCAGCTGACCACACTGGAGGAATCAGTCTTCCACTCGGTGGGCA
ACCTGGAGACACTCATCCTGGACTCCAACCCGCTGGCCTGCGACTGTCGGCTCCTGTGGGTGTTCCGGCGCCGC
TGGCGGCTCAACTTCAACCGGCAGCAGCCCACGTGCGCCACGCCCGAGTTTGTCCAGGGCAAGGAGTTCAAGGA
CTTCCCTGATGTGCTACTGCCCAACTACTTCACCTGCCGCCGCCCCGCATCCGGGACCGCAAGGCCCAGCAGG
TGTTTGTGGACGAGGGCCACACGGTGCAGTTTGTGTGCCGGGCCGATGGCGACCCGCCGCCCGCCATCCTCTGG
CTCTCACCCCGAAAGCACCTGGTCTCAGCCAAGAGCAATGGGCGGCTCACAGTCTTCCCTGATGGCACGCTGGA
GGTGCGCTACGCCCAGGTACAGGACAACGGCACGTACCTGTGCATCGCGGCCAACGCGGGCGGCAACGACTCCA
TGCCCGCCCACCTGCATGTGCGCAGCTACTCGCCCGACTGGCCCCATCAGCCCAACAAGACCTTCGCTTTCATC
TCCAACCAGCCGGGCGAGGGAGAGGCCAACAGCACCCGCGCCACTGTGCCTTTCCCCTTCGACATCAAGACCCT
CATCATCGCCACCACCATGGGCTTCATCTCTTTCCTGGGCGTCGTCCTCTTCTGCCTGGTGCTGCTGTTTCTCT
GGAGCCGGGGCAAGGGCAACACAAAGCACAACATCGAGATCGAGTATGTGCCCCGAAAGTCGGACGCAGGCATC
AGCTCCGCCGACGCGCCCCGCAAGTTCAACATGAAGATGATATGAGGCCGGGGCGGGGGGCAGGGACCCCCGGG
CGGCCGGGCAGGGGAAGGGGCCTGGTCGCCACCTGCTCACTCTCCAGTCCTTCCCACCTCCTCCCTACCCTTCT
ACACACGTTCTCTTTCTCCCTCCCGCCTCCGTCCCCTGCTGCCCCCGCCAGCCCTCACCACCTGCCCTCCTTC
TACCAGGACCTCAGAAGCCCAGACCTGGGGACCCCACCTACACAGGGGCATTGACAGACTGGAGTTGAAAGCCG
ACGAACCGACACGCGGCAGAGTCAATAATTCAATAAAAAAGTTACGAACTTTCTCTGTAACTTGGGTTTCAATA
ATTATGGATTTTTATGAAAACTTGAAATAATAAAAAGAGAAAAAAACTAAAAAAAAAAAAAAAAAAAAA

FIG. 2

MQVSKRMLAGGVRSMPSPLLACWQPILLLVLGSVLSGSATGCPPRCECSAQDRAVLCHRKCFVAVPEGIPTE
TRLLDLGKNRIKTLNQDEFASFPHLEELELNENIVSAVEPGAFNNLFNLRTLGLRSNRLKLIPLGVFTGLSNLT
KQDISENKIVILLDYMFQDLYNLKSLEVGDNDLVYISHRAFSGLNSLEQLTLEKCNLTSIPTEALSHLHGLIVL
RLRHLNINAIRDYSFKRLYRLKVLEISHWPYLDTMTPNCLYGLNLTSLSITHCNLTAVPYLAVRHLVYLRFLN
LSYNPISTIEGSMLHELLRLQEIQLVGGQLAVVEPYAFRGLNYLRVLNVSGNQLTTLEESVFHSVGNLETLILD
SNPLACDCRLLWVFRRRWRLNFNRQQPTCATPEFVQGKEFKDFPDVLLPNYFTCRRARIRDRKAQQVFVDE
GHTVQFVCRADGDPPPAILWLSPRKHLVSAKSNGRLTVFPDGTLEVRYAQVQDNGTYLCIAANAGGNDSMP
AHLHVRSYSPDWPHQPNKTFAFISNQPGEGEANSTRATVPFPFDIKTLIIATTMGFISFLGVVLFCLVLLFLWS
RGKGNTKHNIEIEYVPRKSDAGISSADAPRKFNMKMI

Important features:

Signal sequence:

amino acids 1-41

Transmembrane domain:

amino acids 556-578

N-glycosylation site.

amino acids 144-148, 202-206, 264-268, 274-278, 293-297, 341-345, 492-496, 505-509, 526-530, 542-546

Casein kinase II phosphorylation site.

amino acids 49-53, 108-112, 146-150, 300-304, 348-352, 349-353, 607-611

Tyrosine kinase phosphorylation site.

amino acids 590-598

N-myristoylation site.

amino acids 10-16, 32-38, 37-43, 113-119, 125-131, 137-143, 262-268, 320-326, 344-350, 359-365, 493-499, 503-509, 605-611

Prokaryotic membrane lipoprotein lipid attachment site.

amino acids 32-43

FIG. 3

CCCACGCGTCCGCTGGTGTTAGATCGAGCAACCCTCTAAAAGCAGTTTAGAGTGGTAAAAAAAAAAAAAAACAC
ACCAAACGCTCGCAGCCACAAAAGGGATGAAATTTCTTCTGGACATCCTCCTGCTTCTCCCGTTACTGATCGTC
TGCTCCCTAGAGTCCTTCGTGAAGCTTTTTATTCCTAAGAGGAGAAAATCAGTCACCGGCGAAATCGTGCTGAT
TACAGGAGCTGGGCATGGAATTGGGAGACTGACTGCCTATGAATTTGCTAAACTTAAAAGCAAGCTGGTTCTCT
GGGATATAAATAAGCATGGACTGGAGGAAACAGCTGCCAAATGCAAGGGACTGGGTGCCAAGGTTCATACCTTT
GTGGTAGACTGCAGCAACCGAGAAGATATTTACAGCTCTGCAAAGAAGGTGAAGGCAGAAATTGGAGATGTTAG
TATTTTAGTAAATAATGCTGGTGTAGTCTATACATCAGATTTGTTTGCTACACAAGATCCTCAGATTGAAAAGA
CTTTTGAAGTTAATGTACTTGCACATTTCTGGACTACAAAGGCATTTCTTCCTGCAATGACGAAGAATAACCAT
GGCCATATTGTCACTGTGGCTTCGGCAGCTGGACATGTCTCGGTCCCCTTCTTACTGGCTTACTGTTCAAGCAA
GTTGCTGCTGTTGGATTTCATAAAACTTTGACAGATGAACTGGCTGCCTTACAAATAACTGGAGTCAAAACAA
CATGTCTGTGTCCTAATTTCGTAAACACTGGCTTCATCAAAAATCCAAGTACAAGTTTGGGACCCACTCTGGAA
CCTGAGGAAGTGGTAAACAGGCTGATGCATGGGATTCTGACTGAGCAGAAGATGATTTTTATTCCATCTTCTAT
AGCTTTTTTAACAACATTGGAAAGGATCCTTCCTGAGCGTTTCCTGGCAGTTTTAAAACGAAAAATCAGTGTTA
AGTTTGATGCAGTTATTGGATATAAAATGAAAGCGCAATAAGCACCTAGTTTCTGAAAACTGATTTACCAGGT
TTAGGTTGATGTCATCTAATAGTGCCAGAATTTTAATGTTTGAACTTCTGTTTTTCTAATTATCCCCATTTCT
TCAATATCATTTTTGAGGCTTTGGCAGTCTTCATTTACTACCACTTGTTCTTTAGCCAAAAGCTGATTACATAT
GATATAAACAGAGAAATACCTTTAGAGGTGACTTTAAGGAAAATGAAGAAAAAGAACCAAAATGACTTTATTAA
AATAATTTCCAAGATTATTTGTGGCTCACCTGAAGGCTTTGCAAAATTTGTACCATAACCGTTTATTTAACATA
TATTTTATTTTTGATTGCACTTAAATTTTGTATAATTTGTGTTTCTTTTTCTGTTCTACATAAAATCAGAAAC
TTCAAGCTCTCTAAATAAAATGAAGGACTATATCTAGTGGTATTTCACAATGAATATCATGAACTCTCAATGGG
TAGGTTTCATCCTACCCATTGCCACTCTGTTTCCTGAGAGATACCTCACATTCCAATGCCAAACATTTCTGCAC
AGGGAAGCTAGAGGTGGATACACGTGTTGCAAGTATAAAAGCATCACTGGGATTTAAGGAGAATTGAGAGAATG
TACCCACAAATGGCAGCAATAATAAATGGATCACACTTAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAAAAAAAA

FIG. 4

MKFLLDILLLLPLLIVCSLESFVKLFIPKRRKSVTGEIVLITGAGHGIGRLTAYEFAKLKS
KLVLWDINKHGLEETAAKCKGLGAKVHTFVVDCSNREDIYSSAKKVKAEIGDVSILVNNAG
VVYTSDLFATQDPQIEKTFEVNVLAHFWTTKAFLPAMTKNNHGHIVTVASAAGHVSVPFLL
AYCSSKFAAVGFHKTLTDELAALQITGVKTTCLCPNFVNTGFIKNPSTSLGPTLEPEEVVN
RLMHGILTEQKMIFIPSSIAFLTTLERILPERFLAVLKRKISVKFDAVIGYKMKAQ

Signal sequence:
amino acids 1-19 cAMP- and cGMP-dependent protein kinase phosphorylation site.
amino acids 30-34, 283-287

Casein kinase II phosphorylation site.
amino acids 52-56, 95-99, 198-202, 267-271

N-myristoylation site.
amino acids 43-49, 72-78, 122-128, 210-216

FIG. 5

ACTGCACTCGGTTCTATCGATTGAATTCCCCGGGGATCCTCTAGAGATCCCTCGACCTCGA
CCCACGCGTCCGCGGACGCGTGGGCGGACGCGTGGGCCGGCTACCAGGAAGAGTCTGCCGA
AGGTGAAGGCCATGGACTTCATCACCTCCACAGCCATCCTGCCCTGCTGTTCGGCTGCCT
GGGCGTCTTCGGCCTCTTCCGGCTGCTGCAGTGGGTGCGCGGGAAGGCCTACCTGCGGAAT
GCTGTGGTGATCACAGGCGCCACCTCAGGGCTGGGCAAAGAATGTGCAAAAGTCTTCT
ATGCTGCGGGTGCTAAACTGGTGCTCTGTGGCCGGAATGGTGGGGCCCTAGAAGAGCTCAT
CAGAGAACTTACCGCTTCTCATGCCACCAAGGTGCAGACACACAAGCCTTACTTGGTGACC
TTCGACCTCACAGACTCTGGGGCCATAGTTGCAGCAGCAGCTGAGATCCTGCAGTGCTTTG
GCTATGTCGACATACTTGTCAACAATGCTGGGATCAGCTACCGTGGTACCATCATGGACAC
CACAGTGGATGTGGACAAGAGGGTCATGGAGACAAACTACTTTGGCCCAGTTGCTCTAACG
AAAGCACTCCTGCCCTCCATGATCAAGAGGAGGCAAGGCCACATTGTCGCCATCAGCAGCA
TCCAGGGCAAGATGAGCATTCCTTTTCGATCAGCATATGCAGCCTCCAAGCACGCAACCCA
GGCTTTCTTTGACTGTCTGCGTGCCGAGATGGAACAGTATGAAATTGAGGTGACCGTCATC
AGCCCCGGCTACATCCACACCAACCTCTCTGTAAATGCCATCACCGCGGATGGATCTAGGT
ATGGAGTTATGGACACCACCACAGCCCAGGGCCGAAGCCCTGTGGAGGTGGCCCAGGATGT
TCTTGCTGCTGTGGGGAAGAAGAAGAAAGATGTGATCCTGGCTGACTTACTGCCTTCCTTG
GCTGTTTATCTTCGAACTCTGGCTCCTGGGCTCTTCTTCAGCCTCATGGCCTCCAGGGCCA
GAAAAGAGCGGAAATCCAAGAACTCCTAGTACTCTGACCAGCCAGGGCCAGGGCAGAGAAG
CAGCACTCTTAGGCTTGCTTACTCTACAAGGGACAGTTGCATTTGTTGAGACTTTAATGGA
GATTTGTCTCACAAGTGGGAAAGACTGAAGAAACACATCTCGTGCAGATCTGCTGGCAGAG
GACAATCAAAAACGACAACAAGCTTCTTCCCAGGGTGAGGGGAAACACTTAAGGAATAAAT
ATGGAGCTGGGGTTTAACACTAAAAACTAGAAATAAACATCTCAAACAGTAAAAAAAAAAA
AAAAGGGCGGCCGCGACTCTAGAGTCGACCTGCAGAAGCTTGGCCGCCATGGCCCAACTTG
TTTATTGCAGCTTATAATGGTTAC

FIG. 6

MDFITSTAILPLLFGCLGVFGLFRLLQWVRGKAYLRNAVVITGATSGLGKECAKVFYAAG
AKLVLCGRNGGALEELIRELTASHATKVQTHKPYLVTFDLTDSGAIVAAAAEILQCFGYVD
ILVNNAGISYRGTIMDTTVDVDKRVMETNYFGPVALTKALLPSMIKRRQGHIVAISSIQGK
MSIPFRSAYAASKHATQAFFDCLRAEMEQYEIEVTVISPGYIHTNLSVNAITADGSRYGVM
DTTTAQGRSPVEVAQDVLAAVGKKKKDVILADLLPSLAVYLRTLAPGLFFSLMASRARKER
KSKNS

Signal sequence:
amino acids 1-21

Transmembrane domain:
amino acids 104-120, 278-292

N-glycosylation site.
amino acids 228-232

Glycosaminoglycan attachment site.
amino acids 47-51

Casein kinase II phosphorylation site.
amino acids 135-139, 139-143, 253-257

Tyrosine kinase phosphorylation site.
amino acids 145-153, 146-153

N-myristoylation site.
amino acids 44-50, 105-111, 238-244, 242-248, 291-297

Amidation site.
amino acids 265-269

Prokaryotic membrane lipoprotein lipid attachment site.
amino acids 6-17

FIG. 7

CGGTGGCCATGACTGCGGCCGTGTTCTTCGGCTGCGCCTTCATTGCCTTCGGGCCTGCGCT
CGCCCTTTATGTCTTCACCATCGCCATCGAGCCGTTGCGTATCATCTTCCTCATCGCCGGA
GCTTTCTTCTGGTTGGTGTCTCTACTGATTCGTCCCTTGTTTGGTTCATGGCAAGAGTCA
TTATTGACAACAAAGATGGACCAACACAGAAATATCTGCTGATCTTTGGAGCGTTTGTCTC
TGTCTATATCCAAGAAATGTTCCGATTTGCATATTATAAACTCTTAAAAAAGCCAGTGAA
GGTTTGAAGAGTATAAACCCAGGTGAGACAGCACCCTCTATGCGACTGCTGGCCTATGTTT
CTGGCTTGGGCTTTGGAATCATGAGTGGAGTATTTTCCTTTGTGAATACCCTATCTGACTC
CTTGGGGCCAGGCACAGTGGGCATTCATGGAGATTCTCCTCAATTCTTCCTTTATTCAGCT
TTCATGACGCTGGTCATTATCTTGCTGCATGTATTCTGGGGCATTGTATTTTTTGATGGCT
GTGAGAAGAAAAAGTGGGGCATCCTCCTTATCGTTCTCCTGACCCACCTGCTGGTGTCAGC
CCAGACCTTCATAAGTTCTTATTATGGAATAAACCTGGCGTCAGCATTTATAATCCTGGTG
CTCATGGGCACCTGGGCATTCTTAGCTGCGGGAGGCAGCTGCCGAAGCCTGAAACTCTGCC
TGCTCTGCCAAGACAAGAACTTTCTTCTTTACAACCAGCGCTCCAGATAACCTCAGGGAAC
CAGCACTTCCCAAACCGCAGACTACATCTTTAGAGGAAGCACAACTGTGCCTTTTTCTGAA
AATCCCTTTTTCTGGTGGAATTGAGAAGAAATAAAACTATGCAGATA

FIG. 8

MTAAVFFGCAFIAFGPALALYVFTIAIEPLRIIFLIAGAFFWLVSLLISSLVWFMARVIID
NKDGPTQKYLLIFGAFVSVYIQEMFRFAYYKLLKKASEGLKSINPGETAPSMRLLAYVSGL
GFGIMSGVFSFVNTLSDSLGPGTVGIHGDSPQFFLYSAFMTLVIILLHVFWGIVFFDGCEK
KKWGILLIVLLTHLLVSAQTFISSYYGINLASAFIILVLMGTWAFLAAGGSCRSLKLCLLC
QDKNFLLYNQRSR

Important features of the protein:
Signal peptide:
amino acids 1-19

Transmembrane domains:
amino acids 32-51, 119-138, 152-169, 216-235

Glycosaminoglycan attachment site.
amino acids 120-123

Sodium:neurotransmitter symporter family protein
amino acids 31-65

FIG. 9

CGGCTCCGAGGCTCCCGCCAGGAGAAAGGAACATTCTGAGGGGAGTCTACACCCTGTGGAGCTCAAGATGGTCCT
GAGTGGGGCGCTGTGCTTCCGAATGAAGGACTCGGCATTGAAGGTGCTTTATCTGCATAATAACCAGCTTCTAG
CTGGAGGGCTGCATGCAGGGAAGGTCATTAAAGGTGAAGAGATCAGCGTGGTCCCCAATCGGTGGCTGGATGCC
AGCCTGTCCCCCGTCATCCTGGGTGTCCAGGGTGGAAGCCAGTGCCTGTCATGTGGGGTGGGGCAGGAGCCGAC
TCTAACACTAGAGCCAGTGAACATCATGGAGCTCTATCTTGGTGCCAAGGAATCCAAGAGCTTCACCTTCTACC
GGCGGGACATGGGGCTCACCTCCAGCTTCGAGTCGGCTGCCTACCCGGGCTGGTTCCTGTGCACGGTGCCTGAA
GCCCATCAGCCTGTCAGACTCACCCAGCTTCCCGAGAATGGTGGCTGGAATGCCCCCATCACAGACTTCTACTT
CCAGCAGTGTGACTAGGCAACGTGCCCCCAGAACTCCCTGGGCAGAGCCAGCTCGGGTGAGGGTCAGTGGA
GGAGACCCATGGCGGACAATCACTCTCTCTGCTCTCAGGACCCCCACGTCTGACTTAGTGGGCACCTGACCACT
TTGTCTTCTGGTTCCCAGTTTGGATAAATTCTGAGATTTGGAGCTCAGTCCACGGTCCTCCCCCACTGGATGGT
GCTACTGCTGTGGAACCTTGTAAAAACCATGTGGGGTAAACTGGGAATAACATGAAAAGATTTCTGTGGGGGTG
GGGTGGGGGAGTGGTGGGAATCATTCCTGCTTAATGGTAACTGACAAGTGTTACCCTGAGCCCCGCAGGCCAAC
CCATCCCCAGTTGAGCCTTATAGGGTCAGTAGCTCTCCACATGAAGTCCTGTCACTCACCACTGTGCAGGAGAG
GGAGGTGGTCATAGAGTCAGGGATCTATGGCCCTTGGCCCAGCCCCACCCCCTTCCCTTTAATCCTGCCACTGT
CATATGCTACCTTTCCTATCTCTTCCCTCATCATCTTGTTGTGGGCATGAGGAGGTGGTGATGTCAGAAGAAAT
GGCTCGAGCTCAGAAGATAAAAGATAAGTAGGGTATGCTGATCCTCTTTTAAAAACCCAAGATACAATCAAAAT
CCCAGATGCTGGTCTCTATTCCCATGAAAAAGTGCTCATGACATATTGAGAAGACCTACTTACAAAGTGGCATA
TATTGCAATTTATTTTAATTAAAAGATACCTATTTATATATTTCTTTATAGAAAAAAGTCTGGAAGAGTTTACT
TCAATTGTAGCAATGTCAGGGTGGTGGCAGTATAGGTGATTTTTCTTTTAATTCTGTTAATTTATCTGTATTTC
CTAATTTTTCTACAATGAAGATGAATTCCTTGTATAAAAATAAGAAAAGAAATTAATCTTGAGGTAAGCAGAGC
AGACATCATCTCTGATTGTCCTCAGCCTCCACTTCCCCAGAGTAAATTCAAATTGAATCGAGCTCTGCTGCTCT
GGTTGGTTGTAGTAGTGATCAGGAAACAGATCTCAGCAAAGCCACTGAGGAGGAGGCTGTGCTGAGTTTGTGTG
GCTGGAATCTCTGGGTAAGGAACTTAAAGAACAAAAATCATCTGGTAATTCTTTCCTAGAAGGATCACAGCCCC
TGGGATTCCAAGGCATTGGATCCAGTCTCTAAGAAGGCTGCTGTACTGGTTGAATTGTGTCCCCCTCAAATTCA
CATCCTTCTTGGAATCTCAGTCTGTGAGTTTATTTGGAGATAAGGTCTCTGCAGATGTAGTTAGTTAAGACAAG
GTCATGCTGGATGAAGGTAGACCTAAATTCAATATGACTGGTTTCCTTGTATGAAAAGGAGAGGACACAGAGAC
AGAGGAGACGCGGGAAGACTATGTAAAGATGAAGGCAGAGATCGGAGTTTTGCAGCCACAAGCTAAGAAACAC
CAAGGATTGTGGCAACCATCAGAAGCTTGGAAGAGGCAAAGAAGAATTCTTCCCTAGAGGCTTTAGAGGGATAA
CGGCTCTGCTGAAACCTTAATCTCAGACTTCCAGCCTCCTGAACGAAGAAAGAATAAATTTCGGCTGTTTTAAG
CCACCAAGGATAATTGGTTACAGCAGCTCTAGGAAACTAATACAGCTGCTAAAATGATCCCTGTCTCCTCGTGT
TTACATTCTGTGTGTGTCCCCTCCCACAATGTACCAAAGTTGTCTTTGTGACCAATAGAATATGGCAGAAGTGA
TGGCATGCCACTTCCAAGATTAGGTTATAAAAGACACTGCAGCTTCTACTTGAGCCCTCTCTCTCTGCCACCCA
CCGCCCCCAATCTATCTTGGCTCACTCGCTCTGGGGGAAGCTAGCTGCCATGCTATGAGCAGGCCTATAAAGAG
ACTTACGTGGTAAAAAATGAAGTCTCCTGCCCACAGCCACATTAGTGAACCTAGAAGCAGAGACTCTGTGACAT
AATCGATGTTTGTTGTTTTAAGTTGCTCAGTTTTGGTCTAACTTGTTATGCAGCAATAGATAAATAATATGCAG
AGAAAGAG

FIG. 10

MVLSGALCFRMKDSALKVLYLHNNQLLAGGLHAGKVIKGEEISVVPNRWLDASLSPVILGVQGGSQCLSCGVGQ
EPTLTLEPVNIMELYLGAKESKSFTFYRRDMGLTSSFESAAYPGWFLCTVPEADQPVRLTQLPENGGWNAPITD
FYFQQCD

N-myristoylation sites:

amino acids 29-34, 30-35, 60-65, 63-68, 73-78, 91-96, 106-111

Interleukin-1 signature:

amino acids 111-131

Interleukin-1 proteins:

amino acids 8-29, 83-120, 95-134, 64-103

FIG. 11

```
   1 gtcagccgca tggctccoct gtgcoccagc ccctggctcc ctctgttgat cccggccoct
  61 gctccaggcc tcactgtgca actgctgctg tcactgctgc ttctgatgcc tgtccatccc
 121 cagaggttgc cccggatgca ggaggattcc ccttgggag gaggctcttc tggggaagat
 181 gacccactgg gcgaggagga tctgcccagt gaagaggatt cacccagaga ggaggatcca
 241 ccggagagg aggatctacc tggagaggag gatctacctg gagaggagga tctacctgaa
 301 gttaagccta atcagaaga agagggctcc ctgaagttag aggatctacc tactgttgag
 361 gctcctggag atcctcaaga acccagaat aatgcccaca gggacaaaga agggatgac
 421 cagagtcatt ggcgctatgg aggcgacccg ccctggcccc gggtgtcccc agcctgcgcg
 481 ggccgcttcc agtccccgt ggatatccgc cccagctcg ccgccttctg ccggccctg
 541 cgccccctgg aactcctggg cttccagctc ccgccgctcc cagaactgcg cctgcgcaac
 601 aatggccaca gtgtgcaact gaccctgcct cctgggctag agatggctct gggtcccggg
 661 cgggagtacc gggctctgca gctgcatctg cactgggggg ctgcaggtcg tcgggctcg
 721 gagcacactg tggaaggcca ccgtttccct gccgagatcc acgtggttca cctcagcacc
 781 gcctttgcca gagttgacga ggccttgggg cgcccggag gcctggccgt gttggccgcc
 841 tttctggagg agggcccgga agaaaacagt gcctatgagc agttgctgtc tgcttggaa
 901 gaaatcgctg aggaaggctc agagactcag gtcccaggac tggacatatc tgcactcctg
 961 ccctctgact tcagccgcta cttccaatat gagggtctc tgactacacc gccctgtgcc
1021 cagggtgtca tctggactgt gtttaaccag acagtgatgc tgagtgctaa gcagctccac
1081 accctctctg cacccctgtg gggacctggt gactctcggc tacagctgaa cttccgagcg
1141 acgcagcctt tgaatgggcg agtgattgag gcctccttcc ctgctggagt ggacagcagt
1201 cctcgggctg ctgagccagt ccagctgaat tcctgcctgg ctgctggtga catcctagcc
1261 ctggttttg gcctccttt tgctgtcacc agcgtcgcgt tccttgtgca gatgagaagg
1321 cagcacagaa ggggaaccaa aggggtgtg agctaccgcc agcagaggt agccgagact
1381 ggagcctaga ggctggatct tggagaatgt gagaagccag ccagaggcat ctgaggggga
1441 gccggtaact gtcctgtcct gctcattatg ccacttcctt ttaactgcaa agaaattttt
1501 taaataaat atttataat
```

FIG. 12

></usr/seqdb2/sst/DNA/Dnaseqs.min/ss.DNA108809
><subunit 1 of 1, 459 aa, 1 stop
><MW: 49726, pI: 4.70, NX(S/T): 1
MAPLCPSPWLPLLIPAPAPGLTVQLLLSLLLLVPVHPQRLPRMQEDSPLGGGSSGEDDPL
GEEDLPSEEDSPREEDPPGEEDLPGEEDLPGEEDLPEVKPKSEEEGSLKLEDLPTVEAPG
DPQEPQNNAHRDKEGDDQSHWRYGGDPPWPRVSPACAGRFQSPVDIRPQLAAFCPALRPL
ELLGFQLPPLPELRLRNNGHSVQLTLPPGLEMALGPGREYRALQLHLHWGAAGRPGSEHT
VEGHRFPAEIHVVHLSTAFARVDEALGRPGGLAVLAAFLEEGPEENSAYEQLLSRLEEIA
EEGSETQVPGLDISALLPSDFSRYFRYEGSLTTPPCAQGVIWTVFNQTVMLSAKQLHTLS
DTLWGPGDSRLQLNFRATQPLNGRVIEASFPAGVDSSPRAAEPVQLNSCLAAGDILALVF
GLLFAVTSVAFLVQMRRQHRRGTKGGVSYRPAEVAETGA

FIG. 13

```
CTTCAGAACAGGTTCTCCTTCCCCAGTCACCAGTTGCTCGAGTTAGAATTGTCTGCAATGGCCGCCCTGCAGAA
ATCTGTGAGCTCTTTCCTTATGGGGACCCTGGCCACCAGCTGCCTCCTTCTCTTGGCCCTCTTGGTACAGGGAG
GAGCAGCTGCGCCCATCAGCTCCCACTGCAGGCTTGACAAGTCCAACTTCCAGCAGCCCTATATCACCAACCGC
ACCTTCATGCTGGCTAAGGAGGCTAGCTTGGCTGATAACAACACAGACGTTCGTCTCATTGGGGAGAAACTGTT
CCACGGAGTCAGTATGAGTGAGCGCTGCTATCTGATGAAGCAGGTGCTGAACTTCACCCTTGAAGAAGTGCTGT
TCCCTCAATCTGATAGGTTCCAGCCTTATATGCAGGAGGTGGTGCCCTTCCTGGCCAGGCTCAGCAACAGGCTA
AGCACATGTCATATTGAAGGTGATGACCTGCATATCCAGAGGAATGTGCAAAAGCTGAAGGACACAGTGAAAAA
GCTTGGAGAGAGTGGAGAGATCAAAGCAATTGGAGAACTGGATTTGCTGTTTATGTCTCTGAGAAATGCCTGCA
TTTGACCAGAGCAAAGCTGAAAAATGAATAACTAACCCCCTTTCCCTGCTAGAAATAACAATTAGATGCCCCAA
AGCGATTTTTTTAACCAAAAGGAAGATGGGAAGCCAAACTCCATCATGATGGGTGGATTCCAAATGAACCCCT
GCGTTAGTTACAAAGGAAACCAATGCCACTTTGTTTATAAGACCAGAAGGTAGACTTTCTAAGCATAGATATT
TATTGATAACATTTCATTGTAACTGGTGTTCTATACACAGAAAACAATTTATTTTTTAAATAATTGTCTTTTTC
CATAAAAAAGATTACTTTCCATTCCTTTAGGGGAAAAAACCCCTAAATAGCTTCATGTTTCCATAATCAGTACT
TTATATTTATAAATGTATTTATTATTATTATAAGACTGCATTTTATTTATATCATTTTATTAATATGGATTTAT
TTATAGAAACATCATTCGATATTGCTACTTGAGTGTAAGGCTAATATTGATATTTATGACAATAATTATAGAGC
TATAACATGTTTATTTGACCTCAATAAACACTTGGATATCCC
```

FIG. 14

MAALQKSVSSFLMGTLATSCLLLLALLVQGGAAAPISSHCRLDKSNFQQPYITNRTFMLAKEASLADNNTDVRL
IGEKLFHGVSMSERCYLMKQVLNFTLEEVLFPQSDRFQPYMQEVVPFLARLSNRLSTCHIEGDDLHIQRNVQKL
KDTVKKLGESGEIKAIGELDLLFMSLRNACI

Important features of the protein:
Signal peptide:
amino acids 1-33

N-glycosylation sites.
amino acids 54-58, 68-72, 97-101

N-myristoylation sites.
amino acids 14-20, 82-88

Prokaryotic membrane lipoprotein lipid attachment site.
amino acids 10-21

FIG. 15

```
CACCAGACAGCACTCCAGCACTCTGTTTGGGGGGCATTCGAAACAGCAAAATCACTCATAAAAGGCAAAAATT
GCAAAAAAAATAGTAATAACCAGCATGGCACTAAATAGACCATGAAAAGACATGTGTGTGCAGTATGAAAATT
GAGACAGGAAGGCAGAGTGTCAGCTTGTTCCACCTCAGCTGGGAATGTGCATCAGGCAACTCAAGTTTTTCACC
ACGGCATGTGTCTGTGAATGTCCGCAAAACATTCTCTCTCCCCAGCCTTCATGTGTTAACCTGGGGATGATGTG
GACCTGGGCACTGTGGATGCTCCCTTCACTCTGCAAATTCAGCCTGGCAGCTCTGCCAGCTAAGCCTGAGAACA
TTTCCTGTGTCTACTACTATAGGAAAAATTTAACCTGCACTTGGAGTCCAGGAAAGGAAACCAGTTATACCCAG
TACACAGTTAAGAGAACTTACGCTTTTGGAGAAAAACATGATAATTGTACAACCAATAGTTCTACAAGTGAAAA
TCGTGCTTCGTGCTCTTTTTTCCTTCCAAGAATAACGATCCCAGATAATTATACCATTGAGGTGGAAGCTGAAA
ATGGAGATGGTGTAATTAAATCTCATATGACATACTGGAGATTAGAGAACATAGCGAAAACTGAACCACCTAAG
ATTTTCCGTGTGAAACCAGTTTTGGGCATCAAACGAATGATTCAAATTGAATGGATAAAGCCTGAGTTGGCGCC
TGTTTCATCTGATTTAAAATACACACTTCGATTCAGGACAGTCAACAGTACCAGCTGGATGGAAGTCAACTTCG
CTAAGAACCGTAAGGATAAAAACCAAACGTACAACCTCACGGGGCTGCAGCCTTTTACAGAATATGTCATAGCT
CTGCGATGTGCGGTCAAGGAGTCAAAGTTCTGGAGTGACTGGAGCCAAGAAAAAATGGGAATGACTGAGGAAGA
AGCTCCATGTGGCCTGGAACTGTGGAGAGTCCTGAAACCAGCTGAGGCGGATGGAAGAAGGCCAGTGCGGTTGT
TATGGAAGAAGGCAAGAGGAGCCCCAGTCCTAGAGAAAACACTTGGCTACAACATATGGTACTATCCAGAAAGC
AACACTAACCTCACAGAAACAATGAACACTACTAACCAGCAGCTTGAACTGCATCTGGGAGGCGAGAGCTTTTG
GGTGTCTATGATTTCTTATAATTCTCTTGGGAAGTCTCCAGTGGCCACCCTGAGGATTCCAGCTATTCAAGAAA
AATCATTTCAGTGCATTGAGGTCATGCAGGCCTGCGTTGCTGAGGACCAGCTAGTGGTGAAGTGGCAAAGCTCT
GCTCTAGACGTGAACACTTGGATGATTGAATGGTTTCCGGATGTGGACTCAGAGCCCACCACCCTTTCCTGGGA
ATCTGTGTCTCAGGCCACGAACTGGACGATCCAGCAAGATAAATTAAAACCTTCTGGTGCTATAACATCTCTG
TGTATCCAATGTTGCATGACAAAGTTGGCGAGCCATATTCCATCCAGGCTTATGCCAAAGAAGGCGTTCCATCA
GAAGGTCCTGAGACCAAGGTGGAGAACATTGGCGTGAAGACGGTCACGATCACATGGAAAGAGATTCCCAAGAG
TGAGAGAAAGGGTATCATCTGCAACTACACCATCTTTTACCAAGCTGAAGGTGGAAAAGGATTCTGTAAGCACG
CCCATAGCGAAGTGGAAAAAAACCCCAAGCCCCAGATAGATGCTATGGATAGACCTGTTGTAGGCATGGCTCCC
CCATCTCATTGTGACTTGCAACCTGGCATGAATCACTTAGCTTCTTTAAATCTCTCTGAAAATGGGGCCAAGAG
CACCCACCTTTTGGGGTTTTGGGGGTTAAATGAGAGTGAAGTGACAGTACCTGAGAGGAGAGTCCTGAGGAAAT
GGAAGGAGTTGTTATAAATTTGTCCTGGTTAGGCCCTGAATTGACCTCCCGGGAGCTCCCCGACCATCATTCCCA
GGAATGGCGTGCCTGGCTTAAAGAGTGAGGAGGAACAGACCCTGTCACCATGACTTCTACTGCCCCTGCCAAAT
CATGCTTTTGTTTTCAGTCCACCTTATCTCCTGACATCTTAAATACTGGGCAAGGCTTGGATTCTTGCTTAGG
CTAAATAATTTTTTCTTATGGTAAAATACACGTAAAATATTTTCCAGTTTAAACATTTGAAAGTGTACAATTT
AGTGGCATTAGAAGCATTCACAATATTGTGCAACCATCACCACTATTTCCAGAACTCTTCTATTTCTGCCCAAA
TAGAAGCCCTATACCCATTCATTAGTCACTCCCCATTCCTCTCCTCCCACAGCCCCTGGCAACTACCAAACTGC
TTTGTGTCTCTATGGATTGCCTATTTTGGATATTTCATATACATAGAATCATAAANTAAAAAAAAAAAAAAAA
AAA
```

FIG. 16

></usr/seqdb2/sst/DNA/Dnaseqs.min/ss.DNA177313
><​subunit 1 of 1, 582 aa, 1 stop
><MW: 66605, pI: 8.14, NX(S/T): 15
MCIRQLKFFTTACVCECPQNILSPQPSCVNLGMMWTWALWMLPSLCKFSLAALPAKPENIS
CVYYRKNLTCTWSPGKETSYTQYTVKRTYAFGEKHDNCTTNSSTSENRASCSFFLPRITI
PDNYTIEVEAENGDGVIKSHMTYWRLENIAKTEPPKIFRVKPVLGIKRMIQIEWIKPELAP
VSSDLKYTLRFRTVNSTSWMEVNFAKNRKDKNQTYNLTGLQPFTEYVIALRCAVKESKFWS
DWSQEKMGMTEEEAPCGLELWRVLKPAEADGRRPVRLLWKKARGAPVLEKTLGYNIWYYPE
SNTNLTETMNTTNQQLELHLGGESFWVSMISYNSLGKSPVATLRIPAIQEKSFQCIEVMQA
CVAEDQLVVKWQSSALDVNTWMIEWFPDVDSEPTTLSWESVSQATNWTIQQDKLKPFWCYN
ISVYPMLHDKVGEPYSIQAYAKEGVPSEGPETKVENIGVKTVTITWKEIPKSERKGIICNY
TIFYQAEGGKGFCKHAHSEVEKNPKPQIDAMDRPVVGMAPPSHCDLQPGMNHLASLNLSEN
GAKSTHLLGFWGLNESEVTVPERRVLRKWKELL Important features of the protein:

Signal peptide:

Amino acids    1-46

N-glycosylation sites:

Amino acids    59-63;69-73;99-103;103-107;125-129;198-202;
               215-219;219-223;309-313;315-319;412-416;
               427-431;487-491;545-549;563-567

N-myristoylation sites:

Amino acids    32-38;137-143;483-489;550-556;561-567

Amidation site:

Amino acids    274-278

Growth factor and cytokines receptors family signature 1:

Amino acids    62-75

Fibronectin type III domain:

Amino acids    54-144;154-247

FIG. 17

```
CACTTTCTCCCTCTCTTCCTTTACTTTCGAGAAACCGCGCTTCCGCTTCTGGTCGCAGAGACCTCGGAGACCGC
GCCGGGGAGACGGAGGTGCTGTGGGTGGGGGGACCTGTGGCTGCTCGTACCGCCCCCCACCCTCCTCTTCTGC
ACTGCCGTCCTCCGGAAGACCTTTTCCCCTGCTCTGTTTCCTTCACCGAGTCTGTGCATCGCCCCGGACCTGGC
CGGGAGGAGGCTTGGCCGGCGGGAGATGCTCTAGGGGCGGCGCGGGAGGAGCGGCCGGCGGGACGGAGGGCCCG
GCAGGAAGATGGGCTCCCGTGGACAGGGACTCTTGCTGGCGTACTGCCTGCTCCTTGCCTTTGCCTCTGGCCTG
GTCCTGAGTCGTGTGCCCCATGTCCAGGGGAACAGCAGGAGTGGGAGGGGACTGAGGAGCTGCCGTCGCCTCC
GGACCATGCCGAGAGGGCTGAAGAACAACATGAAAAATACAGGCCCAGTCAGGACCAGGGGCTCCCTGCTTCCC
GGTGCTTGCGCTGCTGTGACCCCGGTACCTCCATGTACCCGGCGACCGCCGTGCCCCAGATCAACATCACTATC
TTGAAAGGGGAGAAGGGTGACCGCGGAGATCGAGGCCTCCAAGGGAAATATGGCAAAACAGGCTCAGCAGGGGC
CAGGGGCCACACTGGACCCAAAGGGCAGAAGGGCTCCATGGGGGCCCTGGGGAGCGGTGCAAGAGCCACTACG
CCGCCTTTTCGGTGGGCCGGAAGAAGCCCATGCACAGCAACCACTACTACCAGACGGTGATCTTCGACACGGAG
TTCGTGAACCTCTACGACCACTTCAACATGTTCACCGGCAAGTTCTACTGCTACGTGCCCGGCCTCTACTTCTT
CAGCCTCAACGTGCACACCTGGAACCAGAAGGAGACCTACCTGCACATCATGAAGAACGAGGAGGAGGTGGTGA
TCTTGTTCGCCAGGTGGGCGACCGCAGCATCATGCAAAGCCAGAGCCTGATGCTGGAGCTGCGAGAGCAGGAC
CAGGTGTGGGTACGCCTCTACAAGGGCGAACGTGAGAACGCCATCTTCAGCGAGGAGCTGGACACCTACATCAC
CTTCAGTGGCTACCTGGTCAAGCACGCCACCGAGCCCTAGCTGGCCGGCCACCTCCTTTCCTCTCGCCACCTTC
CACCCCTGCGCTGTGCTGACCCCACCGCCTCTTCCCCGATCCCTGGACTCCGACTCCCTGGCTTTGGCATTCAG
TGAGACGCCCTGCACACACAGAAAGCCAAAGCGATCGGTGCTCCCAGATCCCGCAGCCTCTGGAGAGAGCTGAC
GGCAGATGAAATCACCAGGGCGGGGCACCCGCGAGAACCCTCTGGGACCTTCCGCGGCCCTCTCTGCACACATC
CTCAAGTGACCCCGCACGGCGAGACGCGGGTGGCGGCAGGGCGTCCCAGGGTGCGGCACCGCGGCTCCAGTCCT
TGGAAATAATTAGGCAAATTCTAAAGGTCTCAAAAGGAGCAAAGTAAACCGTGGAGGACAAAGAAAAGGGTTGT
TATTTTTGTCTTTCCAGCCAGCCTGCTGGCTCCCAAGAGAGAGGCCTTTTCAGTTGAGACTCTGCTTAAGAGAA
GATCCAAAGTTAAAGCTCTGGGGTCAGGGGAGGGGCCGGGGGCAGGAAACTACCTCTGGCTTAATTCTTTTAAG
CCACGTAGGAACTTTCTTGAGGGATAGGTGGACCCTGACATCCCTGTGGCCTTGCCCAAGGGCTCTGCTGGTCT
TTCTGAGTCACAGCTGCGAGGTGATGGGGGCTGGGGCCCCAGGCGTCAGCCTCCCAGAGGGACAGCTGAGCCCC
CTGCCTTGGCTCCAGGTTGGTAGAAGCAGCCGAAGGGCTCCTGACAGTGGCCAGGGACCCCTGGGTCCCCCAGG
CCTGCAGATGTTTCTATGAGGGGCAGAGCTCCTTGGTACATCCATGTGTGGCTCTGCTCCACCCCTGTGCCACC
CCAGAGCCCTGGGGGGTGGTCTCCATGCCTGCCACCCTGGCATCGGCTTTCTGTGCCGCCTCCCACACAAATCA
GCCCCAGAAGGCCCCGGGGCCTTGGCTTCTGTTTTTATAAAACACCTCAAGCAGCACTGCAGTCTCCCATCTC
CTCGTGGGCTAAGCATCACCGCTTCCACGTGTGTTGTGTTGGTTGGCAGCAAGGCTGATCCAGACCCCTTCTGC
CCCCACTGCCCTCATCCAGGCCTCTGACCAGTAGCCTGAGAGGGCTTTTTCTAGGCTTCAGAGCAGGGGAGAG
CTGGAAGGGGCTAGAAAGCTCCCGCTTGTCTGTTTCTCAGGCCTCCTGTGAGCCTCAGTCCTGAGACCAGAGTCA
AGAGGAAGTACACGTCCCAATCACCCGTGTCAGGATTCACTCTCAGGAGCTGGGTGGCAGGAGAGGCAATAGCC
CCTGTGGCAATTGCAGGACCAGCTGGAGCAGGGTTGCGGTGTCTCCACGGTGCTCTCGCCCTGCCCATGGCCAC
CCCAGACTCTGATCTCCAGGAACCCCATAGCCCCTCTCCACCTCACCCCATGTTGATGCCCAGGGTCACTCTTG
CTACCCGCTGGGCCCCAAACCCCCGCTGCCTCTCTTCCTTCCCCCCATCCCCCACCTGGTTTTGACTAATCCT
GCTTCCCTCTCTGGGCCTGGCTGCCGGGATCTGGGGTCCCTAAGTCCCTCTCTTTAAAGAACTTCTGCGGGTCA
GACTCTGAAGCCGAGTTGCTGTGGGCGTGCCCGGAAGCAGAGCGCCACACTCGCTGCTTAAGCTCCCCCAGCTC
TTTCCAGAAAACATTAAACTCAGAATTGTGTTTTCAA
```

FIG. 18

MGSRGQGLLLAYCLLLAFASGLVLSRVPHVQGEQQEWEGTEELPSPPDHAERAEEQHEKYRPSQDQGLPASRCL
RCCDPGTSMYPATAVPQINITILKGEKGDRGDRGLQGKYGKTGSAGARGHTGPKGQKGSMGAPGERCKSHYAAF
SVGRKKPMHSNHYYQTVIFDTEFVNLYDHFNMFTGKFYCYVPGLYFFSLNVHTWNQKETYLHIMKNEEEVVILF
AQVGDRSIMQSQSLMLELPEQDQVWVRLYKGERENAIFSEELDTYITFSGYLVKHATEP

Important features:
Signal sequence.
amino acids 1-25

N-glycosylation site.
amino acids 93-97

N-myristoylation sites.
amino acids 7-13, 21-27, 67-73, 117-123, 129-135

Amidation site.
amino acids 150-154

Cell attachment sequence.
amino acids 104-107

FIG. 19

```
AAGTCATTCAGTGGATGTGATCTTGGCTCACAGGGGACGATGTCAAGCTCTTCCTGGCTCCTTCTCAGCCTTGT
TGCTGTAACTGCTGCTCAGTCCACCATTGAGGAACAGGCCAAGACATTTTTGGACAAGTTTAACCACGAAGCCG
AAGACCTGTTCTATCAAAGTTCACTTGCTTCTTGGAATTATAACACCAATATTACTGAAGAGAATGTCCAAAAC
ATGAATAATGCTGGGGACAAATGGTCTGCCTTTTTAAAGGAACAGTCCACACTTGCCCAAATGTATCCACTACA
AGAAATTCAGAATCTCACAGTCAAGCTTCAGCTGCAGGCTCTTCAGCAAAATGGGTCTTCAGTGCTCTCAGAAG
ACAAGAGCAAACGGTTGAACACAATTCTAAATACAATGAGCACCATCTACAGTACTGGAAAAGTTTGTAACCCA
GATAATCCACAAGAATGCTTATTACTTGAACCAGGTTTGAATGAAATAATGGCAAACAGTTTAGACTACAATGA
GAGGCTCTGGGCTTGGGAAAGCTGGAGATCTGAGGTCGGCAAGCAGCTGAGGCCATTATATGAAGAGTATGTGG
TCTTGAAAAATGAGATGGCAAGAGCAAATCATTATGAGGACTATGGGGATTATTGGAGAGGAGACTATGAAGTA
AATGGGGTAGATGGCTATGACTACAGCCGCGGCCAGTTGATTGAAGATGTGGAACATACCTTTGAAGAGATTAA
ACCATTATATGAACATCTTCATGCCTATGTGAGGGCAAAGTTGATGAATGCCTATCCTTCCTATATCAGTCCAA
TTGGATGCCTCCCTGCTCATTTGCTTGGTGATATGTGGGGTAGATTTTGGACAAATCTGTACTCTTTGACAGTT
CCCTTTGGACAGAAACCAAACATAGATGTTACTGATGCAATGGTGGACCAGGCCTGGGATGCACAGAGAATATT
CAAGGAGGCCGAGAAGTTCTTTGTATCTGTTGGTCTTCCTAATATGACTCAAGGATTCTGGGAAAATTCCATGC
TAACGGACCCAGGAAATGTTCAGAAAGCAGTCTGCCATCCCACAGCTTGGGACCTGGGGAAGGGCGACTTCAGG
ATCCTTATGTGCACAAAGGTGACAATGGACGACTTCCTGACAGCTCATCATGAGATGGGGCATATCCAGTATGA
TATGGCATATGCTGCACAACCTTTTCTGCTAAGAAATGGAGCTAATGAAGGATTCCATGAAGCTGTTGGGGAAA
TCATGTCACTTTCTGCAGCCACACCTAAGCATTTAAAATCCATTGGTCTTCTGTCACCCGATTTTCAAGAAGAC
AATGAAACAGAAATAAACTTCCTGCTCAAACAAGCACTCACGATTGTTGGGACTCTGCCATTTACTTACATGTT
AGAGAAGTGGAGGTGGATGGTCTTTAAAGGGGAAATTCCCAAAGACCAGTGGATGAAAAAGTGGTGGGAGATGA
AGCGAGAGATAGTTGGGGTGGTGGAACCTGTGCCCCATGATGAAACATACTGTGACCCCGCATCTCTGTTCCAT
GTTTCTGATGATTACTCATTCATTCGGATATTACACAGGACCCTTTACCAATTCCAGTTTCAAGAAGCACTTTG
TCAAGCAGCTAAACATGAAGGCCCTCTGCACAAATGTGACATCTCAAACTCTACGAAGCTGGACAGAAACTGT
TGTAAGAAATACCTCAAAATGTTGAACCTCTCCTAGTATTCAGTATTACTCATTTCCATGCCTAGGTTTGTATT
TGATTTCTTTGTTCTAAAAAGAAAATTTTATGGCCTCAAAATGTCCTCATTTACAAACCAAACATTTAATTTGT
GGTCAGACAGGAACCTAGACCATACAACAATTGGGTGGGCCACCTCTTTTCTCCCTATCATAACTACAGCCCTC
TCTTCCTGGTAATTGGAAGGAAAGAGCGGTTTAGGGTGGAATATATCTGTTAATATGCATTCTTTTCTTATCTG
CCAGAAGCAAATTTAGCCAAGTCAAAGAGAAGAAACCATAGATCATAGATGTAAATATATGTACATCTGGAACC
CCTCAAAAGGCCCTGAACCCCCTTTTTTGTGTAGCAATATGCTGAGGCTTGGAAAATCAGAACCCTGGACCCT
AGCATTGGAAAATGTTGTAGGAGCAAGAACATGAATGTAAGGCCACTGCTCAACTACTTTGAGCCCTTATTTAC
CTGGCTGAAAGACCAGAACAAGAATTCTTTTGTGGGATGGAGTACCGACTGGAGTCCATATGCAGACCCAAAGC
ATCAAAGTGAGGATAAGCCTAAAATCAGCTCTTGGAGATAAAGCATATGAATGGAACGACAATGAAATGTACCT
GTTCCGATCATCTGTTGCATATGCTATGAGGCAGTACTTTTTAAAAGTAAAAAATCAGATGATTCTTTTTGGGG
AGGAGGATGTGCGAGTGGCTAATTTGAAACCAAGAATCTCCTTTAATTTCTTTGTCACTGCACCTAAAAATGTG
TCTGATATCATTCCTAGAACTGAAGTTGAAAAGGCCATCAGGATGTCCCGGAGCCGTATCAATGATGCTTTCCG
TCTGAATGACAACAGCCTAGAGTTTCTGGGGATACAGCCAACACTTGGACCTCCTAACCAGCCCCCTGTTTCCA
TATGGCTGATTGTTTTTGGAGTTGTGATGGGAGTGATAGTGGTTGGCCATTGTCATCCTGATCTTCACTGGGATC
AGAGATCGGAAGAAGAAAAATAAAGCAAGAAGTGGAGAAAATCCTTATGCCTCCATCGATATTAGCAAAGGAGA
AAATAATCCAGGATTCCAAAACACTGATGATGTTCAGACCTCCTTTTAGAAAAATCTATGTTTTTCCTCTTGAG
GTGATTTTGTTGTATGTAAATGTTAATTTCATGGTATAGAAAATATAAGATGATAAAGATATCATTAAATGTCA
AAACTATGACTCTGTTCAGAAAAAAAATTGTCCAAAGACAACATGGCCAAGGAGAGAGCATCTTCATTGACATT
GCTTTCAGTATTTATTTCTGTCTCTGGATTTGACTTCTGTTCTGTTTCTTAATAAGGATTTTGTATTAGAGTAT
ATTAGGGAAAGTGTGTATTTGGTCTCACAGGCTGTTCAGGGATAATCTAAATGTAAATGTCTGTTGAATTTCTG
AAGTTGAAAACAAGGATATATCATTGGAGCAAGTGTTGGATCTTGTATGGAATATGGATGGATCACTTGTAAGG
ACAGTGCCTGGGAACTGGTGTAGCTGCAAGGATTGAGAATGGCATGCATTAGCTCACTTTCATTTAATCCATTG
TCAAGGATGACATGCTTTCTTCACAGTAACTCAGTTCAAGTACTATGGTGATTTGCCTACAGTGATGTTTGGAA
TCGATCATGCTTTCTTCAAGGTGACAGGTCTAAAGAGAGAAGAATCCAGGGAACAGGTAGAGGACATTGCTTTT
TCACTTCCAAGGTGCTTGATCAACATCTCCCTGACAACACAAAACTAGAGCCAGGGGCCTCCGTGAACTCCCCA
GAGCATGCCTGATAGAAACTCATTTCTACTGTTCTCTAACTGTGGAGTGAATGGAAATTCCAACTGTATGTTCA
CCCTCTGAAGTGGGTACCCAGTCTCTTAAATCTTTTGTATTTGCTCACAGTGTTTGAGCAGTGCTGAGCACAAA
GCAGACACTCAATAAATGCTAGATTTACAAAA
```

FIG. 20

MSSSSWLLLSLVAVTAAQSTIEEQAKTFLDKFNHEAEDLFYQSSLASWNYNTNITEENVQNMNNAGDKWSAFLK
EQSTLAQMYPLQEIQNLTVKLQLQALQQNGSSVLSEDKSKRLNTILNTMSTIYSTGKVCNPDNPQECLLLEPGL
NEIMANSLDYNERLWAWESWRSEVGKQLRPLYEEYVVLKNEMARANHYEDYGDYWRGDYEVNGVDGYDYSRGQL
IEDVEHTFEEIKPLYEHLHAYVRAKLMNAYPSYISPIGCLPAHLLGDMWGRFWTNLYSLTVPFGQKPNIDVTDA
MVDQAWDAQRIFKEAEKFFVSVGLPNMTQGFWENSMLTDPGNVQKAVCHPTAWDLGKGDFRILMCTKVTMDDFL
TAHHEMGHIQYDMAYAAQPFLLRNGANEGFHEAVGEIMSLSAATPKHLKSIGLLSPDFQEDNETEINFLLKQAL
TIVGTLPFTYMLEKWRWMVFKGEIPKDQWMKKWEMKREIVGVVEPVPHDETYCDPASLFHVSDDYSFIRYYTR
TLYQFQFQEALCQAAKHEGPLHKCDISNSTEAGQKLL

Important features of the protein:

Signal peptide:
amino acids 1-17

N-glycosylation sites.
amino acids 53-57, 90-94, 103-107, 322-326, 432-438, 546-550

N-myristoylation sites.
amino acids 260-266, 286-292, 395-401

Cell attachment sequence.
amino acids 204-207

Neutral zinc metallopeptidases, zinc-binding region signature.
amino acids 371-381

SEQUENCE LISTING

```
<160> NUMBER OF SEQ ID NOS: 41

<210> SEQ ID NO 1
<211> LENGTH: 2290
<212> TYPE: DNA
<213> ORGANISM: Homo sapiens

<400> SEQUENCE: 1
accgagccga gcggaccgaa ggcgcgcccg agatgcaggt gagcaagagg        50
atgctggcgg ggggcgtgag gagcatgccc agcccctcc tggcctgctg        100 gcagcccatc ctcctgctgg tgctgggctc agtgctgtca ggctcggcca       150
cgggctgccc gccccgctgc gagtgctccg cccaggaccg cgctgtgctg       200
tgccaccgca agtgctttgt ggcagtcccc gagggcatcc ccaccgagac       250
gcgcctgctg gacctaggca agaaccgcat caaaacgctc aaccaggacg       300
agttcgccag cttcccgcac ctggaggagc tggagctcaa cgagaacatc       350
gtgagcgccg tggagcccgg cgccttcaac aacctcttca acctccggac       400
gctgggtctc cgcagcaacc gcctgaagct catcccgcta ggcgtcttca       450
ctggcctcag caacctgacc aagcaggaca tcagcgagaa caagatcgtt       500
atcctactgg actacatgtt tcaggacctg tacaacctca gtcactgga       550 ggttggcgac aatgacctcg tctacatctc tcaccgcgcc ttcagcggcc       600
tcaacagcct ggagcagctg acgctggaga aatgcaacct gacctccatc       650
cccaccgagg cgctgtccca cctgcacggc ctcatcgtcc tgaggctccg       700
gcacctcaac atcaatgcca tccgggacta ctccttcaag aggctgtacc       750
gactcaaggt cttggagatc tcccactggc cctacttgga ccatgaca       800 cccaactgcc tctacggcct caacctgacg tccctgtcca tcacacactg       850
```

| | |
|---|---|
| caatctgacc gctgtgccct acctggccgt ccgccaccta gtctatctcc | 900 |
| gcttcctcaa cctctcctac aaccccatca gcaccattga gggctccatg | 950 |
| ttgcatgagc tgctccggct gcaggagatc cagctggtgg gcgggcagct | 1000 |
| ggccgtggtg gagccctatg ccttccgcgg cctcaactac ctgcgcgtgc | 1050 |
| tcaatgtctc tggcaaccag ctgaccacac tggaggaatc agtcttccac | 1100 |
| tcggtgggca acctggagac actcatcctg gactccaacc cgctggcctg | 1150 |
| cgactgtcgg ctcctgtggg tgttccggcg ccgctggcgg ctcaacttca | 1200 |
| accggcagca gccacgtgc gccacgcccg agtttgtcca gggcaaggag | 1250 |
| ttcaaggact ccctgatgt gctactgccc aactacttca cctgccgccg | 1300 |
| cgcccgcatc cgggaccgca aggcccagca ggtgtttgtg gacgagggcc | 1350 |
| acacggtgca gtttgtgtgc cgggccgatg gcgacccgcc gcccgccatc | 1400 |
| ctctggctct caccccgaaa gcacctggtc tcagccaaga gcaatgggcg | 1450 |
| gctcacagtc ttccctgatg gcacgctgga ggtgcgctac gcccaggtac | 1500 |
| aggacaacgg cacgtacctg tgcatcgcgc ccaacgcggg cggcaacgac | 1550 |
| tccatgcccg cccacctgca tgtgcgcagc tactcgcccg actggcccca | 1600 |
| tcagcccaac aagaccttcg ctttcatctc caaccagccg ggcgagggag | 1650 |
| aggccaacag cacccgcgcc actgtgcctt tccccttcga catcaagacc | 1700 |
| ctcatcatcg ccaccaccat gggcttcatc tctttcctgg gcgtcgtcct | 1750 |
| cttctgcctg gtgctgctgt ttctctggag ccggggcaag ggcaacacaa | 1800 |
| agcacaacat cgagatcgag tatgtgcccc gaaagtcgga cgcaggcatc | 1850 |
| agctccgccg acgcgccccg caagttcaac atgaagatga tatgaggccg | 1900 |
| gggcgggggg cagggacccc cgggcggccg ggcaggggaa ggggcctggt | 1950 |
| cgccacctgc tcactctcca gtccttccca cctcctccct accttctac | 2000 |
| acacgttctc tttctccctc ccgcctccgt ccctgctgc cccccgccag | 2050 |
| ccctcaccac ctgccctcct tctaccagga cctcagaagc ccagacctgg | 2100 |
| ggaccccacc tacacagggg cattgacaga ctggagttga agccgacga | 2150 |
| accgacacgc ggcagagtca ataattcaat aaaaagtta cgaactttct | 2200 |
| ctgtaacttg ggtttcaata attatggatt tttatgaaaa cttgaaataa | 2250 |
| taaaaagaga aaaaactaa aaaaaaaaaa aaaaaaaaa | 2290 |

<210> SEQ ID NO 2
<211> LENGTH: 620
<212> TYPE: PRT
<213> ORGANISM: Homo sapiens

<400> SEQUENCE: 2

Met Gln Val Ser Lys Arg Met Leu Ala Gly Gly Val Arg Ser Met
1               5                   10                  15

Pro Ser Pro Leu Leu Ala Cys Trp Gln Pro Ile Leu Leu Leu Val
                20                  25                  30

Leu Gly Ser Val Leu Ser Gly Ser Ala Thr Gly Cys Pro Pro Arg
                35                  40                  45

Cys Glu Cys Ser Ala Gln Asp Arg Ala Val Leu Cys His Arg Lys
                50                  55                  60

Cys Phe Val Ala Val Pro Glu Gly Ile Pro Thr Glu Thr Arg Leu
                65                  70                  75

-continued

```
Leu Asp Leu Gly Lys Asn Arg Ile Lys Thr Leu Asn Gln Asp Glu
             80                  85                  90

Phe Ala Ser Phe Pro His Leu Glu Glu Leu Glu Leu Asn Glu Asn
             95                 100                 105

Ile Val Ser Ala Val Glu Pro Gly Ala Phe Asn Asn Leu Phe Asn
            110                 115                 120

Leu Arg Thr Leu Gly Leu Arg Ser Asn Arg Leu Lys Leu Ile Pro
            125                 130                 135

Leu Gly Val Phe Thr Gly Leu Ser Asn Leu Thr Lys Gln Asp Ile
            140                 145                 150

Ser Glu Asn Lys Ile Val Ile Leu Leu Asp Tyr Met Phe Gln Asp
            155                 160                 165

Leu Tyr Asn Leu Lys Ser Leu Glu Val Gly Asp Asn Asp Leu Val
            170                 175                 180

Tyr Ile Ser His Arg Ala Phe Ser Gly Leu Asn Ser Leu Glu Gln
            185                 190                 195

Leu Thr Leu Glu Lys Cys Asn Leu Thr Ser Ile Pro Thr Glu Ala
            200                 205                 210

Leu Ser His Leu His Gly Leu Ile Val Leu Arg Leu Arg His Leu
            215                 220                 225

Asn Ile Asn Ala Ile Arg Asp Tyr Ser Phe Lys Arg Leu Tyr Arg
            230                 235                 240

Leu Lys Val Leu Glu Ile Ser His Trp Pro Tyr Leu Asp Thr Met
            245                 250                 255

Thr Pro Asn Cys Leu Tyr Gly Leu Asn Leu Thr Ser Leu Ser Ile
            260                 265                 270

Thr His Cys Asn Leu Thr Ala Val Pro Tyr Leu Ala Val Arg His
            275                 280                 285

Leu Val Tyr Leu Arg Phe Leu Asn Leu Ser Tyr Asn Pro Ile Ser
            290                 295                 300

Thr Ile Glu Gly Ser Met Leu His Glu Leu Leu Arg Leu Gln Glu
            305                 310                 315

Ile Gln Leu Val Gly Gly Gln Leu Ala Val Val Glu Pro Tyr Ala
            320                 325                 330

Phe Arg Gly Leu Asn Tyr Leu Arg Val Leu Asn Val Ser Gly Asn
            335                 340                 345

Gln Leu Thr Thr Leu Glu Glu Ser Val Phe His Ser Val Gly Asn
            350                 355                 360

Leu Glu Thr Leu Ile Leu Asp Ser Asn Pro Leu Ala Cys Asp Cys
            365                 370                 375

Arg Leu Leu Trp Val Phe Arg Arg Arg Trp Arg Leu Asn Phe Asn
            380                 385                 390

Arg Gln Gln Pro Thr Cys Ala Thr Pro Glu Phe Val Gln Gly Lys
            395                 400                 405

Glu Phe Lys Asp Phe Pro Asp Val Leu Leu Pro Asn Tyr Phe Thr
            410                 415                 420

Cys Arg Arg Ala Arg Ile Arg Asp Arg Lys Ala Gln Gln Val Phe
            425                 430                 435

Val Asp Glu Gly His Thr Val Gln Phe Val Cys Arg Ala Asp Gly
            440                 445                 450

Asp Pro Pro Pro Ala Ile Leu Trp Leu Ser Pro Arg Lys His Leu
            455                 460                 465

Val Ser Ala Lys Ser Asn Gly Arg Leu Thr Val Phe Pro Asp Gly
            470                 475                 480
```

```
Thr Leu Glu Val Arg Tyr Ala Gln Val Gln Asp Asn Gly Thr Tyr
            485                 490                 495

Leu Cys Ile Ala Ala Asn Ala Gly Gly Asn Asp Ser Met Pro Ala
        500                 505                 510

His Leu His Val Arg Ser Tyr Ser Pro Asp Trp Pro His Gln Pro
    515                 520                 525

Asn Lys Thr Phe Ala Phe Ile Ser Asn Gln Pro Gly Glu Gly Glu
530                 535                 540

Ala Asn Ser Thr Arg Ala Thr Val Pro Phe Pro Phe Asp Ile Lys
            545                 550                 555

Thr Leu Ile Ile Ala Thr Thr Met Gly Phe Ile Ser Phe Leu Gly
        560                 565                 570

Val Val Leu Phe Cys Leu Val Leu Leu Phe Leu Trp Ser Arg Gly
    575                 580                 585

Lys Gly Asn Thr Lys His Asn Ile Glu Ile Glu Tyr Val Pro Arg
590                 595                 600

Lys Ser Asp Ala Gly Ile Ser Ser Ala Asp Ala Pro Arg Lys Phe
            605                 610                 615

Asn Met Lys Met Ile
        620

<210> SEQ ID NO 3
<211> LENGTH: 1771
<212> TYPE: DNA
<213> ORGANISM: Homo sapiens

<400> SEQUENCE: 3
cccacgcgtc cgctggtgtt agatcgagca accctctaaa agcagtttag            50
agtggtaaaa aaaaaaaaaa acacaccaaa cgctcgcagc cacaaagggg           100
atgaaatttc ttctggacat cctcctgctt ctcccgttac tgatcgtctg           150
ctccctagag tccttcgtga agcttttat tcctaagagg agaaaatcag            200
tcaccggcga aatcgtgctg attacaggag ctgggcatgg aattgggaga           250
ctgactgcct atgaatttgc taaacttaaa agcaagctgg ttctctggga           300
tataaataag catggactgg aggaaacagc tgccaaatgc aagggactgg           350
gtgccaaggt tcatacccttt gtggtagact gcagcaaccg agaagatatt          400
tacagctctg caaagaaggt gaaggcagaa attggagatg ttagtatttt           450
agtaaataat gctggtgtag tctatacatc agatttgttt gctacacaag           500
atcctcagat tgaaaagact tttgaagtta atgtacttgc acatttctgg           550
actacaaagg catttcttcc tgcaatgacg aagaataacc atggccatat            600
tgtcactgtg gcttcggcag ctggacatgt ctcggtcccc ttcttactgg           650
cttactgttc aagcaagttt gctgctgttg gatttcataa aactttgaca           700
gatgaactgg ctgccttaca ataactgga gtcaaaacaa catgtctgtg            750
tcctaatttc gtaaacactg gcttcatcaa aaatccaagt acaagtttgg           800
gacccactct ggaacctgag gaagtggtaa acaggctgat gcatgggatt           850
ctgactgagc agaagatgat ttttattcca tcttctatag cttttttaac           900
aacattggaa aggatccttc ctgagcgttt cctggcagtt ttaaaacgaa           950
aaatcagtgt taagtttgat gcagttattg gatataaaat gaaagcgcaa          1000
taagcaccta gttttctgaa aactgattta ccaggtttag gttgatgtca          1050
```

```
tctaatagtg ccagaatttt aatgtttgaa cttctgtttt ttctaattat        1100
ccccatttct tcaatatcat ttttgaggct ttggcagtct tcatttacta        1150
ccacttgttc tttagccaaa agctgattac atatgatata aacagagaaa        1200
tacctttaga ggtgacttta aggaaaatga agaaaaagaa ccaaaatgac        1250
tttattaaaa taatttccaa gattatttgt ggctcacctg aaggctttgc        1300
aaaatttgta cctaaccgt ttatttaaca tatatttta tttttgattg          1350 cacttaaatt ttgtataatt tgtgtttctt tttctgttct acataaaatc        1400
agaaacttca agctctctaa ataaaatgaa ggactatatc tagtggtatt        1450
tcacaatgaa tatcatgaac tctcaatggg taggtttcat cctacccatt        1500
gccactctgt ttcctgagag atacctcaca ttccaatgcc aaacatttct        1550
gcacagggaa gctagaggtg gatacacgtg ttgcaagtat aaaagcatca        1600
ctgggattta aggagaattg agagaatgta cccacaaatg gcagcaataa        1650
taaatggatc acacttaaaa aaaaaaaaaa aaaaaaaaaa aaaaaaaaaa        1700
aaaaaaaaaa aaaaaaaaaa aaaaaaaaaa aaaaaaaaaa aaaaaaaaaa        1750
aaaaaaaaaa aaaaaaaaaa  a                                     1771
```

<210> SEQ ID NO 4
<211> LENGTH: 300
<212> TYPE: PRT
<213> ORGANISM: Homo sapiens

<400> SEQUENCE: 4

```
Met Lys Phe Leu Leu Asp Ile Leu Leu Leu Leu Pro Leu Leu Ile
 1               5                  10                  15

Val Cys Ser Leu Glu Ser Phe Val Lys Leu Phe Ile Pro Lys Arg
                20                  25                  30

Arg Lys Ser Val Thr Gly Glu Ile Val Leu Ile Thr Gly Ala Gly
                35                  40                  45

His Gly Ile Gly Arg Leu Thr Ala Tyr Glu Phe Ala Lys Leu Lys
                50                  55                  60

Ser Lys Leu Val Leu Trp Asp Ile Asn Lys His Gly Leu Glu Glu
                65                  70                  75

Thr Ala Ala Lys Cys Lys Gly Leu Gly Ala Lys Val His Thr Phe
                80                  85                  90

Val Val Asp Cys Ser Asn Arg Glu Asp Ile Tyr Ser Ser Ala Lys
                95                 100                 105

Lys Val Lys Ala Glu Ile Gly Asp Val Ser Ile Leu Val Asn Asn
               110                 115                 120

Ala Gly Val Val Tyr Thr Ser Asp Leu Phe Ala Thr Gln Asp Pro
               125                 130                 135

Gln Ile Glu Lys Thr Phe Glu Val Asn Val Leu Ala His Phe Trp
               140                 145                 150

Thr Thr Lys Ala Phe Leu Pro Ala Met Thr Lys Asn Asn His Gly
               155                 160                 165

His Ile Val Thr Val Ala Ser Ala Ala Gly His Val Ser Val Pro
               170                 175                 180

Phe Leu Leu Ala Tyr Cys Ser Ser Lys Phe Ala Ala Val Gly Phe
               185                 190                 195

His Lys Thr Leu Thr Asp Glu Leu Ala Ala Leu Gln Ile Thr Gly
               200                 205                 210
```

| | | | | | | | | | | |
|---|---|---|---|---|---|---|---|---|---|---|
|Val|Lys|Thr|Thr|Cys|Leu|Cys|Pro|Asn|Phe|Val|Asn|Thr|Gly|Phe|
| | |215| | | | |220| | | |225|

Ile Lys Asn Pro Ser Thr Ser Leu Gly Pro Thr Leu Glu Pro Glu
             230                 235                 240

Glu Val Val Asn Arg Leu Met His Gly Ile Leu Thr Glu Gln Lys
             245                 250                 255

Met Ile Phe Ile Pro Ser Ser Ile Ala Phe Leu Thr Thr Leu Glu
             260                 265                 270

Arg Ile Leu Pro Glu Arg Phe Leu Ala Val Leu Lys Arg Lys Ile
             275                 280                 285

Ser Val Lys Phe Asp Ala Val Ile Gly Tyr Lys Met Lys Ala Gln
             290                 295                 300

<210> SEQ ID NO 5
<211> LENGTH: 1427
<212> TYPE: DNA
<213> ORGANISM: Homo sapiens

<400> SEQUENCE: 5

```
actgcactcg gttctatcga ttgaattccc cggggatcct ctagagatcc          50
ctcgacctcg acccacgcgt ccgcggacgc gtgggcggac gcgtgggccg         100
gctaccagga agagtctgcc gaaggtgaag gccatggact tcatcacctc         150
cacagccatc ctgcccctgc tgttcggctg cctgggcgtc ttcggcctct         200
tccggctgct gcagtgggtg cgcgggaagg cctacctgcg gaatgctgtg         250
gtggtgatca caggcgccac ctcagggctg gcaaagaat gtgcaaaagt          300 cttctatgct gcgggtgcta aactggtgct ctgtggccgg aatggtgggg         350
ccctagaaga gctcatcaga gaacttaccg cttctcatgc caccaaggtg         400
cagacacaca agccttactt ggtgaccttc gacctcacag actctggggc         450
catagttgca gcagcagctg agatcctgca gtgctttggc tatgtcgaca         500
tacttgtcaa caatgctggg atcagctacc gtggtaccat catggacacc         550
acagtggatg tggacaagag ggtcatggag acaaactact tggcccagt          600 tgctctaacg aaagcactcc tgcccctccat gatcaagagg aggcaaggcc         650
acattgtcgc catcagcagc atccagggca agatgagcat tccttttcga         700
tcagcatatg cagcctccaa gcacgcaacc caggcttct ttgactgtct          750 gcgtgccgag atgaacagt atgaaattga ggtgaccgtc atcagcccg           800 gctacatcca caccaacctc tctgtaaatg ccatcaccgc ggatggatct         850
aggtatggaa ttatggacac caccacagcc cagggccgaa gccctgtgga         900
ggtggcccag gatgttcttg ctgctgtggg gaagaagaag aaagatgtga         950
tcctggctga cttactgcct tccttggctg tttatcttcg aactctggct        1000
cctgggctct tcttcagcct catggcctcc agggccagaa agagcggaa         1050 atccaagaac tcctagtact ctgaccagcc agggccaggg cagagaagca        1100
gcactcttag gcttgcttac tctacaaggg acagttgcat tgttgagac          1150 tttaatggag atttgtctca caagtgggaa agactgaaga aacacatctc        1200
gtgcagatct gctggcagag acaatcaaa aacgacaaca agcttcttcc         1250
cagggtgagg ggaaacactt aaggaataaa tatggagctg ggtttaaca         1300 ctaaaaacta gaaataaaca tctcaaacag taaaaaaaaa aaaaagggc         1350
```

```
ggccgcgact ctagagtcga cctgcagaag cttggccgcc atggcccaac              1400
ttgtttattg cagcttataa tggttac                                       1427
```

<210> SEQ ID NO 6
<211> LENGTH: 310
<212> TYPE: PRT
<213> ORGANISM: Homo sapiens

<400> SEQUENCE: 6

```
Met Asp Phe Ile Thr Ser Thr Ala Ile Leu Pro Leu Leu Phe Gly
  1               5                  10                  15

Cys Leu Gly Val Phe Gly Leu Phe Arg Leu Leu Gln Trp Val Arg
                 20                  25                  30

Gly Lys Ala Tyr Leu Arg Asn Ala Val Val Ile Thr Gly Ala
                 35                  40                  45

Thr Ser Gly Leu Gly Lys Glu Cys Ala Lys Val Phe Tyr Ala Ala
                 50                  55                  60

Gly Ala Lys Leu Val Leu Cys Gly Arg Asn Gly Gly Ala Leu Glu
                 65                  70                  75

Glu Leu Ile Arg Glu Leu Thr Ala Ser His Ala Thr Lys Val Gln
                 80                  85                  90

Thr His Lys Pro Tyr Leu Val Thr Phe Asp Leu Thr Asp Ser Gly
                 95                 100                 105

Ala Ile Val Ala Ala Ala Ala Glu Ile Leu Gln Cys Phe Gly Tyr
                110                 115                 120

Val Asp Ile Leu Val Asn Asn Ala Gly Ile Ser Tyr Arg Gly Thr
                125                 130                 135

Ile Met Asp Thr Thr Val Asp Val Asp Lys Arg Val Met Glu Thr
                140                 145                 150

Asn Tyr Phe Gly Pro Val Ala Leu Thr Lys Ala Leu Leu Pro Ser
                155                 160                 165

Met Ile Lys Arg Arg Gln Gly His Ile Val Ala Ile Ser Ser Ile
                170                 175                 180

Gln Gly Lys Met Ser Ile Pro Phe Arg Ser Ala Tyr Ala Ala Ser
                185                 190                 195

Lys His Ala Thr Gln Ala Phe Phe Asp Cys Leu Arg Ala Glu Met
                200                 205                 210

Glu Gln Tyr Glu Ile Glu Val Thr Val Ile Ser Pro Gly Tyr Ile
                215                 220                 225

His Thr Asn Leu Ser Val Asn Ala Ile Thr Ala Asp Gly Ser Arg
                230                 235                 240

Tyr Gly Val Met Asp Thr Thr Thr Ala Gln Gly Arg Ser Pro Val
                245                 250                 255

Glu Val Ala Gln Asp Val Leu Ala Ala Val Gly Lys Lys Lys
                260                 265                 270

Asp Val Ile Leu Ala Asp Leu Pro Ser Leu Ala Val Tyr Leu
                275                 280                 285

Arg Thr Leu Ala Pro Gly Leu Phe Phe Ser Leu Met Ala Ser Arg
                290                 295                 300

Ala Arg Lys Glu Arg Lys Ser Lys Asn Ser
                305                 310
```

<210> SEQ ID NO 7
<211> LENGTH: 902
<212> TYPE: DNA
<213> ORGANISM: Homo sapiens

<400> SEQUENCE: 7

```
cggtggccat gactgcggcc gtgttcttcg gctgcgcctt cattgccttc        50
gggcctgcgc tcgcccttta tgtcttcacc atcgccatcg agccgttgcg       100
tatcatcttc ctcatcgccg gagctttctt ctggttggtg tctctactga       150
tttcgtccct tgtttggttc atggcaagag tcattattga caacaaagat       200
ggaccaacac agaaatatct gctgatcttt ggagcgtttg tctctgtcta       250
tatccaagaa atgttccgat tgcatatta taaactctta aaaaaagcca       300
gtgaaggttt gaagagtata aacccaggtg agacagcacc ctctatgcga       350
ctgctggcct atgtttctgg cttgggcttt ggaatcatga gtggagtatt       400
ttcctttgtg aatacccta ctgactcctt ggggccaggc acagtgggca        450
ttcatggaga ttctcctcaa ttcttccttt attcagcttt catgacgctg       500
gtcattatct gctgcatgt attctggggc attgtatttt ttgatggctg        550
tgagaagaaa aagtggggca tcctccttat cgttctcctg acccacctgc       600
tggtgtcagc ccagaccttc ataagttctt attatggaat aaacctggcg       650
tcagcattta taatcctggt gctcatgggc acctgggcat tcttagctgc       700
gggaggcagc tgccgaagcc tgaaactctg cctgctctgc aagacaaga        750
actttcttct ttacaaccag cgctccagat aacctcaggg aaccagcact       800
tcccaaaccg cagactacat ctttagagga agcacaactg tgccttttc        850
tgaaaatccc tttttctggt ggaattgaga agaaataaa actatgcaga        900
ta                                                            902
```

<210> SEQ ID NO 8
<211> LENGTH: 257
<212> TYPE: PRT
<213> ORGANISM: Homo sapiens

<400> SEQUENCE: 8

```
Met Thr Ala Ala Val Phe Phe Gly Cys Ala Phe Ile Ala Phe Gly
  1               5                  10                  15

Pro Ala Leu Ala Leu Tyr Val Phe Thr Ile Ala Ile Glu Pro Leu
                 20                  25                  30

Arg Ile Ile Phe Leu Ile Ala Gly Ala Phe Phe Trp Leu Val Ser
                 35                  40                  45

Leu Leu Ile Ser Ser Leu Val Trp Phe Met Ala Arg Val Ile Ile
                 50                  55                  60

Asp Asn Lys Asp Gly Pro Thr Gln Lys Tyr Leu Leu Ile Phe Gly
                 65                  70                  75

Ala Phe Val Ser Val Tyr Ile Gln Glu Met Phe Arg Phe Ala Tyr
                 80                  85                  90

Tyr Lys Leu Leu Lys Lys Ala Ser Glu Gly Leu Lys Ser Ile Asn
                 95                 100                 105

Pro Gly Glu Thr Ala Pro Ser Met Arg Leu Leu Ala Tyr Val Ser
                110                 115                 120

Gly Leu Gly Phe Gly Ile Met Ser Gly Val Phe Ser Phe Val Asn
                125                 130                 135

Thr Leu Ser Asp Ser Leu Gly Pro Gly Thr Val Gly Ile His Gly
                140                 145                 150

Asp Ser Pro Gln Phe Phe Leu Tyr Ser Ala Phe Met Thr Leu Val
                155                 160                 165
```

```
Ile Ile Leu Leu His Val Phe Trp Gly Ile Val Phe Phe Asp Gly
            170                 175                 180
Cys Glu Lys Lys Lys Trp Gly Ile Leu Leu Ile Val Leu Leu Thr
            185                 190                 195
His Leu Leu Val Ser Ala Gln Thr Phe Ile Ser Ser Tyr Tyr Gly
            200                 205                 210
Ile Asn Leu Ala Ser Ala Phe Ile Ile Leu Val Leu Met Gly Thr
            215                 220                 225
Trp Ala Phe Leu Ala Ala Gly Gly Ser Cys Arg Ser Leu Lys Leu
            230                 235                 240
Cys Leu Leu Cys Gln Asp Lys Asn Phe Leu Leu Tyr Asn Gln Arg
            245                 250                 255
Ser Arg

<210> SEQ ID NO 9
<211> LENGTH: 2598
<212> TYPE: DNA
<213> ORGANISM: Homo sapiens

<400> SEQUENCE: 9
```

| | | | | | |
|---|---|---|---|---|---|
| cggctcgagg | ctcccgccag | gagaaaggaa | cattctgagg | ggagtctaca | 50 |
| ccctgtggag | ctcaagatgg | tcctgagtgg | ggcgctgtgc | ttccgaatga | 100 |
| aggactcggc | attgaaggtg | ctttatctgc | ataataacca | gcttctagct | 150 |
| ggagggctgc | atgcagggaa | ggtcattaaa | ggtgaagaga | tcagcgtggt | 200 |
| ccccaatcgg | tggctggatg | ccagcctgtc | ccccgtcatc | ctgggtgtcc | 250 |
| agggtggaag | ccagtgcctg | tcatgtgggg | tggggcagga | gccgactcta | 300 |
| acactagagc | cagtgaacat | catggagctc | tatcttggtg | ccaaggaatc | 350 |
| caagagcttc | accttctacc | ggcgggacat | ggggctcacc | tccagcttcg | 400 |
| agtcggctgc | ctacccgggc | tggttcctgt | gcacggtgcc | tgaagccgat | 450 |
| cagcctgtca | gactcaccca | gcttcccgag | aatggtggct | ggaatgcccc | 500 |
| catcacagac | ttctacttcc | agcagtgtga | ctagggcaac | gtgccccca | 550 |
| gaactccctg | gcagagcca | gctcgggtga | ggggtgagtg | gaggagaccc | 600 |
| atggcggaca | tcactctct | ctgctctcag | gaccccacg | tctgacttag | 650 |
| tgggcacctg | accactttgt | cttctggttc | ccagtttgga | taaattctga | 700 |
| gatttggagc | tcagtccacg | gtcctccccc | actggatggt | gctactgctg | 750 |
| tggaaccttg | taaaaaccat | gtggggtaaa | ctgggaataa | catgaaaaga | 800 |
| tttctgtggg | ggtggggtgg | gggagtggtg | ggaatcattc | ctgcttaatg | 850 |
| gtaactgaca | agtgttaccc | tgagccccgc | aggccaaccc | atccccagtt | 900 |
| gagccttata | gggtcagtag | ctctccacat | gaagtcctgt | cactcaccac | 950 |
| tgtgcaggag | agggaggtgg | tcatagagtc | agggatctat | ggcccttggc | 1000 |
| ccagccccac | ccccttccct | ttaatcctgc | cactgtcata | tgctaccttt | 1050 |
| cctatctctt | ccctcatcat | cttgttgtgg | gcatgaggag | gtggtgatgt | 1100 |
| cagaagaaat | ggctcgagct | cagaagataa | agataagta | gggtatgctg | 1150 |
| atcctctttt | aaaacccaa | gatacaatca | aaatcccaga | tgctggtctc | 1200 |
| tattcccatg | aaaagtgct | catgacatat | tgagaagacc | tacttacaaa | 1250 |
| gtggcatata | ttgcaatttta | ttttaattaa | aagataccta | tttatatatt | 1300 |

```
tctttataga aaaaagtctg gaagagttta cttcaattgt agcaatgtca         1350
gggtggtggc agtataggtg attttctttt taattctgtt aatttatctg         1400
tatttcctaa tttttctaca atgaagatga attccttgta taaaaataag         1450
aaaagaaatt aatcttgagg taagcagagc agacatcatc tctgattgtc         1500
ctcagcctcc acttccccag agtaaattca aattgaatcg agctctgctg         1550
ctctggttgg ttgtagtagt gatcaggaaa cagatctcag caaagccact         1600
gaggaggagg ctgtgctgag tttgtgtggc tggaatctct gggtaaggaa         1650
cttaaagaac aaaaatcatc tggtaattct ttcctagaag gatcacagcc         1700
cctgggattc caaggcattg gatccagtct ctaagaaggc tgctgtactg         1750
gttgaattgt gtccccctca aattcacatc cttcttggaa tctcagtctg         1800
tgagtttatt tggagataag gtctctgcag atgtagttag ttaagacaag         1850
gtcatgctgg atgaaggtag acctaaattc aatatgactg gtttccttgt         1900
atgaaaagga gaggacacag agacagagga gacgcgggga agactatgta         1950
aagatgaagg cagagatcgg agttttgcag ccacaagcta agaaacacca         2000
aggattgtgg caaccatcag aagcttggaa gaggcaaaga agaattcttc         2050
cctagaggct ttagagggat aacggctctg ctgaaacctt aatctcagac         2100
ttccagcctc ctgaacgaag aaagaataaa tttcggctgt tttaagccac         2150
caaggataat tggttacagc agctctagga aactaataca gctgctaaaa         2200
tgatccctgt ctcctcgtgt ttacattctg tgtgtgtccc ctcccacaat         2250
gtaccaaagt tgtctttgtg accaatagaa tatggcagaa gtgatggcat         2300
gccacttcca agattaggtt ataaaagaca ctgcagcttc tacttgagcc         2350
ctctctctct gccacccacc gcccccaatc tatcttggct cactcgctct         2400
gggggaagct agctgccatg ctatgagcag gcctataaag agacttacgt         2450
ggtaaaaaat gaagtctcct gcccacagcc acattagtga acctagaagc         2500
agagactctg tgagataatc gatgtttgtt gttttaagtt gctcagtttt         2550
ggtctaactt gttatgcagc aatagataaa taatatgcag  agaaagag           2598
```

<210> SEQ ID NO 10
<211> LENGTH: 155
<212> TYPE: PRT
<213> ORGANISM: Homo sapiens

<400> SEQUENCE: 10

```
Met Val Leu Ser Gly Ala Leu Cys Phe Arg Met Lys Asp Ser Ala
  1               5                  10                  15

Leu Lys Val Leu Tyr Leu His Asn Asn Gln Leu Leu Ala Gly Gly
                 20                  25                  30

Leu His Ala Gly Lys Val Ile Lys Gly Glu Glu Ile Ser Val Val
                 35                  40                  45

Pro Asn Arg Trp Leu Asp Ala Ser Leu Ser Pro Val Ile Leu Gly
                 50                  55                  60

Val Gln Gly Gly Ser Gln Cys Leu Ser Cys Gly Val Gly Gln Glu
                 65                  70                  75

Pro Thr Leu Thr Leu Glu Pro Val Asn Ile Met Glu Leu Tyr Leu
                 80                  85                  90

Gly Ala Lys Glu Ser Lys Ser Phe Thr Phe Tyr Arg Arg Asp Met
                 95                 100                 105
```

```
Gly Leu Thr Ser Ser Phe Glu Ser Ala Ala Tyr Pro Gly Trp Phe
            110                 115                 120

Leu Cys Thr Val Pro Glu Ala Asp Gln Pro Val Arg Leu Thr Gln
            125                 130                 135

Leu Pro Glu Asn Gly Gly Trp Asn Ala Pro Ile Thr Asp Phe Tyr
            140                 145                 150

Phe Gln Gln Cys Asp
            155

<210> SEQ ID NO 11
<211> LENGTH: 1519
<212> TYPE: DNA
<213> ORGANISM: Homo sapiens

<400> SEQUENCE: 11
gtcagccgca tggctcccct gtgcccagc ccctggctcc ctctgttgat            50
cccggcccct gctccaggcc tcactgtgca actgctgctg tcactgctgc           100
ttctgatgcc tgtccatccc cagaggttgc cccggatgca ggaggattcc           150
cccttgggag gaggctcttc tggggaagat gacccactgg gcgaggagga           200
tctgcccagt gaagaggatt cacccagaga ggaggatcca cccggagagg           250
aggatctacc tggagaggag gatctacctg gagaggagga tctacctgaa           300
gttaagccta atcagaaga agagggctcc ctgaagttag aggatctacc            350
tactgttgag gctcctggag atcctcaaga accccagaat aatgcccaca           400
gggacaaaga aggggatgac cagagtcatt ggcgctatgg aggcgacccg           450
ccctggcccc gggtgtcccc agcctgcgcg ggccgcttcc agtccccggt           500
ggatatccgc cccagctcg ccgccttctg cccggccctg cgcccctgg             550 aactcctggg cttccagctc ccgccgctcc cagaactgcg cctgcgcaac           600
aatggccaca gtgtgcaact gaccctgcct cctgggctag agatggctct           650
gggtcccggg cgggagtacc gggctctgca gctgcatctg cactgggggg          700
ctgcaggtcg tccgggctcg gagcacactg tggaaggcca ccgtttccct          750
gccgagatcc acgtggttca cctcagcacc gcctttgcca gagttgacga          800
ggccttgggg cgcccgggag gcctggccgt gttggccgcc tttctggagg          850
agggcccgga agaaaacagt gcctatgagc agttgctgtc tcgcttggaa          900
gaaatcgctg aggaaggctc agagactcag gtcccaggac tggacatatc          950
tgcactcctg ccctctgact tcagccgcta cttccaatat gagggtctc           1000 tgactacacc gccctgtgcc cagggtgtca tctggactgt gtttaaccag         1050
acagtgatgc tgagtgctaa gcagctccac accctctctg acaccctgtg         1100
gggacctggt gactctcggc tacagctgaa cttccgagcg acgcagcctt         1150
tgaatgggcg agtgattgag gcctccttcc ctgctggagt ggacagcagt         1200
cctcgggctg ctgagccagt ccagctgaat tcctgcctgg ctgctggtga         1250
catcctagcc ctggttttg gcctcctttt tgctgtcacc agcgtcgcgt          1300
tccttgtgca gatgagaagg cagcacagaa ggggaaccaa aggggtgtg          1350 agctaccgcc cagcagaggt agccgagact ggagcctaga ggctggatct         1400
tggagaatgt gagaagccag ccagaggcat ctgaggggga gccggtaact         1450
```

```
gtcctgtcct gctcattatg ccacttcctt ttaactgcaa agaaattttt          1500
taaaataaat atttataat                                            1519
```

<210> SEQ ID NO 12
<211> LENGTH: 459
<212> TYPE: PRT
<213> ORGANISM: Homo sapiens

<400> SEQUENCE: 12

```
Met Ala Pro Leu Cys Pro Ser Pro Trp Leu Pro Leu Leu Ile Pro
 1               5                  10                  15

Ala Pro Ala Pro Gly Leu Thr Val Gln Leu Leu Ser Leu Leu
            20                  25                  30

Leu Leu Val Pro Val His Pro Gln Arg Leu Pro Arg Met Gln Glu
            35                  40                  45

Asp Ser Pro Leu Gly Gly Gly Ser Ser Gly Glu Asp Pro Leu
            50                  55                  60

Gly Glu Glu Asp Leu Pro Ser Glu Asp Ser Pro Arg Glu Glu
            65                  70                  75

Asp Pro Pro Gly Glu Glu Asp Leu Pro Gly Glu Glu Asp Leu Pro
            80                  85                  90

Gly Glu Glu Asp Leu Pro Glu Val Lys Pro Lys Ser Glu Glu
            95                  100                 105

Gly Ser Leu Lys Leu Glu Asp Leu Pro Thr Val Glu Ala Pro Gly
            110                 115                 120

Asp Pro Gln Glu Pro Gln Asn Asn Ala His Arg Asp Lys Glu Gly
            125                 130                 135

Asp Asp Gln Ser His Trp Arg Tyr Gly Gly Asp Pro Pro Trp Pro
            140                 145                 150

Arg Val Ser Pro Ala Cys Ala Gly Arg Phe Gln Ser Pro Val Asp
            155                 160                 165

Ile Arg Pro Gln Leu Ala Ala Phe Cys Pro Ala Leu Arg Pro Leu
            170                 175                 180

Glu Leu Leu Gly Phe Gln Leu Pro Pro Leu Pro Glu Leu Arg Leu
            185                 190                 195

Arg Asn Asn Gly His Ser Val Gln Leu Thr Leu Pro Pro Gly Leu
            200                 205                 210

Glu Met Ala Leu Gly Pro Gly Arg Glu Tyr Arg Ala Leu Gln Leu
            215                 220                 225

His Leu His Trp Gly Ala Ala Gly Arg Pro Gly Ser Glu His Thr
            230                 235                 240

Val Glu Gly His Arg Phe Pro Ala Glu Ile His Val Val His Leu
            245                 250                 255

Ser Thr Ala Phe Ala Arg Val Asp Glu Ala Leu Gly Arg Pro Gly
            260                 265                 270

Gly Leu Ala Val Leu Ala Ala Phe Leu Glu Glu Gly Pro Glu Glu
            275                 280                 285

Asn Ser Ala Tyr Glu Gln Leu Leu Ser Arg Leu Glu Glu Ile Ala
            290                 295                 300

Glu Glu Gly Ser Glu Thr Gln Val Pro Gly Leu Asp Ile Ser Ala
            305                 310                 315

Leu Leu Pro Ser Asp Phe Ser Arg Tyr Phe Arg Tyr Glu Gly Ser
            320                 325                 330

Leu Thr Thr Pro Pro Cys Ala Gln Gly Val Ile Trp Thr Val Phe
            335                 340                 345
```

```
Asn Gln Thr Val Met Leu Ser Ala Lys Gln Leu His Thr Leu Ser
            350                 355                 360

Asp Thr Leu Trp Gly Pro Gly Asp Ser Arg Leu Gln Leu Asn Phe
        365                 370                 375

Arg Ala Thr Gln Pro Leu Asn Gly Arg Val Ile Glu Ala Ser Phe
            380                 385                 390

Pro Ala Gly Val Asp Ser Ser Pro Arg Ala Ala Glu Pro Val Gln
            395                 400                 405

Leu Asn Ser Cys Leu Ala Ala Gly Asp Ile Leu Ala Leu Val Phe
            410                 415                 420

Gly Leu Leu Phe Ala Val Thr Ser Val Ala Phe Leu Val Gln Met
            425                 430                 435

Arg Arg Gln His Arg Arg Gly Thr Lys Gly Gly Val Ser Tyr Arg
            440                 445                 450

Pro Ala Glu Val Ala Glu Thr Gly Ala
            455

<210> SEQ ID NO 13
<211> LENGTH: 1152
<212> TYPE: DNA
<213> ORGANISM: Homo sapiens

<400> SEQUENCE: 13
cttcagaaca ggttctcctt ccccagtcac cagttgctcg agttagaatt          50
gtctgcaatg ccgccctgc agaaatctgt gagctctttc cttatgggga          100
ccctggccac cagctgcctc cttctcttgg ccctcttggt acagggagga          150
gcagctgcgc ccatcagctc ccactgcagg cttgacaagt ccaacttcca          200
gcagccctat atcaccaacc gcaccttcat gctggctaag gaggctagct          250
tggctgataa caacacagac gttcgtctca ttggggagaa actgttccac          300
ggagtcagta tgagtgagcg ctgctatctg atgaagcagg tgctgaactt          350 caccccttgaa gaagtgctgt tccctcaatc tgataggttc cagccttata          400
tgcaggaggt ggtgcccttc ctggccaggc tcagcaacag gctaagcaca          450
tgtcatattg aaggtgatga cctgcatatc cagaggaatg tgcaaaagct          500
gaaggacaca gtgaaaaagc ttggagagag tggagagatc aaagcaattg          550
gagaactgga tttgctgttt atgtctctga gaaatgcctg catttgacca          600
gagcaaagct gaaaaatgaa taactaaccc cctttccctg ctagaaataa          650
caattagatg ccccaaagcg attttttta accaaaagga agatgggaag          700
ccaaactcca tcatgatggg tggattccaa atgaacccct gcgttagtta          750
caaaggaaac caatgccact tttgtttata agaccagaag gtagactttc          800
taagcataga tatttattga taacatttca ttgtaactgg tgttctatac          850
acagaaaaca atttattttt taaataattg tcttttcca taaaaagat          900 tactttccat tccttaggg gaaaaaccc ctaaatagct tcatgtttcc          950
ataatcagta cttatatttt ataaatgtat ttattattat tataagactg          1000 catttttattt atatcatttt attaatatgg atttatttat agaaacatca          1050
ttcgatattg ctacttgagt gtaaggctaa tattgatatt tatgacaata          1100
attatagagc tataacatgt ttatttgacc tcaataaaca cttggatatc          1150
cc                                                             1152
```

<210> SEQ ID NO 14
<211> LENGTH: 179
<212> TYPE: PRT
<213> ORGANISM: Homo sapiens

<400> SEQUENCE: 14

Met Ala Ala Leu Gln Lys Ser Val Ser Ser Phe Leu Met Gly Thr
1               5                   10                  15

Leu Ala Thr Ser Cys Leu Leu Leu Ala Leu Leu Val Gln Gly
                20                  25                  30

Gly Ala Ala Ala Pro Ile Ser Ser His Cys Arg Leu Asp Lys Ser
                35                  40                  45

Asn Phe Gln Gln Pro Tyr Ile Thr Asn Arg Thr Phe Met Leu Ala
                50                  55                  60

Lys Glu Ala Ser Leu Ala Asp Asn Asn Thr Asp Val Arg Leu Ile
                65                  70                  75

Gly Glu Lys Leu Phe His Gly Val Ser Met Ser Glu Arg Cys Tyr
                80                  85                  90

Leu Met Lys Gln Val Leu Asn Phe Thr Leu Glu Val Leu Phe
                95                  100                 105

Pro Gln Ser Asp Arg Phe Gln Pro Tyr Met Gln Glu Val Val Pro
                110                 115                 120

Phe Leu Ala Arg Leu Ser Asn Arg Leu Ser Thr Cys His Ile Glu
                125                 130                 135

Gly Asp Asp Leu His Ile Gln Arg Asn Val Gln Lys Leu Lys Asp
                140                 145                 150

Thr Val Lys Lys Leu Gly Glu Ser Gly Glu Ile Lys Ala Ile Gly
                155                 160                 165

Glu Leu Asp Leu Leu Phe Met Ser Leu Arg Asn Ala Cys Ile
                170                 175

<210> SEQ ID NO 15
<211> LENGTH: 2445
<212> TYPE: DNA
<213> ORGANISM: Homo sapiens
<220> FEATURE:
<221> NAME/KEY: Unsure
<222> LOCATION: 2424
<223> OTHER INFORMATION: Unknown base

<400> SEQUENCE: 15

| | | |
|---|---|---|
| caccagacag cactccagca ctctgtttgg ggggcattcg aaacagcaaa | 50 |
| atcactcata aaaggcaaaa aattgcaaaa aaaaatagta ataaccagca | 100 |
| tggcactaaa tagaccatga aaagacatgt gtgtgcagta tgaaaattga | 150 |
| gacaggaagg cagagtgtca gcttgttcca cctcagctgg gaatgtgcat | 200 |
| caggcaactc aagttttca ccacggcatg tgtctgtgaa tgtccgcaaa | 250 |
| acattctctc tccccagcct tcatgtgtta acctggggat gatgtggacc | 300 |
| tgggcactgt ggatgctccc ttcactctgc aaattcagcc tggcagctct | 350 |
| gccagctaag cctgagaaca tttcctgtgt ctactactat aggaaaaatt | 400 |
| taacctgcac ttggagtcca ggaaaggaaa ccagttatac ccagtacaca | 450 |
| gttaagagaa cttacgcttt tggagaaaaa catgataatt gtacaaccaa | 500 |
| tagttctaca agtgaaaatc gtgcttcgtg ctcttttttc cttccaagaa | 550 |
| taacgatccc agataattat accattgagg tggaagctga aaatggagat | 600 |

| | |
|---|---|
| ggtgtaatta aatctcatat gacatactgg agattagaga acatagcgaa | 650 |
| aactgaacca cctaagattt tccgtgtgaa accagttttg ggcatcaaac | 700 |
| gaatgattca aattgaatgg ataaagcctg agttggcgcc tgtttcatct | 750 |
| gatttaaaat acacacttcg attcaggaca gtcaacagta ccagctggat | 800 |
| ggaagtcaac ttcgctaaga accgtaagga taaaaaccaa acgtacaacc | 850 |
| tcacggggct gcagccttt acagaatatg tcatagctct gcgatgtgcg | 900 |
| gtcaaggagt caaagttctg gagtgactgg agccaagaaa aaatgggaat | 950 |
| gactgaggaa gaagctccat gtggcctgga actgtggaga gtcctgaaac | 1000 |
| cagctgaggc ggatggaaga aggccagtgc ggttgttatg gaagaaggca | 1050 |
| agaggagccc cagtcctaga gaaaacactt ggctacaaca tatggtacta | 1100 |
| tccagaaagc aacactaacc tcacagaaac aatgaacact actaaccagc | 1150 |
| agcttgaact gcatctggga ggcgagagct tttgggtgtc tatgatttct | 1200 |
| tataattctc ttgggaagtc tccagtggcc accctgagga ttccagctat | 1250 |
| tcaagaaaaa tcatttcagt gcattgaggt catgcaggcc tgcgttgctg | 1300 |
| aggaccagct agtggtgaag tggcaaagct ctgctctaga cgtgaacact | 1350 |
| tggatgattg aatggtttcc ggatgtggac tcagagccca ccaccctttc | 1400 |
| ctgggaatct gtgtctcagg ccacgaactg gacgatccag caagataaat | 1450 |
| taaaacctt ctggtgctat aacatctctg tgtatccaat gttgcatgac | 1500 |
| aaagttggcg agccatattc catccaggct tatgccaaag aaggcgttcc | 1550 |
| atcagaaggt cctgagacca agtggagaa cattggcgtg aagacggtca | 1600 |
| cgatcacatg gaaagagatt cccaagagtg agagaaaggg tatcatctgc | 1650 |
| aactacacca tcttttacca agctgaaggt ggaaaaggat tctgtaagca | 1700 |
| cgcccatagc gaagtggaaa aaaacccaa gccccagata gatgctatgg | 1750 |
| atagacctgt tgtaggcatg gctcccccat ctcattgtga cttgcaacct | 1800 |
| ggcatgaatc acttagcttc tttaaatctc tctgaaaatg gggccaagag | 1850 |
| caccccacctt tgggggtttt gggggttaaa tgagagtgaa gtgacagtac | 1900 |
| ctgagaggag agtcctgagg aaatggaagg agttgttata atttgtcctg | 1950 |
| gttaggccct gaattgacct cccgggagct ccccgaccat cattcccagg | 2000 |
| aatggcgtgc ctggcttaaa gagtgaggag gaacagaccc tgtcaccatg | 2050 |
| acttctactg ccctgccaa atcatgcttt tgttttcag tccacctttat | 2100 |
| ctcctgacat cttaaatact gggcaaggct tggattcttg cttaggctaa | 2150 |
| ataatttttt cttatggtaa aatacacgta aaatattttt ccagtttaaa | 2200 |
| catttgaaag tgtacaattt agtggcatta gaagcattca caatattgta | 2250 |
| caaccatcac cactatttcc agaactcttc tatttctgcc caaatagaag | 2300 |
| ccctataccc attcattagt cactccccat tcctctcctc ccacagcccc | 2350 |
| tggcaactac caaactgctt tgtgtctcta tggattgcct attttggata | 2400 |
| tttcatatac atagaatcat aaantaaaaa aaaaaaaaa aaaaa | 2445 |

<210> SEQ ID NO 16
<211> LENGTH: 582
<212> TYPE: PRT
<213> ORGANISM: Homo sapiens

```
<400> SEQUENCE: 16

Met Cys Ile Arg Gln Leu Lys Phe Phe Thr Ala Cys Val Cys
  1               5                  10                  15

Glu Cys Pro Gln Asn Ile Leu Ser Pro Gln Pro Ser Cys Val Asn
                 20                  25                  30

Leu Gly Met Met Trp Thr Trp Ala Leu Trp Met Leu Pro Ser Leu
                 35                  40                  45

Cys Lys Phe Ser Leu Ala Ala Leu Pro Ala Lys Pro Glu Asn Ile
                 50                  55                  60

Ser Cys Val Tyr Tyr Tyr Arg Lys Asn Leu Thr Cys Thr Trp Ser
                 65                  70                  75

Pro Gly Lys Glu Thr Ser Tyr Thr Gln Tyr Thr Val Lys Arg Thr
                 80                  85                  90

Tyr Ala Phe Gly Glu Lys His Asp Asn Cys Thr Thr Asn Ser Ser
                 95                 100                 105

Thr Ser Glu Asn Arg Ala Ser Cys Ser Phe Phe Leu Pro Arg Ile
                110                 115                 120

Thr Ile Pro Asp Asn Tyr Thr Ile Glu Val Glu Ala Glu Asn Gly
                125                 130                 135

Asp Gly Val Ile Lys Ser His Met Thr Tyr Trp Arg Leu Glu Asn
                140                 145                 150

Ile Ala Lys Thr Glu Pro Pro Lys Ile Phe Arg Val Lys Pro Val
                155                 160                 165

Leu Gly Ile Lys Arg Met Ile Gln Ile Glu Trp Ile Lys Pro Glu
                170                 175                 180

Leu Ala Pro Val Ser Ser Asp Leu Lys Tyr Thr Leu Arg Phe Arg
                185                 190                 195

Thr Val Asn Ser Thr Ser Trp Met Glu Val Asn Phe Ala Lys Asn
                200                 205                 210

Arg Lys Asp Lys Asn Gln Thr Tyr Asn Leu Thr Gly Leu Gln Pro
                215                 220                 225

Phe Thr Glu Tyr Val Ile Ala Leu Arg Cys Ala Val Lys Glu Ser
                230                 235                 240

Lys Phe Trp Ser Asp Trp Ser Gln Glu Lys Met Gly Met Thr Glu
                245                 250                 255

Glu Glu Ala Pro Cys Gly Leu Glu Leu Trp Arg Val Leu Lys Pro
                260                 265                 270

Ala Glu Ala Asp Gly Arg Arg Pro Val Arg Leu Leu Trp Lys Lys
                275                 280                 285

Ala Arg Gly Ala Pro Val Leu Glu Lys Thr Leu Gly Tyr Asn Ile
                290                 295                 300

Trp Tyr Tyr Pro Glu Ser Asn Thr Asn Leu Thr Glu Thr Met Asn
                305                 310                 315

Thr Thr Asn Gln Gln Leu Glu Leu His Leu Gly Gly Glu Ser Phe
                320                 325                 330

Trp Val Ser Met Ile Ser Tyr Asn Ser Leu Gly Lys Ser Pro Val
                335                 340                 345

Ala Thr Leu Arg Ile Pro Ala Ile Gln Glu Lys Ser Phe Gln Cys
                350                 355                 360

Ile Glu Val Met Gln Ala Cys Val Ala Glu Asp Gln Leu Val Val
                365                 370                 375

Lys Trp Gln Ser Ser Ala Leu Asp Val Asn Thr Trp Met Ile Glu
                380                 385                 390
```

```
Trp Phe Pro Asp Val Asp Ser Glu Pro Thr Thr Leu Ser Trp Glu
            395                 400                 405

Ser Val Ser Gln Ala Thr Asn Trp Thr Ile Gln Gln Asp Lys Leu
            410                 415                 420

Lys Pro Phe Trp Cys Tyr Asn Ile Ser Val Tyr Pro Met Leu His
            425                 430                 435

Asp Lys Val Gly Glu Pro Tyr Ser Ile Gln Ala Tyr Ala Lys Glu
            440                 445                 450

Gly Val Pro Ser Glu Gly Pro Glu Thr Lys Val Glu Asn Ile Gly
            455                 460                 465

Val Lys Thr Val Thr Ile Thr Trp Lys Glu Ile Pro Lys Ser Glu
            470                 475                 480

Arg Lys Gly Ile Ile Cys Asn Tyr Thr Ile Phe Tyr Gln Ala Glu
            485                 490                 495

Gly Gly Lys Gly Phe Cys Lys His Ala His Ser Glu Val Glu Lys
            500                 505                 510

Asn Pro Lys Pro Gln Ile Asp Ala Met Asp Arg Pro Val Val Gly
            515                 520                 525

Met Ala Pro Pro Ser His Cys Asp Leu Gln Pro Gly Met Asn His
            530                 535                 540

Leu Ala Ser Leu Asn Leu Ser Glu Asn Gly Ala Lys Ser Thr His
            545                 550                 555

Leu Leu Gly Phe Trp Gly Leu Asn Glu Ser Glu Val Thr Val Pro
            560                 565                 570

Glu Arg Arg Val Leu Arg Lys Trp Lys Glu Leu Leu
            575                 580

<210> SEQ ID NO 17
<211> LENGTH: 2849
<212> TYPE: DNA
<213> ORGANISM: Homo sapiens

<400> SEQUENCE: 17
cactttctcg ctctcttcct ttactttcga gaaaccgcgc ttccgcttct          50
ggtcgcagag acctcggaga ccgcgccggg gagacggagg tgctgtgggt         100 ggggggggacc tgtggctgct cgtaccgccc cccaccctcc tcttctgcac        150
tgccgtcctc cggaagacct tttcccctgc tctgtttcct tcaccgagtc         200
tgtgcatcgc cccggacctg gccgggagga ggcttggccg gcgggagatg         250 ctctagggc ggcgcgggag gagcggccgg cgggacggag ggcccggcag          300
gaagatgggc tcccgtggac agggactctt gctggcgtac tgcctgctcc         350
ttgcctttgc ctctggcctg gtcctgagtc gtgtgcccca tgtccagggg         400
gaacagcagg agtgggaggg gactgaggag ctgccgtcgc ctccggacca         450
tgccgagagg gctgaagaac aacatgaaaa atacaggccc agtcaggacc         500
aggggctccc tgcttcccgg tgcttgcgct gctgtgaccc cggtacctcc         550
atgtacccgg cgaccgccgt gccccagatc aacatcacta tcttgaaagg         600
ggagaagggt gaccgcggag atcgaggcct ccaagggaaa tatggcaaaa         650
caggctcagc aggggccagg ggccacactg gacccaaagg gcagaagggc         700
tccatggggg cccctgggga gcggtgcaag agccactacg ccgccttttc         750
ggtgggccga aagaagccca tgcacagcaa ccactactac cagacggtga         800
tcttcgacac ggagttcgtg aacctctacg accacttcaa catgttcacc         850
```

-continued

| | |
|---|---|
| ggcaagttct actgctacgt gcccggcctc tacttcttca gcctcaacgt | 900 |
| gcacacctgg aaccagaagg agacctacct gcacatcatg aagaacgagg | 950 |
| aggaggtggt gatcttgttc gcgcaggtgg gcgaccgcag catcatgcaa | 1000 |
| agccagagcc tgatgctgga gctgcgagag caggaccagg tgtgggtacg | 1050 |
| cctctacaag ggcgaacgtg agaacgccat cttcagcgag gagctggaca | 1100 |
| cctacatcac cttcagtggc tacctggtca agcacgccac cgagccctag | 1150 |
| ctggccggcc acctcctttc ctctcgccac cttccacccc tgcgctgtgc | 1200 |
| tgaccccacc gcctcttccc cgatccctgg actccgactc cctggctttg | 1250 |
| gcattcagtg agacgccctg cacacacaga aagccaaagc gatcggtgct | 1300 |
| cccagatccc gcagcctctg gagagagctg acggcagatg aaatcaccag | 1350 |
| ggcggggcac ccgcgagaac cctctgggac cttccgcggc cctctctgca | 1400 |
| cacatcctca agtgaccccg cacggcgaga cgcgggtggc ggcagggcgt | 1450 |
| cccagggtgc ggcaccgcgg ctccagtcct tggaaataat taggcaaatt | 1500 |
| ctaaaggtct caaaggagc aaagtaaacc gtggaggaca agaaaagggg | 1550 |
| ttgttatttt tgtctttcca gccagcctgc tggctcccaa gagagaggcc | 1600 |
| ttttcagttg agactctgct taagagaaga tccaaagtta aagctctggg | 1650 |
| gtcaggggag gggccggggg caggaaacta cctctggctt aattctttta | 1700 |
| agccacgtag gaactttctt gagggatagg tggaccctga catccctgtg | 1750 |
| gccttgccca agggctctgc tggtctttct gagtcacagc tgcgaggtga | 1800 |
| tgggggctgg ggccccaggc gtcagcctcc cagagggaca gctgagcccc | 1850 |
| ctgccttggc tccaggttgg tagaagcagc cgaagggctc ctgacagtgg | 1900 |
| ccagggaccc ctgggtcccc caggcctgca gatgtttcta tgaggggcag | 1950 |
| agctccttgg tacatccatg tgtggctctg ctccaccct gtgccacccc | 2000 |
| agagccctgg ggggtggtct ccatgcctgc caccctggca tcggctttct | 2050 |
| gtgccgcctc ccacacaaat cagccccaga aggccccggg gccttggctt | 2100 |
| ctgttttta taaaacacct caagcagcac tgcagtctcc catctcctcg | 2150 |
| tgggctaagc atcaccgctt ccacgtgtgt tgtgttggtt ggcagcaagg | 2200 |
| ctgatccaga ccccttctgc ccccactgcc ctcatccagg cctctgacca | 2250 |
| gtagcctgag aggggctttt tctaggcttc agagcagggg agagctggaa | 2300 |
| ggggctagaa agctcccgct tgtctgtttc tcaggctcct gtgagcctca | 2350 |
| gtcctgagac cagagtcaag aggaagtaca cgtcccaatc accgtgtca | 2400 |
| ggattcactc tcaggagctg ggtggcagga gaggcaatag cccctgtggc | 2450 |
| aattgcagga ccagctggag cagggttgcg gtgtctccac ggtgctctcg | 2500 |
| ccctgcccat ggccacccca gactctgatc tccaggaacc ccatagcccc | 2550 |
| tctccacctc accccatgtt gatgcccagg gtcactcttg ctacccgctg | 2600 |
| ggcccccaaa ccccgctgc ctctcttcct tcccccatc cccacctgg | 2650 |
| ttttgactaa tcctgcttcc ctctctgggc ctggctgccg ggatctgggg | 2700 |
| tccctaagtc cctctctta aagaacttct gcgggtcaga ctctgaagcc | 2750 |
| gagttgctgt gggcgtgccc ggaagcagag cgccacactc gctgcttaag | 2800 |
| ctcccccagc tctttccaga aaacattaaa ctcagaattg tgttttcaa | 2849 |

<210> SEQ ID NO 18
<211> LENGTH: 281
<212> TYPE: PRT
<213> ORGANISM: Homo sapiens

<400> SEQUENCE: 18

```
Met Gly Ser Arg Gly Gln Gly Leu Leu Ala Tyr Cys Leu Leu
 1               5                  10                  15

Leu Ala Phe Ala Ser Gly Leu Val Leu Ser Arg Val Pro His Val
                20                  25                  30

Gln Gly Glu Gln Gln Glu Trp Glu Gly Thr Glu Glu Leu Pro Ser
            35                  40                  45

Pro Pro Asp His Ala Glu Arg Ala Glu Glu Gln His Glu Lys Tyr
        50                  55                  60

Arg Pro Ser Gln Asp Gln Gly Leu Pro Ala Ser Arg Cys Leu Arg
 65                  70                  75

Cys Cys Asp Pro Gly Thr Ser Met Tyr Pro Ala Thr Ala Val Pro
            80                  85                  90

Gln Ile Asn Ile Thr Ile Leu Lys Gly Glu Lys Gly Asp Arg Gly
            95                 100                 105

Asp Arg Gly Leu Gln Gly Lys Tyr Gly Lys Thr Gly Ser Ala Gly
            110                 115                 120

Ala Arg Gly His Thr Gly Pro Lys Gly Gln Lys Gly Ser Met Gly
            125                 130                 135

Ala Pro Gly Glu Arg Cys Lys Ser His Tyr Ala Ala Phe Ser Val
            140                 145                 150

Gly Arg Lys Lys Pro Met His Ser Asn His Tyr Tyr Gln Thr Val
            155                 160                 165

Ile Phe Asp Thr Glu Phe Val Asn Leu Tyr Asp His Phe Asn Met
            170                 175                 180

Phe Thr Gly Lys Phe Tyr Cys Tyr Val Pro Gly Leu Tyr Phe Phe
            185                 190                 195

Ser Leu Asn Val His Thr Trp Asn Gln Lys Glu Thr Tyr Leu His
            200                 205                 210

Ile Met Lys Asn Glu Glu Val Val Ile Leu Phe Ala Gln Val
            215                 220                 225

Gly Asp Arg Ser Ile Met Gln Ser Gln Ser Leu Met Leu Glu Leu
            230                 235                 240

Arg Glu Gln Asp Gln Val Trp Val Arg Leu Tyr Lys Gly Glu Arg
            245                 250                 255

Glu Asn Ala Ile Phe Ser Glu Glu Leu Asp Thr Tyr Ile Thr Phe
            260                 265                 270

Ser Gly Tyr Leu Val Lys His Ala Thr Glu Pro
            275                 280
```

<210> SEQ ID NO 19
<211> LENGTH: 3732
<212> TYPE: DNA
<213> ORGANISM: Homo sapiens

<400> SEQUENCE: 19

| | |
|---|---|
| aagtcattca gtggatgtga tcttggctca caggggacga tgtcaagctc | 50 |
| ttcctggctc cttctcagcc ttgttgctgt aactgctgct cagtccacca | 100 |
| ttgaggaaca ggccaagaca ttttttggaca agtttaacca cgaagccgaa | 150 |
| gacctgttct atcaaagttc acttgcttct tggaattata cacaccaatat | 200 |

```
tactgaagag  aatgtccaaa  acatgaataa  tgctggggac  aaatggtctg      250 ccttttaaa   ggaacagtcc  acacttgccc  aaatgtatcc  actacaagaa      300
attcagaatc  tcacagtcaa  gcttcagctg  caggctcttc  agcaaaatgg      350
gtcttcagtg  ctctcagaag  acaagagcaa  acggttgaac  acaattctaa      400
atacaatgag  caccatctac  agtactggaa  aagtttgtaa  cccagataat      450
ccacaagaat  gcttattact  tgaaccaggt  ttgaatgaaa  taatggcaaa      500
cagtttagac  tacaatgaga  ggctctgggc  ttgggaaagc  tggagatctg      550
aggtcggcaa  gcagctgagg  ccattatatg  aagagtatgt  ggtcttgaaa      600
aatgagatgg  caagagcaaa  tcattatgag  gactatgggg  attattggag      650
aggagactat  gaagtaaatg  gggtagatgg  ctatgactac  agccgcggcc      700
agttgattga  agatgtggaa  cataccttg   aagagattaa  accattatat      750
gaacatcttc  atgcctatgt  gagggcaaag  ttgatgaatg  cctatccttc      800
ctatatcagt  ccaattggat  gcctccctgc  tcatttgctt  ggtgatatgt      850
ggggtagatt  ttgacaaat   ctgtactctt  tgacagttcc  ctttggacag      900
aaaccaaaca  tagatgttac  tgatgcaatg  gtggaccagg  cctgggatgc      950
acagagaata  ttcaaggagg  ccgagaagtt  ctttgtatct  gttggtcttc      1000
ctaatatgac  tcaaggattc  tgggaaaatt  ccatgctaac  ggacccagga     1050
aatgttcaga  aagcagtctg  ccatcccaca  gcttgggacc  tggggaaggg     1100
cgacttcagg  atccttatgt  gcacaaaggt  gacaatggac  gacttcctga     1150
cagctcatca  tgagatgggg  catatccagt  atgatatggc  atatgctgca     1200 caacctttc   tgctaagaaa  tggagctaat  gaaggattcc  atgaagctgt     1250
tgggaaaatc  atgtcacttt  ctgcagccac  acctaagcat  ttaaaatcca     1300
ttggtcttct  gtcacccgat  tttcaagaag  acaatgaaac  agaaataaac     1350
ttcctgctca  aacaagcact  cacgattgtt  gggactctgc  catttactta     1400
catgttagag  aagtggaggt  ggatggtctt  taaaggggaa  attcccaaag     1450
accagtggat  gaaaaagtgg  tgggagatga  agcgagagat  agttggggtg     1500
gtggaacctg  tgcccatga   tgaaacatac  tgtgaccccg  catctctgtt     1550
ccatgtttct  gatgattact  cattcattcg  atattacaca  aggacccttt     1600
accaattcca  gtttcaagaa  gcactttgtc  aagcagctaa  acatgaaggc     1650
cctctgcaca  aatgtgacat  ctcaaactct  acagaagctg  acagaaact     1700 gttgtaagaa  atacctcaaa  atgttgaacc  tctcctagta  ttcagtatta     1750
ctcatttcca  tgcctaggtt  tgtatttgat  ttctttgttc  taaaaagaaa     1800
attttatggc  ctcaaaatgt  cctcatttac  aaaccaaaca  tttaatttgt     1850
ggtcagacag  gaacctagac  catacaacaa  ttgggtgggc  cacctctttt     1900
ctccctatca  taactacagc  cctctcttcc  tggtaattgg  aaggaaagag     1950
cggtttaggg  tggaatatat  ctgttaatat  gcattctttt  cttatctgcc     2000
agaagcaaat  ttagccaagt  caaagagaag  aaaccataga  tcatagatgt     2050
aaatatatgt  acatctggaa  cccctcaaaa  ggccctgaac  ccccttttt     2100 tgtgtagcaa  tatgctgagg  cttggaaaat  cagaaccctg  gacccctagca    2150 ttggaaaatg  ttgtaggagc  aagaacatga  atgtaaggcc  actgctcaac     2200
```

| | |
|---|---|
| tactttgagc ccttatttac ctggctgaaa gaccagaaca agaattcttt | 2250 |
| tgtgggatgg agtaccgact ggagtccata tgcagaccca agcatcaaa | 2300 |
| gtgaggataa gcctaaaatc agctcttgga gataaagcat atgaatggaa | 2350 |
| cgacaatgaa atgtacctgt tccgatcatc tgttgcatat gctatgaggc | 2400 |
| agtactttt aaaagtaaaa aatcagatga ttctttttgg ggaggaggat | 2450 |
| gtgcgagtgg ctaatttgaa accaagaatc tcctttaatt tctttgtcac | 2500 |
| tgcacctaaa aatgtgtctg atatcattcc tagaactgaa gttgaaaagg | 2550 |
| ccatcaggat gtcccggagc cgtatcaatg atgctttccg tctgaatgac | 2600 |
| aacagcctag agtttctggg gatacagcca acacttggac ctcctaacca | 2650 |
| gcccctgtt tccatatggc tgattgtttt tggagttgtg atgggagtga | 2700 |
| tagtggttgg cattgtcatc ctgatcttca ctgggatcag agatcggaag | 2750 |
| aagaaaata aagcaagaag tggagaaaat cctttatgcct ccatcgatat | 2800 |
| tagcaaagga gaaataatc caggattcca aaacactgat gatgttcaga | 2850 |
| cctcctttta gaaaaatcta tgttttcct cttgaggtga ttttgttgta | 2900 |
| tgtaaatgtt aatttcatgg tatagaaaat ataagatgat aaagatatca | 2950 |
| ttaaatgtca aaactatgac tctgttcaga aaaaaaattg tccaaagaca | 3000 |
| acatggccaa ggagagagca tcttcattga cattgctttc agtatttatt | 3050 |
| tctgtctctg gatttgactt ctgttctgtt tcttaataag gattttgtat | 3100 |
| tagagtatat tagggaaagt gtgtatttgg tctcacaggc tgttcaggga | 3150 |
| taatctaaat gtaaatgtct gttgaattc tgaagttgaa aacaaggata | 3200 |
| tatcattgga gcaagtgttg gatcttgtat ggaatatgga tggatcactt | 3250 |
| gtaaggacag tgcctgggaa ctggtgtagc tgcaaggatt gagaatggca | 3300 |
| tgcattagct cactttcatt taatccattg tcaaggatga catgctttct | 3350 |
| tcacagtaac tcagttcaag tactatggtg atttgcctac agtgatgttt | 3400 |
| ggaatcgatc atgctttctt caaggtgaca ggtctaaaga gagaagaatc | 3450 |
| cagggaacag gtagaggaca ttgcttttc acttccaagg tgcttgatca | 3500 |
| acatctccct gacaacacaa aactagagcc aggggcctcc gtgaactccc | 3550 |
| cagagcatgc ctgatagaaa ctcatttcta ctgttctcta actgtggagt | 3600 |
| gaatggaaat tccaactgta tgttcaccct ctgaagtggg tacccagtct | 3650 |
| cttaaatctt ttgtatttgc tcacagtgtt tgagcagtgc tgagcacaaa | 3700 |
| gcagacactc aataaatgct agatttacaa aa | 3732 |

<210> SEQ ID NO 20
<211> LENGTH: 555
<212> TYPE: PRT
<213> ORGANISM: Homo sapiens

<400> SEQUENCE: 20

Met Ser Ser Ser Ser Trp Leu Leu Leu Ser Leu Val Ala Val Thr
1               5                   10                  15

Ala Ala Gln Ser Thr Ile Glu Glu Gln Ala Lys Thr Phe Leu Asp
            20                  25                  30

Lys Phe Asn His Glu Ala Glu Asp Leu Phe Tyr Gln Ser Ser Leu
        35                  40                  45

-continued

```
Ala Ser Trp Asn Tyr Asn Thr Asn Ile Thr Glu Glu Asn Val Gln
                 50                  55                  60

Asn Met Asn Asn Ala Gly Asp Lys Trp Ser Ala Phe Leu Lys Glu
             65                  70                  75

Gln Ser Thr Leu Ala Gln Met Tyr Pro Leu Gln Glu Ile Gln Asn
             80                  85                  90

Leu Thr Val Lys Leu Gln Leu Gln Ala Leu Gln Gln Asn Gly Ser
             95                 100                 105

Ser Val Leu Ser Glu Asp Lys Ser Lys Arg Leu Asn Thr Ile Leu
            110                 115                 120

Asn Thr Met Ser Thr Ile Tyr Ser Thr Gly Lys Val Cys Asn Pro
            125                 130                 135

Asp Asn Pro Gln Glu Cys Leu Leu Leu Glu Pro Gly Leu Asn Glu
            140                 145                 150

Ile Met Ala Asn Ser Leu Asp Tyr Asn Glu Arg Leu Trp Ala Trp
            155                 160                 165

Glu Ser Trp Arg Ser Glu Val Gly Lys Gln Leu Arg Pro Leu Tyr
            170                 175                 180

Glu Glu Tyr Val Val Leu Lys Asn Glu Met Ala Arg Ala Asn His
            185                 190                 195

Tyr Glu Asp Tyr Gly Asp Tyr Trp Arg Gly Asp Tyr Glu Val Asn
            200                 205                 210

Gly Val Asp Gly Tyr Asp Tyr Ser Arg Gly Gln Leu Ile Glu Asp
            215                 220                 225

Val Glu His Thr Phe Glu Glu Ile Lys Pro Leu Tyr Glu His Leu
            230                 235                 240

His Ala Tyr Val Arg Ala Lys Leu Met Asn Ala Tyr Pro Ser Tyr
            245                 250                 255

Ile Ser Pro Ile Gly Cys Leu Pro Ala His Leu Leu Gly Asp Met
            260                 265                 270

Trp Gly Arg Phe Trp Thr Asn Leu Tyr Ser Leu Thr Val Pro Phe
            275                 280                 285

Gly Gln Lys Pro Asn Ile Asp Val Thr Asp Ala Met Val Asp Gln
            290                 295                 300

Ala Trp Asp Ala Gln Arg Ile Phe Lys Glu Ala Glu Lys Phe Phe
            305                 310                 315

Val Ser Val Gly Leu Pro Asn Met Thr Gln Gly Phe Trp Glu Asn
            320                 325                 330

Ser Met Leu Thr Asp Pro Gly Asn Val Gln Lys Ala Val Cys His
            335                 340                 345

Pro Thr Ala Trp Asp Leu Gly Lys Gly Asp Phe Arg Ile Leu Met
            350                 355                 360

Cys Thr Lys Val Thr Met Asp Asp Phe Leu Thr Ala His His Glu
            365                 370                 375

Met Gly His Ile Gln Tyr Asp Met Ala Tyr Ala Ala Gln Pro Phe
            380                 385                 390

Leu Leu Arg Asn Gly Ala Asn Glu Gly Phe His Glu Ala Val Gly
            395                 400                 405

Glu Ile Met Ser Leu Ser Ala Ala Thr Pro Lys His Leu Lys Ser
            410                 415                 420

Ile Gly Leu Leu Ser Pro Asp Phe Gln Glu Asp Asn Glu Thr Glu
            425                 430                 435

Ile Asn Phe Leu Leu Lys Gln Ala Leu Thr Ile Val Gly Thr Leu
            440                 445                 450
```

```
Pro Phe Thr Tyr Met Leu Glu Lys Trp Arg Trp Met Val Phe Lys
                455                 460                 465

Gly Glu Ile Pro Lys Asp Gln Trp Met Lys Lys Trp Trp Glu Met
            470                 475                 480

Lys Arg Glu Ile Val Gly Val Val Glu Pro Val Pro His Asp Glu
        485                 490                 495

Thr Tyr Cys Asp Pro Ala Ser Leu Phe His Val Ser Asp Asp Tyr
    500                 505                 510

Ser Phe Ile Arg Tyr Tyr Thr Arg Thr Leu Tyr Gln Phe Gln Phe
515                 520                 525

Gln Glu Ala Leu Cys Gln Ala Ala Lys His Glu Gly Pro Leu His
                530                 535                 540

Lys Cys Asp Ile Ser Asn Ser Thr Glu Ala Gly Gln Lys Leu Leu
            545                 550                 555

<210> SEQ ID NO 21
<211> LENGTH: 43
<212> TYPE: DNA
<213> ORGANISM: Artificial sequence
<220> FEATURE:
<223> OTHER INFORMATION: oligonucleotide probe

<400> SEQUENCE: 21
tgtaaaacga cggccagtta aatagacctg caattattaa tct            43

<210> SEQ ID NO 22
<211> LENGTH: 41
<212> TYPE: DNA
<213> ORGANISM: Artificial sequence
<220> FEATURE:
<223> OTHER INFORMATION: oligonucleotide probe

<400> SEQUENCE: 22
caggaaacag ctatgaccac ctgcacacct gcaaatccat t              41

<210> SEQ ID NO 23
<211> LENGTH: 22
<212> TYPE: DNA
<213> ORGANISM: Artificial sequence
<220> FEATURE:
<223> OTHER INFORMATION: oligonucleotide probe

<400> SEQUENCE: 23
agcaaccgcc tgaagctcat cc                                   22

<210> SEQ ID NO 24
<211> LENGTH: 24
<212> TYPE: DNA
<213> ORGANISM: Artificial sequence
<220> FEATURE:
<223> OTHER INFORMATION: oligonucleotide probe

<400> SEQUENCE: 24
aaggcgcggt gaaagatgta gacg                                 24

<210> SEQ ID NO 25
<211> LENGTH: 50
<212> TYPE: DNA
<213> ORGANISM: Artificial sequence
<220> FEATURE:
<223> OTHER INFORMATION: oligonucleotide probe

<400> SEQUENCE: 25
gactacatgt ttcaggacct gtacaacctc aagtcactgg aggttggcga     50
```

```
<210> SEQ ID NO 26
<211> LENGTH: 23
<212> TYPE: DNA
<213> ORGANISM: Artificial sequence
<220> FEATURE:
<223> OTHER INFORMATION: oligonucleotide probe

<400> SEQUENCE: 26
ggtgaaggca gaaattggag atg                                              23

<210> SEQ ID NO 27
<211> LENGTH: 24
<212> TYPE: DNA
<213> ORGANISM: Artificial sequence
<220> FEATURE:
<223> OTHER INFORMATION: oligonucleotide probe

<400> SEQUENCE: 27
atcccatgca tcagcctgtt tacc                                             24

<210> SEQ ID NO 28
<211> LENGTH: 48
<212> TYPE: DNA
<213> ORGANISM: Artificial sequence
<220> FEATURE:
<223> OTHER INFORMATION: oligonucleotide probe

<400> SEQUENCE: 28
gctggtgtag tctatacatc agatttgttt gctacacaag atcctcag                   48

<210> SEQ ID NO 29
<211> LENGTH: 24
<212> TYPE: DNA
<213> ORGANISM: Artificial sequence
<220> FEATURE:
<223> OTHER INFORMATION: oligonucleotide probe

<400> SEQUENCE: 29
ggtgctaaac tggtgctctg tggc                                             24

<210> SEQ ID NO 30
<211> LENGTH: 20
<212> TYPE: DNA
<213> ORGANISM: Artificial sequence
<220> FEATURE:
<223> OTHER INFORMATION: oligonucleotide probe

<400> SEQUENCE: 30
cagggcaaga tgagcattcc                                                  20

<210> SEQ ID NO 31
<211> LENGTH: 24
<212> TYPE: DNA
<213> ORGANISM: Artificial sequence
<220> FEATURE:
<223> OTHER INFORMATION: oligonucleotide probe

<400> SEQUENCE: 31
tcatactgtt ccatctcggc acgc                                             24

<210> SEQ ID NO 32
<211> LENGTH: 50
<212> TYPE: DNA
<213> ORGANISM: Artificial sequence
<220> FEATURE:
<223> OTHER INFORMATION: oligonucleotide probe
```

```
<400> SEQUENCE: 32
aatggtgggg ccctagaaga gctcatcaga gaactcaccg cttctcatgc                50

<210> SEQ ID NO 33
<211> LENGTH: 30
<212> TYPE: DNA
<213> ORGANISM: Artificial sequence
<220> FEATURE:
<223> OTHER INFORMATION: oligonucleotide probe

<400> SEQUENCE: 33
gtcaaggagt caaagttctg gagtgactgg                                      30

<210> SEQ ID NO 34
<211> LENGTH: 27
<212> TYPE: DNA
<213> ORGANISM: Artificial sequence
<220> FEATURE:
<223> OTHER INFORMATION: oligonucleotide probe

<400> SEQUENCE: 34
cgcacatcgc agagctatga  catattc                                        27

<210> SEQ ID NO 35
<211> LENGTH: 33
<212> TYPE: DNA
<213> ORGANISM: Artificial sequence
<220> FEATURE:
<223> OTHER INFORMATION: oligonucleotide probe

<400> SEQUENCE: 35
cgtacaacct cacggggctg cagccttttta  cag                                33

<210> SEQ ID NO 36
<211> LENGTH: 24
<212> TYPE: DNA
<213> ORGANISM: Artificial sequence
<220> FEATURE:
<223> OTHER INFORMATION: oligonucleotide probe

<400> SEQUENCE: 36
tacaggccca gtcaggacca  gggg                                           24

<210> SEQ ID NO 37
<211> LENGTH: 24
<212> TYPE: DNA
<213> ORGANISM: Artificial sequence
<220> FEATURE:
<223> OTHER INFORMATION: oligonucleotide probe

<400> SEQUENCE: 37
ctgaagaagt agaggccggg  cacg                                           24

<210> SEQ ID NO 38
<211> LENGTH: 45
<212> TYPE: DNA
<213> ORGANISM: Artificial sequence
<220> FEATURE:
<223> OTHER INFORMATION: oligonucleotide probe

<400> SEQUENCE: 38
cccggtgctt gcgctgctgt gaccccggta  cctccatgta  cccgg                   45
```

```
<210> SEQ ID NO 39
<211> LENGTH: 24
<212> TYPE: DNA
<213> ORGANISM: Artificial sequence
<220> FEATURE:
<223> OTHER INFORMATION: oligonucleotide probe

<400> SEQUENCE: 39
ggctcacagg ggacgatgtc  aagc                                           24

<210> SEQ ID NO 40
<211> LENGTH: 24
<212> TYPE: DNA
<213> ORGANISM: Artificial sequence
<220> FEATURE:
<223> OTHER INFORMATION: oligonucleotide probe

<400> SEQUENCE: 40
ctccagcttt cccaagccca  gagc                                           24

<210> SEQ ID NO 41
<211> LENGTH: 45
<212> TYPE: DNA
<213> ORGANISM: Artificial sequence
<220> FEATURE:
<223> OTHER INFORMATION: oligonucleotide probe

<400> SEQUENCE: 41
tggctccttc tcagccttgt tgctgtaact gctgctcagt  ccacc                    45
```

METHODS OF IDENTIFYING AGENTS THAT AMELIORATE OR MODULATE EFFECTS OF PRO1328 GENE DISRUPTIONS

CROSS-REFERENCE TO RELATED APPLICATIONS

This application is a divisional of, and claims the benefit under 35 U.S.C. §120 of, parent application Ser. No. 12/221,669, filed Aug. 4, 2008 now abandoned, which application is a continuation of U.S. application Ser. No. 11/457,708, filed Jun. 3, 2009, which is a continuation of, and claims the benefit under 35 U.S.C. §120 of, international application PCT/US2005/02723, filed Jan. 27, 2005, which claims priority under 35 U.S.C. §119(e) to U.S. Provisional Application Ser. No. 60/544,195 filed Feb. 12, 2004.

INCORPORATION-BY-REFERENCE

The contents of the text file named "Sequence Listing P5202R1" and created Sep. 6, 2006, being 62 kB in size, which was filed with the United States Patent and Trademark Office on Sep. 27, 2006 regarding U.S. application Ser. No. 11/457,708, and which was later filed regarding related application U.S. Ser. No. 12/221,669, filed Aug. 4, 2008, are hereby incorporated by reference in their entirety.

FIELD OF THE INVENTION

The present invention relates to compositions, including transgenic and knockout animals and methods of using such compositions for the diagnosis and treatment of diseases or disorders.

BACKGROUND OF THE INVENTION

Extracellular proteins play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents. Efforts are being undertaken by both industry and academia to identify new, native secreted proteins. Many efforts are focused on the screening of mammalian recombinant DNA libraries to identify the coding sequences for novel secreted proteins. Examples of screening methods and techniques are described in the literature [see, for example, Klein et al., Proc. Natl. Acad. Sci. 93:7108-7113 (1996); U.S. Pat. No. 5,536,637)].

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesion molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immuno-adhesions, for instance, can be employed as therapeutic agents to block receptor-ligand interactions. The membrane-bound proteins can also be employed for screening of potential peptide or small molecule inhibitors of the relevant receptor/ligand interaction.

Efforts are being undertaken by both industry and academia to identify new, native receptor or membrane-bound proteins. Many efforts are focused on the screening of mammalian recombinant DNA libraries to identify the coding sequences for novel receptor or membrane-bound proteins.

Given the importance of secreted and membrane-bound proteins in biological and disease processes, in vivo studies and characterizations may provide valuable identification and discovery of therapeutics and/or treatments useful in the prevention, amelioration or correction of diseases or dysfunctions. In this regard, genetically engineered mice have proven to be invaluable tools for the functional dissection of biological processes relevant to human disease, including immunology, cancer, neuro-biology, cardiovascular biology, obesity and many others. Gene knockouts can be viewed as modeling the biological mechanism of drug action by presaging the activity of highly specific antagonists in vivo. Knockout mice have been shown to model drug activity; phenotypes of mice deficient for specific pharmaceutical target proteins can resemble the human clinical phenotype caused by the corresponding antagonist drug. Gene knockouts enable the discovery of the mechanism of action of the target, the predominant physiological role of the target, and mechanism-based side-effects that might result from inhibition of the target in mammals. Examples of this type include mice deficient in the angiotensin converting enzyme (ACE) [Esther, C. R. et al., Lab. Invest., 74:953-965 (1996)] and cyclooxygenase-1 (COX1) genes [Langenbach, R. et al., Cell, 83:483-492 (1995)]. Conversely, knocking the gene out in the mouse can have an opposite phenotypic effect to that observed in humans after administration of an agonist drug to the corresponding target. Examples include the erythropoietin knockout [Wu, C. S. et al., Cell, 83:59-67 (1996)], in which a consequence of the mutation is deficient red blood cell production, and the GABA(A)-R-β3 knockout [DeLorey, T. M., J. Neurosci., 18:8505-8514 (1998)], in which the mutant mice show hyper-activity and hyper-responsiveness. Both these phenotypes are opposite to the effects of erythropoietin and benzodiazepine administration in humans. A striking example of a target validated using mouse genetics is the ACC2 gene. Although the human ACC2 gene had been identified several years ago, interest in ACC2 as a target for drug development was stimulated only recently after analysis of ACC2 function using a knockout mouse. ACC2 mutant mice eat more than their wild-type littermates, yet burn more fat and store less fat in their adipocytes, making this enzyme a probable target for chemical antagonism in the treatment of obesity [Abu-Elheiga, L. et al., Science, 291:2613-2616 (2001)].

In the instant application, mutated gene disruptions have resulted in phenotypic observations related to various disease conditions or dysfunctions including: CNS/neurological disturbances or disorders such as anxiety; eye abnormalities and associated diseases; cardiovascular, endothelial or angiogenic disorders including atherosclerosis; abnormal metabolic disorders including diabetes and dyslipidemias associated with elevated serum triglycerides and cholesterol levels; immunological and inflammatory disorders; oncological disorders; bone metabolic abnormalities or disorders such as arthritis, osteoporosis and osteopetrosis; or a developmental disease such as embryonic lethality.

SUMMARY OF THE INVENTION

A. Embodiments

The invention provides an isolated nucleic acid molecule comprising a nucleotide sequence that encodes a PRO227, PRO233, PRO238, PRO1328, PRO4342, PRO7423, PRO10096, PRO21384, PRO353 or PRO1885 polypeptide.

In one aspect, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule encoding a PRO227, PRO233, PRO238, PRO1328, PRO4342, PRO7423, PRO10096, PRO21384, PRO353 or PRO1885 polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule comprising the coding sequence of a full-length PRO227, PRO233, PRO238, PRO1328, PRO4342, PRO7423, PRO10096, PRO21384, PRO353 or PRO1885 polypeptide cDNA as disclosed herein, the coding sequence of a PRO227, PRO233, PRO238, PRO1328, PRO4342, PRO7423, PRO10096, PRO21384, PRO353 or PRO1885 polypeptide lacking the signal peptide as disclosed herein, the coding sequence of an extracellular domain of a transmembrane PRO227, PRO233, PRO238, PRO1328, PRO4342, PRO7423, PRO10096, PRO21384, PRO353 or PRO1885 polypeptide, with or without the signal peptide, as disclosed herein or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule that encodes the same mature polypeptide encoded by any of the human protein cDNAs deposited with the ATCC as disclosed herein, or (b) the complement of the DNA molecule of (a).

Another aspect of the invention provides an isolated nucleic acid molecule comprising a nucleotide sequence encoding a PRO227, PRO233, PRO238, PRO1328, PRO4342, PRO7423, PRO10096, PRO21384, PRO353 or PRO1885 polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO227, PRO233, PRO238, PRO1328, PRO4342, PRO7423, PRO10096, PRO21384, PRO353 or PRO1885 polypeptides are contemplated.

The invention also provides fragments of a PRO227, PRO233, PRO238, PRO1328, PRO4342, PRO7423, PRO10096, PRO21384, PRO353 or PRO1885 polypeptide coding sequence, or the complement thereof, that may find use as, for example, hybridization probes, for encoding fragments of a PRO227, PRO233, PRO238, PRO1328, PRO4342, PRO7423, PRO10096, PRO21384, PRO353 or PRO1885 polypeptide that may optionally encode a polypeptide comprising a binding site for an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody or as antisense oligonucleotide probes. Such nucleic acid fragments usually are or are at least about 10 nucleotides in length, alternatively are or are at least about 15 nucleotides in length, alternatively are or are at least about 20 nucleotides in length, alternatively are or are at least about 30 nucleotides in length, alternatively are or are at least about 40 nucleotides in length, alternatively are or are at least about 50 nucleotides in length, alternatively are or are at least about 60 nucleotides in length, alternatively are or are at least about 70 nucleotides in length, alternatively are or are at least about 80 nucleotides in length, alternatively are or are at least about 90 nucleotides in length, alternatively are or are at least about 100 nucleotides in length, alternatively are or are at least about 110 nucleotides in length, alternatively are or are at least about 120 nucleotides in length, alternatively are or are at least about 130 nucleotides in length, alternatively are or are at least about 140 nucleotides in length, alternatively are or are at least about 150 nucleotides in length, alternatively are or are at least about 160 nucleotides in length, alternatively are or are at least about 170 nucleotides in length, alternatively are or are at least about 180 nucleotides in length, alternatively are or are at least about 190 nucleotides in length, alternatively are or are at least about 200 nucleotides in length, alternatively are or are at least about 250 nucleotides in length, alternatively are or are at least about 300 nucleotides in length, alternatively are or are at least about 350 nucleotides in length, alternatively are or are at least about 400 nucleotides in length, alternatively are or are at least about 450 nucleotides in length, alternatively are or are at least about 500 nucleotides in length, alternatively are or are at least about 600 nucleotides in length, alternatively are or are at least about 700 nucleotides in length, alternatively are or are at least about 800 nucleotides in length, alternatively are or are at least about 900 nucleotides in length and alternatively are or are at least about 1000 nucleotides in length, wherein in this context the term "about" means the referenced nucleotide sequence length plus or minus 10% of that referenced length. It is noted that novel fragments of a PRO227, PRO233, PRO238, PRO1328, PRO4342, PRO7423, PRO10096, PRO21384, PRO353 or PRO1885 polypeptide-encoding nucleotide sequence may be determined in a routine manner by aligning the PRO227, PRO233, PRO238, PRO1328, PRO4342, PRO7423, PRO10096, PRO21384, PRO353 or PRO1885 polypeptide-encoding nucleotide sequence with other known nucleotide sequences using any of a number of well known sequence alignment programs and determining which PRO227, PRO233, PRO238, PRO1328, PRO4342, PRO7423, PRO10096, PRO21384, PRO353 or PRO1885 polypeptide-encoding nucleotide sequence fragment(s) are novel. All of such PRO227, PRO233, PRO238, PRO1328, PRO4342, PRO7423, PRO10096, PRO21384, PRO353 or PRO1885 polypeptide-encoding nucleotide sequences are contemplated herein. Also contemplated are the PRO227, PRO233, PRO238, PRO1328, PRO4342, PRO7423, PRO10096, PRO21384, PRO353 or PRO1885 polypeptide fragments encoded by these nucleotide molecule fragments, preferably those PRO227, PRO233, PRO238, PRO1328, PRO4342, PRO7423, PRO10096, PRO21384, PRO353 or PRO1885 polypeptide fragments that comprise a binding site for an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

The invention provides isolated PRO227, PRO233, PRO238, PRO1328, PRO4342, PRO7423, PRO10096, PRO21384, PRO353 or PRO1885 polypeptides encoded by any of the isolated nucleic acid sequences hereinabove identified.

In a certain aspect, the invention concerns an isolated PRO227, PRO233, PRO238, PRO1328, PRO4342, PRO7423, PRO10096, PRO21384, PRO353 or PRO1885 polypeptide, comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a PRO227, PRO233, PRO238, PRO1328, PRO4342, PRO7423, PRO10096, PRO21384, PRO353 or PRO1885 polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a further aspect, the invention concerns an isolated PRO227, PRO233, PRO238, PRO1328, PRO4342, PRO7423, PRO10096, PRO21384, PRO353 or PRO1885 polypeptide comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to an amino acid sequence encoded by any of the human protein cDNAs deposited with the ATCC as disclosed herein.

In one aspect, the invention concerns PRO227, PRO233, PRO238, PRO1328, PRO4342, PRO7423, PRO10096, PRO21384, PRO353 or PRO1885 variant polypeptides which are or are at least about 10 amino acids in length, alternatively are or are at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, PRO227, PRO233, PRO238, PRO1328, PRO4342, PRO7423, PRO10096, PRO21384, PRO353 or PRO1885 variant polypeptides will have or have no more than one conservative amino acid substitution as compared to the native PRO227, PRO233, PRO238, PRO1328, PRO4342, PRO7423, PRO10096, PRO21384, PRO353 or PRO1885 polypeptide sequence, alternatively will have or will have no more than 2, 3, 4, 5, 6, 7, 8, 9, or 10 conservative amino acid substitution as compared to the native PRO227, PRO233, PRO238, PRO1328, PRO4342, PRO7423, PRO10096, PRO21384, PRO353 or PRO1885 polypeptide sequence.

In a specific aspect, the invention provides an isolated PRO227, PRO233, PRO238, PRO1328, PRO4342, PRO7423, PRO10096, PRO21384, PRO353 or PRO1885 polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO227, PRO233, PRO238, PRO1328, PRO4342, PRO7423, PRO10096, PRO21384, PRO353 or PRO1885 polypeptide and recovering the PRO227, PRO233, PRO238, PRO1328, PRO4342, PRO7423, PRO10096, PRO21384, PRO353 or PRO1885 polypeptide from the cell culture.

Another aspect the invention provides an isolated PRO227, PRO233, PRO238, PRO1328, PRO4342, PRO7423, PRO10096, PRO21384, PRO353 or PRO1885 polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO227, PRO233, PRO238, PRO1328, PRO4342, PRO7423, PRO10096, PRO21384, PRO353 or PRO1885 polypeptide and recovering the PRO227, PRO233, PRO238, PRO1328, PRO4342, PRO7423, PRO10096, PRO21384, PRO353 or PRO1885 polypeptide from the cell culture.

The invention provides agonists and antagonists of a native PRO227, PRO233, PRO238, PRO1328, PRO4342, PRO7423, PRO10096, PRO21384, PRO353 or PRO1885 polypeptide as defined herein. In particular, the agonist or antagonist is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody or a small molecule.

The invention provides a method of identifying agonists or antagonists to a PRO227, PRO233, PRO238, PRO1328, PRO4342, PRO7423, PRO10096, PRO21384, PRO353 or PRO1885 polypeptide which comprise contacting the PRO227, PRO233, PRO238, PRO1328, PRO4342, PRO7423, PRO10096, PRO21384, PRO353 or PRO1885 polypeptide with a candidate molecule and monitoring a biological activity mediated by said PRO227, PRO233, PRO238, PRO1328, PRO4342, PRO7423, PRO10096, PRO21384, PRO353 or PRO1885 polypeptide. Preferably, the PRO227, PRO233, PRO238, PRO1328, PRO4342, PRO7423, PRO10096, PRO21384, PRO353 or PRO1885 polypeptide is a native PRO227, PRO233, PRO238, PRO1328, PRO4342, PRO7423, PRO10096, PRO21384, PRO353 or PRO1885 polypeptide.

The invention provides a composition of matter comprising a PRO227, PRO233, PRO238, PRO1328, PRO4342, PRO7423, PRO10096, PRO21384, PRO353 or PRO1885 polypeptide, or an agonist or antagonist of a PRO227, PRO233, PRO238, PRO1328, PRO4342, PRO7423, PRO10096, PRO21384, PRO353 or PRO1885 polypeptide as herein described, or an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody, in combination with a carrier. Optionally, the carrier is a pharmaceutically acceptable carrier.

The invention provides the use of a PRO227, PRO233, PRO238, PRO1328, PRO4342, PRO7423, PRO10096, PRO21384, PRO353 or PRO1885 polypeptide, or an agonist or antagonist thereof as hereinbefore described, or an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody, for the preparation of a medicament useful in the treatment of a condition which is responsive to the anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

The invention provides vectors comprising DNA encoding any of the herein described polypeptides. Host cell comprising any such vector are also provided. By way of example, the host cells may be CHO cells, *E. coli*, or yeast. A process for producing any of the herein described polypeptides is further provided and comprises culturing host cells under conditions suitable for expression of the desired polypeptide and recovering the desired polypeptide from the cell culture.

The invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

The invention provides an antibody which binds, preferably specifically, to any of the above or below described polypeptides. Optionally, the antibody is a monoclonal antibody, humanized antibody, antibody fragment or single-chain antibody.

The invention provides oligonucleotide probes which may be useful for isolating genomic and cDNA nucleotide sequences, measuring or detecting expression of an associated gene or as antisense probes, wherein those probes may be derived from any of the above or below described nucleotide sequences. Preferred probe lengths are described above.

The invention also provides a method of identifying a phenotype associated with a disruption of a gene which encodes for a PRO227, PRO233, PRO238, PRO1328, PRO4342, PRO7423, PRO10096, PRO21384, PRO353 or PRO1885 polypeptide, the method comprising:

(a) providing a non-human transgenic animal whose genome comprises a disruption of the gene which encodes for a PRO227, PRO233, PRO238, PRO1328, PRO4342, PRO7423, PRO10096, PRO21384, PRO353 or PRO1885 polypeptide;

(b) measuring a physiological characteristic of the non-human transgenic animal; and (c) comparing the measured physiological characteristic with that of a gender matched wild-type animal, wherein the physiological characteristic of the non-human transgenic animal that differs from the physiological characteristic of the wild-type animal is identified as a phenotype resulting from the gene disruption in the non-human transgenic animal. In one aspect, the non-human transgenic animal is a mammal. In another aspect, the mammal is a rodent. In still another aspect, the mammal is a rat or a mouse. In one aspect, the non-human transgenic animal is heterozygous for the disruption of a gene which encodes for a PRO227, PRO233, PRO238, PRO1328, PRO4342, PRO7423, PRO10096, PRO21384, PRO353 or PRO1885 polypeptide. In another aspect, the phenotype exhibited by the non-human transgenic animal as compared with gender matched wild-type littermates is at least one of the following: a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

In still another aspect, the developmental abnormality comprises embryonic lethality or reduced viability.

In still yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still another aspect, the immunological disorders are consistent with systemic lupus erythematosis; rheumatoid arthritis; juvenile chronic arthritis; spondyloarthropathies;

systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In still another aspect, the bone metabolic abnormality or disorder is arthritis, osteoporosis, osteopenia or osteopetrosis.

In another aspect, the non-human transgenic animal exhibits at least one of the following physiological characteristics compared with gender matched wild-type littermates: an increased anxiety-like response during open field activity testing; an increased anxiety response during home-cage activity testing (circadian test) and in functional observation battery (FOB) testing resulting in balding, absent whiskers and exothalamus observations; a decreased anxiety-like response during open field testing; depigmentation spots and an increased mean artery-to-vein ratio associated with retinal degeneration; yellow-tinted coats in albino male (0/−) mice and female (+/−) mice; an increased blood glucose level; an increased mean serum cholesterol level; an increased mean serum triglyceride level; increased levels of urobilinogen, ketones and blood in the urine; a decreased mean percentage of B cells in peripheral blood; an increased mean percentage of CD4+ cells in peripheral blood; an increased mean percentage of mature B cells and increased mean percentages of IgM+ and B220Hi IgD+ cells in bone marrow; in an increased percentage of immature B cells in bone marrow; an increased cell number for TcR+ cells, CD19+ cells and GR1-cells in lymph node; an increased mean percentages of TcR Beta, CD4 and CD8 cells in thymus; an increased mean serum IgG2a response to an ovalbumin challenge; an increased mean TNF-alpha response and MCP-1 response to LPS challenge in acute phase response testing; an increased mean IL-6 response to a LPS challenge in acute phase response testing; mobilization of neutrophils in response to peritoneal inflammation by a zymosan challenge; a decreased mean bone mineral content and density in total body, femur and vertebrate including a decreased mean trabecular bone volume, decreased thickness, and decreased connectivity density; a decreased femoral midshaft cross-sectional area; growth retardation with decreased body weight and length, total tissue mass, and lean body mass; an increased total tissue mass, increased lean body mass, an increased percent total body fat; increased total body bone mineral content, increased total body and increased femoral bone mineral density; degeneration of seminiferous tubules; embryonic lethality; or embryonic lethality wherein heterozygous adults exhibited decreased serum IgM, IgG1, IgG2a, IgG2b and IgG3 levels; embryonic lethality wherein necropsy shows multiple histological defects involving GI, hematopoietic, respiratory, neuromuscular, and reproductive systems.

The invention also provides an isolated cell derived from a non-human transgenic animal whose genome comprises a disruption of the gene which encodes for a PRO227, PRO233, PRO238, PRO1328, PRO4342, PRO7423, PRO10096, PRO21384, PRO353 or PRO1885 polypeptide. In one aspect, the isolated cell is a murine cell. In yet another aspect, the murine cell is an embryonic stem cell. In still another aspect, the isolated cell is derived from a non-human transgenic animal which exhibits at least one of the following phenotypes compared with gender matched wild-type littermates: a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

The invention also provides a method of identifying an agent that modulates a phenotype associated with a disruption of a gene which encodes for a PRO227, PRO233, PRO238, PRO1328, PRO4342, PRO7423, PRO10096, PRO21384, PRO353 or PRO1885 polypeptide, the method comprising:

(a) providing a non-human transgenic animal whose genome comprises a disruption of the gene which encodes for the PRO227, PRO233, PRO238, PRO1328, PRO4342, PRO7423, PRO10096, PRO21384, PRO353 or PRO1885 polypeptide;

(b) measuring a physiological characteristic of the non-human transgenic animal of (a);

(c) comparing the measured physiological characteristic of (b) with that of a gender matched wild-type animal, wherein the physiological characteristic of the non-human transgenic animal that differs from the physiological characteristic of the wild-type animal is identified as a phenotype resulting from the gene disruption in the non-human transgenic animal;

(d) administering a test agent to the non-human transgenic animal of (a); and (e) determining whether the test agent modulates the identified phenotype associated with gene disruption in the non-human transgenic animal.

In one aspect, the phenotype associated with the gene disruption comprises a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In yet another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism, or Conradi syndrome.

In still another aspect, the developmental abnormality comprises embryonic lethality or reduced viability.

In still another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

In still another aspect, the non-human transgenic animal exhibits at least one of the following physiological characteristics compared with gender matched wild-type littermates: an increased anxiety-like response during open field activity testing; an increased anxiety response during home-cage activity testing (circadian test) and in functional observation battery (FOB) testing resulting in balding, absent whiskers and exothalamus observations; a decreased anxiety-like response during open field testing; depigmentation spots and an increased mean artery-to-vein ratio associated with retinal degeneration; yellow-tinted coats in albino male (0/−) mice and female (+/−) mice; an increased blood glucose level; an increased mean serum cholesterol level; an increased mean serum triglyceride level; increased levels of urobilinogen, ketones and blood in the urine; a decreased mean percentage of B cells in peripheral blood; an increased mean percentage of CD4+ cells in peripheral blood; an increased mean percentage of mature B cells and increased mean percentages of IgM+ and B220Hi IgD+ cells in bone marrow; in an increased percentage of immature B cells in bone marrow; an increased cell number for TcR+ cells, CD19+ cells and GR1-cells in lymph node; an increased mean percentages of TcR Beta, CD4 and CD8 cells in thymus; an increased mean serum IgG2a response to an ovalbumin challenge; an increased mean TNF-alpha response and MCP-1 response to LPS challenge in acute phase response testing; an increased mean IL-6 response to a LPS challenge in acute phase response testing; mobilization of neutrophils in response to peritoneal inflammation by a zymosan challenge; a decreased mean bone mineral content and density in total body, femur and vertebrate including a decreased mean trabecular bone volume, decreased thickness, and decreased connectivity density; a decreased femoral midshaft cross-sectional area; growth retardation with decreased body weight and length, total tissue mass, and lean body mass; an increased total tissue mass, increased lean body mass, an increased percent total body fat; increased total body bone mineral content, increased total body and increased femoral bone mineral density; degeneration of seminiferous tubules; embryonic lethality; or embryonic lethality wherein heterozygous adults exhibited decreased serum IgM, IgG1, IgG2a, IgG2b and IgG3 levels; embryonic lethality wherein necropsy shows multiple histological defects involving GI, hematopoietic, respiratory, neuromuscular, and reproductive systems.

The invention also provides an agent which modulates the phenotype associated with gene disruption. In one aspect, the agent is an agonist or antagonist of a PRO227, PRO233, PRO238, PRO1328, PRO4342, PRO7423, PRO10096, PRO21384, PRO353 or PRO1885 polypeptide. In yet another aspect, the agonist agent is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody. In still another aspect, the antagonist agent is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

The invention also provides a method of identifying an agent that modulates a physiological characteristic associated with a disruption of the gene which encodes for a PRO227, PRO233, PRO238, PRO1328, PRO4342, PRO7423, PRO10096, PRO21384, PRO353 or PRO1885 polypeptide, the method comprising:

(a) providing a non-human transgenic animal whose genome comprises a disruption of the gene which encodes for a PRO227, PRO233, PRO238, PRO1328, PRO4342, PRO7423, PRO10096, PRO21384, PRO353 or PRO1885 polypeptide;

(b) measuring a physiological characteristic exhibited by the non-human transgenic animal of (a);

(c) comparing the measured physiological characteristic of (b) with that of a gender matched wild-type animal, wherein the physiological characteristic exhibited by the non-human transgenic animal that differs from the physiological characteristic exhibited by the wild-type animal is identified as a physiological characteristic associated with gene disruption;

(d) administering a test agent to the non-human transgenic animal of (a); and (e) determining whether the physiological characteristic associated with gene disruption is modulated.

In one aspect, the non-human transgenic animal exhibits at least one of the following physiological characteristics compared with gender matched wild-type littermates: an increased anxiety-like response during open field activity testing; an increased anxiety response during home-cage activity testing (circadian test) and in functional observation battery (FOB) testing resulting in balding, absent whiskers and exothalamus observations; a decreased anxiety-like response during open field testing; depigmentation spots and an increased mean artery-to-vein ratio associated with retinal degeneration; yellow-tinted coats in albino male (0/−) mice and female (+/−) mice; an increased blood glucose level; an increased mean serum cholesterol level; an increased mean serum triglyceride level; increased levels of urobilinogen, ketones and blood in the urine; a decreased mean percentage of B cells in peripheral blood; an increased mean percentage of CD4+ cells in peripheral blood; an increased mean percentage of mature B cells and increased mean percentages of IgM+ and B220Hi IgD+ cells in bone marrow; in an increased percentage of immature B cells in bone marrow; an increased cell number for TcR+ cells, CD19+ cells and GR1-cells in lymph node; an increased mean percentages of TcR Beta, CD4 and CD8 cells in thymus; an increased mean serum IgG2a response to an ovalbumin challenge; an increased mean TNF-alpha response and MCP-1 response to LPS challenge in acute phase response testing; an increased mean IL-6 response to a LPS challenge in acute phase response testing; mobilization of neutrophils in response to peritoneal inflammation by a zymosan challenge; a decreased mean bone mineral content and density in total body, femur and vertebrate including a decreased mean trabecular bone volume, decreased thickness, and decreased connectivity density; a decreased femoral midshaft cross-sectional area; growth retardation with decreased body weight and length, total tissue mass, and lean body mass; an increased total tissue mass, increased lean body mass, an increased percent total body fat; increased total body bone mineral content, increased total body and increased femoral bone mineral density; degeneration of seminiferous tubules; embryonic lethality; or embryonic lethality wherein heterozygous adults exhibited decreased serum IgM, IgG1, IgG2a, IgG2b and IgG3 levels; embryonic lethality wherein necropsy shows multiple histological defects involving GI, hematopoietic, respiratory, neuromuscular, and reproductive systems.

The invention also provides an agent that modulates a physiological characteristic which is associated with gene disruption. In one aspect, the agent is an agonist or antagonist of the phenotype associated with a disruption of a gene which encodes for a PRO227, PRO233, PRO238, PRO1328, PRO4342, PRO7423, PRO10096, PRO21384, PRO353 or PRO1885 polypeptide. In yet another aspect, the agent is an agonist or antagonist of a PRO227, PRO233, PRO238, PRO1328, PRO4342, PRO7423, PRO10096, PRO21384, PRO353 or PRO1885 polypeptide. In yet another aspect, the agonist agent is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody. In still another aspect, the antagonist agent is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

The invention also provides a method of identifying an agent which modulates a behavior associated with a disruption of the gene which encodes for a PRO227, PRO233, PRO238, PRO1328, PRO4342, PRO7423, PRO10096, PRO21384, PRO353 or PRO1885 polypeptide, the method comprising:

(a) providing a non-human transgenic animal whose genome comprises a disruption of the gene which encodes for a PRO227, PRO233, PRO238, PRO1328, PRO4342, PRO7423, PRO10096, PRO21384, PRO353 or PRO1885 polypeptide;

(b) observing the behavior exhibited by the non-human transgenic animal of (a);

(c) comparing the observed behavior of (b) with that of a gender matched wild-type animal, wherein the observed behavior exhibited by the non-human transgenic animal that differs from the observed behavior exhibited by the wild-type animal is identified as a behavior associated with gene disruption;

(d) administering a test agent to the non-human transgenic animal of (a); and (e) determining whether the agent modulates the behavior associated with gene disruption.

In one aspect, the observed behavior is an increased anxiety-like response during open field activity testing. In yet another aspect, the observed behavior is a decreased anxiety-like response during open field activity testing. In yet another aspect, the observed behavior is an abnormal circadian rhythm during home-cage activity testing. In yet another aspect, the observed behavior is an enhanced motor coordination during inverted screen testing. In yet another aspect, the observed behavior is impaired motor coordination during inverted screen testing. In yet another aspect, the observed behavior includes depression, generalized anxiety disorders, attention deficit disorder, sleep disorder, hyperactivity disorder, obsessive compulsive disorder, schizophrenia, cognitive disorders, hyperalgesia and sensory disorders. Such disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

The invention also provides an agent that modulates a behavior which is associated with gene disruption. In one aspect, the agent is an agonist or antagonist of the phenotype associated with a disruption of a gene which encodes for a PRO227, PRO233, PRO238, PRO1328, PRO4342, PRO7423, PRO10096, PRO21384, PRO353 or PRO1885 polypeptide. In yet another aspect, the agent is an agonist or antagonist of a PRO227, PRO233, PRO238, PRO1328, PRO4342, PRO7423, PRO10096, PRO21384, PRO353 or PRO1885 polypeptide. In yet another aspect, the agonist agent is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody. In still another aspect, the antagonist agent is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

The invention also provides a method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO227, PRO233, PRO238, PRO1328, PRO4342, PRO7423, PRO10096, PRO21384, PRO353 or PRO1885 polypeptide, the method comprising:

(a) providing a non-human transgenic animal whose genome comprises a disruption of the gene which encodes for a PRO227, PRO233, PRO238, PRO1328, PRO4342, PRO7423, PRO10096, PRO21384, PRO353 or PRO1885 polypeptide;

(b) administering a test agent to said non-human transgenic animal; and (c) determining whether the test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality associated with the gene disruption in the non-human transgenic animal.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In still another aspect, the developmental abnormality comprises embryonic lethality or reduced viability.

In yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still yet another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

In still another aspect, the non-human transgenic animal exhibits at least one of the following physiological characteristics compared with gender matched wild-type littermates: an increased anxiety-like response during open field activity testing; an increased anxiety response during home-cage activity testing (circadian test) and in functional observation battery (FOB) testing resulting in balding, absent whiskers and exothalamus observations; a decreased anxiety-like response during open field testing; depigmentation spots and an increased mean artery-to-vein ratio associated with retinal degeneration; yellow-tinted coats in albino male (0/−) mice and female (+/−) mice; an increased blood glucose level; an increased mean serum cholesterol level; an increased mean serum triglyceride level; increased levels of urobilinogen, ketones and blood in the urine; a decreased mean percentage of B cells in peripheral blood; an increased mean percentage of CD4+ cells in peripheral blood; an increased mean percentage of mature B cells and increased mean percentages of IgM+ and B220Hi IgD+ cells in bone marrow; in an increased percentage of immature B cells in bone marrow; an increased cell number for TcR+ cells, CD19+ cells and GR1-cells in lymph node; an increased mean percentages of TcR Beta, CD4 and CD8 cells in thymus; an increased mean serum IgG2a response to an ovalbumin challenge; an increased mean TNF-alpha response and MCP-1 response to LPS challenge in acute phase response testing; an increased mean IL-6 response to a LPS challenge in acute phase response testing; mobilization of neutrophils in response to peritoneal inflammation by a zymosan challenge; a decreased mean bone mineral content and density in total body, femur and vertebrate including a decreased mean trabecular bone volume, decreased thickness, and decreased connectivity density; a decreased femoral midshaft cross-sectional area; growth retardation with decreased body weight and length, total tissue mass, and lean body mass; an increased total tissue mass, increased lean body mass, an increased percent total body fat; increased total body bone mineral content, increased total body and increased femoral bone mineral density; degeneration of seminiferous tubules; embryonic lethality; or embryonic lethality wherein heterozygous adults exhibited decreased serum IgM, IgG1, IgG2a, IgG2b and IgG3 levels; embryonic lethality wherein necropsy shows multiple histological defects involving GI, hematopoietic, respiratory, neuromuscular, and reproductive systems.

The invention also provides an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality which is associated with gene disruption. In one aspect, the agent is an agonist or antagonist of the phenotype associated with a disruption of a gene which encodes for a PRO227, PRO233, PRO238, PRO1328, PRO4342, PRO7423, PRO10096, PRO21384, PRO353 or PRO1885 polypeptide. In yet another aspect, the agent is an agonist or antagonist of a PRO227, PRO233, PRO238, PRO1328, PRO4342, PRO7423, PRO10096, PRO21384, PRO353 or PRO1885 polypeptide. In yet another aspect, the agonist agent is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody. In still another aspect, the antagonist agent is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

The invention also provides a therapeutic agent for the treatment of a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

The invention also provides a method of identifying an agent that modulates the expression of a PRO227, PRO233, PRO238, PRO1328, PRO4342, PRO7423, PRO10096, PRO21384, PRO353 or PRO1885 polypeptide, the method comprising:

(a) contacting a test agent with a host cell expressing a PRO227, PRO233, PRO238, PRO1328, PRO4342, PRO7423, PRO10096, PRO21384, PRO353 or PRO1885 polypeptide; and (b) determining whether the test agent modulates the expression of the PRO227, PRO233, PRO238, PRO1328, PRO4342, PRO7423, PRO10096, PRO21384, PRO353 or PRO1885 polypeptide by the host cell.

The invention also provides an agent that modulates the expression of a PRO227, PRO233, PRO238, PRO1328, PRO4342, PRO7423, PRO10096, PRO21384, PRO353 or PRO1885 polypeptide. In one aspect, the agent is an agonist or antagonist of the phenotype associated with a disruption of a gene which encodes for a PRO227, PRO233, PRO238, PRO1328, PRO4342, PRO7423, PRO10096, PRO21384, PRO353 or PRO1885 polypeptide. In yet another aspect, the agent is an agonist or antagonist of a PRO227, PRO233, PRO238, PRO1328, PRO4342, PRO7423, PRO10096, PRO21384, PRO353 or PRO1885 polypeptide. In yet another aspect, the agonist agent is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody. In still another aspect, the antagonist agent is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

The invention also provides a method of evaluating a therapeutic agent capable of affecting a condition associated with a disruption of a gene which encodes for a PRO227, PRO233, PRO238, PRO1328, PRO4342, PRO7423, PRO10096, PRO21384, PRO353 or PRO1885 polypeptide, the method comprising:

(a) providing a non-human transgenic animal whose genome comprises a disruption of the gene which encodes for the PRO227, PRO233, PRO238, PRO1328, PRO4342, PRO7423, PRO10096, PRO21384, PRO353 or PRO1885 polypeptide;

(b) measuring a physiological characteristic of the non-human transgenic animal of (a);

(c) comparing the measured physiological characteristic of (b) with that of a gender matched wild-type animal, wherein the physiological characteristic of the non-human transgenic animal that differs from the physiological characteristic of the wild-type animal is identified as a condition resulting from the gene disruption in the non-human transgenic animal;

(d) administering a test agent to the non-human transgenic animal of (a); and (e) evaluating the effects of the test agent on the identified condition associated with gene disruption in the non-human transgenic animal.

In one aspect, the condition is a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality. The invention also provides a therapeutic agent which is capable of affecting a condition associated with gene disruption. In one aspect, the agent is an agonist or antagonist of the phenotype associated with a disruption of a gene which encodes for a PRO227, PRO233, PRO238, PRO1328, PRO4342, PRO7423, PRO10096, PRO21384, PRO353 or PRO1885 polypeptide. In yet another aspect, the agent is an agonist or antagonist of a PRO227, PRO233, PRO238, PRO1328, PRO4342, PRO7423, PRO10096, PRO21384, PRO353 or PRO1885 polypeptide. In yet another aspect, the agonist agent is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody. In still another aspect, the antagonist agent is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

The invention also provides a pharmaceutical composition comprising a therapeutic agent capable of affecting the condition associated with gene disruption.

The invention also provides a method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO227, PRO233, PRO238, PRO1328, PRO4342, PRO7423, PRO10096, PRO21384, PRO353 or PRO1885 polypeptide, the method comprising administering to a subject in need of such treatment whom may already have the disorder, or may be prone to have the disorder or may be in whom the disorder is to be prevented, a therapeutically effective amount of a therapeutic agent, or agonists or antagonists thereof, thereby effectively treating or preventing or ameliorating said disorder or disease.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

In still another aspect, the developmental abnormality comprises embryonic lethality or reduced viability.

In yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still yet another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

In another aspect the therapeutic agent is an agonist or antagonist of the phenotype associated with a disruption of a gene which encodes for a PRO227, PRO233, PRO238, PRO1328, PRO4342, PRO7423, PRO10096, PRO21384, PRO353 or PRO1885 polypeptide. In yet another aspect, the agent is an agonist or antagonist of a PRO227, PRO233, PRO238, PRO1328, PRO4342, PRO7423, PRO10096, PRO21384, PRO353 or PRO1885 polypeptide. In yet another aspect, the agonist agent is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody. In still another aspect, the antagonist agent is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

The invention also provides a method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO227, PRO233, PRO238, PRO1328, PRO4342, PRO7423, PRO10096, PRO21384, PRO353 or PRO1885 polypeptide, the method comprising:

(a) providing a non-human transgenic animal cell culture, each cell of said culture comprising a disruption of the gene which encodes for a PRO227, PRO233, PRO238, PRO1328, PRO4342, PRO7423, PRO10096, PRO21384, PRO353 or PRO1885 polypeptide;

(b) administering a test agent to said cell culture; and (c) determining whether the test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality in said culture.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

In still another aspect, the developmental abnormality comprises embryonic lethality or reduced viability.

In yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still yet another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

The invention also provides an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality which is associated with gene disruption in said culture. In one aspect, the agent is an agonist or antagonist of the phenotype associated with a disruption of a gene which encodes for a PRO227, PRO233, PRO238, PRO1328, PRO4342, PRO7423, PRO10096, PRO21384, PRO353 or PRO1885 polypeptide. In yet another aspect, the agent is an agonist or antagonist of a PRO227, PRO233, PRO238, PRO1328, PRO4342, PRO7423, PRO10096, PRO21384, PRO353 or PRO1885 polypeptide. In yet another aspect, the agonist agent is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody. In still another aspect, the antagonist agent is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

The invention also provides a method of modulating a phenotype associated with a disruption of a gene which encodes for a PRO227, PRO233, PRO238, PRO1328, PRO4342, PRO7423, PRO10096, PRO21384, PRO353 or PRO1885 polypeptide, the method comprising administering to a subject whom may already have the phenotype, or may be prone to have the phenotype or may be in whom the phenotype is to be prevented, an effective amount of an agent identified as modulating said phenotype, or agonists or antagonists thereof, thereby effectively modulating the phenotype.

The invention also provides a method of modulating a physiological characteristic associated with a disruption of a gene which encodes for a PRO227, PRO233, PRO238, PRO1328, PRO4342, PRO7423, PRO10096, PRO21384, PRO353 or PRO1885 polypeptide, the method comprising administering to a subject whom may already exhibit the physiological characteristic, or may be prone to exhibit the physiological characteristic or may be in whom the physiological characteristic is to be prevented, an effective amount of an agent identified as modulating said physiological characteristic, or agonists or antagonists thereof, thereby effectively modulating the physiological characteristic.

The invention also provides a method of modulating a behavior associated with a disruption of a gene which encodes for a PRO227, PRO233, PRO238, PRO1328, PRO4342, PRO7423, PRO10096, PRO21384, PRO353 or PRO1885 polypeptide, the method comprising administering to a subject whom may already exhibit the behavior, or may be prone to exhibit the behavior or may be in whom the exhibited behavior is to be prevented, an effective amount of an agent identified as modulating said behavior, or agonists or antagonists thereof, thereby effectively modulating the behavior.

The invention also provides a method of modulating the expression of a PRO227, PRO233, PRO238, PRO1328, PRO4342, PRO7423, PRO10096, PRO21384, PRO353 or PRO1885 polypeptide, the method comprising administering to a host cell expressing said PRO227, PRO233, PRO238, PRO1328, PRO4342, PRO7423, PRO10096, PRO21384, PRO353 or PRO1885 polypeptide, an effective amount of an agent identified as modulating said expression, or agonists or antagonists thereof, thereby effectively modulating the expression of said polypeptide.

The invention also provides a method of modulating a condition associated with a disruption of a gene which encodes for a PRO227, PRO233, PRO238, PRO1328, PRO4342, PRO7423, PRO10096, PRO21384, PRO353 or PRO1885 polypeptide, the method comprising administering to a subject whom may have the condition, or may be prone to have the condition or may be in whom the condition is to be prevented, a therapeutically effective amount of a therapeutic agent identified as modulating said condition, or agonists or antagonists thereof, thereby effectively modulating the condition.

The invention also provides a method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO227, PRO233, PRO238, PRO1328, PRO4342, PRO7423, PRO10096, PRO21384, PRO353 or PRO1885 polypeptide, the method comprising administering to a non-human transgenic animal cell culture, each cell of said culture comprising a disruption of the gene which encodes for a PRO227, PRO233, PRO238, PRO1328, PRO4342, PRO7423, PRO10096, PRO21384, PRO353 or PRO1885 polypeptide, an effective amount of an agent identified as treating or preventing or ameliorating said disorder, or agonists or antagonists thereof, thereby effectively treating or preventing or ameliorating said disorder.

In yet further embodiments, the invention is directed to the following set of potential claims for this application:

1. A method of identifying a phenotype associated with a disruption of a gene which encodes for a PRO227, PRO233, PRO238, PRO1328, PRO4342, PRO7423, PRO10096, PRO21384, PRO353 or PRO1885 polypeptide, the method comprising:

(a) providing a non-human transgenic animal whose genome comprises a disruption of the gene which encodes for a PRO227, PRO233, PRO238, PRO1328, PRO4342, PRO7423, PRO10096, PRO21384, PRO353 or PRO1885 polypeptide;

(b) measuring a physiological characteristic of the non-human transgenic animal; and (c) comparing the measured physiological characteristic with that of a gender matched wild-type animal, wherein the physiological characteristic of the non-human transgenic animal that differs from the physiological characteristic of the wild-type animal is identified as a phenotype resulting from the gene disruption in the non-human transgenic animal.

2. The method of claim 1, wherein the non-human transgenic animal is heterozygous for the disruption of a gene which encodes for a PRO227, PRO233, PRO238, PRO1328, PRO4342, PRO7423, PRO10096, PRO21384, PRO353 or PRO1885 polypeptide.

3. The method of claim 1, wherein the phenotype exhibited by the non-human transgenic animal as compared with gender matched wild-type littermates is at least one of the following: a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

4. The method of claim 3, wherein the neurological disorder is an increased anxiety-like response during open field activity testing.

5. The method of claim 3, wherein the neurological disorder is a decreased anxiety-like response during open field activity testing.

6. The method of claim 3, wherein the neurological disorder is an abnormal circadian rhythm during home-cage activity testing.

7. The method of claim 3, wherein the neurological disorder is an enhanced motor coordination during inverted screen testing.

8. The method of claim 3, wherein the neurological disorder is an impaired motor coordination during inverted screen testing.

9. The method of claim 3, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

10. The method of claim 3, wherein the eye abnormality is a retinal abnormality.

11. The method of claim 3, wherein the eye abnormality is consistent with vision problems or blindness.

12. The method of claim 10, wherein the retinal abnormality is consistent with retinitis pigmentosa.

13. The method of claim 10, wherein the retinal abnormality is characterized by retinal degeneration or retinal dysplasia.

14. The method of claim 10, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

15. The method of claim 3, wherein the eye abnormality is a cataract.

16. The method of claim 15, wherein the cataract is consistent with systemic diseases such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

17. The method of claim 3, wherein the developmental abnormality comprises embryonic lethality or reduced viability.

18. The method of claim 3, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

19. The method of claim 3, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonias, idiopathic pulmonary fibrosis and hypersensitivity pneumonitis; or transplantation associated diseases including graft rejection and graft-versus-host disease.

20. The method of claim 3, wherein the bone metabolic abnormality or disorder is arthritis, osteoporosis or osteopetrosis.

21. The method of claim 1, wherein the non-human transgenic animal exhibits at least one of the following physiological characteristics compared with gender matched wild-type littermates: an increased anxiety-like response during open field activity testing; an increased anxiety response during home-cage activity testing (circadian test) and in functional observation battery (FOB) testing resulting in balding, absent whiskers and exothalamus observations; a decreased anxiety-like response during open field testing; depigmentation spots and an increased mean artery-to-vein ratio associated with retinal degeneration; yellow-tinted coats in albino male (0/−) mice and female (+/−) mice; an increased blood glucose level; an increased mean serum cholesterol level; an increased mean serum triglyceride level; increased levels of urobilinogen, ketones and blood in the urine; a decreased mean percentage of B cells in peripheral blood; an increased mean percentage of CD4+ cells in peripheral blood; an increased mean percentage of mature B cells and increased mean percentages of IgM+ and B220Hi IgD+ cells in bone marrow; in an increased percentage of immature B cells in bone marrow; an increased cell number for TcR+ cells, CD19+ cells and GR1-cells in lymph node; an increased mean percentages of TcR Beta, CD4 and CD8 cells in thymus; an increased mean serum IgG2a response to an ovalbumin challenge; an increased mean TNF-alpha response and MCP-1 response to LPS challenge in acute phase response testing; an increased mean IL-6 response to a LPS challenge in acute phase response testing; mobilization of neutrophils in response to peritoneal inflammation by a zymosan challenge; a decreased mean bone mineral content and density in total body, femur and vertebrate including a decreased mean trabecular bone volume, decreased thickness, and decreased connectivity density; a decreased femoral midshaft cross-sectional area; growth retardation with decreased body weight and length, total tissue mass, and lean body mass; an increased total tissue mass, increased lean body mass, an increased percent total body fat; increased total body bone mineral content, increased total body and increased femoral bone mineral density; degeneration of seminiferous tubules; embryonic lethality; or embryonic lethality wherein heterozygous adults exhibited decreased serum IgM, IgG1, IgG2a, IgG2b and IgG3 levels; embryonic lethality wherein necropsy shows multiple histological defects involving GI, hematopoietic, respiratory, neuromuscular, and reproductive systems.

22. An isolated cell derived from a non-human transgenic animal whose genome comprises a disruption of the gene which encodes for a PRO227, PRO233, PRO238, PRO1328, PRO4342, PRO7423, PRO10096, PRO21384, PRO353 or PRO1885 polypeptide.

23. The isolated cell of claim 22 which is a murine cell.

24. The isolated cell of claim 23, wherein the murine cell is an embryonic stem cell.

25. The isolated cell of claim 22, wherein the non-human transgenic animal exhibits at least one of the following phenotypes compared with gender matched wild-type littermates: a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

26. A method of identifying an agent that modulates a phenotype associated with a disruption of a gene which encodes for a PRO227, PRO233, PRO238, PRO1328, PRO4342, PRO7423, PRO10096, PRO21384, PRO353 or PRO1885 polypeptide, the method comprising:
(a) providing a non-human transgenic animal whose genome comprises a disruption of the gene which encodes for the PRO227, PRO233, PRO238, PRO1328, PRO4342, PRO7423, PRO10096, PRO21384, PRO353 or PRO1885 polypeptide;
(b) measuring a physiological characteristic of the non-human transgenic animal of (a);
(c) comparing the measured physiological characteristic of (b) with that of a gender matched wild-type animal, wherein the physiological characteristic of the non-human transgenic animal that differs from the physiological characteristic of the wild-type animal is identified as a phenotype resulting from the gene disruption in the non-human transgenic animal;
(d) administering a test agent to the non-human transgenic animal of (a); and
(e) determining whether the test agent modulates the identified phenotype associated with gene disruption in the non-human transgenic animal.

27. The method of claim 26, wherein the phenotype associated with the gene disruption comprises a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

28. The method of claim 27, wherein the neurological disorder is an increased anxiety-like response during open field activity testing.

29. The method of claim 27, wherein the neurological disorder is a decreased anxiety-like response during open field activity testing.

30. The method of claim 27, wherein the neurological disorder is an abnormal circadian rhythm during home-cage activity testing.

31. The method of claim 27, wherein the neurological disorder is an enhanced motor coordination during inverted screen testing.

32. The method of claim 27, wherein the neurological disorder is an impaired motor coordination during inverted screen testing.

33. The method of claim 27, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

34. The method of claim 27, wherein the eye abnormality is a retinal abnormality.

35. The method of claim 27, wherein the eye abnormality is consistent with vision problems or blindness.

36. The method of claim 34, wherein the retinal abnormality is consistent with retinitis pigmentosa.

37. The method of claim 34, wherein the retinal abnormality is characterized by retinal degeneration or retinal dysplasia.

38. The method of claim 34, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

39. The method of claim 27, wherein the eye abnormality is a cataract.

40. The method of claim 39, wherein the cataract is consistent with systemic diseases such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

41. The method of claim 27, wherein the developmental abnormality comprises embryonic lethality or reduced viability.

42. The method of claim 27, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

43. The method of claim 27, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation-associated diseases including graft rejection and graft-versus-host disease.

44. The method of claim 27, wherein said bone metabolic abnormality or disorder is arthritis, osteoporosis or osteopetrosis.

45. The method of claim 26, wherein the non-human transgenic animal exhibits at least one of the following physiological characteristics compared with gender matched wild-type littermates: an increased anxiety-like response during open field activity testing; an increased anxiety response during home-cage activity testing (circadian test) and in functional observation battery (FOB) testing resulting in balding, absent whiskers and exothalamus observations; a decreased anxiety-like response during open field testing; depigmentation spots and an increased mean artery-to-vein ratio associated with retinal degeneration; yellow-tinted coats in albino male (0/−) mice and female (+/−) mice; an increased blood glucose level; an increased mean serum cholesterol level; an increased mean serum triglyceride level; increased levels of urobilinogen, ketones and blood in the urine; a decreased mean percentage of B cells in peripheral blood; an increased mean percentage of CD4+ cells in peripheral blood; an increased mean percentage of mature B cells and increased mean percentages of IgM+ and B220Hi IgD+ cells in bone marrow; in an increased percentage of immature B cells in bone marrow; an increased cell number for TcR+ cells, CD19+ cells and GR1-cells in lymph node; an increased mean percentages of TcR Beta, CD4 and CD8 cells in thymus; an increased mean serum IgG2a response to an ovalbumin challenge; an increased mean TNF-alpha response and MCP-1 response to LPS challenge in acute phase response testing; an increased mean IL-6 response to a LPS challenge in acute phase response testing; mobilization of neutrophils in response to peritoneal inflammation by a zymosan challenge; a decreased mean bone mineral content and density in total body, femur and vertebrate including a decreased mean trabecular bone volume, decreased thickness, and decreased connectivity density; a decreased femoral midshaft cross-sectional area; growth retardation with decreased body weight and length, total tissue mass, and lean body mass; an increased total tissue mass, increased lean body mass, an increased percent total body fat; increased total body bone mineral content, increased total body and increased femoral bone mineral density; degeneration of seminiferous tubules; embryonic lethality; or embryonic lethality wherein heterozygous adults exhibited decreased serum IgM, IgG1, IgG2a, IgG2b and IgG3 levels; embryonic lethality wherein necropsy shows multiple histological defects involving GI, hematopoietic, respiratory, neuromuscular, and reproductive systems.

46. An agent identified by the method of claim 26.

47. The agent of claim 46 which is an agonist or antagonist of a PRO227, PRO233, PRO238, PRO1328, PRO4342, PRO7423, PRO10096, PRO21384, PRO353 or PRO1885 polypeptide.

48. The agent of claim 47, wherein the agonist is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

49. The agent of claim 47, wherein the antagonist is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

50. A method of identifying an agent that modulates a physiological characteristic associated with a disruption of the gene which encodes for a PRO227, PRO233, PRO238, PRO1328, PRO4342, PRO7423, PRO10096, PRO21384, PRO353 or PRO1885 polypeptide, the method comprising:

(a) providing a non-human transgenic animal whose genome comprises a disruption of the gene which encodes for a PRO227, PRO233, PRO238, PRO1328, PRO4342, PRO7423, PRO10096, PRO21384, PRO353 or PRO1885 polypeptide;

(b) measuring a physiological characteristic exhibited by the non-human transgenic animal of (a);

(c) comparing the measured physiological characteristic of (b) with that of a gender matched wild-type animal, wherein the physiological characteristic exhibited by the non-human transgenic animal that differs from the physiological characteristic exhibited by the wild-type animal is identified as a physiological characteristic associated with gene disruption;

(d) administering a test agent to the non-human transgenic animal of (a); and (e) determining whether the physiological characteristic associated with gene disruption is modulated.

51. The method of claim 50, wherein the non-human transgenic animal exhibits at least one of the following physiological characteristics compared with gender matched wild-type littermates: an increased anxiety-like response during open field activity testing; an increased anxiety response during home-cage activity testing (circadian test) and in functional observation battery (FOB) testing resulting in balding, absent whiskers and exothalamus observations; a decreased anxiety-like response during open field testing; depigmentation spots and an increased mean artery-to-vein ratio associated with retinal degeneration; yellow-tinted coats in albino male (0/−) mice and female (+/−) mice; an increased blood glucose level; an increased mean serum cholesterol level; an increased mean serum triglyceride level; increased levels of urobilinogen, ketones and blood in the urine; a decreased mean percentage of B cells in peripheral blood; an increased mean percentage of CD4+ cells in peripheral blood; an increased mean percentage of mature B cells and increased mean percentages of IgM+ and B220Hi IgD+ cells in bone marrow; in an increased percentage of immature B cells in bone marrow; an increased cell number for TcR+ cells, CD19+ cells and GR1-cells in lymph node; an increased mean percentages of TcR Beta, CD4 and CD8 cells in thymus; an increased mean serum IgG2a response to an ovalbumin challenge; an increased mean TNF-alpha response and MCP-1 response to LPS challenge in acute phase response testing; an increased mean IL-6 response to a LPS challenge in acute phase response testing; mobilization of neutrophils in response to peritoneal inflammation by a zymosan challenge; a decreased mean bone mineral content and density in total body, femur and vertebrate including a decreased mean trabecular bone volume, decreased thickness, and decreased connectivity density; a decreased femoral midshaft cross-sectional area; growth retardation with decreased body weight and length, total tissue mass, and lean body mass; an increased total tissue mass, increased lean body mass, an increased percent total body fat; increased total body bone mineral content, increased total body and increased femoral bone mineral density; degeneration of seminiferous tubules; embryonic lethality; or embryonic lethality wherein heterozygous adults exhibited decreased serum IgM, IgG1, IgG2a, IgG2b and IgG3 levels; embryonic lethality wherein necropsy shows multiple histological defects involving GI, hematopoietic, respiratory, neuromuscular, and reproductive systems.

52. An agent identified by the method of claim 50.

53. The agent of claim 52 which is an agonist or antagonist of a PRO227, PRO233, PRO238, PRO1328, PRO4342, PRO7423, PRO10096, PRO21384, PRO353 or PRO1885 polypeptide.

54. The agent of claim 53, wherein the agonist is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

55. The agent of claim 53, wherein the antagonist is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

56. A method of identifying an agent which modulates a behavior associated with a disruption of the gene which encodes for a PRO227, PRO233, PRO238, PRO1328, PRO4342, PRO7423, PRO10096, PRO21384, PRO353 or PRO1885 polypeptide, the method comprising:

(a) providing a non-human transgenic animal whose genome comprises a disruption of the gene which encodes for a PRO227, PRO233, PRO238, PRO1328, PRO4342, PRO7423, PRO10096, PRO21384, PRO353 or PRO1885 polypeptide;

(b) observing the behavior exhibited by the non-human transgenic animal of (a);

(c) comparing the observed behavior of (b) with that of a gender matched wild-type animal, wherein the observed behavior exhibited by the non-human transgenic animal that differs from the observed behavior exhibited by the wild-type animal is identified as a behavior associated with gene disruption;

(d) administering a test agent to the non-human transgenic animal of (a); and (e) determining whether the agent modulates the behavior associated with gene disruption.

57. The method of claim 56, wherein the behavior is an increased anxiety-like response during open field activity testing.

58. The method of claim 56, wherein the behavior is a decreased anxiety-like response during open field activity testing.

59. The method of claim 56, wherein the behavior is an abnormal circadian rhythm during home-cage activity testing.

60. The method of claim 56, wherein the behavior is an enhanced motor coordination during inverted screen testing.

61. The method of claim 56, wherein the behavior is an impaired motor coordination during inverted screen testing.

62. The method of claim 56, wherein the behavior is depression, generalized anxiety disorders, attention deficit disorder, sleep disorder, hyperactivity disorder, obsessive compulsive disorder, schizophrenia, cognitive disorders, hyperalgesia or sensory disorders.

63. An agent identified by the method of claim 56.

64. The agent of claim 63 which is an agonist or antagonist of a PRO227, PRO233, PRO238, PRO1328, PRO4342, PRO7423, PRO10096, PRO21384, PRO353 or PRO1885 polypeptide.

65. The agent of claim 64, wherein the agonist is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

66. The agent of claim 64, wherein the antagonist is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

67. A method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO227, PRO233, PRO238, PRO1328, PRO4342, PRO7423, PRO10096, PRO21384, PRO353 or PRO1885 polypeptide, the method comprising:

(a) providing a non-human transgenic animal whose genome comprises a disruption of the gene which encodes for a PRO227, PRO233, PRO238, PRO1328, PRO4342, PRO7423, PRO10096, PRO21384, PRO353 or PRO1885 polypeptide;

(b) administering a test agent to said non-human transgenic animal; and (c) determining whether said test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality in the non-human transgenic animal.

68. The method of claim 67, wherein the neurological disorder is an increased anxiety-like response during open field activity testing.

69. The method of claim 67, wherein the neurological disorder is a decreased anxiety-like response during open field activity testing.

70. The method of claim 67, wherein the neurological disorder is an abnormal circadian rhythm during home-cage activity testing.

71. The method of claim 67, wherein the neurological disorder is an enhanced motor coordination during inverted screen testing.

72. The method of claim 67, wherein the neurological disorder is an impaired motor coordination during inverted screen testing.

73. The method of claim 67, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

74. The method of claim 67, wherein the eye abnormality is a retinal abnormality.

75. The method of claim 67, wherein the eye abnormality is consistent with vision problems or blindness.

76. The method of claim 74, wherein the retinal abnormality is consistent with retinitis pigmentosa.

77. The method of claim 74, wherein the retinal abnormality is characterized by retinal degeneration or retinal dysplasia.

78. The method of claim 74, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congenita, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

79. The method of claim 67, wherein the eye abnormality is a cataract.

80. The method of claim 79, wherein the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

81. The method of claim 67, wherein the developmental abnormality comprises embryonic lethality or reduced viability.

82. The method of claim 67, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

83. The method of claim 67, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

84. The method of claim 67, wherein said bone metabolic abnormality or disorder is arthritis, osteoporosis or osteopetrosis.

85. The method of claim 67, wherein the non-human transgenic animal exhibits at least one of the following physiological characteristics compared with gender matched wild-type littermates: an increased anxiety-like response during open field activity testing; an increased anxiety response during home-cage activity testing (circadian test) and in functional observation battery (FOB) testing resulting in balding, absent whiskers and exothalamus observations; a decreased anxiety-like response during open field testing; depigmentation spots and an increased mean artery-to-vein ratio associated with retinal degeneration; yellow-tinted coats in albino male (0/−) mice and female (+/−) mice; an increased blood glucose level; an increased mean serum cholesterol level; an increased mean serum triglyceride level; increased levels of urobilinogen, ketones and blood in the urine; a decreased mean percentage of B cells in peripheral blood; an increased mean percentage of CD4+ cells in peripheral blood; an increased mean percentage of mature B cells and increased mean percentages of IgM+ and B220Hi IgD+ cells in bone marrow; in an increased percentage of immature B cells in bone marrow; an increased cell number for TcR+ cells, CD19+ cells and GR1-cells in lymph node; an increased mean percentages of TcR Beta, CD4 and CD8 cells in thymus; an increased mean serum IgG2a response to an ovalbumin challenge; an increased mean TNF-alpha response and MCP-1 response to LPS challenge in acute phase response testing; an increased mean IL-6 response to a LPS challenge in acute phase response testing; mobilization of neutrophils in response to peritoneal inflammation by a zymosan challenge; a decreased mean bone mineral content and density in total body, femur and vertebrate including a decreased mean trabecular bone volume, decreased thickness, and decreased connectivity density; a decreased femoral midshaft cross-sectional area; growth retardation with decreased body weight and length, total tissue mass, and lean body mass; an increased total tissue mass, increased lean body mass, an increased percent total body fat; increased total body bone mineral content, increased total body and increased femoral bone mineral density; degeneration of seminiferous tubules; embryonic lethality; or embryonic lethality wherein heterozygous adults exhibited decreased serum IgM, IgG1, IgG2a, IgG2b and IgG3 levels; embryonic lethality wherein necropsy shows multiple histological defects involving GI, hematopoietic, respiratory, neuromuscular, and reproductive systems.

86. An agent identified by the method of claim 67.

87. The agent of claim 82 which is an agonist or antagonist of a PRO227, PRO233, PRO238, PRO1328, PRO4342, PRO7423, PRO10096, PRO21384, PRO353 or PRO1885 polypeptide.

88. The agent of claim 87, wherein the agonist is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

89. The agent of claim 87, wherein the antagonist is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

90. A therapeutic agent identified by the method of claim 67.

91. A method of identifying an agent that modulates the expression of a PRO227, PRO233, PRO238, PRO1328, PRO4342, PRO7423, PRO10096, PRO21384, PRO353 or PRO1885 polypeptide, the method comprising:

(a) contacting a test agent with a host cell expressing a PRO227, PRO233, PRO238, PRO1328, PRO4342, PRO7423, PRO10096, PRO21384, PRO353 or PRO1885 polypeptide; and (b) determining whether the test agent modulates the expression of the PRO227, PRO233, PRO238, PRO1328, PRO4342, PRO7423, PRO10096, PRO21384, PRO353 or PRO1885 polypeptide by the host cell.

92. An agent identified by the method of claim 91.

93. The agent of claim 92 which is an agonist or antagonist of a PRO227, PRO233, PRO238, PRO1328, PRO4342, PRO7423, PRO10096, PRO21384, PRO353 or PRO1885 polypeptide.

94. The agent of claim 93, wherein the agonist is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

95. The agent of claim 93, wherein the antagonist is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

96. A method of evaluating a therapeutic agent capable of affecting a condition associated with a disruption of a gene which encodes for a PRO227, PRO233, PRO238, PRO1328, PRO4342, PRO7423, PRO10096, PRO21384, PRO353 or PRO1885 polypeptide, the method comprising:

(a) providing a non-human transgenic animal whose genome comprises a disruption of the gene which encodes for the PRO227, PRO233, PRO238, PRO1328, PRO4342, PRO7423, PRO10096, PRO21384, PRO353 or PRO1885 polypeptide;

(b) measuring a physiological characteristic of the non-human transgenic animal of (a);

(c) comparing the measured physiological characteristic of (b) with that of a gender matched wild-type animal, wherein the physiological characteristic of the non-human transgenic animal that differs from the physiological characteristic of the wild-type animal is identified as a condition resulting from the gene disruption in the non-human transgenic animal;

(d) administering a test agent to the non-human transgenic animal of (a); and (e) evaluating the effects of the test agent on the identified condition associated with gene disruption in the non-human transgenic animal.

97. The method of claim 96, wherein the condition is a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

98. A therapeutic agent identified by the method of claim 96.

99. The therapeutic agent of claim 98 which is an agonist or antagonist of a PRO227, PRO233, PRO238, PRO1328, PRO4342, PRO7423, PRO10096, PRO21384, PRO353 or PRO1885 polypeptide.

100. The therapeutic agent of claim 99, wherein the agonist is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

101. The therapeutic agent of claim 99, wherein the antagonist is an anti-PRO227, anti-PRO233, anti-PRO238, anti-PRO4342, anti-PRO7423, anti-PRO10096, anti-PRO21384, anti-PRO353 or anti-PRO1885 antibody.

102. A pharmaceutical composition comprising the therapeutic agent of claim 98.

103. A method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO227, PRO233, PRO238, PRO1328, PRO4342, PRO7423, PRO10096, PRO21384, PRO353 or PRO1885 polypeptide, the method comprising administering to a subject in need of such treatment whom may already have the disorder, or may be prone to have the disorder or may be in whom the disorder is to be prevented, a therapeutically effective amount of the therapeutic agent of claim 94, or agonists or antagonists thereof, thereby effectively treating or preventing or ameliorating said disorder.

104. The method of claim 103, wherein the neurological disorder is an increased anxiety-like response during open field activity testing.

105. The method of claim 103, wherein the neurological disorder is a decreased anxiety-like response during open field activity testing.

106. The method of claim 103, wherein the neurological disorder is an abnormal circadian rhythm during home-cage activity testing.

107. The method of claim 103, wherein the neurological disorder is an enhanced motor coordination during inverted screen testing.

108. The method of claim 103, wherein the neurological disorder is an impaired motor coordination during inverted screen testing.

109. The method of claim 103, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

110. The method of claim 103, wherein the eye abnormality is a retinal abnormality.

111. The method of claim 103, wherein the eye abnormality is consistent with vision problems or blindness.

112. The method of claim 110, wherein the retinal abnormality is consistent with retinitis pigmentosa.

113. The method of claim 110, wherein the retinal abnormality is characterized by retinal degeneration or retinal dysplasia.

114. The method of claim 110, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

115. The method of claim 103, wherein the eye abnormality is a cataract.

116. The method of claim 115, wherein the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

117. The method of claim 103, wherein the developmental abnormality comprises embryonic lethality or reduced viability.

118. The method of claim 103, wherein the cardiovascular, endothelial or angiogenic disorders are arterial iseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

119. The method of claim 103, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

120. The method of claim 103, wherein said bone metabolic abnormality or disorder is arthritis, osteoporosis or osteopetrosis.

121. A method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO227, PRO233, PRO238, PRO1328, PRO4342, PRO7423, PRO10096, PRO21384, PRO353 or PRO1885 polypeptide, the method comprising:

(a) providing a non-human transgenic animal cell culture, each cell of said culture comprising a disruption of the gene which encodes for a PRO227, PRO233, PRO238, PRO1328, PRO4342, PRO7423, PRO10096, PRO21384, PRO353 or PRO1885 polypeptide;

(b) administering a test agent to said cell culture; and (c) determining whether said test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality in said cell culture.

122. The method of claim 121, wherein the neurological disorder is an increased anxiety-like response during open field activity testing.

123. The method of claim 121, wherein the neurological disorder is a decreased anxiety-like response during open field activity testing.

124. The method of claim 121, wherein the neurological disorder is an abnormal circadian rhythm during home-cage activity testing.

125. The method of claim 121, wherein the neurological disorder is an enhanced motor coordination during inverted screen testing.

126. The method of claim 121, wherein the neurological disorder is an impaired motor coordination during inverted screen testing.

127. The method of claim 121, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

128. The method of claim 121, wherein the eye abnormality is a retinal abnormality.

129. The method of claim 121, wherein the eye abnormality is consistent with vision problems or blindness.

130. The method of claim 128, wherein the retinal abnormality is consistent with retinitis pigmentosa.

131. The method of claim 128, wherein the retinal abnormality is characterized by retinal degeneration or retinal dysplasia.

132. The method of claim 128, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

133. The method of claim 121, wherein the eye abnormality is a cataract.

134. The method of claim 133, wherein the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

135. The method of claim 121, wherein the developmental abnormality comprises embryonic lethality or reduced viability.

136. The method of claim 121, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

137. The method of claim 121, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

138. The method of claim 121, wherein said bone metabolic abnormality or disorder is arthritis, osteoporosis or osteopetrosis.

139. An agent identified by the method of claim 121.

140. The agent of claim 139 which is an agonist or antagonist of a PRO227, PRO233, PRO238, PRO1328, PRO4342, PRO7423, PRO10096, PRO21384, PRO353 or PRO1885 polypeptide.

141. The agent of claim 140, wherein the agonist is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

142. The agent of claim 140, wherein the antagonist is an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody.

143. A therapeutic agent identified by the method of claim 121.

144. A method of modulating a phenotype associated with a disruption of a gene which encodes for a PRO227, PRO233, PRO238, PRO1328, PRO4342, PRO7423, PRO10096, PRO21384, PRO353 or PRO1885 polypeptide, the method comprising administering to a subject whom may already have the phenotype, or may be prone to have the phenotype or may be in whom the phenotype is to be prevented, an effective amount of the agent of claim 46, or agonists or antagonists thereof, thereby effectively modulating the phenotype.

145. A method of modulating a physiological characteristic associated with a disruption of a gene which encodes for a PRO227, PRO233, PRO238, PRO1328, PRO4342, PRO7423, PRO10096, PRO21384, PRO353 or PRO1885 polypeptide, the method comprising administering to a subject whom may already exhibit the physiological characteristic, or may be prone to exhibit the physiological characteristic or may be in whom the physiological characteristic is to be prevented, an effective amount of the agent of claim 52, or agonists or antagonists thereof, thereby effectively modulating the physiological characteristic.

146. A method of modulating a behavior associated with a disruption of a gene which encodes for a PRO227, PRO233, PRO238, PRO1328, PRO4342, PRO7423, PRO10096, PRO21384, PRO353 or PRO1885 polypeptide, the method comprising administering to a subject whom may already exhibit the behavior, or may be prone to exhibit the behavior or may be in whom the exhibited behavior is to be prevented, an effective amount of the agent of claim 63, or agonists or antagonists thereof, thereby effectively modulating the behavior.

147. A method of modulating the expression of a PRO227, PRO233, PRO238, PRO1328, PRO4342, PRO7423, PRO10096, PRO21384, PRO353 or PRO1885 polypeptide, the method comprising administering to a host cell expressing said PRO227, PRO233, PRO238, PRO1328, PRO4342, PRO7423, PRO10096, PRO21384, PRO353 or PRO1885 polypeptide, an effective amount of the agent of claim 92, or agonists or antagonists thereof, thereby effectively modulating the expression of said polypeptide.

148. A method of modulating a condition associated with a disruption of a gene which encodes for a PRO227, PRO233, PRO238, PRO1328, PRO4342, PRO7423, PRO10096, PRO21384, PRO353 or PRO1885 polypeptide, the method comprising administering to a subject whom may have the condition, or may be prone to have the condition or may be in whom the condition is to be prevented, a therapeutically effective amount of the therapeutic agent of claim 98, or agonists or antagonists thereof, thereby effectively modulating the condition.

149. A method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO227, PRO233, PRO238, PRO1328, PRO4342, PRO7423, PRO10096, PRO21384, PRO353 or PRO1885 polypeptide, the method comprising administering to a non-human transgenic animal cell culture, each cell of said culture comprising a disruption of the gene which encodes for a PRO227, PRO233, PRO238, PRO1328, PRO4342, PRO7423, PRO10096, PRO21384, PRO353 or PRO1885 polypeptide, a therapeutically effective amount of the agent of claim 139, or agonists or antagonists thereof, thereby effectively treating or preventing or ameliorating said disorder.

BRIEF DESCRIPTION OF THE DRAWINGS

FIG. 1 shows a nucleotide sequence (SEQ ID NO:1) of a native sequence PRO227 cDNA, wherein SEQ ID NO:1 is a clone designated herein as "DNA33786-1132" (UNQ201).

FIG. 2 shows the amino acid sequence (SEQ ID NO:2) derived from the coding sequence of SEQ ID NO:1 shown in FIG. 1.

FIG. 3 shows a nucleotide sequence (SEQ ID NO:3) of a native sequence PRO233 cDNA, wherein SEQ ID NO:3 is a clone designated herein as "DNA34436-1238" (UNQ207).

FIG. 4 shows the amino acid sequence (SEQ ID NO:4) derived from the coding sequence of SEQ ID NO:3 shown in FIG. 3.

FIG. 5 shows a nucleotide sequence (SEQ ID NO:5) of a native sequence PRO238 cDNA, wherein SEQ ID NO:5 is a clone designated herein as "DNA35600-1162" (UNQ212).

FIG. 6 shows the amino acid sequence (SEQ ID NO:6) derived from the coding sequence of SEQ ID NO:5 shown in FIG. 5.

FIG. 7 shows a nucleotide sequence (SEQ ID NO:7) of a native sequence PRO1328 cDNA, wherein SEQ ID NO:7 is a clone designated herein as "DNA66658-1584" (UNQ688).

FIG. 8 shows the amino acid sequence (SEQ ID NO:8) derived from the coding sequence of SEQ ID NO:7 shown in FIG. 7.

FIG. 9 shows a nucleotide sequence (SEQ ID NO:9) of a native sequence PRO4342 cDNA, wherein SEQ ID NO:9 is a clone designated herein as "DNA96787-2534-1" (UNQ1896).

FIG. 10 shows the amino acid sequence (SEQ ID NO:10) derived from the coding sequence of SEQ ID NO:9 shown in FIG. 9.

FIG. 11 shows a nucleotide sequence (SEQ ID NO:11) of a native sequence PRO7423 cDNA, wherein SEQ ID NO:11 is a clone designated herein as "DNA108809" (UNQ2964).

FIG. 12 shows the amino acid sequence (SEQ ID NO:12) derived from the coding sequence of SEQ ID NO:11 shown in FIG. 11.

FIG. 13 shows a nucleotide sequence (SEQ ID NO:13) of a native sequence PRO10096 cDNA, wherein SEQ ID NO:13 is a clone designated herein as "DNA125185-2806" (UNQ3099).

FIG. 14 shows the amino acid sequence (SEQ ID NO:14) derived from the coding sequence of SEQ ID NO:13 shown in FIG. 13.

FIG. 15 shows a nucleotide sequence (SEQ ID NO:15) of a native sequence PRO21384 cDNA, wherein SEQ ID NO:15 is a clone designated herein as "DNA177313-2982" (UNQ6368).

FIG. 16 shows the amino acid sequence (SEQ ID NO:16) derived from the coding sequence of SEQ ID NO:15 shown in FIG. 15.

FIG. 17 shows a nucleotide sequence (SEQ ID NO:17) of a native sequence PRO353 cDNA, wherein SEQ ID NO:17 is a clone designated herein as "DNA41234-1242-1" (UNQ310).

FIG. 18 shows the amino acid sequence (SEQ ID NO:18) derived from the coding sequence of SEQ ID NO:17 shown in FIG. 17.

FIG. 19 shows a nucleotide sequence (SEQ ID NO:19) of a native sequence PRO1885 cDNA, wherein SEQ ID NO:19 is a clone designated herein as "DNA79302-2521" (UNQ868).

FIG. 20 shows the amino acid sequence (SEQ ID NO:20) derived from the coding sequence of SEQ ID NO:19 shown in FIG. 19.

DETAILED DESCRIPTION OF THE PREFERRED EMBODIMENTS

I. Definitions

The terms "PRO polypeptide" and "PRO" as used herein and when immediately followed by a numerical designation refer to various polypeptides, wherein the complete designation (i.e., PRO/number) refers to specific polypeptide sequences as described herein. The terms "PRO/number polypeptide" and "PRO/number" wherein the term "number" is provided as an actual numerical designation as used herein encompass native sequence polypeptides and polypeptide variants (which are further defined herein). The PRO227, PRO233, PRO238, PRO1328, PRO4342, PRO7423, PRO10096, PRO21384, PRO353 or PRO1885 polypeptides described herein may be isolated from a variety of sources, such as from human tissue types or from another source, or prepared by recombinant or synthetic methods. The term "PRO polypeptide" refers to each individual PRO/number polypeptide disclosed herein. All disclosures in this specification which refer to the "PRO polypeptide" refer to each of the polypeptides individually as well as jointly. For example, descriptions of the preparation of, purification of, derivation of, formation of antibodies to or against, administration of, compositions containing, treatment of a disease with, etc., pertain to each polypeptide of the invention individually. The term "PRO polypeptide" also includes variants of the PRO/number polypeptides disclosed herein.

A "native sequence PRO227, PRO233, PRO238, PRO1328, PRO4342, PRO7423, PRO10096, PRO21384, PRO353 or PRO1885 polypeptide" comprises a polypeptide having the same amino acid sequence as the corresponding PRO227, PRO233, PRO238, PRO1328, PRO4342, PRO7423, PRO10096, PRO21384, PRO353 or PRO1885 polypeptide derived from nature. Such native sequence PRO227, PRO233, PRO238, PRO1328, PRO4342, PRO7423, PRO10096, PRO21384, PRO353 or PRO1885 polypeptides can be isolated from nature or can be produced by recombinant or synthetic means. The term "native sequence PRO227, PRO233, PRO238, PRO1328, PRO4342, PRO7423, PRO10096, PRO21384, PRO353 or PRO1885 polypeptide" specifically encompasses naturally-occurring truncated or secreted forms of the specific PRO227, PRO233, PRO238, PRO1328, PRO4342, PRO7423, PRO10096, PRO21384, PRO353 or PRO1885 polypeptide (e.g., an extracellular domain sequence), naturally-occurring variant forms (e.g., alternatively spliced forms) and naturally-occurring allelic variants of the polypeptide. The invention provides native sequence PRO227, PRO233, PRO238, PRO1328, PRO4342, PRO7423, PRO10096, PRO21384, PRO353 or PRO1885 polypeptides disclosed herein which are mature or full-length native sequence polypeptides comprising the full-length amino acids sequences shown in the accompanying figures. Start and stop codons are shown in bold font and underlined in the figures. However, while the PRO227, PRO233, PRO238, PRO1328, PRO4342, PRO7423, PRO10096, PRO21384, PRO353 or PRO1885 polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO227, PRO233, PRO238, PRO1328, PRO4342, PRO7423, PRO10096, PRO21384, PRO353 or PRO1885 polypeptides.

The PRO227, PRO233, PRO238, PRO1328, PRO4342, PRO7423, PRO10096, PRO21384, PRO353 or PRO1885 polypeptide "extracellular domain" or "ECD" refers to a form of the PRO227, PRO233, PRO238, PRO1328, PRO4342, PRO7423, PRO10096, PRO21384, PRO353 or PRO1885 polypeptide which is essentially free of the transmembrane and cytoplasmic domains. Ordinarily, a PRO227, PRO233, PRO238, PRO1328, PRO4342, PRO7423, PRO10096, PRO21384, PRO353 or PRO1885 polypeptide ECD will have less than 1% of such transmembrane and/or cytoplasmic domains and preferably, will have less than 0.5% of such domains. It will be understood that any transmembrane domains identified for the PRO227, PRO233, PRO238, PRO1328, PRO4342, PRO7423, PRO10096, PRO21384, PRO353 or PRO1885 polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO227, PRO233, PRO238, PRO1328, PRO4342, PRO7423, PRO10096, PRO21384, PRO353 or PRO1885 polypeptide may contain from about 5 or fewer amino acids on either side of the transmembrane domain/extracellular domain boundary as identified in the Examples or specification and such polypeptides, with or without the associated signal peptide, and nucleic acid encoding them, are contemplated by the present invention.

The approximate location of the "signal peptides" of the various PRO227, PRO233, PRO238, PRO1328, PRO4342, PRO7423, PRO10096, PRO21384, PRO353 or PRO1885 polypeptides disclosed herein are shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1-6 (1997) and von Heinje et al., *Nucl. Acids. Res.* 14:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"PRO227, PRO233, PRO238, PRO1328, PRO4342, PRO7423, PRO10096, PRO21384, PRO353 or PRO1885 polypeptide variant" means a PRO227, PRO233, PRO238, PRO1328, PRO4342, PRO7423, PRO10096, PRO21384, PRO353 or PRO1885 polypeptide, preferably an active PRO227, PRO233, PRO238, PRO1328, PRO4342, PRO7423, PRO10096, PRO21384, PRO353 or PRO1885 polypeptide, as defined herein having at least about 80% amino acid sequence identity with a full-length native sequence PRO227, PRO233, PRO238, PRO1328, PRO4342, PRO7423, PRO10096, PRO21384, PRO353 or PRO1885 polypeptide sequence as disclosed herein, a PRO227, PRO233, PRO238, PRO1328, PRO4342, PRO7423, PRO10096, PRO21384, PRO353 or PRO1885 polypeptide sequence lacking the signal peptide as disclosed herein, an extracellular domain of a PRO227, PRO233, PRO238, PRO1328, PRO4342, PRO7423, PRO10096, PRO21384, PRO353 or PRO1885 polypeptide, with or without the signal peptide, as disclosed herein or any other fragment of a full-length PRO227, PRO233, PRO238, PRO1328, PRO4342, PRO7423, PRO10096, PRO21384, PRO353 or PRO1885 polypeptide sequence as disclosed herein (such as those encoded by a nucleic acid that represents only a portion of the complete coding sequence for a full-length PRO227, PRO233, PRO238, PRO1328, PRO4342, PRO7423, PRO10096, PRO21384, PRO353 or PRO1885 polypeptide). Such PRO227, PRO233, PRO238, PRO1328, PRO4342, PRO7423, PRO10096, PRO21384, PRO353 or PRO1885 polypeptide variants include, for instance, PRO227, PRO233, PRO238, PRO1328, PRO4342, PRO7423, PRO10096, PRO21384, PRO353 or PRO1885 polypeptides wherein one or more amino acid residues are added, or deleted, at the N- or C-terminus of the full-length native amino acid sequence. Ordinarily, a PRO227, PRO233, PRO238, PRO1328, PRO4342, PRO7423, PRO10096, PRO21384, PRO353 or PRO1885 polypeptide variant will have or will have at least about 80% amino acid sequence identity, alternatively will have or will have at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence PRO227, PRO233, PRO238, PRO1328, PRO4342, PRO7423, PRO10096, PRO21384, PRO353 or PRO1885 polypeptide sequence as disclosed herein, a PRO227, PRO233, PRO238, PRO1328, PRO4342, PRO7423, PRO10096, PRO21384, PRO353 or PRO1885 polypeptide sequence lacking the signal peptide as disclosed herein, an extracellular domain of a PRO227, PRO233, PRO238, PRO1328, PRO4342, PRO7423, PRO10096, PRO21384, PRO353 or PRO1885 polypeptide, with or without the signal peptide, as disclosed herein or any other specifically defined fragment of a full-length PRO227, PRO233, PRO238, PRO1328, PRO4342, PRO7423, PRO10096, PRO21384, PRO353 or PRO1885 polypeptide sequence as disclosed herein. Ordinarily, PRO227, PRO233, PRO238, PRO1328, PRO4342, PRO7423, PRO10096, PRO21384, PRO353 or PRO1885 variant polypeptides are or are at least about 10 amino acids in length, alternatively are or are at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, PRO227, PRO233, PRO238, PRO1328, PRO4342, PRO7423, PRO10096, PRO21384, PRO353 or PRO1885 variant polypeptides will have no more than one conservative amino acid substitution as compared to the native PRO227, PRO233, PRO238, PRO1328, PRO4342, PRO7423, PRO10096, PRO21384, PRO353 or PRO1885 polypeptide sequence, alternatively will have or will have no more than 2, 3, 4, 5, 6, 7, 8, 9, or 10 conservative amino acid substitution as compared to the native PRO227, PRO233, PRO238, PRO1328, PRO4342, PRO7423, PRO10096, PRO21384, PRO353 or PRO1885 polypeptide sequence.

"Percent (%) amino acid sequence identity" with respect to the PRO227, PRO233, PRO238, PRO1328, PRO4342, PRO7423, PRO10096, PRO21384, PRO353 or PRO1885 polypeptide sequences identified herein is defined as the percentage of amino acid residues in a candidate sequence that are identical with the amino acid residues in the specific PRO227, PRO233, PRO238, PRO1328, PRO4342, PRO7423, PRO10096, PRO21384, PRO353 or PRO1885 polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNAS-TAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "PRO", wherein "PRO" represents the amino acid sequence of a hypothetical PRO polypeptide of interest, "Comparison Protein" represents the amino acid sequence of a polypeptide against which the "PRO" polypeptide of interest is being compared, and "X," "Y" and "Z" each represent different hypothetical amino acid residues. Unless specifically stated otherwise, all % amino acid sequence identity values used herein are obtained as described in the immediately preceding paragraph using the ALIGN-2 computer program.

"PRO227, PRO233, PRO238, PRO1328, PRO4342, PRO7423, PRO10096, PRO21384, PRO353 or PRO1885 variant polynucleotide" or "PRO227, PRO233, PRO238, PRO1328, PRO4342, PRO7423, PRO10096, PRO21384, PRO353 or PRO1885 variant nucleic acid sequence" means a nucleic acid molecule which encodes a PRO227, PRO233, PRO238, PRO1328, PRO4342, PRO7423, PRO10096, PRO21384, PRO353 or PRO1885 polypeptide, preferably an active PRO227, PRO233, PRO238, PRO1328, PRO4342, PRO7423, PRO10096, PRO21384, PRO353 or PRO1885 polypeptide, as defined herein and which has at least about 80% nucleic acid sequence identity with a nucleotide acid sequence encoding a full-length native sequence PRO227, PRO233, PRO238, PRO1328, PRO4342, PRO7423, PRO10096, PRO21384, PRO353 or PRO1885 polypeptide sequence as disclosed herein, a full-length native sequence PRO227, PRO233, PRO238, PRO1328, PRO4342, PRO7423, PRO10096, PRO21384, PRO353 or PRO1885 polypeptide sequence lacking the signal peptide as disclosed herein, an extracellular domain of a PRO227, PRO233, PRO238, PRO1328, PRO4342, PRO7423, PRO10096, PRO21384, PRO353 or PRO1885 polypeptide, with or without the signal peptide, as disclosed herein or any other fragment of a full-length PRO227, PRO233, PRO238, PRO1328, PRO4342, PRO7423, PRO10096, PRO21384, PRO353 or PRO1885 polypeptide sequence as disclosed herein (such as those encoded by a nucleic acid that represents only a portion of the complete coding sequence for a full-length PRO227, PRO233, PRO238, PRO1328, PRO4342, PRO7423, PRO10096, PRO21384, PRO353 or PRO1885 polypeptide). Ordinarily, a PRO227, PRO233, PRO238, PRO1328, PRO4342, PRO7423, PRO10096, PRO21384, PRO353 or PRO1885 variant polynucleotide will have or will have at least about 80% nucleic acid sequence identity, alternatively will have or will have at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding a full-length native sequence PRO227, PRO233, PRO238, PRO1328, PRO4342, PRO7423, PRO10096, PRO21384, PRO353 or PRO1885 polypeptide sequence as disclosed herein, a full-length native sequence PRO227, PRO233, PRO238, PRO1328, PRO4342, PRO7423, PRO10096, PRO21384, PRO353 or PRO1885 polypeptide sequence lacking the signal peptide as disclosed herein, an extracellular domain of a PRO227, PRO233, PRO238, PRO1328, PRO4342, PRO7423, PRO10096, PRO21384, PRO353 or PRO1885 polypeptide, with or without the signal sequence, as disclosed herein or any other fragment of a full-length PRO227, PRO233, PRO238, PRO1328, PRO4342, PRO7423, PRO10096, PRO21384, PRO353 or PRO1885 polypeptide sequence as disclosed herein. Variants do not encompass the native nucleotide sequence.

Ordinarily, PRO227, PRO233, PRO238, PRO1328, PRO4342, PRO7423, PRO10096, PRO21384, PRO353 or PRO1885 variant polynucleotides are or are at least about 5 nucleotides in length, alternatively are or are at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

"Percent (%) nucleic acid sequence identity" with respect to PRO227-, PRO233-, PRO238-, PRO1328-, PRO4342-, PRO7423-, PRO10096-, PRO21384-, PRO353- or PRO1885-encoding nucleic acid sequences identified herein is defined as the percentage of nucleotides in a candidate sequence that are identical with the nucleotides in the PRO227, PRO233, PRO238, PRO1328, PRO4342, PRO7423, PRO10096, PRO21384, PRO353 or PRO1885 nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "PRO-DNA", wherein "PRO-DNA" represents a hypothetical PRO-encoding nucleic acid sequence of interest, "Comparison DNA" represents the nucleotide sequence of a nucleic acid molecule against which the "PRO-DNA" nucleic acid molecule of interest is being compared, and "N", "L" and "V" each represent different hypothetical nucleotides. Unless specifically stated otherwise, all % nucleic acid sequence identity values used herein are obtained as described in the immediately preceding paragraph using the ALIGN-2 computer program.

The invention also provides PRO227, PRO233, PRO238, PRO1328, PRO4342, PRO7423, PRO10096, PRO21384, PRO353 or PRO1885 variant polynucleotides which are nucleic acid molecules that encode a PRO227, PRO233, PRO238, PRO1328, PRO4342, PRO7423, PRO10096, PRO21384, PRO353 or PRO1885 polypeptide and which are capable of hybridizing, preferably under stringent hybridization and wash conditions, to nucleotide sequences encoding a full-length PRO227, PRO233, PRO238, PRO1328, PRO4342, PRO7423, PRO10096, PRO21384, PRO353 or PRO1885 polypeptide as disclosed herein. PRO227, PRO233, PRO238, PRO1328, PRO4342, PRO7423, PRO10096, PRO21384, PRO353 or PRO1885 variant polypeptides may be those that are encoded by a PRO227, PRO233, PRO238, PRO1328, PRO4342, PRO7423, PRO10096, PRO21384, PRO353 or PRO1885 variant polynucleotide.

The term "full-length coding region" when used in reference to a nucleic acid encoding a PRO227, PRO233, PRO238, PRO1328, PRO4342, PRO7423, PRO10096, PRO21384, PRO353 or PRO1885 polypeptide refers to the sequence of nucleotides which encode the full-length PRO227, PRO233, PRO238, PRO1328, PRO4342, PRO7423, PRO10096, PRO21384, PRO353 or PRO1885 polypeptide of the invention (which is often shown between start and stop codons, inclusive thereof, in the accompanying figures). The term "full-length coding region" when used in reference to an ATCC deposited nucleic acid refers to the PRO227, PRO233, PRO238, PRO1328, PRO4342, PRO7423, PRO10096, PRO21384, PRO353 or PRO1885 polypeptide-encoding portion of the cDNA that is inserted into the vector deposited with the ATCC (which is often shown between start and stop codons, inclusive thereof, in the accompanying figures).

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. The invention provides that the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO227, PRO233, PRO238, PRO1328, PRO4342, PRO7423, PRO10096, PRO21384, PRO353 or PRO1885 polypeptide natural environment will not be present. Ordinarily, however, isolated polypeptide will be prepared by at least one purification step.

An "isolated" PRO227, PRO233, PRO238, PRO1328, PRO4342, PRO7423, PRO10096, PRO21384, PRO353 or PRO1885 polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a PRO227, PRO233, PRO238, PRO1328, PRO4342, PRO7423, PRO10096, PRO21384, PRO353 or PRO1885 polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" for the purposes herein refers to form(s) of a PRO227, PRO233, PRO238, PRO1328, PRO4342, PRO7423, PRO10096, PRO21384, PRO353 or PRO1885 polypeptide which retain a biological and/or an immunological activity of native or naturally-occurring PRO227, PRO233, PRO238, PRO1328, PRO4342, PRO7423, PRO10096, PRO21384, PRO353 or PRO1885 polypeptide, wherein "biological" activity refers to a biological function (either inhibitory or stimulatory) caused by a native or naturally-occurring PRO227, PRO233, PRO238, PRO1328, PRO4342, PRO7423, PRO10096, PRO21384, PRO353 or PRO1885 polypeptide other than the ability to induce the production of an antibody against an antigenic epitope possessed by a native or naturally-occurring PRO227, PRO233, PRO238, PRO1328, PRO4342, PRO7423, PRO10096, PRO21384, PRO353 or PRO1885 polypeptide and an "immunological" activity refers to the ability to induce the production of an antibody against an antigenic epitope possessed by a native or naturally-occurring PRO227, PRO233, PRO238, PRO1328, PRO4342, PRO7423, PRO10096, PRO21384, PRO353 or PRO1885 polypeptide.

The term "antagonist" is used in the broadest sense [unless otherwise qualified], and includes any molecule that partially or fully blocks, inhibits, or neutralizes a biological activity of a native PRO227, PRO233, PRO238, PRO1328, PRO4342, PRO7423, PRO10096, PRO21384, PRO353 or PRO1885 polypeptide disclosed herein. In a similar manner, the term "agonist" is used in the broadest sense [unless otherwise qualified] and includes any molecule that mimics a biological activity of a native PRO227, PRO233, PRO238, PRO1328, PRO4342, PRO7423, PRO10096, PRO21384, PRO353 or PRO1885 polypeptide disclosed herein. Suitable agonist or antagonist molecules specifically include agonist or antagonist antibodies or antibody fragments, fragments or amino acid sequence variants of native PRO227, PRO233, PRO238, PRO1328, PRO4342, PRO7423, PRO10096, PRO21384, PRO353 or PRO1885 polypeptides, peptides, antisense oligonucleotides, small organic molecules, etc. Methods for identifying agonists or antagonists of a PRO227, PRO233, PRO238, PRO1328, PRO4342, PRO7423, PRO10096, PRO21384, PRO353 or PRO1885 polypeptide may comprise contacting a PRO227, PRO233, PRO238, PRO1328, PRO4342, PRO7423, PRO10096, PRO21384, PRO353 or PRO1885 polypeptide with a candidate agonist or antagonist molecule and measuring a detectable change in one or more biological activities normally associated with the PRO227, PRO233, PRO238, PRO1328, PRO4342, PRO7423, PRO10096, PRO21384, PRO353 or PRO1885 polypeptide.

"Treating" or "treatment" or "alleviation" refers to both therapeutic treatment and prophylactic or preventative measures, wherein the object is to prevent or slow down (lessen) the targeted pathologic condition or disorder. A subject in need of treatment may already have the disorder, or may be prone to have the disorder or may be in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, rodents such as rats or mice, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. Depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO227, PRO233, PRO238, PRO1328, PRO4342, PRO7423, PRO10096, PRO21384, PRO353 or PRO1885 polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

An "effective amount" of a PRO227, PRO233, PRO238, PRO1328, PRO4342, PRO7423, PRO10096, PRO21384, PRO353 or PRO1885 polypeptide, an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody, a PRO227, PRO233, PRO238, PRO1328, PRO4342, PRO7423, PRO10096, PRO21384, PRO353 or PRO1885 binding oligopeptide, a PRO227, PRO233, PRO238, PRO1328, PRO4342, PRO7423, PRO10096, PRO21384, PRO353 or PRO1885 binding organic molecule or an agonist or antagonist thereof as disclosed herein is an amount sufficient to carry out a specifically stated purpose. An "effective amount" may be determined empirically and in a routine manner, in relation to the stated purpose.

The term "therapeutically effective amount" refers to an amount of an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody, a PRO227, PRO233, PRO238, PRO1328, PRO4342, PRO7423, PRO10096, PRO21384, PRO353 or PRO1885 polypeptide, a PRO227, PRO233, PRO238, PRO1328, PRO4342, PRO7423, PRO10096, PRO21384, PRO353 or PRO1885 binding oligopeptide, a PRO227, PRO233, PRO238, PRO1328, PRO4342, PRO7423, PRO10096, PRO21384, PRO353 or PRO1885 binding organic molecule or other drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the drug may prevent growth and/or kill existing cancer cells, it may be cytostatic and/or cytotoxic.

The phrases "cardiovascular, endothelial and angiogenic disorder", "cardiovascular, endothelial and angiogenic dysfunction", "cardiovascular, endothelial or angiogenic disorder" and "cardiovascular, endothelial or angiogenic dysfunction" are used interchangeably and refer in part to systemic disorders that affect vessels, such as diabetes mellitus, as well as diseases of the vessels themselves, such as of the arteries, capillaries, veins, and/or lymphatics. This would include indications that stimulate angiogenesis and/or cardiovascularization, and those that inhibit angiogenesis and/or cardiovascularization. Such disorders include, for example, arterial disease, such as atherosclerosis, hypertension, inflammatory vasculitides, Reynaud's disease and Reynaud's phenomenon, aneurysms, and arterial restenosis; venous and lymphatic disorders such as thrombophlebitis, lymphangitis, and lymphedema; and other vascular disorders such as peripheral vascular disease, cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma, tumor angiogenesis, trauma such as wounds, burns, and other injured tissue, implant fixation, scarring, ischemia reperfusion injury, rheumatoid arthritis, cerebrovascular disease, renal diseases such as acute renal failure, or osteoporosis. This would also include angina, myocardial infarctions such as acute myocardial infarctions, cardiac hypertrophy, and heart failure such as CHF.

"Hypertrophy", as used herein, is defined as an increase in mass of an organ or structure independent of natural growth that does not involve tumor formation. Hypertrophy of an organ or tissue is due either to an increase in the mass of the individual cells (true hypertrophy), or to an increase in the number of cells making up the tissue (hyperplasia), or both. Certain organs, such as the heart, lose the ability to divide shortly after birth. Accordingly, "cardiac hypertrophy" is defined as an increase in mass of the heart, which, in adults, is characterized by an increase in myocyte cell size and contractile protein content without concomitant cell division. The character of the stress responsible for inciting the hypertrophy, (e.g., increased preload, increased afterload, loss of myocytes, as in myocardial infarction, or primary depression of contractility), appears to play a critical role in determining the nature of the response. The early stage of cardiac hypertrophy is usually characterized morphologically by increases in the size of myofibrils and mitochondria, as well as by enlargement of mitochondria and nuclei. At this stage, while muscle cells are larger than normal, cellular organization is largely preserved. At a more advanced stage of cardiac hypertrophy, there are preferential increases in the size or number of specific organelles, such as mitochondria, and new contractile elements are added in localized areas of the cells, in an irregular manner. Cells subjected to long-standing hypertrophy show more obvious disruptions in cellular organization, including markedly enlarged nuclei with highly lobulated membranes, which displace adjacent myofibrils and cause breakdown of normal Z-band registration. The phrase "cardiac hypertrophy" is used to include all stages of the progression of this condition, characterized by various degrees of structural damage of the heart muscle, regardless of the underlying cardiac disorder. Hence, the term also includes physiological conditions instrumental in the development of cardiac hypertrophy, such as elevated blood pressure, aortic stenosis, or myocardial infarction.

"Heart failure" refers to an abnormality of cardiac function where the heart does not pump blood at the rate needed for the requirements of metabolizing tissues. The heart failure can be caused by a number of factors, including ischemic, congenital, rheumatic, or idiopathic forms.

"Congestive heart failure" (CHF) is a progressive pathologic state where the heart is increasingly unable to supply adequate cardiac output (the volume of blood pumped by the heart over time) to deliver the oxygenated blood to peripheral tissues. As CHF progresses, structural and hemodynamic damages occur. While these damages have a variety of manifestations, one characteristic symptom is ventricular hypertrophy. CHF is a common end result of a number of various cardiac disorders.

"Myocardial infarction" generally results from atherosclerosis of the coronary arteries, often with superimposed coronary thrombosis. It may be divided into two major types: transmural infarcts, in which myocardial necrosis involves the full thickness of the ventricular wall, and subendocardial (nontransmural) infarcts, in which the necrosis involves the subendocardium, the intramural myocardium, or both, without extending all the way through the ventricular wall to the epicardium. Myocardial infarction is known to cause both a change in hemodynamic effects and an alteration in structure in the damaged and healthy zones of the heart. Thus, for example, myocardial infarction reduces the maximum cardiac output and the stroke volume of the heart. Also associated with myocardial infarction is a stimulation of the DNA synthesis occurring in the interstice as well as an increase in the formation of collagen in the areas of the heart not affected.

As a result of the increased stress or strain placed on the heart in prolonged hypertension due, for example, to the increased total peripheral resistance, cardiac hypertrophy has long been associated with "hypertension". A characteristic of the ventricle that becomes hypertrophic as a result of chronic pressure overload is an impaired diastolic performance. Fouad et al., *J. Am. Coll. Cardiol.*, 4: 1500-1506 (1984); Smith et al., *J. Am. Coll. Cardiol.*, 5: 869-874 (1985). A prolonged left ventricular relaxation has been detected in early essential hypertension, in spite of normal or supranormal systolic function. Hartford et al., *Hypertension*, 6: 329-338 (1984). However, there is no close parallelism between blood pressure levels and cardiac hypertrophy. Although improvement in left ventricular function in response to antihypertensive therapy has been reported in humans, patients variously treated with a diuretic (hydrochlorothiazide), a β-blocker (propranolol), or a calcium channel blocker (diltiazem), have shown reversal of left ventricular hypertrophy, without improvement in diastolic function. Inouye et al., *Am. J. Cardiol.*, 53: 1583-7 (1984).

Another complex cardiac disease associated with cardiac hypertrophy is "hypertrophic cardiomyopathy". This condition is characterized by a great diversity of morphologic, functional, and clinical features (Maron et al., *N. Engl. J. Med.*, 316: 780-789 (1987); Spirito et al., *N. Engl. J. Med.*, 320: 749-755 (1989); Louie and Edwards, *Prog. Cardiovasc. Dis.*, 36: 275-308 (1994); Wigle et al., *Circulation*, 92: 1680-1692 (1995)), the heterogeneity of which is accentuated by the fact that it afflicts patients of all ages. Spirito et al., *N. Engl. J. Med.*, 336: 775-785 (1997). The causative factors of hypertrophic cardiomyopathy are also diverse and little understood. In general, mutations in genes encoding sarcomeric proteins are associated with hypertrophic cardiomyopathy. Recent data suggest that β-myosin heavy chain mutations may account for approximately 30 to 40 percent of cases of familial hypertrophic cardiomyopathy. Watkins et al., *N. Engl. J. Med.*, 326: 1108-1114 (1992); Schwartz et al, *Circulation*, 91: 532-540 (1995); Marian and Roberts, *Circulation*, 92: 1336-1347 (1995); Thierfelder et al., *Cell*, 77: 701-712 (1994); Watkins et al., *Nat. Gen.*, 11: 434-437 (1995). Besides β-myosin heavy chain, other locations of genetic mutations include cardiac troponin T, alpha topomyosin, cardiac myosin binding protein C, essential myosin light chain, and regulatory myosin light chain. See, Malik and Watkins, *Curr. Opin. Cardiol.*, 12: 295-302 (1997).

Supravalvular "aortic stenosis" is an inherited vascular disorder characterized by narrowing of the ascending aorta, but other arteries, including the pulmonary arteries, may also be affected. Untreated aortic stenosis may lead to increased intracardiac pressure resulting in myocardial hypertrophy and eventually heart failure and death. The pathogenesis of this disorder is not fully understood, but hypertrophy and possibly hyperplasia of medial smooth muscle are prominent features of this disorder. It has been reported that molecular variants of the elastin gene are involved in the development and pathogenesis of aortic stenosis. U.S. Pat. No. 5,650,282 issued Jul. 22, 1997.

"Valvular regurgitation" occurs as a result of heart diseases resulting in disorders of the cardiac valves. Various diseases, like rheumatic fever, can cause the shrinking or pulling apart of the valve orifice, while other diseases may result in endocarditis, an inflammation of the endocardium or lining membrane of the atrioventricular orifices and operation of the heart. Defects such as the narrowing of the valve stenosis or the defective closing of the valve result in an accumulation of blood in the heart cavity or regurgitation of blood past the valve. If uncorrected, prolonged valvular stenosis or insufficiency may result in cardiac hypertrophy and associated damage to the heart muscle, which may eventually necessitate valve replacement.

The term "immune related disease" means a disease in which a component of the immune system of a mammal causes, mediates or otherwise contributes to a morbidity in the mammal. Also included are diseases in which stimulation or intervention of the immune response has an ameliorative effect on progression of the disease. Included within this term are immune-mediated inflammatory diseases, non-immune-mediated inflammatory diseases, infectious diseases, immunodeficiency diseases, neoplasia, etc.

The term "T cell mediated disease" means a disease in which T cells directly or indirectly mediate or otherwise contribute to a morbidity in a mammal. The T cell mediated disease may be associated with cell mediated effects, lymphokine mediated effects, etc., and even effects associated with B cells if the B cells are stimulated, for example, by the lymphokines secreted by T cells.

Examples of immune-related and inflammatory diseases, some of which are immune or T cell mediated, include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonia, idiopathic pulmonary fibrosis and hypersensitivity pneumonitis, or transplantation associated diseases including graft rejection and graft-versus-host-disease. Infectious diseases including viral diseases such as AIDS (HIV infection), hepatitis A, B, C, D, and E, herpes, etc., bacterial infections, fungal infections, protozoal infections and parasitic infections.

An "autoimmune disease" herein is a disease or disorder arising from and directed against an individual's own tissues or a co-segregate or manifestation thereof or resulting condition therefrom. Examples of autoimmune diseases or disorders include, but are not limited to arthritis (rheumatoid arthritis, juvenile rheumatoid arthritis, osteoarthritis, psoriatic arthritis, and ankylosing spondylitis), psoriasis, dermatitis including atopic dermatitis; chronic idiopathic urticaria, including chronic autoimmune urticaria, polymyositis/dermatomyositis, toxic epidermal necrolysis, systemic scleroderma and sclerosis, responses associated with inflammatory bowel disease (IBD) (Crohn's disease, ulcerative colitis), and IBD with co-segregate of pyoderma gangrenosum, erythema nodosum, primary sclerosing cholangitis, and/or episcleritis), respiratory distress syndrome, including adult respiratory distress syndrome (ARDS), meningitis, IgE-mediated diseases such as anaphylaxis and allergic rhinitis, encephalitis such as Rasmussen's encephalitis, uveitis, colitis such as microscopic colitis and collagenous colitis, glomerulonephritis (GN) such as membranous GN, idiopathic membranous GN, membranous proliferative GN (MPGN), including Type I and Type II, and rapidly progressive GN, allergic conditions, eczema, asthma, conditions involving infiltration of T cells and chronic inflammatory responses, atherosclerosis, autoimmune myocarditis, leukocyte adhesion deficiency, systemic lupus erythematosus (SLE) such as cutaneous SLE, lupus (including nephritis, cerebritis, pediatric, non-renal, discoid, alopecia), juvenile onset diabetes, multiple sclerosis (MS) such as spino-optical MS, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including Large Vessel vasculitis (including Polymyalgia Rheumatica and Giant Cell (Takayasu's) Arteritis), Medium Vessel vasculitis (including Kawasaki's Disease and Polyarteritis Nodosa), CNS vasculitis, and ANCA-associated vasculitis, such as Churg-Strauss vasculitis or syndrome (CSS)), aplastic anemia, Coombs positive anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome, myasthenia gravis, antigen-antibody complex mediated diseases, anti-glomerular basement membrane disease, anti-phospholipid antibody syndrome, allergic neuritis, Bechet disease, Castleman's syndrome, Goodpasture's Syndrome, Lambert-Eaton Myasthenic Syndrome, Reynaud's syndrome, Sjorgen's syndrome, Stevens-Johnson syndrome, solid organ transplant rejection (including pretreatment for high panel reactive antibody titers, IgA deposit in tissues, and rejection arising from renal transplantation, liver transplantation, intestinal transplantation, cardiac transplantation, etc.), graft versus host disease (GVHD), pemphigoid bullous, pemphigus (including vulgaris, foliaceus, and pemphigus mucus-membrane pemphigoid), autoimmune polyendocrinopathies, Reiter's disease, stiff-man syndrome, immune complex nephritis, IgM polyneuropathies or IgM mediated neuropathy, idiopathic thrombocytopenic purpura (ITP), thrombotic throbocytopenic purpura (TTP), thrombocytopenia (as developed by myocardial infarction patients, for example), including autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM), including pediatric IDDM, and Sheehan's syndrome; autoimmune hepatitis, Lymphoid interstitial pneumonitis (HIV), bronchiolitis obliterans (non-transplant) vs NSIP, Guillain-Barré Syndrome, Berger's Disease (IgA nephropathy), primary biliary cirrhosis, celiac sprue (gluten enteropathy), refractory sprue with co-segregate dermatitis herpetiformis, cryoglobulinemia, amylotrophic lateral sclerosis (ALS; Lou Gehrig's disease), coronary artery disease, autoimmune inner ear disease (AIED), autoimmune hearing loss, opsoclonus myoclonus syndrome (OMS), polychondritis such as refractory polychondritis, pulmonary alveolar proteinosis, amyloidosis, giant cell hepatitis, scleritis, monoclonal gammopathy of uncertain/unknown significance (MGUS), peripheral neuropathy, paraneoplastic syndrome, channelopathies such as epilepsy, migraine, arrhythmia, muscular disorders, deafness, blindness, periodic paralysis, and channelopathies of the CNS; autism, inflammatory myopathy, and focal segmental glomerulosclerosis (FSGS).

The phrase "anxiety related disorders" refers to disorders of anxiety, mood, and substance abuse, including but not limited to: depression, generalized anxiety disorders, attention deficit disorder, sleep disorder, hyperactivity disorder, obsessive compulsive disorder, schizophrenia, cognitive disorders, hyperalgesia and sensory disorders. Such disorders include the mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

The term "lipid metabolic disorder" refers to abnormal clinical chemistry levels of cholesterol and triglycerides, wherein elevated levels of these lipids is an indication for atherosclerosis. Additionally, abnormal serum lipid levels may be an indication of various cardiovascular diseases including hypertension, stroke, coronary artery diseases, diabetes and/or obesity.

The phrase "eye abnormality" refers to such potential disorders of the eye as they may be related to atherosclerosis or various ophthalmological abnormalities. Such disorders include but are not limited to the following: retinal dysplasia, various retinopathies, restenosis, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congenita, Flynn- Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis. Cataracts are also considered an eye abnormality and are associated with such systemic diseases as: Human Down's syndrome, Hallerman-Streiff syndrome, Lowe syndrome, galactosemia, Marfan syndrome, Trismoy 13-15 condition, Alport syndrome, myotonic dystrophy, Fabry disease, hypothroidisms, or Conradi syndrome. Other ocular developmental anomalies include: Aniridia, anterior segment and dysgenesis syndrome. Cataracts may also occur as a result of an intraocular infection or inflammation (uveitis).

A "growth inhibitory amount" of an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody, PRO227, PRO233, PRO238, PRO1328, PRO4342, PRO7423, PRO10096, PRO21384, PRO353 or PRO1885 polypeptide, PRO227, PRO233, PRO238, PRO1328, PRO4342, PRO7423, PRO10096, PRO21384, PRO353 or PRO1885 binding oligopeptide or PRO227, PRO233, PRO238, PRO1328, PRO4342, PRO7423, PRO10096, PRO21384, PRO353 or PRO1885 binding organic molecule is an amount capable of inhibiting the growth of a cell, especially tumor, e.g., cancer cell, either in vitro or in vivo. A "growth inhibitory amount" of an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody, PRO227, PRO233, PRO238, PRO1328, PRO4342, PRO7423, PRO10096, PRO21384, PRO353 or PRO1885 polypeptide, PRO227, PRO233, PRO238, PRO1328, PRO4342, PRO7423, PRO10096, PRO21384, PRO353 or PRO1885 binding oligopeptide or PRO227, PRO233, PRO238, PRO1328, PRO4342, PRO7423, PRO10096, PRO21384, PRO353 or PRO1885 binding organic molecule for purposes of inhibiting neoplastic cell growth may be determined empirically and in a routine manner.

A "cytotoxic amount" of an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody, PRO227, PRO233, PRO238, PRO1328, PRO4342, PRO7423, PRO10096, PRO21384, PRO353 or PRO1885 polypeptide, PRO227, PRO233, PRO238, PRO1328, PRO4342, PRO7423, PRO10096, PRO21384, PRO353 or PRO1885 binding oligopeptide or PRO227, PRO233, PRO238, PRO1328, PRO4342, PRO7423, PRO10096, PRO21384, PRO353 or PRO1885 binding organic molecule is an amount capable of causing the destruction of a cell, especially tumor, e.g., cancer cell, either in vitro or in vivo. A "cytotoxic amount" of an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody, PRO227, PRO233, PRO238, PRO1328, PRO4342, PRO7423, PRO10096, PRO21384, PRO353 or PRO1885 polypeptide, PRO227, PRO233, PRO238, PRO1328, PRO4342, PRO7423, PRO10096, PRO21384, PRO353 or PRO1885 binding oligopeptide or PRO227, PRO233, PRO238, PRO1328, PRO4342, PRO7423, PRO10096, PRO21384, PRO353 or PRO1885 binding organic molecule for purposes of inhibiting neoplastic cell growth may be determined empirically and in a routine manner.

The term "antibody" is used in the broadest sense and specifically covers, for example, single anti-PRO227, anti-PRO233, anti-PRO238, anti-PRO1328, anti-PRO4342, anti-PRO7423, anti-PRO10096, anti-PRO21384, anti-PRO353 or anti-PRO1885 monoclonal antibodies (including agonist, antagonist, and neutralizing antibodies), anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody compositions with polyepitopic specificity, polyclonal antibodies, single chain anti-PRO227, anti-PRO233, anti-PRO238, anti-PRO1328, anti-PRO4342, anti-PRO7423, anti-PRO10096, anti-PRO21384, anti-PRO353 or anti-PRO1885 antibodies, and fragments of anti-PRO227, anti-PRO233, anti-PRO238, anti-PRO1328, anti-PRO4342, anti-PRO7423, anti-PRO10096, anti-PRO21384, anti-PRO353 or anti-PRO1885 antibodies (see below) as long as they exhibit the desired biological or immunological activity. The term "immunoglobulin" (Ig) is used interchangeable with antibody herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. The invention provides that the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology*, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 1-35 (H1), 50-65 (H2) and 95-102 (H3) in the $V_H$; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 53-55 (H2) and 96-101 (H3) in the $V_H$; Chothia and Lesk *J. Mol. Biol.* 196:901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., *Nature*, 256:495 (1975), or may be made using recombinant DNA methods in bacterial, eukaryotic animal or plant cells (see, e.g., U.S. Pat. No. 4,816, 567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a $C_L$ and at least heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., *Protein Eng.* 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., *Proc. Natl. Acad. Sci. USA*, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992).

A "species-dependent antibody," e.g., a mammalian antihuman IgE antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1 \times 10^{-7}$ M, preferably no more than about $1 \times 10^{-8}$ and most preferably no more than about $1 \times 10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

A "PRO227, PRO233, PRO238, PRO1328, PRO4342, PRO7423, PRO10096, PRO21384, PRO353 or PRO1885 binding oligopeptide" is an oligopeptide that binds, preferably specifically, to a PRO227, PRO233, PRO238, PRO1328, PRO4342, PRO7423, PRO10096, PRO21384, PRO353 or PRO1885 polypeptide as described herein. PRO227, PRO233, PRO238, PRO1328, PRO4342, PRO7423, PRO10096, PRO21384, PRO353 or PRO1885 binding oligopeptides may be chemically synthesized using known oligopeptide synthesis methodology or may be prepared and purified using recombinant technology. PRO227, PRO233, PRO238, PRO1328, PRO4342, PRO7423, PRO10096, PRO21384, PRO353 or PRO1885 binding oligopeptides usually are or are at least about 5 amino acids in length, alternatively are or are at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a PRO227, PRO233, PRO238, PRO1328, PRO4342, PRO7423, PRO10096, PRO21384, PRO353 or PRO1885 polypeptide as described herein. PRO227, PRO233, PRO238, PRO1328, PRO4342, PRO7423, PRO10096, PRO21384, PRO353 or PRO1885 binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708, 871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in *Synthetic Peptides as Antigens*, 130-149 (1986); Geysen et al., *J. Immunol. Meth.*, 102:259-274 (1987); Schoofs et al., *J. Immunol.*, 140:611-616 (1988), Cwirla, S. E. et al. (1990) *Proc. Natl. Acad. Sci. USA*, 87:6378; Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A. S. et al. (1991) *Proc. Natl. Acad. Sci. USA*, 88:8363, and Smith, G. P. (1991) *Current Opin. Biotechnol.*, 2:668).

A "PRO227, PRO233, PRO238, PRO1328, PRO4342, PRO7423, PRO10096, PRO21384, PRO353 or PRO1885 binding organic molecule" is an organic molecule other than an oligopeptide or antibody as defined herein that binds, preferably specifically, to a PRO227, PRO233, PRO238, PRO1328, PRO4342, PRO7423, PRO10096, PRO21384, PRO353 or PRO1885 polypeptide as described herein. PRO227, PRO233, PRO238, PRO1328, PRO4342, PRO7423, PRO10096, PRO21384, PRO353 or PRO1885 binding organic molecules may be identified and chemically synthesized using known methodology (see, e.g., PCT Publication Nos. WO00/00823 and WO00/39585). PRO227, PRO233, PRO238, PRO1328, PRO4342, PRO7423, PRO10096, PRO21384, PRO353 or PRO1885 binding organic molecules are usually less than about 2000 daltons in size, alternatively less than about 1500, 750, 500, 250 or 200 daltons in size, wherein such organic molecules that are capable of binding, preferably specifically, to a PRO227, PRO233, PRO238, PRO1328, PRO4342, PRO7423, PRO10096, PRO21384, PRO353 or PRO1885 polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585).

An antibody, oligopeptide or other organic molecule "which binds" an antigen of interest, e.g. a tumor-associated polypeptide antigen target, is one that binds the antigen with sufficient affinity such that the antibody, oligopeptide or other organic molecule is preferably useful as a diagnostic and/or therapeutic agent in targeting a cell or tissue expressing the antigen, and does not significantly cross-react with other proteins. The extent of binding of the antibody, oligopeptide or other organic molecule to a "non-target" protein will be less than about 10% of the binding of the antibody, oligopeptide or other organic molecule to its particular target protein as determined by fluorescence activated cell sorting (FACS) analysis or radioimmunoprecipitation (RIA). With regard to the binding of an antibody, oligopeptide or other organic molecule to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. The term "specific binding" refers to binding where a molecule binds to a particular polypeptide or epitope on a particular polypeptide without substantially binding to any other polypeptide or polypeptide epitope.

An antibody, oligopeptide or other organic molecule that "inhibits the growth of tumor cells expressing a "PRO227, PRO233, PRO238, PRO1328, PRO4342, PRO7423, PRO10096, PRO21384, PRO353 or PRO1885" or a "growth inhibitory" antibody, oligopeptide or other organic molecule is one which results in measurable growth inhibition of cancer cells expressing or overexpressing the appropriate PRO227, PRO233, PRO238, PRO1328, PRO4342, PRO7423, PRO10096, PRO21384, PRO353 or PRO1885 polypeptide. The PRO227, PRO233, PRO238, PRO1328, PRO4342, PRO7423, PRO10096, PRO21384, PRO353 or PRO1885 polypeptide may be a transmembrane polypeptide expressed on the surface of a cancer cell or may be a polypeptide that is produced and secreted by a cancer cell. Preferred growth inhibitory anti-PRO227, anti-PRO233, anti-PRO238, anti-PRO1328, anti-PRO4342, anti-PRO7423, anti-PRO10096, anti-PRO21384, anti-PRO353 or anti-PRO1885 antibodies, oligopeptides or organic molecules inhibit growth of PRO227-, PRO233-, PRO238-, PRO1328-, PRO4342-, PRO7423-, PRO10096-, PRO21384-, PRO353- or PRO1885-expressing tumor cells by or by greater than 20%, preferably from about 20% to about 50%, and even more preferably, by or by greater than 50% (e.g., from about 50% to about 100%) as compared to the appropriate control, the control typically being tumor cells not treated with the antibody, oligopeptide or other organic molecule being tested. Growth inhibition can be measured at an antibody concentration of about 0.1 to 30 µg/ml or about 0.5 nM to 200 nM in cell culture, where the growth inhibition is determined 1-10 days after exposure of the tumor cells to the antibody. Growth inhibition of tumor cells in vivo can be determined in various ways. The antibody is growth inhibitory in vivo if administration of the anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody at about 1 µg/kg to about 100 mg/kg body weight results in reduction in tumor size or tumor cell proliferation within about 5 days to 3 months from the first administration of the antibody, preferably within about 5 to 30 days.

An antibody, oligopeptide or other organic molecule which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses a PRO227, PRO233, PRO238, PRO1328, PRO4342, PRO7423, PRO10096, PRO21384, PRO353 or PRO1885 polypeptide. Preferably the cell is a tumor cell, e.g., a prostate, breast, ovarian, stomach, endometrial, lung, kidney, colon, bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody, oligopeptide or other organic molecule which induces apoptosis is one which results in or in about 2 to 50 fold, preferably in or in about 5 to 50 fold, and most preferably in or in about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Natl. Acad. Sci. U.S.A.* 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol.* 9:457-492 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202:163 (1996), may be performed.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD). Preferably, the cancer comprises a tumor that expresses an IGF receptor, more preferably breast cancer, lung cancer, colorectal cancer, or prostate cancer, and most preferably breast or prostate cancer.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, *Chem. Intl. Ed. Engl.*, 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON•toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

The terms "cell proliferative disorder" and "proliferative disorder" refer to disorders that are associated with some degree of abnormal cell proliferation. In one aspect of the invention, the cell proliferative disorder is cancer.

"Tumor", as used herein, refers to all neoplastic cell growth and proliferation, whether malignant or benign, and all pre-cancerous and cancerous cells and tissues.

An antibody, oligopeptide or other organic molecule which "induces cell death" is one which causes a viable cell to become nonviable. The cell is one which expresses a PRO227, PRO233, PRO238, PRO1328, PRO4342, PRO7423, PRO10096, PRO21384, PRO353 or PRO1885 polypeptide, preferably a cell that overexpresses a PRO227, PRO233, PRO238, PRO1328, PRO4342, PRO7423, PRO10096, PRO21384, PRO353 or PRO1885 polypeptide as compared to a normal cell of the same tissue type. The PRO227, PRO233, PRO238, PRO1328, PRO4342, PRO7423, PRO10096, PRO21384, PRO353 or PRO1885 polypeptide may be a transmembrane polypeptide expressed on the surface of a cancer cell or may be a polypeptide that is produced and secreted by a cancer cell. Preferably, the cell is a cancer cell, e.g., a breast, ovarian, stomach, endometrial, salivary gland, lung, kidney, colon, thyroid, pancreatic or bladder cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody, oligopeptide or other organic molecule is able to induce cell death, loss of membrane integrity as evaluated by uptake of propidium iodide (PI), trypan blue (see Moore et al. *Cytotechnology* 17:1-11 (1995)) or 7AAD can be assessed relative to untreated cells. Preferred cell death-inducing antibodies, oligopeptides or other organic molecules are those which induce PI uptake in the PI uptake assay in BT474 cells.

As used herein, the term "immunoadhesion" designates antibody-like molecules which combine the binding specificity of a heterologous protein (an "adhesion") with the effector functions of immunoglobulin constant domains. Structurally, the immunoadhesions comprise a fusion of an amino acid sequence with the desired binding specificity which is other than the antigen recognition and binding site of an antibody (i.e., is "heterologous"), and an immunoglobulin constant domain sequence. The adhesion part of an immunoadhesion molecule typically is a contiguous amino acid sequence comprising at least the binding site of a receptor or a ligand. The immunoglobulin constant domain sequence in the immunoadhesion may be obtained from any immunoglobulin, such as IgG-1, IgG-2, IgG-3, or IgG-4 subtypes, IgA (including IgA-1 and IgA-2), IgE, IgD or IgM.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

"Replication-preventing agent" is an agent wherein replication, function, and/or growth of the cells is inhibited or prevented, or cells are destroyed, no matter what the mechanism, such as by apoptosis, angiostasis, cytosis, tumoricide, mytosis inhibition, blocking cell cycle progression, arresting cell growth, binding to tumors, acting as cellular mediators, etc. Such agents include a chemotherapeutic agent, cytotoxic agent, cytokine, growth-inhibitory agent, or anti-hormonal agent, e.g., an anti-estrogen compound such as tamoxifen, an anti-progesterone such as onapristone (see, EP 616 812); or an anti-androgen such as flutamide, as well as aromidase inhibitors, or a hormonal agent such as an androgen.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chloranbucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

Preferred cytotoxic agents herein for the specific tumor types to use in combination with the antagonists herein are as follows:

1. Prostate cancer: androgens, docetaxel, paclitaxel, estramustine, doxorubicin, mitoxantrone, antibodies to ErbB2 domain(s) such as 2C4 (WO 01/00245; hybridoma ATCC HB-12697), which binds to a region in the extracellular domain of ErbB2 (e.g., any one or more residues in the region from about residue 22 to about residue 584 of ErbB2, inclusive), AVASTIN™ anti-vascular endothelial growth factor (VEGF), TARCEVA™ OSI-774 (erlotinib) (Genenetech and OSI Pharmaceuticals), or other epidermal growth factor receptor tyrosine kinase inhibitors (EGFR TKI's).
2. Stomach cancer: 5-fluorouracil (5FU), XELODA™ capecitabine, methotrexate, etoposide, cisplatin/carboplatin, paclitaxel, docetaxel, gemcitabine, doxorubicin, and CPT-11 (camptothcin-11; irinotecan, USA Brand Name: CAMPTOSAR®).
3. Pancreatic cancer: gemcitabine, 5FU, XELODA™ capecitabine, CPT-11, docetaxel, paclitaxel, cisplatin, carboplatin, TARCEVA™ erlotinib, and other EGFR TKI's.
4. Colorectal cancer: 5FU, XELODA™ capecitabine, CPT-11, oxaliplatin, AVASTIN™ anti-VEGF, TARCEVA™ erlotinib and other EGFR TKI's, and ERBITUXT™ (formerly known as IMC-C225) human:murine-chimerized monoclonal antibody that binds to EGFR and blocks the ability of EGF to initiate receptor activation and signaling to the tumor.
5. Renal cancer: IL-2, interferon alpha, AVASTIN™ anti-VEGF, MEGACE™ (Megestrol acetate) progestin, vinblastine, TARCEVA™ erlotinib, and other EGFR TKI's.

A "growth inhibitory agent" when used herein refers to a compound or composition which inhibits growth of a cell, especially a PRO227-, PRO233-, PRO238-, PRO1328-, PRO4342-, PRO7423-; PRO10096-; PRO21384-; PRO353- or PRO1885-expressing cancer cell, either in vitro or in vivo. Thus, the growth inhibitory agent may be one which significantly reduces the percentage of PRO227-, PRO233-, PRO238-, PRO1328-, PRO4342-, PRO7423-, PRO10096-, PRO21384-, PRO353- or PRO1885-expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3,6-trideoxy-α-L-lyxo-hexapyranosyl)oxy]-7,8,9,10-tetrahydro-6,8,1 1-trihydroxy-8-(hydroxyacetyl)-1-methoxy-5,12-naphthacenedione.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "package insert" is used to refer to instructions customarily included in commercial packages of therapeutic products, that contain information about the indications, usage, dosage, administration, contraindications and/or warnings concerning the use of such therapeutic products.

The term "gene" refers to (a) a gene containing at least one of the DNA sequences disclosed herein; (b) any DNA sequence that encodes the amino acid sequence encoded by the DNA sequences disclosed herein and/or; (c) any DNA sequence that hybridizes to the complement of the coding sequences disclosed herein. Preferably, the term includes coding as well as noncoding regions, and preferably includes all sequences necessary for normal gene expression.

The term "gene targeting" refers to a type of homologous recombination that occurs when a fragment of genomic DNA is introduced into a mammalian cell and that fragment locates and recombines with endogenous homologous sequences. Gene targeting by homologous recombination employs recombinant DNA technologies to replace specific genomic sequences with exogenous DNA of particular design.

The term "homologous recombination" refers to the exchange of DNA fragments between two DNA molecules or chromatids at the site of homologous nucleotide sequences.

The term "target gene" (alternatively referred to as "target gene sequence" or "target DNA sequence") refers to any nucleic acid molecule, polynucleotide, or gene to be modified by homologous recombination. The target sequence includes an intact gene, an exon or intron, a regulatory sequence or any region between genes. The target gene my comprise a portion of a particular gene or genetic locus in the individual's genomic DNA.

"Disruption" of a PRO227, PRO233, PRO238, PRO1328, PRO4342, PRO7423, PRO10096, PRO21384, PRO353 or PRO1885 gene occurs when a fragment of genomic DNA locates and recombines with an endogenous homologous sequence wherein the disruption is a deletion of the native gene or a portion thereof, or a mutation in the native gene or wherein the disruption is the functional inactivation of the native gene. Alternatively, sequence disruptions may be generated by nonspecific insertional inactivation using a gene trap vector (i.e. non-human transgenic animals containing and expressing a randomly inserted transgene; see for example U.S. Pat. No. 6,436,707 issued Aug. 20, 2002). These sequence disruptions or modifications may include insertions, missense, frameshift, deletion, or substitutions, or replacements of DNA sequence, or any combination thereof. Insertions include the insertion of entire genes, which may be of animal, plant, fungal, insect, prokaryotic, or viral origin. Disruption, for example, can alter the normal gene product by inhibiting its production partially or completely or by enhancing the normal gene product's activity. Preferably, the disruption is a null disruption, wherein there is no significant expression of the PRO227, PRO233, PRO238, PRO1328, PRO4342, PRO7423, PRO10096, PRO21384, PRO353 or PRO1885 gene.

The term "native expression" refers to the expression of the full-length polypeptide encoded by the PRO227, PRO233, PRO238, PRO1328, PRO4342, PRO7423, PRO10096, PRO21384, PRO353 or PRO1885 gene, at expression levels present in the wild-type mouse. Thus, a disruption in which there is "no native expression" of the endogenous PRO227, PRO233, PRO238, PRO1328, PRO4342, PRO7423, PRO10096, PRO21384, PRO353 or PRO1885 gene refers to a partial or complete reduction of the expression of at least a portion of a polypeptide encoded by an endogenous PRO227, PRO233, PRO238, PRO1328, PRO4342, PRO7423, PRO10096, PRO21384, PRO353 or PRO1885 gene of a single cell, selected cells, or all of the cells of a mammal.

The term "knockout" refers to the disruption of a PRO227, PRO233, PRO238, PRO1328, PRO4342, PRO7423, PRO10096, PRO21384, PRO353 or PRO1885 gene wherein the disruption results in: the functional inactivation of the native gene; the deletion of the native gene or a portion thereof; or a mutation in the native gene.

The term "knock-in" refers to the replacement of the mouse ortholog (or other mouse gene) with a human cDNA encoding any of the specific human PRO227-, PRO233-, PRO238-, PRO1328-, PRO4342-, PRO7423-, PRO10096-, PRO21384-, PRO353- or PRO1885-encoding genes or variants thereof (ie. the disruption results in a replacement of a native mouse gene with a native human gene).

The term "construct" or "targeting construct" refers to an artificially assembled DNA segment to be transferred into a target tissue, cell line or animal. Typically, the targeting construct will include a gene or a nucleic acid sequence of particular interest, a marker gene and appropriate control sequences. As provided herein, the targeting construct comprises a PRO227, PRO233, PRO238, PRO1328, PRO4342, PRO7423, PRO10096, PRO21384, PRO353 or PRO1885 targeting construct. A "PRO227, PRO233, PRO238, PRO1328, PRO4342, PRO7423, PRO10096, PRO21384, PRO353 or PRO1885 targeting construct" includes a DNA sequence homologous to at least one portion of a PRO227, PRO233, PRO238, PRO1328, PRO4342, PRO7423, PRO10096, PRO21384, PRO353 or PRO1885 gene and is capable of producing a disruption in a PRO227, PRO233, PRO238, PRO1328, PRO4342, PRO7423, PRO10096, PRO21384, PRO353 or PRO1885 gene in a host cell.

The term "transgenic cell" refers to a cell containing within its genome a PRO227, PRO233, PRO238, PRO1328, PRO4342, PRO7423, PRO10096, PRO21384, PRO353 or PRO1885 gene that has been disrupted, modified, altered, or replaced completely or partially by the method of gene targeting.

The term "transgenic animal" refers to an animal that contains within its genome a specific gene that has been disrupted or otherwise modified or mutated by the methods described herein or methods otherwise well known in the art. Preferably the non-human transgenic animal is a mammal. More preferably, the mammal is a rodent such as a rat or mouse. In addition, a "transgenic animal" may be a heterozygous animal (i.e., one defective allele and one wild-type allele) or a homozygous animal (i.e., two defective alleles). An embryo is considered to fall within the definition of an animal. The provision of an animal includes the provision of an embryo or foetus in utero, whether by mating or otherwise, and whether or not the embryo goes to term.

As used herein, the terms "selective marker" and position selection marker" refer to a gene encoding a product that enables only the cells that carry the gene to survive and/or grow under certain conditions. For example, plant and animal cells that express the introduced neomycin resistance ($Neo^r$) gene are resistant to the compound G418. Cells that do not carry the $Neo^r$ gene marker are killed by G418. Other positive selection markers are known to, or are within the purview of, those of ordinary skill in the art.

The term "modulates" or "modulation" as used herein refers to the decrease, inhibition, reduction, amelioration, increase or enhancement of a PRO227, PRO233, PRO238, PRO1328, PRO4342, PRO7423, PRO10096, PRO21384, PRO353 or PRO1885 gene function, expression, activity, or alternatively a phenotype associated with PRO227, PRO233, PRO238, PRO1328, PRO4342, PRO7423, PRO10096, PRO21384, PRO353 or PRO1885 gene.

The term "ameliorates" or "amelioration" as used herein refers to a decrease, reduction or elimination of a condition, disease, disorder, or phenotype, including an abnormality or symptom.

The term "abnormality" refers to any disease, disorder, condition, or phenotype in which PRO227, PRO233, PRO238, PRO1328, PRO4342, PRO7423, PRO10096, PRO21384, PRO353 or PRO1885 is implicated, including pathological conditions and behavioral observations.

TABLE 1

```
/*
*
* C-C increased from 12 to 15
* Z is average of EQ
* B is average of ND
* match with stop is _M; stop-stop = 0; J (joker) match = 0
*/
#define    _M   -8    /* value of a match with a stop */
int    _day[26][26] = {
/*        A B C D E F G H I J K L M N O P Q R S T U V W
X Y Z */
/* A */   { 2, 0,-2, 0, 0,-4, 1,-1,-1, 0,-1,-2,-1, 0,_M, 1, 0,-2, 1, 1, 0, 0,-6, 0,-3, 0},
```

TABLE 1-continued

```
/* B */   { 0, 3,-4, 3, 2,-5, 0, 1,-2, 0, 0,-3,-2, 2,_M,-1, 1, 0, 0, 0, 0,-2,-5, 0,-3, 1},
/* C */   {-2,-4,15,-5,-5,-4,-3,-3,-2, 0,-5,-6,-5,-4,_M,-3,-5,-4, 0,-2, 0,-2,-8, 0, 0,-5},
/* D */   { 0, 3,-5, 4, 3,-6, 1, 1,-2, 0, 0,-4,-3, 2,_M,-1, 2,-1, 0, 0, 0,-2,-7, 0,-4, 2},
/* E */   { 0, 2,-5, 3, 4,-5, 0, 1,-2, 0, 0,-3,-2, 1,_M,-1, 2,-1, 0, 0, 0,-2,-7, 0,-4, 3},
/* F */   {-4,-5,-4,-6,-5, 9,-5,-2, 1, 0,-5, 2, 0,-4,_M,-5,-5,-4,-3,-3, 0,-1, 0, 0, 7,-5},
/* G */   { 1, 0,-3, 1, 0,-5, 5,-2,-3, 0,-2,-4,-3, 0,_M,-1,-1,-3, 1, 0, 0,-1,-7, 0,-5, 0},
/* H */   {-1, 1,-3, 1, 1,-2,-2, 6,-2, 0, 0,-2,-2, 2,_M, 0, 3, 2,-1,-1, 0,-2,-3, 0, 0, 2},
/* I */   {-1,-2,-2,-2,-2, 1,-3,-2, 5, 0,-2, 2, 2,-2,_M,-2,-2,-2,-1, 0, 0, 4,-5, 0,-1,-2},
/* J */   { 0, 0, 0, 0, 0, 0, 0, 0, 0, 0, 0, 0, 0, 0,_M, 0, 0, 0, 0, 0, 0, 0, 0, 0, 0, 0},
/* K */   {-1, 0,-5, 0, 0,-5,-2, 0,-2, 0, 5,-3, 0, 1,_M,-1, 1, 3, 0, 0, 0,-2,-3, 0,-4, 0},
/* L */   {-2,-3,-6,-4,-3, 2,-4,-2, 2, 0,-3, 6, 4,-3,_M,-3,-2,-3,-3,-1, 0, 2,-2, 0,-1,-2},
/* M */   {-1,-2,-5,-3,-2, 0,-3,-2, 2, 0, 0, 4, 6,-2,_M,-2,-1, 0,-2,-1, 0, 2,-4, 0,-2,-1},
/* N */   { 0, 2,-4, 2, 1,-4, 0, 2,-2, 0, 1,-3,-2, 2,_M,-1, 1, 0, 1, 0, 0,-2,-4, 0,-2, 1},
/* O */   {_M,_M,_M,_M,_M,_M,_M,_M,_M,_M,_M,_M,_M,_M,
0,_M,_M,_M,_M,_M,_M,_M,_M,_M,_M,_M},
/* P */   { 1,-1,-3,-1,-1,-5,-1, 0,-2, 0,-1,-3,-2,-1,_M, 6, 0, 0, 1, 0, 0,-1,-6, 0,-5, 0},
/* Q */   { 0, 1,-5, 2, 2,-5,-1, 3,-2, 0, 1,-2,-1, 1,_M, 0, 4, 1,-1,-1, 0,-2,-5, 0,-4, 3},
/* R */   {-2, 0,-4,-1,-1,-4,-3,-2, 2, 0, 3,-3, 0, 0,_M, 0, 1, 6, 0,-1, 0,-2, 2, 0,-4, 0},
/* S */   { 1, 0, 0, 0, 0,-3, 1,-1,-1, 0, 0,-3,-2, 1,_M, 1,-1, 0, 2, 1, 0,-1,-2, 0,-3, 0},
/* T */   { 1, 0,-2, 0, 0,-3, 0,-1, 0, 0, 0,-1,-1, 0,_M, 0,-1,-1, 1, 3, 0, 0,-5, 0,-3, 0},
/* U */   { 0, 0, 0, 0, 0, 0, 0, 0, 0, 0, 0, 0, 0, 0,_M, 0, 0, 0, 0, 0, 0, 0, 0, 0, 0, 0},
/* V */   { 0,-2,-2,-2,-2,-1,-1,-2, 4, 0,-2, 2, 2,-2,_M,-1,-2,-2,-1, 0, 0, 4,-6, 0,-2,-2},
/* W */   {-6,-5,-8,-7,-7, 0,-7,-3,-5, 0,-3,-2,-4,-4,_M,-6,-5, 2,-2,-5, 0,-6,17, 0,-6},
/* X */   { 0, 0, 0, 0, 0, 0, 0, 0, 0, 0, 0, 0, 0, 0,_M, 0, 0, 0, 0, 0, 0, 0, 0, 0, 0, 0},
/* Y */   {-3,-3, 0,-4,-4, 7,-5, 0,-1, 0,-4,-1,-2,-2,_M,-5,-4,-4,-3,-3, 0,-2, 0, 0,10,-4},
/* Z */   { 0, 1,-5, 2, 3,-5, 0, 2,-2, 0, 0,-2,-1, 1,_M, 0, 3, 0, 0, 0, 0,-2,-6, 0,-4, 4}
};
/*
*/
#include <stdio.h>
#include <ctype.h>
#define    MAXJMP    16      /* max jumps in a diag */
#define    MAXGAP    24      /* don't continue to penalize gaps larger than this */
#define    JMPS      1024    /* max jmps in an path */
#define    MX        4       /* save if there's at least MX-1 bases since last jmp */
#define    DMAT      3       /* value of matching bases */
#define    DMIS      0       /* penalty for mismatched bases */
#define    DINS0     8       /* penalty for a gap */
#define    DINS1     1       /* penalty per base */
#define    PINS0     8       /* penalty for a gap */
#define    PINS1     4       /* penalty per residue */
struct jmp {
        short            n[MAXJMP]; /* size of jmp (neg for dely) */
        unsigned short   x[MAXJMP]; /* base no. of jmp in seq x */
};                               /* limits seq to 2^16 -1 */
struct diag {
        int         score;    /* score at last jmp */
        long        offset;   /* offset of prev block */
        short       ijmp;     /* current jmp index */
        struct jmp  jp;       /* list of jmps */
};
struct path {
        int         spc;      /* number of leading spaces */
        short       n[JMPS];  /* size of jmp (gap) */
        int         x[JMPS];  /* loc of jmp (last elem before gap) */
};
char        *ofile;           /* output file name */
char        *namex[2];        /* seq names: getseqs( ) */
char        *prog;            /* prog name for err msgs */
char        *seqx[2];         /* seqs: getseqs( ) */
int         dmax;             /* best diag: nw( ) */
int         dmax( );          /* final diag */
int         dna;              /* set if dna: main( ) */
int         endgaps;          /* set if penalizing end gaps */
int         gapx, gapy;       /* total gaps in seqs */
int         len0, len1;       /* seq lens */
int         ngapx, ngapy;     /* total size of gaps */
int         smax;             /* max score: nw( ) */
int         *xbm;             /* bitmap for matching */
long        offset;           /* current offset in jmp file */
struct diag *dx;              /* holds diagonals */
struct path pp[2];            /* holds path for seqs */
char        *calloc( ), *malloc( ), *index( ), *strcpy( );
char        *getseq( ), *g_calloc( );
/* Needleman-Wunsch alignment program
*
* usage: progs file1 file2
*    where file1 and file2 are two dna or two protein sequences.
*    The sequences can be in upper- or lower-case an may contain ambiguity
*    Any lines beginning with ';', '>' or '<' are ignored
```

TABLE 1-continued

```
*       Max file length is 65535 (limited by unsigned short x in the jmp struct)
*       A sequence with ⅓ or more of its elements ACGTU is assumed to be DNA
*       Output is in the file "align.out"
*
* The program may create a tmp file in /tmp to hold info about traceback.
* Original version developed under BSD 4.3 on a vax 8650
*/
#include "nw.h"
#include "day.h"
static      _dbval[26] = {
            1,14,2,13,0,0,4,11,0,0,12,0,3,15,0,0,0,5,6,8,8,7,9,0,10,0
};
static      _pbval[26] = {
            1, 2|(1<<('D'-'A'))|(1<<('N'-'A')), 4, 8, 16, 32, 64,
            128, 256, 0xFFFFFFFF, 1<<10, 1<<11, 1<<12, 1<<13, 1<<14,
            1<<15, 1<<16, 1<<17, 1<<18, 1<<19, 1<<20, 1<<21, 1<<22,
            1<<23, 1<<24, 1<<25|(1<<('E'-'A'))|(1<<('Q'-'A'))
};
main(ac, av)                                                                                    main
            int         ac;
            char        *av[ ];
{
            prog = av[0];
            if (ac != 3) {
                        fprintf(stderr,"usage: %s file1 file2\n", prog);
                        fprintf(stderr,"where file1 and file2 are two dna or two protein sequences.\n");
                        fprintf(stderr,"The sequences can be in upper- or lower-case\n");
                        fprintf(stderr,"Any lines beginning with ';' or '<' are ignored\n");
                        fprintf(stderr,"Output is in the file \"align.out\"\n");
                        exit(1);
            }
            namex[0] = av[1];
            namex[1] = av[2];
            seqx[0] = getseq(namex[0], &len0);
            seqx[1] = getseq(namex[1], &len1);
            xbm = (dna)? _dbval : _pbval;
endgaps = 0;                /* 1 to penalize endgaps */
ofile = "align.out";        /* output file */
nw( );                      /* fill in the matrix, get the possible jmps */
readjmps( );                /* get the actual jmps */
print( );                   /* print stats, alignment */
cleanup(0);                 /* unlink any tmp files */ }
/* do the alignment, return best score: main( )
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw( )                                                                                           nw
{
            char        *px, *py;               /* seqs and ptrs */
            int         *ndely, *dely;          /* keep track of dely */
            int         ndelx, delx;            /* keep track of delx */
            int         *tmp;                   /* for swapping row( ), row1 */
            int         mis;                    /* score for each type */
            int         ins0, ins1;             /* insertion penalties */
            register                id;         /* diagonal index */
            register                ij;         /* jmp index */
            register    *col0, *col1;           /* score for curr, last row */
            register                xx, yy;     /* index into seqs */
            dx = (struct diag *)g_calloc("to get diags", len0+len1+1, sizeof(struct diag));
            ndely = (int *)g_calloc("to get ndely", len1+1, sizeof(int));
            dely = (int *)g_calloc("to get dely", len1+1, sizeof(int));
            col0 = (int *)g_calloc("to get col0", len1+1, sizeof(int));
            col1 = (int *)g_calloc("to get col1", len1+1, sizeof(int));
            ins0 = (dna)? DINS0 : PINS0;
            ins1 = (dna)? DINS1 : PINS1;
            smax = -10000;
            if (endgaps) {
                        for (col0[0] = dely[0] = -ins0, yy = 1; yy <= len1; yy++) {
                                    col0[yy] = dely[yy] = col0[yy-1] - ins1;
                                    ndely[yy] = yy;
                        }
                        col0[0] = 0; /* Waterman Bull Math Biol 84 */
            }
            else
                        for (yy = 1; yy <= len1; yy++)
                                    dely[yy] = -ins0;
            /* fill in match matrix
```

TABLE 1-continued

```
             */
            for (px = seqx[0], xx = 1; xx <= len0; px++, xx++) {
                    /* initialize first entry in col
                     */
                    if (endgaps) {
            if (xx == 1)
                    col1[0] = delx = -(ins0+ins1);
            else
                    col1[0] = delx = col0[0] - ins1;
            ndelx = xx;
    }
    else {
            col1[0] = 0;
            delx = -ins0;
            ndelx = 0;
    }
                                                                                    ...nw
            for (py = seqx[1], yy = 1; yy <= len1; py++, yy++) {
                    mis = col0[yy-1];
                    if (dna)
                            mis += (xbm[*px-'A']&xbm[*py-'A'])? DMAT : DMIS;
                    else
                            mis += _day[*px-'A'][*py-'A'];
                    /* update penalty for del in x seq;
                     * favor new del over ongong del
                     * ignore MAXGAP if weighting endgaps
                     */
                    if (endgaps || ndely[yy] < MAXGAP) {
                            if (col0[yy] - ins0 >= dely[yy]) {
                                    dely[yy] = col0[yy] - (ins0+ins1);
                                    ndely[yy] = 1;
                            } else {
                                    dely[yy] -= ins1;
                                    ndely[yy]++;
                            }
                    } else {
                            if (col0[yy] - (ins0+ins1) >= dely[yy]) {
                                    dely[yy] = col0[yy] - (ins0+ins1);
                                    ndely[yy] = 1;
                            } else
                                    ndely[yy]++;
                    }
                    /* update penalty for del in y seq;
                     * favor new del over ongong del
                     */
                    if (endgaps || ndelx < MAXGAP) {
                            if (col1[yy-1] - ins0 >= delx) {
                                    delx = col1[yy-1] - (ins0+ins1);
                                    ndelx = 1;
                            } else {
                                    delx -= ins1;
                                    ndelx++;
                            }
                    } else {
                            if (col1[yy-1] - (ins0+ins1) >= delx) {
                                    delx = col1[yy-1] - (ins0+ins1);
                                    ndelx = 1;
                            } else
                                    ndelx++;
                    }
    }
    /* pick the maximum score; we're favoring
     * mis over any del and delx over dely
     */
                                                                                    ...nw
    id = xx - yy + len1 - 1;
    if (mis >= delx && mis >= dely[yy])
            col1[yy] = mis;
                            else if (delx >= dely[yy]) {
                                    col1[yy] = delx;
                                    ij = dx[id].ijmp;
                                    if (dx[id].jp.n[0] && (!dna || (ndelx >= MAXJMP
                                        && xx > dx[id].jp.x[ij]+MX) || mis > dx[id].score+DINS0)) {
                                            dx[id].ijmp++;
                                            if (++ij >= MAXJMP) {
                                                    writejmps(id);
                                                    ij = dx[id].ijmp = 0;
                                                    dx[id].offset = offset;
                                                    offset += sizeof(struct jmp) + sizeof(offset);
                                            }
                                    }
```

TABLE 1-continued

```
                        dx[id].jp.n[ij] = ndelx;
                        dx[id].jp.x[ij] = xx;
                        dx[id].score = delx;
                }
                else {
                        col1[yy] = dely[yy];
                        ij = dx[id].ijmp;
if (dx[id].jp.n[0] && (!dna || (ndely[yy] >= MAXJMP
                        && xx > dx[id].jp.x[ij]+MX) || mis > dx[id].score+DINS0)) {
                                dx[id].ijmp++;
                                if (++ij >= MAXJMP) {
                                        writejmps(id);
                                        ij = dx[id].ijmp = 0;
                                        dx[id].offset = offset;
                                        offset += sizeof(struct jmp) + sizeof(offset);
                                }
                        }
                        dx[id].jp.n[ij] = -ndely[yy];
                        dx[id].jp.x[ij] = xx;
                        dx[id].score = dely[yy];
                }
                if (xx == len0 && yy < len1) {
                        /* last col
                         */
                        if (endgaps)
                                col1[yy] -= ins0+ins1*(len1-yy);
                        if (col1[yy] > smax) {
                                smax = col1[yy];
                                dmax = id;
                        }
                }
        }
        if (endgaps && xx < len0)
                col1[yy-1] -= ins0+ins1*(len0-xx);
        if (col1[yy-1] > smax) {
                smax = col1[yy-1];
                dmax = id;
        }
        tmp = col0; col0 = col1; col1 = tmp;           }
(void) free((char *)ndely);
(void) free((char *)dely);
(void) free((char *)col0);
(void) free((char *)col1);                     }
/*
*
* print( ) -- only routine visible outside this module
*
* static:
* getmat( ) -- trace back best path, count matches: print( )
* pr_align( ) -- print alignment of described in array p[ ]: print( )
* dumpblock( ) -- dump a block of lines with numbers, stars: pr_align( )
* nums( ) -- put out a number line: dumpblock( )
* putline( ) -- put out a line (name, [num], seq, [num]): dumpblock( )
* stars( ) - -put a line of stars: dumpblock( )
* stripname( ) -- strip any path and prefix from a seqname
*/
#include "nw.h"
#define SPC    3
#define P_LINE      256       /* maximum output line */
#define P_SPC       3         /* space between name or num and seq */
extern _day[26][26];
int     olen;           /* set output line length */
FILE    *fx;            /* output file */
print( )                                                                               print
{
        int     lx, ly, firstgap, lastgap;        /* overlap */
        if ((fx = fopen(ofile, "w")) == 0) {
                fprintf(stderr,"%s: can't write %s\n", prog, ofile);
                cleanup(1);
        }
        fprintf(fx, "<first sequence: %s (length = %d)\n", namex[0], len0);
        fprintf(fx, "<second sequence: %s (length = %d)\n", namex[1], len1);
        olen = 60;
        lx = len0;
        ly = len1;
        firstgap = lastgap = 0;
        if (dmax < len1 - 1) { /* leading gap in x */
                pp[0].spc = firstgap = len1 - dmax - 1;
                ly -= pp[0].spc;
        }
```

TABLE 1-continued

```
              else if (dmax > len1 - 1) {      /* leading gap in y */
                      pp[1].spc = firstgap = dmax - (len1 - 1);
                      lx -= pp[1].spc;
      }
if (dmax0 < len0 - 1) {                 /* trailing gap in x */
              lastgap = len0 - dmax0 -1;
              lx -= lastgap;
      }
else if (dmax0 > len0 - 1) {            /* trailing gap in y */
              lastgap = dmax0 - (len0 - 1);
              ly -= lastgap;
      }
getmat(lx, ly, firstgap, lastgap);
pr_align( ); }
/*
* trace back the best path, count matches
*/
static
getmat(lx, ly, firstgap, lastgap)                                                        getmat
      int      lx, ly;                  /* "core" (minus endgaps) */
      int      firstgap, lastgap;       /* leading trailing overlap */
{
      int             nm, i0, i1, siz0, siz1;
      char            outx[32];
      double          pct;
      register                n0, n1;
      register char *p0, *p1;
      /* get total matches, score
       */
      i0 = i1 = siz0 = siz1 = 0;
      p0 = seqx[0] + pp[1].spc;
      p1 = seqx[1] + pp[0].spc;
      n0 = pp[1].spc + 1;
      n1 = pp[0].spc + 1;
      nm = 0;
      while ( *p0 && *p1 ) {
              if (siz0) {
                      p1++;
                      n1++;
                      siz0--;
              }
              else if (siz1) {
                      p0++;
                      n0++;
                      siz1--;
              }
              else {
                      if (xbm[*p0-'A']&xbm[*p1-'A'])
                              nm++;
                      if (n0++ == pp[0].x[i0])
                              siz0 = pp[0].n[i0++];
                      if (n1++ == pp[1].x[i1])
                              siz1 = pp[1].n[i1++];
                      p0++;
                      p1++;
              }
      }
      /* pct homology:
       * if penalizing endgaps, base is the shorter seq
       * else, knock off overhangs and take shorter core
       */
      if (endgaps)
              lx = (len0 < len1)? len0 : len1;
      else
              lx = (lx < ly)? lx : ly;
      pct = 100.*(double)nm/(double)lx;
      fprintf(fx, "\n");
      fprintf(fx, "<%d match%s in an overlap of %d: %.2f percent similarity\n",
              nm, (nm == 1)? "" : "es", lx, pct);
      fprintf(fx, "<gaps in first sequence: %d", gapx);                                  ...getmat
      if (gapx) {
              (void) sprintf(outx, " (%d %s%s)",
                      ngapx, (dna)? "base":"residue", (ngapx == 1)? "":"s");
              fprintf(fx,"%s", outx);
      fprintf(fx, ", gaps in second sequence: %d", gapy);
      if (gapy) {
              (void) sprintf(outx, " (%d %s%s)",
                      ngapy, (dna)? "base":"residue", (ngapy == 1)? "":"s");
              fprintf(fx,"%s", outx);
      }
```

TABLE 1-continued

```
            if (dna)
                    fprintf(fx,
                            "\n<score: %d (match = %d, mismatch = %d, gap penalty = %d + %d per
base)\n",
                            smax, DMAT, DMIS, DINS0, DINS1);
            else
                    fprintf(fx,
                            "\n<score: %d (Dayhoff PAM 250 matrix, gap penalty = %d + %d per
residue)\n",
                            smax, PINS0, PINS1);
            if (endgaps)
                    fprintf(fx,
                            "<endgaps penalized. left endgap: %d %s%s, right endgap: %d %s%s\n",
                            firstgap, (dna)? "base" : "residue", (firstgap == 1)? "" : "s",
                            lastgap, (dna)? "base" : "residue", (lastgap == 1)? "" : "s");
            else
                    fprintf(fx, "<endgaps not penalized\n");
}
static          nm;             /* matches in core -- for checking */
static          lmax;           /* lengths of stripped file names */
static          ij[2];          /* jmp index for a path */
static          nc[2];          /* number at start of current line */
static          ni[2];          /* current elem number -- for gapping */
static          siz[2];
static char     *ps[2];         /* ptr to current element */
static char     *po[2];         /* ptr to next output char slot */
static char     out[2][P_LINE];         /* output line */
static char     star[P_LINE]; /* set by stars( ) */
/*
* print alignment of described in struct path pp[ ]
*/
static
pr_align( )                                                                     pr_align
{
int             nn;     /* char count */
int             more;
register        I;
for (I = 0, lmax = 0; I < 2; I++) {
        nn = stripname(namex[i]);
        if (nn > lmax)
                lmax = nn;
        nc[i] = 1;
        ni[i] = 1;
        siz[i] = ij[i] = 0;
        ps[i] = seqx[i];
        po[i] = out[i];                 }
for (nn = nm = 0, more = 1; more; ) {                                           ...pr_align
        for (I = more = 0; I < 2; I++) {
                /*
                * do we have more of this sequence?
                */
                if (!*ps[i])
                        continue;
                more++;
                if (pp[i].spc) {                /* leading space */
                        *po[i]++ = ' ';
                        pp[i].spc--;
                }
                else if (siz[i]) {              /* in a gap */
                        *po[i]++ = '-';
                        siz[i]--;
                }
                else {          /* we're putting a seq element
                                */
                        *po[i] = *ps[i];
                        if (islower(*ps[i]))
                                *ps[i] = toupper(*ps[i]);
                        po[i]++;
                        ps[i]++;
                        /*
                        * are we at next gap for this seq?
                        */
                        if (ni[i] == pp[i].x[ij[i]]) {
                                /*
                                * we need to merge all gaps
                                * at this location
                                */
                                siz[i] = pp[i].n[ij[i]++];
                                while (ni[i] == pp[i].x[ij[i]])
                                        siz[i] += pp[i].n[ij[i]++];
```

TABLE 1-continued

```
                        }
                        ni[i]++;
                }
        }
        if (++nn == olen || !more && nn) {
                dumpblock( );
                for (I = 0; I < 2; I++)
                        po[i] = out[i];
                nn = 0;
        }
        }
    }
}
/*
 * dump a block of lines, including numbers, stars: pr_align( )
 */
static
dumpblock( )                                                                    dumpblock
{
        register         I;
        for (I = 0; I < 2; I++)
                *po[i]-- = '\0';                                               ...dumpblock
        (void) putc('\n', fx);
        for (I = 0; I < 2; I++) {
                if (*out[i] && (*out[i] != ' ' || *(po[i]) != ' ')) {
                        if (I == 0)
                                nums(I);
                        if (I == 0 && *out[1])
                                stars( );
                        putline(I);
                        if (I == 0 && *out[1])
                                fprintf(fx, star);
                        if (I == 1)
                                nums(I);
                }
        }
}
/*
 * put out a number line: dumpblock( )
 */
static
nums(ix)                                                                        nums
        int      ix;      /* index in out[ ] holding seq line */
{
        char       nline[P_LINE];
        register   I, j;
        register char *pn, *px, *py;
        for (pn = nline, I = 0; I < lmax+P_SPC; I++, pn++)
                *pn = ' ';
        for (I = nc[ix], py = out[ix]; *py; py++, pn++) {
                if (*py == ' ' || *py == '-')
                        *pn = ' ';
                else {
                        if (I%10 == 0 || (I == 1 && nc[ix] != 1)) {
                                j = (I < 0)? -I : I;
                                for (px = pn; j; j /= 10, px--)
                                        *px = j%10 + '0';
                                if (I < 0)
                                        *px = '-';
                        }
                        else
                                *pn = ' ';
                        I++;
                }
        }
        *pn = '\0';
        nc[ix] = I;
        for (pn = nline; *pn; pn++)
                (void) putc(*pn, fx);
        (void) putc('\n', fx);
}
/*
 * put out a line (name, [num], seq, [num]): dumpblock( )
 */
static
putline(ix)                                                                     putline
        int      ix;                    {
                                                                                ...putline
        int         I;
        register char *px;
```

TABLE 1-continued

```
                for (px = namex[ix], I = 0; *px && *px != ':'; px++, I++)
                        (void) putc(*px, fx);
                for (; I < lmax+P_SPC; I++)
                        (void) putc(' ', fx);
                /* these count from 1:
                 * ni[ ] is current element (from 1)
                 * nc[ ] is number at start of current line
                 */
                for (px = out[ix]; *px; px++)
                        (void) putc(*px&0x7F, fx);
                (void) putc('\n', fx);
        }
        /*
         * put a line of stars (seqs always in out[0], out[1]): dumpblock( )
         */
        static
        stars( )                                                                                stars
        {
                int                     I;
                register char *p0, *p1, cx, *px;
                if (!*out[0] || (*out[0] == ' ' && *(po[0]) == ' ') ||
                    !*out[1] || (*out[1] == ' ' && *(po[1]) == ' '))
                        return;
                px = star;
                for (I = lmax+P_SPC; I; I--)
                        *px++ = ' ';
                for (p0 = out[0], p1 = out[1]; *p0 && *p1; p0++, p1++) {
                        if (isalpha(*p0) && isalpha(*p1)) {
                                if (xbm[*p0-'A']&xbm[*p1-'A']) {
                                        cx = '*';
                                        nm++;
                                }
                                else if (!dna && _day[*p0-'A'][*p1-'A'] > 0)
                                        cx = '.';
                                else
                                        cx = ' ';
                        }
                        else
                                cx = ' ';
                        *px++ = cx;
                }
                *px++ = '\n';
                *px = '\0';
        }
        /*
         * strip path or prefix from pn, return len: pr_align( )
         */
        static
        stripname(pn)                                                                           stripname
                char      *pn;    /* file name (may be path) */
        {
                register char *px, *py;
                py = 0;
                for (px = pn; *px; px++)
                        if (*px == '/')
                                py = px + 1;
                if (py)
                        (void) strcpy(pn, py);
                return(strlen(pn));
        }
        /*
         * cleanup( ) -- cleanup any tmp file
         * getseq( ) -- read in seq, set dna, len, maxlen
         * g_calloc( ) -- calloc( ) with error checkin
         * readjmps( ) -- get the good jmps, from tmp file if necessary
         * writejmps( ) -- write a filled array of jmps to a tmp file: nw( )
         */
        #include "nw.h"
        #include <sys/file.h>
        char      *jname = "/tmp/homgXXXXXX";                  /* tmp file for jmps */
        FILE      *fj;
        int       cleanup( );                                   /* cleanup tmp file */
        long      lseek( );
        /*
         * remove any tmp file if we blow
         */
        cleanup(I)                                                                              cleanup
                int       I;
        {
                if (fj)
```

TABLE 1-continued

```
                (void) unlink(jname);
        exit(I);
}
/*
* read, return ptr to seq, set dna, len, maxlen
* skip lines starting with ';', '<', or '>'
* seq in upper or lower case
*/
char    *
getseq(file, len)                                                                       getseq
        char            *file;          /* file name */
        int             *len;           /* seq len */
{
        char            line[1024], *pseq;
        register char   *px, *py;
        int             natgc, tlen;
        FILE            *fp;
        if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
if ((pseq = malloc((unsigned)(tlen+6))) == 0) {
        fprintf(stderr,"%s: malloc( ) failed to get %d bytes for %s\n", prog, tlen+6, file);
        exit(1);
}
pseq[0] = pseq[1] = pseq[2] = pseq[3] = '\0';
                                                                                        ...getseq
        py = pseq + 4;
        *len = tlen;
        rewind(fp);
        while (fgets(line, 1024, fp)) {
                if (*line == ';' || *line == '<' || *line == '>')
                        continue;
                for (px = line; *px != '\n'; px++) {
                        if (isupper(*px))
                                *py++ = *px;
                        else if (islower(*px))
                                *py++ = toupper(*px);
                        if (index("ATGCU",*(py-1)))
                                natgc++;
                }
        }
        *py++ = '\0';
        *py = '\0';
        (void) fclose(fp);
        dna = natgc > (tlen/3);
        return(pseq+4);
}
char    *
g_calloc(msg, nx, sz)                                                                   g_calloc
        char            *msg;           /* program, calling routine */
        int             nx, sz;         /* number and size of elements */
{
        char            *px, *calloc( );
        if ((px = calloc((unsigned)nx, (unsigned)sz)) == 0) {
                if (*msg) {
                        fprintf(stderr, "%s: g_calloc( ) failed %s (n=%d, sz=%d)\n", prog, msg,
nx, sz);
                        exit(1);
                }
        }
        return(px);
}
/*
* get final jmps from dx[ ] or tmp file, set pp[ ], reset dmax: main( )
*/
readjmps( )                                                                             readjmps
{
        int             fd = -1;
        int             siz, i0, i1;
        register        I, j, xx;
        if (fj) {
```

TABLE 1-continued

```
                (void) fclose(fj);
                if ((fd = open(jname, O_RDONLY, 0)) < 0) {
                        fprintf(stderr, "%s: can't open( ) %s\n", prog, jname);
                        cleanup(1);
                }
        }
}
for (I = i0 = i1 = 0, dmax0 = dmax, xx = len0; ; I++) {
        while (1) {
                for (j = dx[dmax].ijmp; j >= 0 && dx[dmax].jp.x[j] >= xx; j--)
                        ;
                                                                          ...readjmps
                        if (j < 0 && dx[dmax].offset && fj) {
                                (void) lseek(fd, dx[dmax].offset, 0);
                                (void) read(fd, (char *)&dx[dmax].jp, sizeof(struct jmp));
                                (void) read(fd, (char *)&dx[dmax].offset,
sizeof(dx[dmax].offset));
                                dx[dmax].ijmp = MAXJMP-1;         }
                        else
                                break;          }
                if (I >= JMPS) {
                        fprintf(stderr, "%s: too many gaps in alignment\n", prog);
                        cleanup(1);
                }
                if (j >= 0) {
                        siz = dx[dmax].jp.n[j];
                        xx = dx[dmax].jp.x[j];
                        dmax += siz;
                        if (siz < 0) {           /* gap in second seq */
                                pp[1].n[i1] = -siz;
                                xx += siz;
                                /* id = xx - yy + len1 - 1                      */
                                pp[1].x[i1] = xx - dmax + len1 - 1;
                                gapy++;
                                ngapy -= siz;
/* ignore MAXGAP when doing endgaps */
                                siz = (-siz < MAXGAP || endgaps)? -siz : MAXGAP;
                                i1++;
                        }
                        else if (siz > 0) {      /* gap in first seq */
                                pp[0].n[i0] = siz;
                                pp[0].x[i0] = xx;
                                gapx++;
                                ngapx += siz;
/* ignore MAXGAP when doing endgaps */
                                siz = (siz < MAXGAP || endgaps)? siz : MAXGAP;
                                i0++;
                        }
                }
                else
                        break;
        }
        /* reverse the order of jmps            */
        for (j = 0, i0--; j < i0; j++, i0--) {
                I = pp[0].n[j]; pp[0].n[j] = pp[0].n[i0]; pp[0].n[i0] = I;
                I = pp[0].x[j]; pp[0].x[j] = pp[0].x[i0]; pp[0].x[i0] = I;
        }
        for (j = 0, i1--; j < i1; j++, i1--) {
                I = pp[1].n[j]; pp[1].n[j] = pp[1].n[i1]; pp[1].n[i1] = I;
                I = pp[1].x[j]; pp[1].x[j] = pp[1].x[i1]; pp[1].x[i1] = I;
        }
        if (fd >= 0)
                (void) close(fd);
        if (fj) {
                (void) unlink(jname);
                fj = 0;
                offset = 0;
        }                               }
/*
 * write a filled jmp struct offset of the prev one (if any): nw( )
 */
writejmps(ix)                                                             writejmps
        int     ix;
{
        char    *mktemp( );
        if (!fj) {
                if (mktemp(jname) < 0) {
                        fprintf(stderr, "%s: can't mktemp( ) %s\n", prog, jname);
                        cleanup(1);
                }
                if ((fj = fopen(jname, "w")) == 0) {
```

TABLE 1-continued

```
            fprintf(stderr, "%s: can't write %s\n", prog, jname);
            exit(1);
        }
    }
    (void) fwrite((char *)&dx[ix].jp, sizeof(struct jmp), 1, fj);
    (void) fwrite((char *)&dx[ix].offset, sizeof(dx[ix].offset), 1, fj);
}
```

TABLE 2

| PRO | XXXXXXXXXXXXXXX | (Length = 15 amino acids) |
|---|---|---|
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the PRO polypeptide) = 5 divided by 15 = 33.3%

TABLE 3

| PRO | XXXXXXXXXX | (Length = 10 amino acids) |
|---|---|---|
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the PRO polypeptide) = 5 divided by 10 = 50%

TABLE 4

| PRO-DNA | NNNNNNNNNNNNNN | (Length = 14 nucleotides) |
|---|---|---|
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 6 divided by 14 = 42.9%

TABLE 5

| PRO-DNA | NNNNNNNNNNNN | (Length = 12 nucleotides) |
|---|---|---|
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 4 divided by 12 = 33.3%

II. Compositions and Methods of the Invention

A. Full-Length PRO227, PRO233, PRO238, PRO1328, PRO4342, PRO7423; PRO10096; PRO21384; PRO353 or PRO1885 Polypeptides The present invention provides newly identified and isolated nucleotide sequences encoding polypeptides referred to in the present application as PRO227, PRO233, PRO238, PRO1328, PRO4342, PRO7423, PRO10096, PRO21384, PRO353 or PRO1885 polypeptides. In particular, cDNAs encoding various PRO227, PRO233, PRO238, PRO1328, PRO4342, PRO7423, PRO10096, PRO21384, PRO353 or PRO1885 polypeptides have been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by the full length native nucleic acid molecules disclosed herein as well as all further native homologues and variants included in the foregoing definition of PRO, will be referred to as "PRO/number", regardless of their origin or mode of preparation.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the PRO227, PRO233, PRO238, PRO1328, PRO4342, PRO7423, PRO10096, PRO21384, PRO353 or PRO1885 polypeptides and encoding nucleic acids described herein, Applicants have identified what is believed to be the reading frame best identifiable with the sequence information available at the time.

B. PRO227, PRO233, PRO238, PRO1328, PRO4342, PRO7423, PRO10096, PRO21384, PRO353 or PRO1885 Polypeptide Variants In addition to the full-length native sequence PRO227, PRO233, PRO238, PRO1328, PRO4342, PRO7423, PRO10096, PRO21384, PRO353 or PRO1885 polypeptides described herein, it is contemplated that PRO227, PRO233, PRO238, PRO1328, PRO4342, PRO7423, PRO10096, PRO21384, PRO353 or PRO1885 variants can be prepared. PRO227, PRO233, PRO238, PRO1328, PRO4342, PRO7423, PRO10096, PRO21384, PRO353 or PRO1885 variants can be prepared by introducing appropriate nucleotide changes into the PRO227, PRO233, PRO238, PRO1328, PRO4342, PRO7423, PRO10096, PRO21384, PRO353 or PRO1885 DNA, and/or by synthesis of the desired PRO227, PRO233, PRO238, PRO1328, PRO4342, PRO7423, PRO10096, PRO21384, PRO353 or PRO1885 polypeptide. Those skilled in the art will appreciate that amino acid changes may alter post-translational processes of the PRO227, PRO233, PRO238, PRO1328, PRO4342, PRO7423, PRO10096, PRO21384, PRO353 or PRO1885 polypeptide, such as changing the number or position of glycosylation sites or altering the membrane anchoring characteristics.

Variations in the native full-length sequence PRO227, PRO233, PRO238, PRO1328, PRO4342, PRO7423, PRO10096, PRO21384, PRO353 or PRO1885 polypeptide or in various domains of the PRO227, PRO233, PRO238, PRO1328, PRO4342, PRO7423, PRO10096, PRO21384, PRO353 or PRO1885 polypeptide described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO227, PRO233, PRO238, PRO1328, PRO4342, PRO7423, PRO10096, PRO21384, PRO353 or PRO1885 polypeptide that results in a change in the amino acid sequence of the PRO227, PRO233, PRO238, PRO1328, PRO4342, PRO7423, PRO10096, PRO21384, PRO353 or PRO1885 polypeptide as compared with the native sequence PRO227, PRO233, PRO238, PRO1328, PRO4342, PRO7423, PRO10096, PRO21384, PRO353 or PRO1885 polypeptide. Optionally the variation is by substitution of at least one amino acid with any other amino acid in one or more of the domains of the PRO227, PRO233, PRO238, PRO1328, PRO4342, PRO7423, PRO10096, PRO21384, PRO353 or PRO1885 polypeptide. Guidance in determining which amino acid residue may be inserted, substituted or deleted without adversely affecting the desired activity may be found by comparing the sequence of the PRO227, PRO233, PRO238, PRO1328, PRO4342, PRO7423, PRO10096, PRO21384, PRO353 or PRO1885 polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO227, PRO233, PRO238, PRO1328, PRO4342, PRO7423, PRO10096, PRO21384, PRO353 or PRO1885 polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the PRO227, PRO233, PRO238, PRO1328, PRO4342, PRO7423, PRO10096, PRO21384, PRO353 or PRO1885 polypeptide.

PRO227, PRO233, PRO238, PRO1328, PRO4342, PRO7423, PRO10096, PRO21384, PRO353 or PRO1885 fragments may be prepared by any of a number of conventional techniques. Desired peptide fragments may be chemically synthesized. An alternative approach involves generating PRO227, PRO233, PRO238, PRO1328, PRO4342, PRO7423, PRO10096, PRO21384, PRO353 or PRO1885 fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO227, PRO233, PRO238, PRO1328, PRO4342, PRO7423, PRO10096, PRO21384, PRO353 or PRO1885 polypeptide fragments share at least one biological and/or immunological activity with the native PRO227, PRO233, PRO238, PRO1328, PRO4342, PRO7423, PRO10096, PRO21384, PRO353 or PRO1885 polypeptide disclosed herein.

Conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are preferably introduced and the products screened.

TABLE 6

| Original Residue | Exemplary Substitutions | Preferred Substitutions |
|---|---|---|
| Ala | Val; Leu; Ile | Val |
| Arg ®) | Lys; Gln; Asn | Lys |
| Asn | Gln; His; Asp, Lys; Arg | Gln |
| Asp | Glu; Asn | Glu |
| Cys ©) | Ser; Ala | Ser |
| Gln | Asn; Glu | Asn |
| Glu | Asp; Gln | Asp |
| Gly | Ala | Ala |
| His | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys | Arg; Gln; Asn | Arg |
| Met | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp | Tyr; Phe | Tyr |
| Tyr | Trp; Phe; Thr; Ser | Phe |
| Val (V) | Ile; Leu; Met; Phe; Ala; Norleucine | Leu |

Substantial modifications in function or immunological identity of the PRO227, PRO233, PRO238, PRO1328, PRO4342, PRO7423, PRO10096, PRO21384, PRO353 or PRO1885 polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

Amino acids may be grouped according to similarities in the properties of their side chains (in A. L. Lehninger, in Biochemistry, second ed., pp. 73-75, Worth Publishers, New York (1975)):
(1) non-polar: Ala (A), Val (V), Leu (L), Ile (I), Pro (P), Phe (F), Trp (W), Met (M)
(2) uncharged polar: Gly (G), Ser (S), Thr (T), Cys©), Tyr (Y), Asn (N), Gln (Q)
(3) acidic: Asp (D), Glu (E)
(4) basic: Lys (K), Arg®), His (H)
Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene,* 34:315 (1985)], restriction selection mutagenesis [Wells et al., *Philos. Trans. R. Soc. London SerA,* 317:415 (1986)] or other known techniques can be performed on the cloned DNA to produce the PRO227, PRO233, PRO238, PRO1328, PRO4342, PRO7423, PRO10096, PRO21384, PRO353 or PRO1885 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science,* 244: 1081-1085 (1989)]. Alanine is also typically preferred because it is the most common amino acid. Further, it is frequently found in both buried and exposed positions [Creighton, *The Proteins,* (W.H. Freeman & Co., N.Y.); Chothia, *J. Mol. Biol.,* 150:1 (1976)]. If alanine substitution does not yield adequate amounts of variant, an isoteric amino acid can be used.

C. Modifications of PRO227, PRO233, PRO238, PRO1328, PRO4342, PRO7423, PRO10096, PRO21384, PRO353 or PRO1885

Covalent modifications of PRO227, PRO233, PRO238, PRO1328, PRO4342, PRO7423, PRO10096, PRO21384, PRO353 or PRO1885 polypeptides are included within the scope of this invention. One type of covalent modification includes reacting targeted amino acid residues of a PRO227, PRO233, PRO238, PRO1328, PRO4342, PRO7423, PRO10096, PRO21384, PRO353 or PRO1885 polypeptide with an organic derivatizing agent that is capable of reacting with selected side chains or the N- or C-terminal residues of the PRO227, PRO233, PRO238, PRO1328, PRO4342, PRO7423, PRO10096, PRO21384, PRO353 or PRO1885 polypeptide. Derivatization with bifunctional agents is useful, for instance, for crosslinking PRO227, PRO233, PRO238, PRO1328, PRO4342, PRO7423, PRO10096, PRO21384, PRO353 or PRO1885 polypeptides to a water-insoluble support matrix or surface for use in the method for purifying anti-PRO227, anti-PRO233, anti-PRO238, anti-PRO1328, anti-PRO4342, anti-PRO7423, anti-PRO10096, anti-PRO21384, anti-PRO353 or anti-PRO1885 antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctionalmaleimides such as bis-N-maleimido-1,8-octane and agents such as ethyl-3-[(p-azidophenyl) dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T.E. Creighton, *Proteins: Structure and Molecular Properties,* W.H. Freeman & Co., San Francisco, pp. 79-86 (1983)], acetylation of the N-terminal amine, and amidation of any C-terminal carboxyl group.

Another type of covalent modification of the PRO227, PRO233, PRO238, PRO1328, PRO4342, PRO7423, PRO10096, PRO21384, PRO353 or PRO1885 polypeptide included within the scope of this invention comprises altering the native glycosylation pattern of the polypeptide. "Altering the native glycosylation pattern" is intended for purposes herein to mean deleting one or more carbohydrate moieties found in native sequence PRO227, PRO233, PRO238, PRO1328, PRO4342, PRO7423, PRO10096, PRO21384, PRO353 or PRO1885 polypeptides (either by removing the underlying glycosylation site or by deleting the glycosylation by chemical and/or enzymatic means), and/or adding one or more glycosylation sites that are not present in the native sequence PRO227, PRO233, PRO238, PRO1328, PRO4342, PRO7423, PRO10096, PRO21384, PRO353 or PRO1885 polypeptide. In addition, the phrase includes qualitative changes in the glycosylation of the native proteins, involving a change in the nature and proportions of the various carbohydrate moieties present.

Addition of glycosylation sites to the PRO227, PRO233, PRO238, PRO1328, PRO4342, PRO7423, PRO10096, PRO21384, PRO353 or PRO1885 polypeptide may be accomplished by altering the amino acid sequence. The alteration may be made, for example, by the addition of, or substitution by, one or more serine or threonine residues to the native sequence PRO227, PRO233, PRO238, PRO1328, PRO4342, PRO7423, PRO10096, PRO21384, PRO353 or PRO1885 (for O-linked glycosylation sites). The PRO227, PRO233, PRO238, PRO1328, PRO4342, PRO7423, PRO10096, PRO21384, PRO353 or PRO1885 amino acid sequence may optionally be altered through changes at the DNA level, particularly by mutating the DNA encoding the PRO227, PRO233, PRO238, PRO1328, PRO4342, PRO7423, PRO10096, PRO21384, PRO353 or PRO1885 polypeptide at preselected bases such that codons are generated that will translate into the desired amino acids.

Another means of increasing the number of carbohydrate moieties on the PRO227, PRO233, PRO238, PRO1328, PRO4342, PRO7423, PRO10096, PRO21384, PRO353 or PRO1885 polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.,* pp. 259-306 (1981).

Removal of carbohydrate moieties present on the PRO227, PRO233, PRO238, PRO1328, PRO4342, PRO7423, PRO10096, PRO21384, PRO353 or PRO1885 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.,* 259:52 (1987) and by Edge et al., *Anal. Biochem.,* 118:131 (1981). Enzymatic cleavage of carbohydrate moieties on polypeptides can be achieved by the use of a variety of endo- and exo-glycosidases as described by Thotakura et al., *Meth. Enzymol.,* 138:350 (1987).

Another type of covalent modification of PRO227, PRO233, PRO238, PRO1328, PRO4342, PRO7423, PRO10096, PRO21384, PRO353 or PRO1885 polypeptides comprises linking the PRO227, PRO233, PRO238, PRO1328, PRO4342, PRO7423, PRO10096, PRO21384, PRO353 or PRO1885 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PRO227, PRO233, PRO238, PRO1328, PRO4342, PRO7423, PRO10096, PRO21384, PRO353 or PRO1885 polypeptides of the present invention may also be modified in a way to form a chimeric molecule comprising the PRO227, PRO233, PRO238, PRO1328, PRO4342, PRO7423, PRO10096, PRO21384, PRO353 or PRO1885 polypeptide fused to another, heterologous polypeptide or amino acid sequence.

Such a chimeric molecule comprises a fusion of the PRO227, PRO233, PRO238, PRO1328, PRO4342, PRO7423, PRO10096, PRO21384, PRO353 or PRO1885 polypeptide with a tag polypeptide which provides an epitope to which an anti-tag antibody can selectively bind. The epitope tag is generally placed at the amino- or carboxyl-terminus of the PRO227, PRO233, PRO238, PRO1328, PRO4342, PRO7423, PRO10096, PRO21384, PRO353 or PRO1885 polypeptide. The presence of such epitope-tagged forms of the PRO227, PRO233, PRO238, PRO1328, PRO4342, PRO7423, PRO10096, PRO21384, PRO353 or PRO1885 polypeptide can be detected using an antibody against the tag polypeptide. Also, provision of the epitope tag enables the PRO227, PRO233, PRO238, PRO1328, PRO4342, PRO7423, PRO10096, PRO21384, PRO353 or PRO1885 polypeptide to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

The chimeric molecule may comprise a fusion of the PRO227, PRO233, PRO238, PRO1328, PRO4342, PRO7423, PRO10096, PRO21384, PRO353 or PRO1885 polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO227, PRO233, PRO238, PRO1328, PRO4342, PRO7423, PRO10096, PRO21384, PRO353 or PRO1885 polypeptide in place of at least one variable region within an Ig molecule. In a particularly preferred aspect of the invention, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of PRO227, PRO233, PRO238, PRO1328, PRO4342, PRO7423, PRO10096, PRO21384, PRO353 or PRO1885 Polypeptides The description below relates primarily to production of PRO227, PRO233, PRO238, PRO1328, PRO4342, PRO7423, PRO10096, PRO21384, PRO353 or PRO1885 polypeptides by culturing cells transformed or transfected with a vector containing PRO227, PRO233, PRO238, PRO1328, PRO4342, PRO7423, PRO10096, PRO21384, PRO353 or PRO1885 nucleic acid. It is, of course, contemplated that alternative methods, which are well known in the art, may be employed to prepare PRO227, PRO233, PRO238, PRO1328, PRO4342, PRO7423, PRO10096, PRO21384, PRO353 or PRO1885 polypeptides. For instance, the PRO227, PRO233, PRO238, PRO1328, PRO4342, PRO7423, PRO10096, PRO21384, PRO353 or PRO1885 sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO227, PRO233, PRO238, PRO1328, PRO4342, PRO7423, PRO10096, PRO21384, PRO353 or PRO1885 polypeptide may be chemically synthesized separately and combined using chemical or enzymatic methods to produce the full-length PRO227, PRO233, PRO238, PRO1328, PRO4342, PRO7423, PRO10096, PRO21384, PRO353 or PRO1885 polypeptide.

1. Isolation of DNA Encoding PRO227, PRO233, PRO238, PRO1328, PRO4342, PRO7423, PRO10096, PRO21384, PRO353 or PRO1885 Polypeptides DNA encoding PRO227, PRO233, PRO238, PRO1328, PRO4342, PRO7423, PRO10096, PRO21384, PRO353 or PRO1885 polypeptides may be obtained from a cDNA library prepared from tissue believed to possess the PRO227, PRO233, PRO238, PRO1328, PRO4342, PRO7423, PRO10096, PRO21384, PRO353 or PRO1885 mRNA and to express it at a detectable level. Accordingly, human PRO227-, PRO233-, PRO238-, PRO1328-, PRO4342-, PRO7423-, PRO10096-, PRO21384-, PRO353- or PRO1885-DNA can be conveniently obtained from a cDNA library prepared from human tissue, such as described in the Examples. The PRO227-, PRO233-, PRO238-, PRO1328-, PRO4342-, PRO7423-, PRO10096-, PRO21384-, PRO353- or PRO1885-encoding gene may also be obtained from a genomic library or by known synthetic procedures (e.g., automated nucleic acid synthesis).

Libraries can be screened with probes (such as antibodies to the PRO227, PRO233, PRO238, PRO1328, PRO4342, PRO7423, PRO10096, PRO21384, PRO353 or PRO1885 polypeptide or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO227, PRO233, PRO238, PRO1328, PRO4342, PRO7423, PRO10096, PRO21384, PRO353 or PRO1885 is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO227, PRO233, PRO238, PRO1328, PRO4342, PRO7423, PRO10096, PRO21384, PRO353 or PRO1885 polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac) 169 degP ompT $kan^r$; *E. coli* W3110 strain 37D6, which has the complete genotype tonA ptr3 phoA E15 (argF-lac) 169 degP ompT rbs7 ilvG $kan^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for PRO227-, PRO233-, PRO238-, PRO1328-, PRO4342-, PRO7423-, PRO10096-, PRO21384-, PRO353- or PRO1885-encoding vectors. *Saccharomyces cerevisiae* is a commonly used lower eukaryotic host microorganism. Others include *Schizosaccharomyces pombe* (Beach and Nurse, *Nature*, 290: 140 [1981]; EP 139,383 published 2 May 1985); *Kluyveromyces* hosts (U.S. Pat. No. 4,943,529; Fleer et al., *Bio/Technology*, 9:968-975 (1991)) such as, e.g., *K. lactis* (MW98-8C, CBS683, CBS4574; Louvencourt et al., *J. Bacteriol.*, 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus*; *yarrowia* (EP 402,226); *Pichia pastoris* (EP 183,070; Sreekrishna et al., *J. Basic Microbiol.*, 28:265-278 [1988]); *Candida*; *Trichoderma reesia* (EP 244,234); *Neurospora crassa* (Case et al., *Proc. Natl. Acad. Sci. USA*, 76:5259-5263 [1979]); *Schwanniomyces* such as *Schwanniomyces occidentalis* (EP 394,538 published 31 Oct. 1990); and filamentous fungi such as, e.g., *Neurospora*, *Penicillium*, *Tolypocladium* (WO 91/00357 published 10 Jan. 1991), and *Aspergillus* hosts such as *A. nidulans* (Ballance et al., *Biochem. Biophys. Res. Commun.*, 112: 284-289 [1983]; Tilburn et al., *Gene*, 26:205-221 [1983]; Yelton et al., *Proc. Natl. Acad. Sci. USA*, 81: 1470-1474 [1984]) and *A. niger* (Kelly and Hynes, *EMBO J.*, 4:475-479 [1985]). Methylotropic yeasts are suitable herein and include, but are not limited to, yeast capable of growth on methanol selected from the genera consisting of *Hansenula*, *Candida*, *Kloeckera*, *Pichia*, *Saccharomyces*, *Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated PRO227, PRO233, PRO238, PRO1328, PRO4342, PRO7423, PRO10096, PRO21384, PRO353 or PRO1885 polypeptides are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/–DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding PRO227, PRO233, PRO238, PRO1328, PRO4342, PRO7423, PRO10096, PRO21384, PRO353 or PRO1885 polypeptides may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO227, PRO233, PRO238, PRO1328, PRO4342, PRO7423, PRO10096, PRO21384, PRO353 or PRO1885 polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO227-, PRO233-, PRO238-, PRO1328-, PRO4342-, PRO7423-, PRO10096-, PRO21384-, PRO353- or PRO1885-encoding DNA that is inserted into the vector. The signal sequence may be a prokaryotic signal sequence selected, for example, from the group of the alkaline phosphatase, penicillinase, 1 pp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the PRO227-, PRO233-, PRO238-, PRO1328-, PRO4342-, PRO7423-, PRO10096-, PRO21384-, PRO353- or PRO1885-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the PRO227-, PRO233-, PRO238-, PRO1328-, PRO4342-, PRO7423-, PRO10096-, PRO21384-, PRO353- or PRO1885-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (tip) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Dalgarno (S.D.) sequence operably linked to the DNA encoding PRO227, PRO233, PRO238, PRO1328, PRO4342, PRO7423, PRO10096, PRO21384, PRO353 or PRO1885 polypeptides.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO227, PRO233, PRO238, PRO1328, PRO4342, PRO7423, PRO10096, PRO21384, PRO353 or PRO1885 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO227, PRO233, PRO238, PRO1328, PRO4342, PRO7423, PRO10096, PRO21384, PRO353 or PRO1885 polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the PRO227, PRO233, PRO238, PRO1328, PRO4342, PRO7423, PRO10096, PRO21384, PRO353 or PRO1885 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO227, PRO233, PRO238, PRO1328, PRO4342, PRO7423, PRO10096, PRO21384, PRO353 or PRO1885 polypeptides.

Still other methods, vectors, and host cells suitable for adaptation to the synthesis of PRO227, PRO233, PRO238, PRO1328, PRO4342, PRO7423, PRO10096, PRO21384, PRO353 or PRO1885 polypeptides in recombinant vertebrate cell culture are described in Gething et al., *Nature*, 293:620-625 (1981); Mantei et al., *Nature*, 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA,* 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO227, PRO233, PRO238, PRO1328, PRO4342, PRO7423, PRO10096, PRO21384, PRO353 or PRO1885 polypeptide or against a synthetic peptide based on the DNA sequences provided herein or against exogenous sequence fused to PRO227, PRO233, PRO238, PRO1328, PRO4342, PRO7423, PRO10096, PRO21384, PRO353 or PRO1885 DNA and encoding a specific antibody epitope.

5. Purification of Polypeptide

Forms of PRO227, PRO233, PRO238, PRO1328, PRO4342, PRO7423, PRO10096, PRO21384, PRO353 or PRO1885 polypeptides may be recovered from culture medium or from host cell lysates. If membrane-bound, it can be released from the membrane using a suitable detergent solution (e.g. Triton-X 100) or by enzymatic cleavage. Cells employed in expression of PRO227, PRO233, PRO238, PRO1328, PRO4342, PRO7423, PRO10096, PRO21384, PRO353 or PRO1885 polypeptides can be disrupted by various physical or chemical means, such as freeze-thaw cycling, sonication, mechanical disruption, or cell lysing agents.

It may be desired to purify PRO227, PRO233, PRO238, PRO1328, PRO4342, PRO7423, PRO10096, PRO21384, PRO353 or PRO1885 polypeptides from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO227, PRO233, PRO238, PRO1328, PRO4342, PRO7423, PRO10096, PRO21384, PRO353 or PRO1885 polypeptide. Various methods of protein purification may be employed and such methods are known in the art and described for example in Deutscher, *Methods in Enzymology,* 182 (1990); Scopes, *Protein Purification: Principles and Practice*, Springer-Verlag, New York (1982). The purification step(s) selected will depend, for example, on the nature of the production process used and the particular PRO227, PRO233, PRO238, PRO1328, PRO4342, PRO7423, PRO10096, PRO21384, PRO353 or PRO1885 polypeptide produced.

E. Uses for PRO227, PRO233, PRO238, PRO1328, PRO4342, PRO7423; PRO10096; PRO21384; PRO353 or PRO1885 Polypeptides Nucleotide sequences (or their complement) encoding PRO227, PRO233, PRO238, PRO1328, PRO4342, PRO7423, PRO10096, PRO21384, PRO353 or PRO1885 polypeptides have various applications in the art of molecular biology, including uses as hybridization probes, in chromosome and gene mapping and in the generation of anti-sense RNA and DNA. PRO227, PRO233, PRO238, PRO1328, PRO4342, PRO7423, PRO10096, PRO21384, PRO353 or PRO1885 nucleic acid will also be useful for the preparation of PRO227, PRO233, PRO238, PRO1328, PRO4342, PRO7423, PRO10096, PRO21384, PRO353 or PRO1885 polypeptides by the recombinant techniques described herein.

The full-length native sequence PRO227, PRO233, PRO238, PRO1328, PRO4342, PRO7423, PRO10096, PRO21384, PRO353 or PRO1885 gene, or portions thereof, may be used as hybridization probes for a cDNA library to isolate the full-length PRO227, PRO233, PRO238, PRO1328, PRO4342, PRO7423, PRO10096, PRO21384, PRO353 or PRO1885 cDNA or to isolate still other cDNAs (for instance, those encoding naturally-occurring variants of PRO227, PRO233, PRO238, PRO1328, PRO4342, PRO7423, PRO10096, PRO21384, PRO353 or PRO1885 polypeptides or PRO227, PRO233, PRO238, PRO1328, PRO4342, PRO7423, PRO10096, PRO21384, PRO353 or PRO1885 polypeptides from other species) which have a desired sequence identity to the native PRO227, PRO233, PRO238, PRO1328, PRO4342, PRO7423, PRO10096, PRO21384, PRO353 or PRO1885 sequence disclosed herein.

Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence PRO227, PRO233, PRO238, PRO1328, PRO4342, PRO7423, PRO10096, PRO21384, PRO353 or PRO1885. By way of example, a screening method will comprise isolating the coding region of the PRO227, PRO233, PRO238, PRO1328, PRO4342, PRO7423, PRO10096, PRO21384, PRO353 or PRO1885 gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the PRO227, PRO233, PRO238, PRO1328, PRO4342, PRO7423, PRO10096, PRO21384, PRO353 or PRO1885 gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the PRO227, PRO233, PRO238, PRO1328, PRO4342, PRO7423, PRO10096, PRO21384, PRO353 or PRO1885 nucleic acids include antisense or sense oligonucleotides comprising a singe-stranded nucleic acid sequence (either RNA or DNA) capable of binding to target PRO227, PRO233, PRO238, PRO1328, PRO4342, PRO7423, PRO10096, PRO21384, PRO353 or PRO1885 mRNA (sense) or PRO227, PRO233, PRO238, PRO1328, PRO4342, PRO7423, PRO10096, PRO21384, PRO353 or PRO1885 DNA (antisense) sequences. Antisense or sense oligonucleotides, according to the present invention, comprise a fragment of the coding region of PRO227, PRO233, PRO238, PRO1328, PRO4342, PRO7423, PRO10096, PRO21384, PRO353 or PRO1885 DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of PRO227, PRO233, PRO238, PRO1328, PRO4342, PRO7423, PRO10096, PRO21384, PRO353 or PRO1885. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

The probes may also be employed in PCR techniques to generate a pool of sequences for identification of closely related PRO227, PRO233, PRO238, PRO1328, PRO4342, PRO7423, PRO10096, PRO21384, PRO353 or PRO1885 coding sequences.

Nucleotide sequences encoding a PRO227, PRO233, PRO238, PRO1328, PRO4342, PRO7423, PRO10096, PRO21384, PRO353 or PRO1885 polypeptide can also be used to construct hybridization probes for mapping the gene which encodes that PRO227, PRO233, PRO238, PRO1328, PRO4342, PRO7423, PRO10096, PRO21384, PRO353 or PRO1885 polypeptide and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO227, PRO233, PRO238, PRO1328, PRO4342, PRO7423, PRO10096, PRO21384, PRO353 or PRO1885 encode a protein which binds to another protein (for example, where the PRO227, PRO233, PRO238, PRO1328, PRO4342, PRO7423, PRO10096, PRO21384, PRO353 or PRO1885 is a receptor), the PRO227, PRO233, PRO238, PRO1328, PRO4342, PRO7423, PRO10096, PRO21384, PRO353 or PRO1885 polypeptide can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO227, PRO233, PRO238, PRO1328, PRO4342, PRO7423, PRO10096, PRO21384, PRO353 or PRO1885 can be used to isolate correlative ligand(s). Screening assays can be designed to find lead compounds that mimic the biological activity of a native PRO227, PRO233, PRO238, PRO1328, PRO4342, PRO7423, PRO10096, PRO21384, PRO353 or PRO1885 polypeptide or a receptor for PRO227, PRO233, PRO238, PRO1328, PRO4342, PRO7423, PRO10096, PRO21384, PRO353 or PRO1885 polypeptides. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode PRO227, PRO233, PRO238, PRO1328, PRO4342, PRO7423, PRO10096, PRO21384, PRO353 or PRO1885 polypeptides or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. The invention provides cDNA encoding a PRO227, PRO233, PRO238, PRO1328, PRO4342, PRO7423, PRO10096, PRO21384, PRO353 or PRO1885 polypeptide which can be used to clone genomic DNA encoding a PRO227, PRO233, PRO238, PRO1328, PRO4342, PRO7423, PRO10096, PRO21384, PRO353 or PRO1885 polypeptide in accordance with established techniques and the genomic sequences used to generate transgenic animals that contain cells which express DNA encoding PRO227, PRO233, PRO238, PRO1328, PRO4342, PRO7423, PRO10096, PRO21384, PRO353 or PRO1885 polypeptides. Any technique known in the art may be used to introduce a target gene transgene into animals to produce the founder lines of transgenic animals. Such techniques include, but are not limited to pronuclear microinjection (U.S. Pat. Nos. 4,873,191, 4,736,866 and 4,870,009); retrovirus mediated gene transfer into germ lines (Van der Putten, et al., *Proc. Natl. Acad. Sci., USA*, 82:6148-6152 (1985)); gene targeting in embryonic stem cells (Thompson, et al., *Cell*, 56:313-321 (1989)); nonspecific insertional inactivation using a gene trap vector (U.S. Pat. No. 6,436,707); electroporation of embryos (Lo, *Mol. Cell. Biol.*, 3:1803-1814 (1983)); and sperm-mediated gene transfer (Lavitrano, et al., *Cell*, 57:717-723 (1989)); etc. Typically, particular cells would be targeted for a PRO227, PRO233, PRO238, PRO1328, PRO4342, PRO7423, PRO10096, PRO21384, PRO353 or PRO1885 transgene incorporation with tissue-specific enhancers. Transgenic animals that include a copy of a transgene encoding a PRO227, PRO233, PRO238, PRO1328, PRO4342, PRO7423, PRO10096, PRO21384, PRO353 or PRO1885 polypeptide introduced into the germ line of the animal at an embryonic stage can be used to examine the effect of increased expression of DNA encoding PRO227, PRO233, PRO238, PRO1328, PRO4342, PRO7423, PRO10096, PRO21384, PRO353 or PRO1885 polypeptides. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PRO227, PRO233, PRO238, PRO1328, PRO4342, PRO7423, PRO10096, PRO21384, PRO353 or PRO1885 polypeptides can be used to construct a PRO227, PRO233, PRO238, PRO1328, PRO4342, PRO7423, PRO10096, PRO21384, PRO353 or PRO1885 "knock out" animal which has a defective or altered gene encoding PRO227, PRO233, PRO238, PRO1328, PRO4342, PRO7423, PRO10096, PRO21384, PRO353 or PRO1885 proteins as a result of homologous recombination between the endogenous gene encoding PRO227, PRO233, PRO238, PRO1328, PRO4342, PRO7423, PRO10096, PRO21384, PRO353 or PRO1885 polypeptides and altered genomic DNA encoding PRO227, PRO233, PRO238, PRO1328, PRO4342, PRO7423, PRO10096, PRO21384, PRO353 or PRO1885 polypeptides introduced into an embryonic stem cell of the animal. Preferably the knock out animal is a mammal. More preferably, the mammal is a rodent such as a rat or mouse. For example, cDNA encoding PRO227, PRO233, PRO238, PRO1328, PRO4342, PRO7423, PRO10096, PRO21384, PRO353 or PRO1885 polypeptides can be used to clone genomic DNA encoding PRO227, PRO233, PRO238, PRO1328, PRO4342, PRO7423, PRO10096, PRO21384, PRO353 or PRO1885 polypeptides in accordance with established techniques. A portion of the genomic DNA encoding the PRO227, PRO233, PRO238, PRO1328, PRO4342, PRO7423, PRO10096, PRO21384, PRO353 or PRO1885 polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the gene encoding the PRO227, PRO233, PRO238, PRO1328, PRO4342, PRO7423, PRO10096, PRO21384, PRO353 or PRO1885 polypeptide.

In addition, knockout mice can be highly informative in the discovery of gene function and pharmaceutical utility for a drug target, as well as in the determination of the potential on-target side effects associated with a given target. Gene function and physiology are so well conserved between mice and humans., since they are both mammals and contain similar numbers of genes, which are highly conserved between the species. It has recently been well documented, for example, that 98% of genes on mouse chromosome 16 have a human ortholog (Mural et al., *Science* 296:1661-71 (2002)).

Although gene targeting in embryonic stem (ES) cells has enabled the construction of mice with null mutations in many genes associated with human disease, not all genetic diseases are attributable to null mutations. One can design valuable mouse models of human diseases by establishing a method for gene replacement (knock-in) which will disrupt the mouse locus and introduce a human counterpart with mutation, Subsequently one can conduct in vivo drug studies targeting the human protein (Kitamoto et. Al., *Biochemical and Biophysical Res. Commun.*, 222:742-47 (1996)).

Nucleic acid encoding the PRO227, PRO233, PRO238, PRO1328, PRO4342, PRO7423, PRO10096, PRO21384, PRO353 or PRO1885 polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

The PRO227, PRO233, PRO238, PRO1328, PRO4342, PRO7423, PRO10096, PRO21384, PRO353 or PRO1885 polypeptides described herein may also be employed as molecular weight markers for protein electrophoresis purposes and the isolated nucleic acid sequences may be used for recombinantly expressing those markers.

The nucleic acid molecules encoding the PRO227, PRO233, PRO238, PRO1328, PRO4342, PRO7423, PRO10096, PRO21384, PRO353 or PRO1885 polypeptides or fragments thereof described herein are useful for chromosome identification. In this regard, there exists an ongoing need to identify new chromosome markers, since relatively few chromosome marking reagents, based upon actual sequence data are presently available. Each PRO227, PRO233, PRO238, PRO1328, PRO4342, PRO7423, PRO10096, PRO21384, PRO353 or PRO1885 nucleic acid molecule of the present invention can be used as a chromosome marker.

The PRO227, PRO233, PRO238, PRO1328, PRO4342, PRO7423, PRO10096, PRO21384, PRO353 or PRO1885 polypeptides and nucleic acid molecules of the present invention may also be used diagnostically for tissue typing, wherein the PRO227, PRO233, PRO238, PRO1328, PRO4342, PRO7423, PRO10096, PRO21384, PRO353 or PRO1885 polypeptides of the present invention may be differentially expressed in one tissue as compared to another, preferably in a diseased tissue as compared to a normal tissue of the same tissue type. PRO227, PRO233, PRO238, PRO1328, PRO4342, PRO7423, PRO10096, PRO21384, PRO353 or PRO1885 nucleic acid molecules will find use for generating probes for PCR, Northern analysis, Southern analysis and Western analysis.

The PRO227, PRO233, PRO238, PRO1328, PRO4342, PRO7423, PRO10096, PRO21384, PRO353 or PRO1885 polypeptides described herein may also be employed as therapeutic agents. The PRO227, PRO233, PRO238, PRO1328, PRO4342, PRO7423, PRO10096, PRO21384, PRO353 or PRO1885 polypeptides of the present invention can be formulated according to known methods to prepare pharmaceutically useful compositions, whereby the PRO227, PRO233, PRO238, PRO1328, PRO4342, PRO7423, PRO10096, PRO21384, PRO353 or PRO1885 product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a PRO227, PRO233, PRO238, PRO1328, PRO4342, PRO7423, PRO10096, PRO21384, PRO353 or PRO1885 polypeptide or agonist or antagonist thereof is employed, normal dosage amounts may vary from about 10 ng/kg to up to 100 mg/kg of mammal body weight or more per day, preferably about 1 μg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a PRO227, PRO233, PRO238, PRO1328, PRO4342, PRO7423, PRO10096, PRO21384, PRO353 or PRO1885 polypeptide is desired in a formulation with release characteristics suitable for the treatment of any disease or disorder requiring administration of the PRO227, PRO233, PRO238, PRO1328, PRO4342, PRO7423, PRO10096, PRO21384, PRO353 or PRO1885 polypeptide, microencapsulation of the PRO227, PRO233, PRO238, PRO1328, PRO4342, PRO7423, PRO10096, PRO21384, PRO353 or PRO1885 polypeptide is contemplated. Microencapsulation of recombinant proteins for sustained release has been successfully performed with human growth hormone (rhGH), interferon-(rhIFN-), interleukin-2, and MN rgp120. Johnson et al., *Nat. Med.,* 2:795-799 (1996); Yasuda, *Biomed. Ther.,* 27:1221-1223 (1993); Hora et al., *Bio/Technology,* 8:755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1-41.

This invention encompasses methods of screening compounds to identify those that mimic the PRO227, PRO233, PRO238, PRO1328, PRO4342, PRO7423, PRO10096, PRO21384, PRO353 or PRO1885 polypeptide (agonists) or prevent the effect of the PRO227, PRO233, PRO238, PRO1328, PRO4342, PRO7423, PRO10096, PRO21384, PRO353 or PRO1885 polypeptide (antagonists). Agonists that mimic a PRO227, PRO233, PRO238, PRO1328, PRO4342, PRO7423, PRO10096, PRO21384, PRO353 or PRO1885 polypeptide would be especially valuable therapeutically in those instances where a negative phenotype is observed based on findings with the non-human transgenic animal whose genome comprises a disruption of the gene which encodes for the PRO227, PRO233, PRO238, PRO1328, PRO4342, PRO7423, PRO10096, PRO21384, PRO353 or PRO1885 polypeptide. Antagonists that prevent the effects of a PRO227, PRO233, PRO238, PRO1328, PRO4342, PRO7423, PRO10096, PRO21384, PRO353 or PRO1885 polypeptide would be especially valuable therapeutically in those instances where a positive phenotype is observed based upon observations with the non-human transgenic knockout animal. Screening assays for antagonist drug candidates are designed to identify compounds that bind or complex with the PRO227, PRO233, PRO238, PRO1328, PRO4342, PRO7423, PRO10096, PRO21384, PRO353 or PRO1885 polypeptide encoded by the genes identified herein, or otherwise interfere with the interaction of the encoded polypeptide with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a PRO227, PRO233, PRO238, PRO1328, PRO4342, PRO7423, PRO10096, PRO21384, PRO353 or PRO1885 polypeptide encoded by a nucleic acid identified herein under conditions and for a time sufficient to allow these two components to interact.

In binding assays, the interaction is binding and the complex formed can be isolated or detected in the reaction mixture. The PRO227, PRO233, PRO238, PRO1328, PRO4342, PRO7423, PRO10096, PRO21384, PRO353 or PRO1885 polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO227, PRO233, PRO238, PRO1328, PRO4342, PRO7423, PRO10096, PRO21384, PRO353 or PRO1885 polypeptide and drying. Alternatively, an immobilized antibody, e.g., a monoclonal antibody, specific for the PRO227, PRO233, PRO238, PRO1328, PRO4342, PRO7423, PRO10096, PRO21384, PRO353 or PRO1885 polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO227, PRO233, PRO238, PRO1328, PRO4342, PRO7423, PRO10096, PRO21384, PRO353 or PRO1885 polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245-246 (1989); Chien et al., *Proc. Natl. Acad. Sci. USA,* 88:9578-9582 (1991)) as disclosed by Chevray and Nathans, *Proc. Natl. Acad. Sci. USA,* 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a PRO227, PRO233, PRO238, PRO1328, PRO4342, PRO7423, PRO10096, PRO21384, PRO353 or PRO1885 polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the PRO227, PRO233, PRO238, PRO1328, PRO4342, PRO7423, PRO10096, PRO21384, PRO353 or PRO1885 polypeptide may be added to a cell along with the compound to be screened for a particular activity and the ability of the compound to inhibit the activity of interest in the presence of the PRO227, PRO233, PRO238, PRO1328, PRO4342, PRO7423, PRO10096, PRO21384, PRO353 or PRO1885 polypeptide indicates that the compound is an antagonist to the PRO227, PRO233, PRO238, PRO1328, PRO4342, PRO7423, PRO10096, PRO21384, PRO353 or PRO1885 polypeptide. Alternatively, antagonists may be detected by combining the PRO227, PRO233, PRO238, PRO1328, PRO4342, PRO7423, PRO10096, PRO21384, PRO353 or PRO1885 polypeptide and a potential antagonist with membrane-bound PRO227, PRO233, PRO238, PRO1328, PRO4342, PRO7423, PRO10096, PRO21384, PRO353 or PRO1885 polypeptide receptors or recombinant receptors under appropriate conditions for a competitive inhibition assay. The PRO227, PRO233, PRO238, PRO1328, PRO4342, PRO7423, PRO10096, PRO21384, PRO353 or PRO1885 polypeptide can be labeled, such as by radioactivity, such that the number of PRO227, PRO233, PRO238, PRO1328, PRO4342, PRO7423, PRO10096, PRO21384, PRO353 or PRO1885 polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.,* 1(2): Chapter 5 (1991). Preferably, expression cloning is employed wherein polyadenylated RNA is prepared from a cell responsive to the PRO227, PRO233, PRO238, PRO1328, PRO4342, PRO7423, PRO10096, PRO21384, PRO353 or PRO1885 polypeptide and a cDNA library created from this RNA is divided into pools and used to transfect COS cells or other cells that are not responsive to the PRO227, PRO233, PRO238, PRO1328, PRO4342, PRO7423, PRO10096, PRO21384, PRO353 or PRO1885 polypeptide. Transfected cells that are grown on glass slides are exposed to labeled PRO227, PRO233, PRO238, PRO1328, PRO4342, PRO7423, PRO10096, PRO21384, PRO353 or PRO1885 polypeptide. The PRO227, PRO233, PRO238, PRO1328, PRO4342, PRO7423, PRO10096, PRO21384, PRO353 or PRO1885 polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, the labeled PRO227, PRO233, PRO238, PRO1328, PRO4342, PRO7423, PRO10096, PRO21384, PRO353 or PRO1885 polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

Another approach in assessing the effect of an antagonist to a PRO227, PRO233, PRO238, PRO1328, PRO4342, PRO7423, PRO10096, PRO21384, PRO353 or PRO1885 polypeptide, would be administering a PRO227, PRO233, PRO238, PRO1328, PRO4342, PRO7423, PRO10096, PRO21384, PRO353 or PRO1885 antagonist to a wild-type mouse in order to mimic a known knockout phenotype. Thus, one would initially knockout the PRO227, PRO233, PRO238, PRO1328, PRO4342, PRO7423, PRO10096, PRO21384, PRO353 or PRO1885 gene of interest and observe the resultant phenotype as a consequence of knocking out or disrupting the PRO227, PRO233, PRO238, PRO1328, PRO4342, PRO7423, PRO10096, PRO21384, PRO353 or PRO1885 gene. Subsequently, one could then assess the effectiveness of an antagonist to the PRO227, PRO233, PRO238, PRO1328, PRO4342, PRO7423, PRO10096, PRO21384, PRO353 or PRO1885 polypeptide by administering an antagonist to the PRO227, PRO233, PRO238, PRO1328, PRO4342, PRO7423, PRO10096, PRO21384, PRO353 or PRO1885 polypeptide to a wild-type mouse. An effective antagonist would be expected to mimic the phenotypic effect that was initially observed in the knockout animal.

Likewise, one could assess the effect of an agonist to a PRO227, PRO233, PRO238, PRO1328, PRO4342, PRO7423, PRO10096, PRO21384, PRO353 or PRO1885 polypeptide, by administering a PRO227, PRO233, PRO238, PRO1328, PRO4342, PRO7423, PRO10096, PRO21384, PRO353 or PRO1885 agonist to a non-human transgenic mouse in order to ameliorate a known negative knockout phenotype. Thus, one would initially knockout the PRO227, PRO233, PRO238, PRO1328, PRO4342, PRO7423, PRO10096, PRO21384, PRO353 or PRO1885 gene of interest and observe the resultant phenotype as a consequence of knocking out or disrupting the PRO227, PRO233, PRO238, PRO1328, PRO4342, PRO7423, PRO10096, PRO21384, PRO353 or PRO1885 gene. Subsequently, one could then assess the effectiveness of an agonist to the PRO227, PRO233, PRO238, PRO1328, PRO4342, PRO7423, PRO10096, PRO21384, PRO353 or PRO1885 polypeptide by administering an agonist to the PRO227, PRO233, PRO238, PRO1328, PRO4342, PRO7423, PRO10096, PRO21384, PRO353 or PRO1885 polypeptide to a the non-human transgenic mouse. An effective agonist would be expected to ameliorate the negative phenotypic effect that was initially observed in the knockout animal In another assay for antagonists, mammalian cells or a membrane preparation expressing the receptor would be incubated with a labeled PRO227, PRO233, PRO238, PRO1328, PRO4342, PRO7423, PRO10096, PRO21384, PRO353 or PRO1885 polypeptide in the presence of the candidate compound. The ability of the compound to enhance or block this interaction could then be measured.

More specific examples of potential antagonists include an oligonucleotide that binds to the fusions of immunoglobulin with the PRO227, PRO233, PRO238, PRO1328, PRO4342, PRO7423, PRO10096, PRO21384, PRO353 or PRO1885 polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO227, PRO233, PRO238, PRO1328, PRO4342, PRO7423, PRO10096, PRO21384, PRO353 or PRO1885 polypeptide that recognizes the receptor but imparts no effect, thereby competitively inhibiting the action of the PRO227, PRO233, PRO238, PRO1328, PRO4342, PRO7423, PRO10096, PRO21384, PRO353 or PRO1885 polypeptide.

Another potential PRO227, PRO233, PRO238, PRO1328, PRO4342, PRO7423, PRO10096, PRO21384, PRO353 or PRO1885 polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature PRO227, PRO233, PRO238, PRO1328, PRO4342, PRO7423, PRO10096, PRO21384, PRO353 or PRO1885 polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6:3073 (1979); Cooney et al., *Science*, 241: 456 (1988); Dervan et al., *Science*, 251:1360 (1991)), thereby preventing transcription and the production of the PRO227, PRO233, PRO238, PRO1328, PRO4342, PRO7423, PRO10096, PRO21384, PRO353 or PRO1885 polypeptide. The antisense RNA oligonucleotide hybridizes to the mRNA in vivo and blocks translation of the mRNA molecule into the PRO227, PRO233, PRO238, PRO1328, PRO4342, PRO7423, PRO10096, PRO21384, PRO353 or PRO1885 polypeptide (antisense—Okano, *Neurochem.*, 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the PRO227, PRO233, PRO238, PRO1328, PRO4342, PRO7423, PRO10096, PRO21384, PRO353 or PRO1885 polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the PRO227, PRO233, PRO238, PRO1328, PRO4342, PRO7423, PRO10096, PRO21384, PRO353 or PRO1885 polypeptide, thereby blocking the normal biological activity of the PRO227, PRO233, PRO238, PRO1328, PRO4342, PRO7423, PRO10096, PRO21384, PRO353 or PRO1885 polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Diagnostic and therapeutic uses of the herein disclosed molecules may also be based upon the positive functional assay hits disclosed and described below.

F. Anti-PRO227, Anti-PRO233, Anti-PRO238, Anti-PRO1328, Anti-PRO4342, Anti-PRO7423; Anti-PRO10096; Anti-PRO21384; Anti-PRO353 or Anti-PRO1885 Antibodies The present invention provides anti-PRO227, anti-PRO233, anti-PRO238, anti-PRO1328, anti-PRO4342, anti-PRO7423, anti-PRO10096, anti-PRO21384, anti-PRO353 or anti-PRO1885 antibodies which may find use herein as therapeutic and/or diagnostic agents. Exemplary antibodies include polyclonal, monoclonal, humanized, bispecific, and heteroconjugate antibodies.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later, the animals are boosted with ⅕ to 1/10 the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice,* pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, *J. Immunol.,* 133:3001 (1984); and Brodeur et al., *Monoclonal Antibody Production Techniques and Applications,* pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., *Anal. Biochem.,* 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice,* pp. 59-103 (Academic Press, 1986)). Suitable culture media for this purpose include, for example, D-MEM or RPMI-1640 medium. In addition, the hybridoma cells may be grown in vivo as ascites tumors in an animal e.g. by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.,* 5:256-262 (1993) and Plückthun, *Immunol. Revs.* 130: 151-188 (1992).

Monoclonal antibodies or antibody fragments can be isolated from antibody phage libraries generated using the techniques described in McCafferty et al., *Nature,* 348:552-554 (1990). Clackson et al., *Nature,* 352:624-628 (1991) and Marks et al., *J. Mol. Biol.,* 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., *Proc. Natl. Acad. Sci. USA,* 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The anti-PRO227, anti-PRO233, anti-PRO238, anti-PRO1328, anti-PRO4342, anti-PRO7423, anti-PRO10096, anti-PRO21384, anti-PRO353 or anti-PRO1885 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature,* 321:522-525 (1986); Riechmann et al., *Nature,* 332:323-329 (1988); and Presta, *Curr. Op. Struct. Biol.,* 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature,* 321:522-525 (1986); Riechmann et al., *Nature,* 332:323-327 (1988); Verhoeyen et al., *Science,* 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.* 151:2296 (1993); Chothia et al., *J. Mol. Biol.,* 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.* 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggemann et al., *Year in Immuno.* 7:33 (1993); U.S. Pat. Nos. 5,545,806, 5,569,825, 5,591,669 (all of GenPharm); 5,545,807; and WO 97/17852.

Alternatively, phage display technology (McCafferty et al., *Nature* 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S, and Chiswell, David J., *Current Opinion in Structural Biology* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

4. Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and ScFv antibody fragments can all be expressed in and secreted from *E. coli,* thus allowing the facile production of large amounts of these fragments. Antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10:163-167 (1992)). According to another approach, $F(ab')_2$ fragments can be isolated directly from recombinant host cell culture. Fab and $F(ab')_2$ fragment with increased in vivo half-life comprising a salvage receptor binding epitope residues are described in U.S. Pat. No. 5,869,046. Other techniques for the production of antibody fragments will be apparent to the skilled practitioner. The antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See *Antibody Engineering,* ed. Borrebaeck, supra. The antibody fragment may also be a "linear antibody", e.g., as described in U.S. Pat. No. 5,641,870 for example. Such linear antibody fragments may be monospecific or bispecific.

5. Bispecific Antibodies

Bispecific antibodies are antibodies that have binding specificities for at least two different epitopes. Exemplary bispecific antibodies may bind to two different epitopes of a PRO227, PRO233, PRO238, PRO1328, PRO4342, PRO7423, PRO10096, PRO21384, PRO353 or PRO1885 protein as described herein. Other such antibodies may combine a PRO227, PRO233, PRO238, PRO1328, PRO4342, PRO7423, PRO10096, PRO21384, PRO353 or PRO1885 binding site with a binding site for another protein. Alternatively, an anti-PRO227, anti-PRO233, anti-PRO238, anti-PRO1328, anti-PRO4342, anti-PRO7423, anti-PRO10096, anti-PRO21384, anti-PRO353 or anti-PRO1885 arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the PRO227-, PRO233-, PRO238-, PRO1328-, PRO4342-, PRO7423-, PRO10096-, PRO21384-, PRO353- or PRO1885-expressing cell. Bispecific antibodies may also be used to localize cytotoxic agents to cells which express a PRO227, PRO233, PRO238, PRO1328, PRO4342, PRO7423, PRO10096, PRO21384, PRO353 or PRO1885 polypeptide. These antibodies possess a PRO227-, PRO233-, PRO238-, PRO1328-, PRO4342-, PRO7423-, PRO10096-, PRO21384-, PRO353- or PRO1885-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., $F(ab')_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.* 10:3655-3659 (1991).

According to a different approach, antibody variable domains with the desired binding specificity (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

The invention provides bispecific antibodies which are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology* 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229:81 (1985) describe a procedure wherein intact antibodies are proteolytically cleaved to generate $F(ab')_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.* 175:217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets. Various techniques for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al., *J. Immunol.* 147:60 (1991).

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-$(X1)_n$-VD2-$(X2)_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

8. Effector Function Engineering

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced antitumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

9. Immunoconjugates

The invention also pertains to immunoconjugates comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$. Conjugates of the antibody and cytotoxic agent are made using a variety of bifunctional protein-coupling agents such as N-succinimidyl-3-(2-pyridyldithiol) propionate (SPDP), iminothiolane (TT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothene, and CC1065, and the derivatives of these toxins that have toxin activity, are also contemplated herein.

Maytansine and Maytansinoids

The invention provides an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody (full length or fragments) which is conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Anti-PRO227, Anti-PRO233, Anti-PRO238, Anti-PRO1328, Anti-PRO4342, Anti-PRO7423, anti-PRO10096, anti-PRO21384, anti-PRO353 or Anti-PRO1885 Antibody-Maytansinoid Conjugates (Immunoconjugates)

Anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody-maytansinoid conjugates are prepared by chemically linking an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131 (1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio)propionate (SPDP) (Carlsson et al., *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hyrdoxymethyl, the C-15 position modified with a hydroxyl group, and the C-20 position having a hydroxyl group. The linkage is formed at the C-3 position of maytansinol or a maytansinol analogue.

Calicheamicin

Another immunoconjugate of interest comprises an anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the anti-PRO227, anti-PRO233, anti-PRO238, anti-PRO1328, anti-PRO4342, anti-PRO7423, anti-PRO10096, anti-PRO21384, anti-PRO353 or anti-PRO1885 antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-PRO227, anti-PRO233, anti-PRO238, anti-PRO1328, anti-PRO4342, anti-PRO7423, anti-PRO10096, anti-PRO21384, anti-PRO353 or anti-PRO1885 antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azido-benzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208,020) may be used.

Alternatively, a fusion protein comprising the anti-PRO227, anti-PRO233, anti-PRO238, anti-PRO1328, anti-PRO4342, anti-PRO7423, anti-PRO10096, anti-PRO21384, anti-PRO353 or anti-PRO1885 antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

The invention provides that the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

10. Immunoliposomes

The anti-PRO227, anti-PRO233, anti-PRO238, anti-PRO1328, anti-PRO4342, anti-PRO7423, anti-PRO10096, anti-PRO21384, anti-PRO353 or anti-PRO1885 antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., *Proc. Natl. Acad. Sci. USA* 82:3688 (1985); Hwang et al., *Proc. Natl. Acad. Sci. USA* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257:286-288 (1982) via a disulfide interchange reaction. A chemotherapeutic agent is optionally contained within the liposome. See Gabizon et al., *J. National Cancer Inst.* 81(19):1484 (1989).

11. Pharmaceutical Compositions of Antibodies

Antibodies specifically binding a PRO227, PRO233, PRO238, PRO1328, PRO4342, PRO7423, PRO10096, PRO21384, PRO353 or PRO1885 polypeptide identified herein, as well as other molecules identified by the screening assays disclosed hereinbefore, can be administered for the treatment of various disorders in the form of pharmaceutical compositions.

If the PRO227, PRO233, PRO238, PRO1328, PRO4342, PRO7423, PRO10096, PRO21384, PRO353 or PRO1885 polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA,* 90: 7889-7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

G. Uses for Anti-PRO227, Anti-PRO233, Anti-PRO238, Anti-PRO1328, Anti-PRO4342, Anti-PRO7423; Anti-PRO10096; Anti-PRO21384; Anti-PRO353 or Anti-PRO1885 Antibodies The anti-PRO227, anti-PRO233, anti-PRO238, anti-PRO1328, anti-PRO4342, anti-PRO7423, anti-PRO10096, anti-PRO21384, anti-PRO353 or anti-PRO1885 antibodies of the invention have various therapeutic and/or diagnostic utilities for a neurological disorder; a cardiovascular, endothelial or angiogenic disorder; an immunological disorder; an oncological disorder; an embryonic developmental disorder or lethality, or a metabolic abnormality. For example, anti-PRO227, anti-PRO233, anti-PRO238, anti-PRO1328, anti-PRO4342, anti-PRO7423, anti-PRO10096, anti-PRO21384, anti-PRO353 or anti-PRO1885 antibodies may be used in diagnostic assays for PRO227, PRO233, PRO238, PRO1328, PRO4342, PRO7423, PRO10096, PRO21384, PRO353 or PRO1885, e.g., detecting its expression (and in some cases, differential expression) in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-PRO227, anti-PRO233, anti-PRO238, anti-PRO1328, anti-PRO4342, anti-PRO7423, anti-PRO10096, anti-PRO21384, anti-PRO353 or anti-PRO1885 antibodies also are useful for the affinity purification of PRO227, PRO233, PRO238, PRO1328, PRO4342, PRO7423, PRO10096, PRO21384, PRO353 or PRO1885 polypeptides from recombinant cell culture or natural sources. In this process, the antibodies against PRO227, PRO233, PRO238, PRO1328, PRO4342, PRO7423, PRO10096, PRO21384, PRO353 or PRO1885 polypeptides are immobilized on a suitable support, such a Sephadex resin or filter paper, using methods well known in the art. The immobilized antibody then is contacted with a sample containing the PRO227, PRO233, PRO238, PRO1328, PRO4342, PRO7423, PRO10096, PRO21384, PRO353 or PRO1885 polypeptide to be purified, and thereafter the support is washed with a suitable solvent that will remove substantially all the material in the sample except the PRO227, PRO233, PRO238, PRO1328, PRO4342, PRO7423, PRO10096, PRO21384, PRO353 or PRO1885 polypeptide, which is bound to the immobilized antibody. Finally, the support is washed with another suitable solvent that will release the PRO227, PRO233, PRO238, PRO1328, PRO4342, PRO7423, PRO10096, PRO21384, PRO353 or PRO1885 polypeptide from the antibody.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Extracellular Domain Homology Screening to Identify Novel Polypeptides and cDNA Encoding Therefor The extracellular domain (ECD) sequences (including the secretion signal sequence, if any) from about 950 known secreted proteins from the Swiss-Prot public database were used to search EST databases. The EST databases included public databases (e.g., Dayhoff, GenBank), and proprietary databases (e.g. LIFESEQ™, Incyte Pharmaceuticals, Palo Alto, Calif.). The search was performed using the computer program BLAST or BLAST-2 (Altschul et al., *Methods in Enzymology*, 266:460-480 (1996)) as a comparison of the ECD protein sequences to a 6 frame translation of the EST sequences. Those comparisons with a BLAST score of 70 (or in some cases 90) or greater that did not encode known proteins were clustered and assembled into consensus DNA sequences with the program "phrap" (Phil Green, University of Washington, Seattle, Wash.).

Using this extracellular domain homology screen, consensus DNA sequences were assembled relative to the other identified EST sequences using phrap. In addition, the consensus DNA sequences obtained were often (but not always) extended using repeated cycles of BLAST or BLAST-2 and phrap to extend the consensus sequence as far as possible using the sources of EST sequences discussed above.

Based upon the consensus sequences obtained as described above, oligonucleotides were then synthesized and used to identify by PCR a cDNA library that contained the sequence of interest and for use as probes to isolate a clone of the full-length coding sequence for a PRO polypeptide. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science,* 253: 1278-1280 (1991)) in the unique XhoI and NotI sites.

Example 2

Isolation of cDNA Clones by Amylase Screening

1. Preparation of Oligo dT Primed cDNA Library mRNA was isolated from a human tissue of interest using reagents and protocols from Invitrogen, San Diego, Calif. (Fast Track 2). This RNA was used to generate an oligo dT primed cDNA library in the vector pRK5D using reagents and protocols from Life Technologies, Gaithersburg, Md. (Super Script Plasmid System). In this procedure, the double stranded cDNA was sized to greater than 1000 bp and the SalI/NotI linkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

2. Preparation of Random Primed cDNA Library

A secondary cDNA library was generated in order to preferentially represent the 5' ends of the primary cDNA clones. Sp6 RNA was generated from the primary library (described above), and this RNA was used to generate a random primed cDNA library in the vector pSST-AMY.0 using reagents and protocols from Life Technologies (Super Script Plasmid System, referenced above). In this procedure the double stranded cDNA was sized to 500-1000 bp, linkered with blunt to NotI adaptors, cleaved with SfiI, and cloned into SfiI/NotI cleaved vector. pSST-AMY.0 is a cloning vector that has a yeast alcohol dehydrogenase promoter preceding the cDNA cloning sites and the mouse amylase sequence (the mature sequence without the secretion signal) followed by the yeast alcohol dehydrogenase terminator, after the cloning sites. Thus, cDNAs cloned into this vector that are fused in frame with amylase sequence will lead to the secretion of amylase from appropriately transfected yeast colonies.

3. Transformation and Detection

DNA from the library described in paragraph 2 above was chilled on ice to which was added electrocompetent DH10B bacteria (Life Technologies, 20 ml). The bacteria and vector mixture was then electroporated as recommended by the manufacturer. Subsequently, SOC media (Life Technologies, 1 ml) was added and the mixture was incubated at 37° C. for 30 minutes. The transformants were then plated onto 20 standard 150 mm LB plates containing ampicillin and incubated for 16 hours (37° C.). Positive colonies were scraped off the plates and the DNA was isolated from the bacterial pellet using standard protocols, e.g. CsCl-gradient. The purified DNA was then carried on to the yeast protocols below.

The yeast methods were divided into three categories: (1) Transformation of yeast with the plasmid/cDNA combined vector; (2) Detection and isolation of yeast clones secreting amylase; and (3) PCR amplification of the insert directly from the yeast colony and purification of the DNA for sequencing and further analysis.

The yeast strain used was HD56-5A (ATCC-90785). This strain has the following genotype: MAT alpha, ura3-52, leu2-3, leu2-112, his3-11, his3-15, MAL+, SUC+, GAL+. Preferably, yeast mutants can be employed that have deficient posttranslational pathways. Such mutants may have translocation deficient alleles in sec71, sec72, sec62, with truncated sec71 being most preferred. Alternatively, antagonists (including antisense nucleotides and/or ligands) which interfere with the normal operation of these genes, other proteins implicated in this post translation pathway (e.g., SEC61p, SEC72p, SEC62p, SEC63p, TDJ1p or SSA1p-4p) or the complex formation of these proteins may also be preferably employed in combination with the amylase-expressing yeast.

Transformation was performed based on the protocol outlined by Gietz et al., *Nucl. Acid. Res.,* 20:1425 (1992). Transformed cells were then inoculated from agar into YEPD complex media broth (100 ml) and grown overnight at 30° C. The YEPD broth was prepared as described in Kaiser et al., *Methods in Yeast Genetics,* Cold Spring Harbor Press, Cold Spring Harbor, N.Y., p. 207 (1994). The overnight culture was then diluted to about $2 \times 10^6$ cells/ml (approx. $OD_{600}$=0.1) into fresh YEPD broth (500 ml) and regrown to $1 \times 10^7$ cells/ml (approx. $OD_{600}$=0.4-0.5).

The cells were then harvested and prepared for transformation by transfer into GS3 rotor bottles in a Sorval GS3 rotor at 5,000 rpm for 5 minutes, the supernatant discarded, and then resuspended into sterile water, and centrifuged again in 50 ml falcon tubes at 3,500 rpm in a Beckman GS-6KR centrifuge. The supernatant was discarded and the cells were subsequently washed with LiAc/TE (10 ml, 10 mM Tris-HCl, 1 mM EDTA pH 7.5, 100 mM $Li_2OOCCH_3$), and resuspended into LiAc/TE (2.5 ml).

Transformation took place by mixing the prepared cells (100 µl) with freshly denatured single stranded salmon testes DNA (Lofstrand Labs, Gaithersburg, Md.) and transforming DNA (1 µg, vol. <10 µl) in microfuge tubes. The mixture was mixed briefly by vortexing, then 40% PEG/TE (600 µl, 40% polyethylene glycol-4000, 10 mM Tris-HCl, 1 mM EDTA, 100 mM $Li_2OOCCH_3$, pH 7.5) was added. This mixture was gently mixed and incubated at 30° C. while agitating for 30 minutes. The cells were then heat shocked at 42° C. for 15 minutes, and the reaction vessel centrifuged in a microfuge at 12,000 rpm for 5-10 seconds, decanted and resuspended into TE (500 µl, 10 mM Tris-HCl, 1 mM EDTA pH 7.5) followed by recentrifugation. The cells were then diluted into TE (1 ml) and aliquots (200 µl) were spread onto the selective media previously prepared in 150 mm growth plates (VWR).

Alternatively, instead of multiple small reactions, the transformation was performed using a single, large scale reaction, wherein reagent amounts were scaled up accordingly.

The selective media used was a synthetic complete dextrose agar lacking uracil (SCD-Ura) prepared as described in Kaiser et al., *Methods in Yeast Genetics,* Cold Spring Harbor Press, Cold Spring Harbor, N.Y., p. 208-210 (1994). Transformants were grown at 30° C. for 2-3 days.

The detection of colonies secreting amylase was performed by including red starch in the selective growth media. Starch was coupled to the red dye (Reactive Red-120, Sigma) as per the procedure described by Biely et al., *Anal. Biochem.,* 172:176-179 (1988). The coupled starch was incorporated into the SCD-Ura agar plates at a final concentration of 0.15% (w/v), and was buffered with potassium phosphate to a pH of 7.0 (50-100 mM final concentration).

The positive colonies were picked and streaked across fresh selective media (onto 150 mm plates) in order to obtain well isolated and identifiable single colonies. Well isolated single colonies positive for amylase secretion were detected by direct incorporation of red starch into buffered SCD-Ura agar. Positive colonies were determined by their ability to break down starch resulting in a clear halo around the positive colony visualized directly.

4. Isolation of DNA by PCR Amplification

When a positive colony was isolated, a portion of it was picked by a toothpick and diluted into sterile water (30 µl) in a 96 well plate. At this time, the positive colonies were either frozen and stored for subsequent analysis or immediately amplified. An aliquot of cells (5 µl) was used as a template for the PCR reaction in a 25 µl volume containing 0.5 µl Klentaq (Clontech, Palo Alto, Calif.); 4.0 µl 10 mM dNTP's (Perkin Elmer-Cetus); 2.5 µl Kentaq buffer (Clontech); 0.25 µl forward oligo 1; 0.25 µl reverse oligo 2; 12.5 µl distilled water. The sequence of the forward oligonucleotide 1 was:

(SEQ ID NO: 21)
5'-TGTAAAACGACGGCCAGTTAAATAGACCTGCAATTATTAATCT-3'

The sequence of reverse oligonucleotide 2 was:

(SEQ ID NO: 22)
5'-CAGGAAACAGCTATGACCACCTGCACACCTGCAAATCCATT-3'

PCR was then performed as follows:

| a. | | Denature | 92° C., 5 minutes |
|---|---|---|---|
| b. | 3 cycles of: | Denature | 92° C., 30 seconds |
| | | Anneal | 59° C., 30 seconds |
| | | Extend | 72° C., 60 seconds |
| c. | 3 cycles of: | Denature | 92° C., 30 seconds |
| | | Anneal | 57° C., 30 seconds |
| | | Extend | 72° C., 60 seconds |
| d. | 25 cycles of: | Denature | 92° C., 30 seconds |
| | | Anneal | 55° C., 30 seconds |
| | | Extend | 72° C., 60 seconds |
| e. | | Hold | 4° C. |

The underlined regions of the oligonucleotides annealed to the ADH promoter region and the amylase region, respectively, and amplified a 307 bp region from vector pSST-AMY.0 when no insert was present. Typically, the first 18 nucleotides of the 5' end of these oligonucleotides contained annealing sites for the sequencing primers. Thus, the total product of the PCR reaction from an empty vector was 343 bp. However, signal sequence-fused cDNA resulted in considerably longer nucleotide sequences.

Following the PCR, an aliquot of the reaction (5 µl) was examined by agarose gel electrophoresis in a 1% agarose gel using a Tris-Borate-EDTA (TBE) buffering system as described by Sambrook et al., supra. Clones resulting in a single strong PCR product larger than 400 bp were further analyzed by DNA sequencing after purification with a 96 Qiaquick PCR clean-up column (Qiagen Inc., Chatsworth, Calif.).

Example 3

Isolation of cDNA Clones Using Signal Algorithm Analysis

Various polypeptide-encoding nucleic acid sequences were identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals. Use of this algorithm resulted in the identification of numerous polypeptide-encoding nucleic acid sequences.

Using the techniques described in Examples 1 to 3 above, numerous full-length cDNA clones were identified as encoding PRO227, PRO233, PRO238, PRO1328, PRO4342, PRO7423, PRO10096, PRO21384, PRO353 or PRO1885 polypeptides as disclosed herein. These cDNAs were then deposited under the terms of the Budapest Treaty with the American Type Culture Collection, 10801 University Blvd., Manassas, Va. 20110-2209, USA (ATCC) as shown in Table 7 below. In addition, the coding sequence of DNA108809 (UNQ2964), was identified from GenBank accession no.: AJ010588.

TABLE 7

| Material | ATCC Dep. No. | Deposit Date |
|---|---|---|
| DNA33786-1132 | 209253 | Sep. 16, 1997 |
| DNA34436-1238 | 209523 | Dec. 10, 1997 |
| DNA35600-1162 | 209370 | Oct. 16, 1997 |
| DNA66658-1584 | 203229 | Sep. 15, 1998 |
| DNA96787-2534-1 | 203589 | Jan. 12, 1999 |
| DNA125185-2806 | PTA-1031 | Dec. 7, 1999 |
| DNA177313-2982 | PTA-2251 | Jul. 19, 2000 |
| DNA41234-1242-1 | 209618 | Feb. 5, 1998 |
| DNA79302-2521 | 203545 | Dec. 22, 1998 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Example 4

Isolation of cDNA Clones Encoding Human PRO227 Polypeptides (UNQ201)

The extracellular domain (ECD) sequences (including the secretion signal, if any) of from about 950 known secreted proteins from the Swiss-Prot public protein database were used to search expressed sequence tag (EST) databases. The EST databases included public EST databases (e.g., GenBank) and a proprietary EST DNA database (LIFESEQ®, Incyte Pharmaceuticals, Palo Alto, Calif.). The search was performed using the computer program BLAST or BLAST2 (Altshul et al., *Methods in Enzymology* 266:460-480 (1996)) as a comparison of the ECD protein sequences to a 6 frame translation of the EST sequence. Those comparisons resulting in a BLAST score of 70 (or in some cases 90) or greater that did not encode known proteins were clustered and assembled into consensus DNA sequences with the program "phrap" (Phil Green, University of Washington, Seattle, Wash.).

A consensus DNA sequence encoding PRO227 was assembled relative to the other identified EST sequences, wherein the consensus sequence was designated herein as DNA28740. Based on the DNA28740 consensus sequence, oligonucleotides were synthesized to identify by PCR a cDNA library that contained the sequence of interest and for use as probes to isolate a clone of the full-length coding sequence for PRO227.

A pair of PCR primers (forward and reverse) were synthesized:

```
forward PCR primer
5'-AGCAACCGCCTGAAGCTCATCC-3'    (SEQ ID NO: 23)

reverse PCR primer
5'-AAGGCGCGGTGAAAGATGTAGACG-3'  (SEQ ID NO: 24)
```

Additionally, a synthetic oligonucleotide hybridization probe was constructed from the consensus DNA28740 sequence which had the following nucleotide sequence:

```
hybridization probe
                                (SEQ ID NO: 25)
5'GACTACATGTTTCAGGACCTGTACAACCTCAAGTCACTGGAGGTTG
GCGA-3'.
```

In order to screen several libraries for a source of a full-length clone, DNA from the libraries was screened by PCR amplification with the PCR primer pair identified above. A positive library was then used to isolate clones encoding the PRO227 gene using the probe oligonucleotide and one of the PCR primers.

RNA for construction of the cDNA libraries was isolated from human fetal lung tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253:1278-1280 (1991)) in the unique XhoI and NotI sites.

DNA sequencing of the clones isolated as described above gave the full-length DNA sequence for PRO227 [herein designated as UNQ201 (DNA33786-1132) and the derived protein sequence for PRO227.

The entire nucleotide sequence of UNQ201 (DNA33786-1132) is shown in FIG. 1 (SEQ ID NO:1). Clone UNQ201 (DNA33786-1132) contains a single open reading frame with an apparent translational initiation site at nucleotide positions 117-119 and ending at the stop codon at nucleotide positions 1989-1991 (FIG. 1, the initiation and stop codons are bold and underlined). The predicted polypeptide precursor is 620 amino acids long (FIG. 2; SEQ ID NO:2). Clone UNQ201 (DNA33786-1132) has been deposited with ATCC on Sep. 16, 1997 and is assigned ATCC deposit no. 209253.

Example 5

Isolation of cDNA Clones Encoding Human PRO233 Polypeptides (UNQ207)

The extracellular domain (ECD) sequences (including the secretion signal, if any) of from about 950 known secreted proteins from the Swiss-Prot public protein database were used to search expressed sequence tag (EST) databases. The EST databases included public EST databases (e.g., GenBank) and a proprietary EST DNA database (LIFESEQ®, Incyte Pharmaceuticals, Palo Alto, Calif.). The search was performed using the computer program BLAST or BLAST2 (Altshul et al., *Methods in Enzymology* 266:460-480 (1996)) as a comparison of the ECD protein sequences to a 6 frame translation of the EST sequence. Those comparisons resulting in a BLAST score of 70 (or in some cases 90) or greater that did not encode known proteins were clustered and assembled into consensus DNA sequences. An expressed sequence tag (EST) was identified by the EST database search and a consensus DNA sequence was assembled relative to other EST sequences using phrap (Phil Green, University of Washington, Seattle, Wash.). This consensus sequence is herein designated "Consen0821", which was used to derive the final consensus sequence, "DNA30945".

Based on the DNA30945 consensus sequence, oligonucleotides were synthesized: 1) to identify by PCR a cDNA library that contained the sequence of interest, and 2) for use as probes to isolate a clone of the full-length coding sequence for PRO233. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as ber Ausubel et al., *Current Protocols in Molecular Biology*, with the PCR primer pair. A positive library was then used to isolate clones encoding the gene of interest by the in vivo cloning procedure using the probe oligonucleotide and one of the primer pairs. Forward and reverse PCR primers were synthesized:

```
forward PCR primer
5'-GGTGAAGGCAGAAATTGGAGATG-3'  (SEQ ID NO: 26)

reverse PCR primer
5'-ATCCCATGCATCAGCCTGTTTACC-3' (SEQ ID NO: 27)
```

Additionally, a synthetic oligonucleotide hybridization probe was constructed from the consensus DNA30945 sequence which had the following nucleotide sequence:

```
hybridization probe
                                (SEQ ID NO: 28)
5'-GCTGGTGTAGTCTATACATCAGATTTGTTTGCTACACAAGATCCT
CAG-3'
```

In order to screen several libraries for a source of a full-length clone, DNA from the libraries was screened by PCR amplification with the PCR primer pair identified above. A positive library was then used to isolate clones encoding the PRO233 gene using the probe oligonucleotide.

RNA for construction of the cDNA libraries was isolated from human fetal brain tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science,* 253:1278-1280 (1991)) in the unique XhoI and NotI sites.

DNA sequencing of the clones isolated as described above gave the full-length DNA sequence for PRO233 [herein designated as UNQ207 (DNA34436-1238)] (SEQ ID NO:3) and the derived protein sequence for PRO233 (SEQ ID NO:4).

The entire nucleotide sequence of UNQ207 (DNA34436-1238) is shown in FIG. 3 (SEQ ID NO:3). Clone UNQ207 (DNA34436-1238) contains a single open reading frame with an apparent translational initiation site at nucleotide positions 101-103 and ending at the stop codon at nucleotide positions 1001-1003 (FIG. 3). The predicted polypeptide precursor is 300 amino acids long (FIG. 4; SEQ ID NO:4). The full-length PRO233 protein shown in FIG. 4 has an estimated molecular weight of about 32964 and a pI of about 9.52. In addition, regions of interest including the signal peptide and a putative oxidoreductase active site, are designated in FIG. 4. Clone UNQ207 (DNA34436-1238) has been deposited with ATCC on Dec. 10, 1997 and is assigned ATCC deposit no. 209523.

Analysis of the amino acid sequence of the full-length PRO233 polypeptide suggests that portions of it possess significant homology to reductase proteins, thereby indicating that PRO233 may be a novel reductase.

Example 6

Isolation of cDNA Clones Encoding Human PRO238 Polypeptides (UNQ212)

A consensus DNA sequence was assembled relative to other EST sequences using phrap as described above in Example 1. This consensus sequence is herein designated DNA30908. Based on the DNA30908 consensus sequence, oligonucleotides were synthesized: 1) to identify by PCR a cDNA library that contained the sequence of interest, and 2) for use as probes to isolate a clone of the full-length coding sequence for PRO238.

PCR primers (forward and reverse) were synthesized:

```
forward PCR primer 1
5'-GGTGCTAAACTGGTGCTCTGTGGC-3'    (SEQ ID NO: 29)

forward PCR primer 2
5'-CAGGGCAAGATGAGCATTCC-3'        (SEQ ID NO: 30)

reverse PCR primer
5'-TCATACTGTTCCATCTCGGCACGC-3'    (SEQ ID NO: 31)
```

Additionally, a synthetic oligonucleotide hybridization probe was constructed from the consensus DNA30908 sequence which had the following nucleotide sequence

```
hybridization probe
                                  (SEQ ID NO: 32)
5'-AATGGTGGGCCCTAGAAGAGCTCATCAGAGAACTCACCGCTTCT
CATGC-3'
```

In order to screen several libraries for a source of a full-length clone, DNA from the libraries was screened by PCR amplification with the PCR primer pair identified above. A positive library was then used to isolate clones encoding the PRO238 gene using the probe oligonucleotide and one of the PCR primers.

RNA for construction of the cDNA libraries was isolated from human fetal liver tissue.

DNA sequencing of the clones isolated as described above gave the full-length DNA sequence for DNA35600-1162 and the derived protein sequence for PRO238.

The entire nucleotide sequence of DNA35600-1162 (UNQ212) is shown in FIG. 5 (SEQ ID NO:5). Clone DNA35600-1162 contains a single open reading frame with an apparent translational initiation site at nucleotide positions 134-136 and ending prior to the stop codon at nucleotide positions 1064-1066 (FIG. 5). The predicted polypeptide precursor is 310 amino acids long (FIG. 6; SEQ ID NO:6). Clone DNA35600-1162 has been deposited with ATCC on Oct. 16, 1997 and is assigned ATCC deposit no. ATCC 209370.

Analysis of the amino acid sequence of the full-length PRO238 polypeptide suggests that portions of it possess significant homology to reductase, particularly oxidoreductase, thereby indicating that PRO238 may be a novel reductase.

Example 7

Isolation of cDNA Clones Encoding Human PRO1328 Polypeptides (UNQ688)

DNA66658-1584 was identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of an EST cluster sequence from the Incyte database, designated Incyte EST cluster sequence no. 40671. This EST cluster sequence was then compared to a variety of expressed sequence tag (EST) databases which included public EST databases (e.g., GenBank) and a proprietary EST DNA database (Lifeseq®, Incyte Pharmaceuticals, Palo Alto, Calif.) to identify existing homologies. The homology search was performed using the computer program BLAST or BLAST2 (Altshul et al., *Methods in Enzymology* 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence is herein designated DNA56749. Proprietary Genentech EST sequences were used in the assembly. In light of the sequence homology between the DNA56749 sequence and the Incyte EST clone no. 4111192, the Incyte EST clone no. 4111192 was purchased and the cDNA insert was obtained and sequenced. The sequence of this cDNA insert is shown in FIG. 7 (SEQ ID NO:7) and is herein designated as DNA66658-1584.

Clone UNQ688 (DNA66658-1584) contains a single open reading frame with an apparent translational initiation site at nucleotide positions 9-11 and ending at the stop codon at nucleotide positions 780-782 (FIG. 7; SEQ ID NO:7). The predicted polypeptide precursor is 257 amino acids long (FIG. 8; SEQ ID NO:8). The full-length PRO1328 protein shown in FIG. 8 has an estimated molecular weight of about 28,472 daltons and a pI of about 9.33. Analysis of the full-length PRO1328 sequence shown in FIG. 8 (SEQ ID NO:8) evidences the presence of the following: a signal peptide from about amino acid 1 to about amino acid 19, transmembrane domains from about amino acid 32 to about amino acid 51, from about amino acid 119 to about amino acid 138, from about amino acid 152 to about amino acid 169 and from about amino acid 216 to about amino acid 235, a glycosaminoglycan attachment site from about amino acid 120 to about amino acid 123 and sodium/neurotransmitter symporter family protein homology block from about amino acid 31 to about amino acid 65. Clone UNQ688 (DNA66658-1584) has been deposited with ATCC on Sep. 15, 1998 and is assigned ATCC deposit no. 203229.

An analysis of the Dayhoff database (version 35.45 SwissProt 35), using a WU-BLAST2 sequence alignment analysis of the full-length PRO1328 amino acid sequence shown in FIG. 8 (SEQ ID NO:8), evidenced significant homology between the PRO1328 amino acid sequence and the following Dayhoff sequences: CEVF36H2L_2, TIP2_TOBAC, AB009466_16, ATU39485_1, P_R60153, P_R77082, S73351, C69392, LEU95008_1 and E64667.

Example 8

Isolation of cDNA Clones Encoding Human PRO4342 Polypeptides (UNQ1896)

A expressed sequence tag (EST) DNA database (LIFESEQ®, Incyte Pharmaceuticals, Palo Alto, Calif.) was searched with human interleukin-1 receptor antagonist (hIL-1Ra) sequence, and the EST, designated 5120028 was identified, which showed homology with the hIL-1Ra known protein. EST clone 5120028 was purchased from Incyte Pharmaceuticals (Palo Alto, Calif.) and the cDNA insert was obtained and sequenced in its entirety.

The entire nucleotide sequence of the clone 5120028, designated UNQ1896 (DNA96787-2534-1), is shown in FIG. 9 (SEQ ID NO:9). Clone UNQ1896 (DNA96787-2534-1) contains a single open reading frame with an apparent translational initiation site at nucleotide positions 1-3, and a stop codon at nucleotide positions 466-468 (FIG. 9; SEQ ID NO:9). The predicted polypeptide precursor (hIL-1Ra3) is 155 amino acids long (FIG. 10; SEQ ID NO:10). The putative signal sequence extends from amino acid positions 1-33. Putative N-myristoylation sites are located at amino acid positions 29-34, 60-65, 63-68, 73-78, 91-96 and 106-111. An interleukin-1-like sequence is located at amino acid positions 111-131.

Clone DNA96787 (designated as DNA96787-2534-1) was deposited with ATCC on Jan. 12, 1999 and was assigned ATCC deposit no. 203589. The full length hIL-1Ra3 protein shown in FIG. 10 (SEQ ID NO:10) has an estimated molecular weight of about 16,961 daltons and a pI of about 4.9.

Based on a BLAST and FastA sequence alignment analysis (using the ALIGN computer program) of the full-length sequence, hIL-1Ra3 shows significant amino acid sequence identity to hicIL-1Ra and hIL-1Ra proteins.

Example 9

Isolation of cDNA Clones Encoding Human PRO10096 Polypeptides (UNQ3099)

DNA125185-2806 (UNQ3099) was identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of an EST cluster sequence from the Incyte database, designated herein as 5086173H1. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., *Methods in Enzymology* 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA110880.

In light of an observed sequence homology between the DNA110880 sequence and an EST sequence encompassed within clone no. 5088384 from the Incyte database, clone no. 5088384 was purchased and the cDNA insert was obtained and sequenced. It was found herein that that cDNA insert encoded a full-length protein. The sequence of this cDNA insert is shown in FIG. 13 (SEQ ID NO:13) and is herein designated as DNA125185-2806.

Clone DNA125185-2806 [UNQ3099] contains a single open reading frame with an apparent translational initiation site at nucleotide positions 58-60 and ending at the stop codon at nucleotide positions 595-597 (FIG. 13). The predicted polypeptide precursor is 179 amino acids long (FIG. 14; SEQ ID NO:14). The full-length PRO10096 (SEQ ID NO:14) protein shown in FIG. 14 has an estimated molecular weight of about 20,011 daltons and a pI of about 8.10. Analysis of the full-length PRO10096 sequence shown in FIG. 14 (SEQ ID NO:14) evidences the presence of a variety of important polypeptide domains as shown in FIG. 14, wherein the locations given for those important polypeptide domains are approximate as described above. Clone DNA125185-2806 has been deposited with ATCC on Dec. 7, 1999 and is assigned ATCC deposit no. PTA-1031.

Example 10

Isolation of cDNA Clones Encoding Human PRO21384 Polypeptides (UNQ6368)

The extracellular domain (ECD) sequences (including the secretion signal, if any) of from about 950 known secreted proteins from the Swiss-Prot public protein database were used to search expressed sequence tag (EST) databases. The EST databases included public EST databases (e.g., Gen-Bank) and a proprietary EST DNA database (LIFESEQ®, Incyte Pharmaceuticals, Palo Alto, Calif.). The search was performed using the computer program BLAST or BLAST2 (Altshul et al., *Methods in Enzymology* 266:460-480 (1996)) as a comparison of the ECD protein sequences to a 6 frame translation of the EST sequence. Those comparisons resulting in a BLAST score of 70 (or in some cases 90) or greater that did not encode known proteins were clustered and assembled into consensus DNA sequences. An expressed sequence tag (EST) was identified by the EST database search and a consensus DNA sequence was assembled relative to other EST sequences using phrap (Phil Green, University of Washington, Seattle, Wash.). This consensus sequence is herein designated "Consen0821", which was used to derive the final consensus sequence, "DNA172257".

Based on the DNA172257 consensus sequence, oligonucleotides were synthesized: 1) to identify by PCR a cDNA library that contained the sequence of interest, and 2) for use as probes to isolate a clone of the full-length coding sequence for PRO233. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as ber Ausubel et al., *Current Protocols in Molecular Biology*, with the PCR primer pair. A positive library was then used to isolate clones encoding the gene of interest by the in vivo cloning procedure using the probe oligonucleotide and one of the primer pairs. Forward and reverse PCR primers were synthesized:

```
forward PCR primer
                            (SEQ ID NO: 33)
5'-GTCAAGGAGTCAAAGTTCTGGAGTGACTGG-3' reverse PCR primer
                            (SEQ ID NO: 34)
5'-CGCACATCGCAGAGCTATGACATATTC-3'
```

Additionally, a synthetic oligonucleotide hybridization probe was constructed from the consensus DNA172257 sequence which had the following nucleotide sequence:

```
hybridization probe
                            (SEQ ID NO: 35)
5'-CGTACAACCTCACGGGGCTGCAGCCTTTTACAG-3'
```

In order to screen several libraries for a source of a full-length clone, DNA from the libraries was screened by PCR amplification with the PCR primer pair identified above. A positive library was then used to isolate clones encoding the PRO21384 gene using the probe oligonucleotide.

RNA for construction of the cDNA libraries was isolated from a mixture of human tissues. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253:1278-1280 (1991)) in the unique XhoI and NotI sites.

DNA sequencing of the clones isolated as described above gave the full-length DNA sequence of PRO21384 [herein designated as UNQ6368 (DNA177313-2982)] (SEQ ID NO:15) and the derived protein sequence of PRO21384 (SEQ ID NO:16).

The entire nucleotide sequence of UNQ6368 (DNA177313-2982) is shown in FIG. 15 (SEQ ID NO:15). Clone UNQ6368 (DNA177313-2982) contains a single open reading frame with an apparent translational initiation site at nucleotide positions 93-95 and ending at the stop codon at nucleotide positions 1939-1941 (FIG. 15). The predicted polypeptide precursor is 582 amino acids long (FIG. 16; SEQ ID NO:16). The full-length PRO21384 protein shown in FIG. 16 has an estimated molecular weight of about 66605 daltons and a pI of about 8.14. Clone UNQ6368 (DNA177313-2982) has been deposited with ATCC on Jul. 19, 2000 and is assigned ATCC deposit no. PTA-2251.

Analysis of the amino acid sequence of the full-length PRO21384 polypeptide evidenced sequence identity between the PRO21384 amino acid sequence and the following Dayhoff sequences: P_R10545, IL6B_MOUSE, GCSR_HUMAN, LIFR_HUMAN, HSU64198_1, P_R85912, P_W70848, P_Y29779, P_Y17825 and P_W70839.

Example 11

Isolation of cDNA Clones Encoding Human PRO353 Polypeptides (UNQ310)

A consensus DNA sequence was assembled relative to other EST sequences using phrap as described in Example 1 above. This consensus sequences is herein designated DNA36363. The consensus DNA sequence was extended using repeated cycles of BLAST and phrap to extend the consensus sequence as far as possible using the sources of EST sequences discussed above. Based on the DNA36363 consensus sequence, oligonucleotides were synthesized: 1) to identify by PCR a cDNA library that contained the sequence of interest, and 2) for use as probes to isolate a clone of the full-length coding sequence for PRO353.

Based on the DNA36363 consensus sequence, forward and reverse PCR primers were synthesized as follows:

```
forward PCR primer
5'-TACAGGCCCAGTCAGGACCAGGGG-3'    (SEQ ID NO: 36)

reverse PCR primer
5'-CTGAAGAAGTAGAGGCCGGGCACG-3'.   (SEQ ID NO: 37)
```

Additionally, a synthetic oligonucleotide hybridization probe was constructed from the DNA36363 consensus sequence which had the following nucleotide sequence:

```
hybridization probe
                            (SEQ ID NO: 38)
5'-CCCGGTGCTTGCGCTGCTGTGACCCCGGTACCTCCATGTACCC
GG-3'
```

In order to screen several libraries for a source of a full-length clone, DNA from the libraries was screened by PCR amplification with one of the PCR primer pairs identified above. A positive library was then used to isolate clones encoding the PRO353 gene using the probe oligonucleotide and one of the PCR primers. RNA for construction of the cDNA libraries was isolated from human fetal kidney tissue.

DNA sequencing of the clones isolated as described above gave the full-length DNA sequence for PRO353 [herein designated as DNA41234-1242-1] (SEQ ID NO:17) and the derived protein sequence for PRO353 (SEQ ID NO:18).

The entire nucleotide sequence of DNA41234-1242-1 [UNQ310] is shown in FIG. 17 (SEQ ID NO:17). Clone DNA41234-1242-1 contains a single open reading frame with an apparent translational initiation site at nucleotide positions 305-307 and ending at the stop codon at nucleotide positions 1148-1150 (FIG. 17). The predicted polypeptide precursor is 281 amino acids long (FIG. 18; SEQ ID NO:18). Important regions of the amino acid sequence encoded by PRO353 include the signal peptide, corresponding to amino acids 1-26, the start of the mature protein at amino acid position 27, a potential N-glycosylation site, corresponding to amino acids 93-98 and a region which has homology to a 30 kd adipocyte complement-related protein precursor, corresponding to amino acids 99-281. Clone DNA41234-1242-1 has been deposited with the ATCC and is assigned ATCC deposit no. ATCC 209618 on Feb. 5, 1998.

Analysis of the amino acid sequence of the full-length PRO353 polypeptides suggests that portions of them possess significant homology to portions of human and murine complement proteins, thereby indicating that PRO353 may be a novel complement protein.

Example 12

Isolation of cDNA Clones Encoding Human PRO1885 Polypeptides (UNQ868) by Amylase Screening 1. Preparation of Oligo dT Primed cDNA Library mRNA was isolated from a human tissue of interest using reagents and protocols from Invitrogen, San Diego, Calif. (Fast Track 2). This RNA was used to generate an oligo dT primed cDNA library in the vector pRK5D using reagents and protocols from Life Technologies, Gaithersburg, Md. (Super Script Plasmid System). In this procedure, the double stranded cDNA was sized to greater than 1000 bp and the SalI/NotI linkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

2. Preparation of Random Primed cDNA Library

A secondary cDNA library was generated in order to preferentially represent the 5' ends of the primary cDNA clones. Sp6 RNA was generated from the primary library (described above), and this RNA was used to generate a random primed cDNA library in the vector pSST-AMY.0 using reagents and protocols from Life Technologies (Super Script Plasmid System, referenced above). In this procedure the double stranded cDNA was sized to 500-1000 bp, linkered with blunt to NotI adaptors, cleaved with SfiI, and cloned into SfiI/NotI cleaved vector. pSST-AMY.0 is a cloning vector that has a yeast alcohol dehydrogenase promoter preceding the cDNA cloning sites and the mouse amylase sequence (the mature sequence without the secretion signal) followed by the yeast alcohol dehydrogenase terminator, after the cloning sites. Thus, cDNAs cloned into this vector that are fused in frame with amylase sequence will lead to the secretion of amylase from appropriately transfected yeast colonies.

3. Transformation and Detection

DNA from the library described in paragraph 2 above was chilled on ice to which was added electrocompetent DH10B bacteria (Life Technologies, 20 ml). The bacteria and vector mixture was then electroporated as recommended by the manufacturer. Subsequently, SOC media (Life Technologies, 1 ml) was added and the mixture was incubated at 37° C. for 30 minutes. The transformants were then plated onto 20 standard 150 mm LB plates containing ampicillin and incubated for 16 hours (37° C.). Positive colonies were scraped off the plates and the DNA was isolated from the bacterial pellet using standard protocols, e.g. CsCl-gradient. The purified DNA was then carried on to the yeast protocols below.

The yeast methods were divided into three categories: (1) Transformation of yeast with the plasmid/cDNA combined vector; (2) Detection and isolation of yeast clones secreting amylase; and (3) PCR amplification of the insert directly from the yeast colony and purification of the DNA for sequencing and further analysis.

The yeast strain used was HD56-5A (ATCC-90785). This strain has the following genotype: MAT alpha, ura3-52, leu2-3, leu2-112, his3-11, his3-15, MAL⁺, SUC⁺, GAL⁺. Preferably, yeast mutants can be employed that have deficient post-translational pathways. Such mutants may have translocation deficient alleles in sec71, sec72, sec62, with truncated sec71 being most preferred. Alternatively, antagonists (including antisense nucleotides and/or ligands) which interfere with the normal operation of these genes, other proteins implicated in this post translation pathway (e.g., SEC61p, SEC72p, SEC62p, SEC63p, TDJ1p or SSA1p-4p) or the complex formation of these proteins may also be preferably employed in combination with the amylase-expressing yeast.

Transformation was performed based on the protocol outlined by Gietz et al., *Nucl. Acid. Res.*, 20:1425 (1992). Transformed cells were then inoculated from agar into YEPD complex media broth (100 ml) and grown overnight at 30° C. The YEPD broth was prepared as described in Kaiser et al., *Methods in Yeast Genetics*, Cold Spring Harbor Press, Cold Spring Harbor, N.Y., p. 207 (1994). The overnight culture was then diluted to about 2×10⁶ cells/ml (approx. $OD_{600}$=0.1) into fresh YEPD broth (500 ml) and regrown to 1×10⁷ cells/ml (approx. $OD_{600}$=0.4-0.5).

The cells were then harvested and prepared for transformation by transfer into GS3 rotor bottles in a Sorval GS3 rotor at 5,000 rpm for 5 minutes, the supernatant discarded, and then resuspended into sterile water, and centrifuged again in 50 ml falcon tubes at 3,500 rpm in a Beckman GS-6KR centrifuge. The supernatant was discarded and the cells were subsequently washed with LiAc/TE (10 ml, 10 mM Tris-HCl, 1 mM EDTA pH 7.5, 100 mM $Li_2OOCCH_3$), and resuspended into LiAc/TE (2.5 ml).

Transformation took place by mixing the prepared cells (100 μl) with freshly denatured single stranded salmon testes DNA (Lofstrand Labs, Gaithersburg, Md.) and transforming DNA (1 μg, vol. <10 μl) in microfuge tubes. The mixture was mixed briefly by vortexing, then 40% PEG/TE (600 μl, 40% polyethylene glycol-4000, 10 mM Tris-HCl, 1 mM EDTA, 100 mM $Li_2OOCCH_3$, pH 7.5) was added. This mixture was gently mixed and incubated at 30° C. while agitating for 30 minutes. The cells were then heat shocked at 42° C. for 15 minutes, and the reaction vessel centrifuged in a microfuge at 12,000 rpm for 5-10 seconds, decanted and resuspended into TE (500 μl, 10 mM Tris-HCl, 1 mM EDTA pH 7.5) followed by recentrifugation. The cells were then diluted into TE (1 ml) and aliquots (200 μl) were spread onto the selective media previously prepared in 150 mm growth plates (VWR).

Alternatively, instead of multiple small reactions, the transformation was performed using a single, large scale reaction, wherein reagent amounts were scaled up accordingly.

The selective media used was a synthetic complete dextrose agar lacking uracil (SCD-Ura) prepared as described in Kaiser et al., *Methods in Yeast Genetics*, Cold Spring Harbor Press, Cold Spring Harbor, N.Y., p. 208-210 (1994). Transformants were grown at 30° C. for 2-3 days.

The detection of colonies secreting amylase was performed by including red starch in the selective growth media. Starch was coupled to the red dye (Reactive Red-120, Sigma) as per the procedure described by Biely et al., *Anal. Biochem.*, 172:176-179 (1988). The coupled starch was incorporated into the SCD-Ura agar plates at a final concentration of 0.15% (w/v), and was buffered with potassium phosphate to a pH of 7.0 (50-100 mM final concentration).

The positive colonies were picked and streaked across fresh selective media (onto 150 mm plates) in order to obtain well isolated and identifiable single colonies. Well isolated single colonies positive for amylase secretion were detected by direct incorporation of red starch into buffered SCD-Ura agar. Positive colonies were determined by their ability to break down starch resulting in a clear halo around the positive colony visualized directly.

4. Isolation of DNA by PCR Amplification

When a positive colony was isolated, a portion of it was picked by a toothpick and diluted into sterile water (30 µl) in a 96 well plate. At this time, the positive colonies were either frozen and stored for subsequent analysis or immediately amplified. An aliquot of cells (5 µl) was used as a template for the PCR reaction in a 25 µl volume containing 0.5 µl Klentaq (Clontech, Palo Alto, Calif.); 4.0 µl 10 mM dNTP's (Perkin Elmer-Cetus); 2.5 µl Kentaq buffer (Clontech); 0.25 µl forward oligo 1; 0.25 µl reverse oligo 2; 12.5 µl distilled water. The sequence of the forward oligonucleotide 1 was:

```
                                          (SEQ ID NO: 21)
5'-TGTAAAACGACGGCCAGTTAAATAGACCTGCAATTATTAATCT-3'
```

The sequence of reverse oligonucleotide 2 was:

```
                                          (SEQ ID NO: 22)
5'-CAGGAAACAGCTATGACCACCTGCACACCTGCAAATCCATT-3'
```

PCR was then performed as follows:

| a. |  | Denature | 92° C., 5 minutes |
|---|---|---|---|
| b. | 3 cycles of: | Denature | 92° C., 30 seconds |
|  |  | Anneal | 59° C., 30 seconds |
|  |  | Extend | 72° C., 60 seconds |
| c. | 3 cycles of: | Denature | 92° C., 30 seconds |
|  |  | Anneal | 57° C., 30 seconds |
|  |  | Extend | 72° C., 60 seconds |
| d. | 25 cycles of: | Denature | 92° C., 30 seconds |
|  |  | Anneal | 55° C., 30 seconds |
|  |  | Extend | 72° C., 60 seconds |
| e. |  | Hold | 4° C. |

The underlined regions of the oligonucleotides annealed to the ADH promoter region and the amylase region, respectively, and amplified a 307 bp region from vector pSST-AMY.0 when no insert was present. Typically, the first 18 nucleotides of the 5' end of these oligonucleotides contained annealing sites for the sequencing primers. Thus, the total product of the PCR reaction from an empty vector was 343 bp. However, signal sequence-fused cDNA resulted in considerably longer nucleotide sequences.

Following the PCR, an aliquot of the reaction (5 µl) was examined by agarose gel electrophoresis in a 1% agarose gel using a Tris-Borate-EDTA (TBE) buffering system as described by Sambrook et al., supra. Clones resulting in a single strong PCR product larger than 400 bp were further analyzed by DNA sequencing after purification with a 96 Qiaquick PCR clean-up column (Qiagen Inc., Chatsworth, Calif.).

5. Identification of Full-Length Clone

A cDNA sequence was isolated in the above screen and compared to a variety of expressed sequence tag (EST) databases which included public EST databases (e.g., GenBank, Merck/Wash. U.) And a proprietary EST DNA database (LIFESEQ®, Incyte Pharmaceuticals, Palo Alto, Calif.) to identify existing homologies. The homology search was performed using the computer program BLAST or BLAST2 (Altshul et al., *Methods in Enzymology* 266:460-480 (1996)). Those comparisons resulting in a BLAST score of 70 (or in some cases 90) or greater that did not encode known proteins were clustered and assembled into consensus DNA sequences with the program "phrap" (Phil Green, University of Washington, Seattle Wash.). The consensus sequence obtained is herein designated: "DNA76621".

Based on the DNA76621 sequence, oligonucleotide probes were generated and used to screen a human testis library prepared as described in paragraph 1 above. The cloning vector was pRK5B (pRK5B is a precursors of pRK5D that does not contain the SfiI site; see Holmes et al., *Science* 253:1278-1280 (1991)), and the cDNA size cut was less than 2800 bp.

PCR primers (forward and reverse) were synthesized:

```
forward PCR primer:
5'-GGCTCACAGGGGACGATGTCAAGC-3'  (SEQ ID NO: 39)

reverse PCR primer:
5'-CTCCAGCTTTCCCAAGCCCAGAGC-3'  (SEQ ID NO: 40)
```

Additionally, a synthetic oligonucleotide hybridization probe was constructed fro the DNA76621 sequence which had the following nucleotide sequence:

```
hybridization probe:
                                          (SEQ ID NO: 41)
5'-TGGCTCCTTCTCAGCCTTGTTGCTGTAACTGCTGCTCAGTCCA

CC-3'
```

In order to screen several libraries for a full-length clone, DNA from the libraries was screened by PCR amplification with the PCR primer pair identified above. A positive library was then used to isolate clones encoding the PRO1885 gene using the probe oligonucleotide and one of the PCR primers.

A full-length clone was identified (designated DNA79302-2521) that contained a single open reading frame with an apparent translational initiation site at nucleotide positions 40-42, and a stop signal at nucleotide positions 1705-1707 (FIG. 19; SEQ ID NO:19). The predicted polypeptide precursor is 555 amino acids long (FIG. 20; SEQ ID NO:20) and has a calculated molecular weight of approximately 63913 daltons and an estimated pI of approximately 4.99. Clone DNA79302-2521 (UNQ868) has been deposited with the ATCC and is assigned ATCC deposit no. 203545 on Dec. 22, 1998.

An analysis of the Dayhoff database (version 35.45 Swiss Prot 35), using a WU-BLAST2 sequence alignment analysis of the full-length sequence shown in FIG. 20 (SEQ ID NO:20); evidenced sequence identity between the PRO1885 amino acid sequence and the following Dayhoff sequences: A31567_1, P_R10426, ACE_HUMAN, P_R04111, A00914_1, ACE_DROME, P_R70013, S81361_1, S57157 and P_R65207.

Example 13

Generation and Analysis of Mice Comprising PRO227, PRO233, PRO238, PRO1328, PRO4342, PRO7423, PRO10096, PRO21384, PRO353 or PRO1885 Gene Disruptions To investigate the role of PRO227, PRO233, PRO238, PRO1328, PRO4342, PRO7423, PRO10096, PRO21384, PRO353 or PRO1885 polypeptides, disruptions in PRO227, PRO233, PRO238, PRO1328, PRO4342, PRO7423, PRO10096, PRO21384, PRO353 or PRO1885 genes were produced by homologous recombination. Specifically, transgenic mice comprising disruptions in PRO227, PRO233, PRO238, PRO1328, PRO4342, PRO7423, PRO10096, PRO21384, PRO353 or PRO1885 genes (i.e., knockout mice) were created by either gene targeting or gene trapping. Mutations were confirmed by southern blot analysis to confirm correct targeting on both the 5' and 3' ends. Gene-specific genotyping was also performed by genomic PCR to confirm the loss of the endogenous native transcript as demonstrated by RT-PCR using primers that anneal to exons flanking the site of insertion. Targeting vectors were electroporated into 129 strain ES cells and targeted clones were identified. Targeted clones were microinjected into host blastocysts to produce chimeras. Chimeras were bred with C57 animals to produce F1 heterozygotes. Heterozygotes were intercrossed to produce F2 wildtype, heterozygote and homozygote cohorts which were used for phenotypic analysis. Rarely, if not enough F1 heterozygotes were produced, the F1 hets were bred to wildtype C57 mice to produce sufficient heterozygotes to breed for cohorts to be analyzed for a phenotype. All phenotypic analysis was performed from 12-16 weeks after birth.

Overall Summary of Results:

A. Generation and Analysis of Mice Comprising DNA33786-1132 (UNQ201) Gene Disruptions In these knockout experiments, the gene encoding PRO227 polypeptides (designated as DNA33786-1132 (UNQ201) was disrupted. The gene specific information for these studies is as follows: the mutated mouse gene corresponds to nucleotide reference: NM_181074: or *Mus musculus* RIKEN cDNA 4930471K13 gene (4930471K13Rik); protein reference: NP_851419 or *Mus musculus* RIKEN cDNA 4930471K13; the human gene sequence reference: BC011057 or *homo sapiens* hypothetical protein FLJ14594 (cDNA clone MGC:17422 IMAGE: 4214343); the human protein sequence corresponds to reference: AAH11057 or *Homo sapiens* hypothetical protein FLJ14594. Mutation Specific Information corresponds to Homologous Recombination (standard) wherein Exon 2 was targeted (NM_181074).

The targeted mouse gene is represented by NCBI accession NM_181074, which is an ortholog of human hypothetical protein FLJ14594. FLJ14594 has features consistent with a type I plasma membrane protein; contains leucine-rich repeats, an immunoglobulin (Ig)-like domain, a transmembrane segment, and possibly a short cytoplasmic C terminus. The hypothetical protein belongs to a gene family comprised of three members, all having no known function (EnsEMBL protein family ENSF00000002632).

Both leucine-rich repeats and Ig-like domains are usually involved in protein-protein interactions and found in a wide variety of proteins (Pfam PF00560 and PF00047). The domain organization and predicted cell location (plasma membrane) of this hypothetical protein suggests that it may function as a cell adhesion molecule, receptor, or ligand.

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice.

|  | wt | het | hom | Total |
|---|---|---|---|---|
| Observed | 19 | 49 | 32 | 100 |
| Expected | 25 | 50 | 25 | 100 |

Chi-Sq. = 3.42 Significance = 0.18087 (hom/n) = 0.32 Avg. Litter Size = 0

Expression of the target gene was detected in embryonic stem (ES) cells and in all 13 adult tissue samples tested by RT-PCR, except bone, small intestine and colon, and adipose. Disruption of the target gene was confirmed by Southern hybridization analysis.

Phenotypic analysis was performed on mice from this generation as described below.

1. Overall Phenotypic Analysis (for Disrupted Gene: DNA33786-1132 (UNQ201)

(a) Overall Phenotypic Summary:

Mutation of the gene encoding the ortholog of human hypothetical protein FLJ14594 (FLJ14594) resulted in growth retardation in (−/−) mice. The homozygous mutant mice were smaller than their wild-type littermates, exhibiting decreased mean body length, total tissue mass, and lean body mass. The (−/−) mice also exhibited a decreased bone mineral-related measurements. Both serum cholesterol and triglycerides were elevated in (−/−) mutant mice. Gene disruption was confirmed by Southern blot.

(b) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

DEXA Results: Both the male and female (−/−) mice exhibited decreased mean total tissue mass and lean body mass when compared with their gender-matched (+/+) littermates and the historical means. These mutant mice also exhibited decreased mean bone mineral content and bone mineral density in total body, femur, and vertebrae.

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 veterbra traebecular bone volume, traebecular thickness, connectivity density and midshaft femur total bone area and cortical thickness. The µCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Micro-CT Analysis Results: The male (−/−) mice exhibited decreased mean vertebral trabecular bone volume, thickness, and connectivity density when compared with their gender-matched (+/+) littermates and the historical means. These mutants also exhibited decreased mean femoral mid-shaft cortical thickness and cross-sectional area.

[Analyzed wt/het/hom: 4/4/8]

Body Measurements: A measurement of length was performed at approximately 16 weeks of age. The (−/−) mice exhibited a decreased weight gain and decreased mean body length, decreased total tissue mass and decreased lean body mass when compared with their gender-matched (+/+) littermates and the historical mean.

These results demonstrate that knockout mutant male mice deficient in the gene encoding PRO227 polypeptides exhibit growth retardation as well as abnormal bone metabolism with significant bone loss characterized by a decrease in bone mass with decreased density and possibly fragility leading to bone fractures. In addition to the observed bone metabolism abnormalities, these studies indicated that (−/−) mutant mice also showed signs of growth retardation. The bony changes may be a result of the decreased body size and mass of these mice as suggested by the fact that the gene is not expressed in the bone. Such growth disorders are associated with the phenotype or physiological condition associated with tissue wasting diseases such as diabetes or cachexia. Thus, PRO227 polypeptides or agonists thereof would be useful for treating diabetes or cachexia.

No hypercalcemia, or hyperglycemia was detected in blood chemistry tests to suggest renal, parathyroid, or adrenal dysfunction that might be related to the decrease in bone mineral density seen on the Dexa scan. However, the (+/−) and (−/−) mice showed more wide variation in their alkaline phosphatase levels. Although the PRO227 encoding gene is not expressed in the bone, the secondary affects caused by growth retardation suggests that PRO227 would be important for maintaining bone homeostasis and bone healing or would be useful for the treatment of arthritis or osteoporosis; whereas antagonists to PRO227 or its encoding gene would lead to abnormal or pathological bone disorders including inflammatory diseases associated with abnormal bone metabolism such as arthritis. [Analyzed wt/het/hom: 14/29/17]

(c) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes, cancer and/or obesity.

The phenotypic tests in this instance included the measurement of serum cholesterol and triglycerides Blood Lipids Procedure:

A cohort of 4 wild type, 4 heterozygotes and 8 homozygotes were tested in this assay. High cholesterol and elevated triglyceride levels are recognized risk factors in the development of cardiovascular disease. Measuring blood lipids allowed finding of the biological switches that regulate blood lipid levels and that upon inhibition would lead to a reduction in the risk for cardiovascular disease. Cholesterol measurements were recorded. The COBAS Integra 400 (mfr: Roche) was used for running blood chemistry tests on mice.

Results:

Both heterozygous (+/−) and homozygous (−/−) mutant mice exhibited an increased mean serum cholesterol and triglyceride levels when compared with their gender-matched (+/+) littermates and the historical mean. (Analyzed wt/het/hom: 4/4/8)

Thus, mutant mice deficient in the PRO227 gene can serve as a model for cardiovascular disease. PRO227 or its encoding gene would be useful in regulating blood lipids and in particular maintaining normal cholesterol and triglyceride levels. Thus PRO227 polypeptides would be useful in the treatment of such cardiovascular diseases as: hypertension, atherosclerosis, heart failure, stroke, various coronary artery diseases and/or diabetes.

B. Generation and Analysis of Mice Comprising DNA34436-1238 (UNQ207) Gene Disruptions In these knockout experiments, the gene encoding PRO233 polypeptides (designated as DNA34436-1238 (UNQ207) was disrupted. The gene specific information for these studies is as follows: the mutated mouse gene corresponds to nucleotide reference: NM_053262: or *Mus musculus* retinal short-chain dehydrogenase/reductase 2 gene; protein reference: NP_444492 or *Mus musculus* retinal short-chain dehydrogenase/reductase 2; the human gene sequence reference: BQ927122 (AGENCOURT_8802906 NIH_MGC_40 *Homo sapiens* cDNA clone IMAGE: 638241); the human protein sequence corresponds to reference: AAH21673 or *Homo sapiens* retinal short-chain dehydrogenase/reductase 2. Mutation Specific Information corresponds to retroviral insertion (OST). Retroviral insertion disrupted the gene prior to the exon encoding amino acid 55 in a protein of 298 amino acids (NCBI accession number NP_444492).

The disrupted mouse gene is retinal short-chain dehydrogenase/reductase 2 (retsdr2), ortholog of human RETSDR2. Aliases include SDR2, Pan1b, RetSDR2, Hsd17b11, hydroxysteroid (17-beta) dehydrogenase 11, retinal short-chain dehydrogenase/reductase SDR2, 17-BETA-HSD11, 17betaHSD11, 17-BETA-HSDXI, and 17-beta-hydroxysteroid dehydrogenase type XI.

RETSDR2 converts 5 alpha-androstane-3 alpha, 17 beta-diol (a metabolite of dihydrostestosterone) into androsterone, such activity being first documented in lung (Brereton et al., *Mol. Cell. Endocrinol.*, 171(1-2): 111-7 (2001)) though expression of the gene is reported in other tissues. Overall, RETSDR2 is well expressed in cells involved with steroidogeneisis and the enzyme is proposed to have an important role in androgen metabolism (Li et al., *Endocr. Res.*, 24(3-4): 663-7 (1998); Chai et al., *Endocrinology*, 144(5):2084-91 (2003)).

Targeted or gene trap mutations were generated in strain 129SvEv$^{Brd}$-derived embryonic stem (ES) cells. The wild-type expression panel resulted in the following observation: expression of the target gene was detected in embryonic stem (ES) cells and, among the 13 adult tissue samples tested by RT-PCR, in bone, skin fibroblast, adipose, and tail. Disruption of the target gene was confirmed by Southern hybridization analysis. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice.

|          | wt | het | hom | Total |
|----------|----|----|----|----|
| Observed | 24 | 46 | 30 | 100 |
| Expected | 25 | 50 | 25 | 100 |

Chi-Sq. = 1.36 Significance = 0.50662 (hom/n) = 0.30 Litter Size = 0

The wild-type expression panel showed that the expression of the gene was detected in embryonic stem (ES) cells and, among the 13 adult tissue samples tested by RT-PCR, in brain, spinal cord, thymus, bone, and adipose. RT-PCR analysis revealed that the transcript was absent in the (−/−) mouse analyzed.

Phenotypic analysis was performed on mice from this generation as described below.

1. Phenotypic Analysis (for Disrupted Gene: DNA34436-1238 (UNQ207)

(a) Overall Phenotypic Summary:

Mutation of the gene encoding the ortholog of human retinal short-chain dehydrogenase/reductase 2 (RETSDR2) resulted in a 2½ fold increased percentage of immature B cells in bone marrow. In addition, (−/−) mice exhibited consistent alterations in bone marrow, but no effects were seen in thymus or spleen. Lymph node FACS showed trends in increased cell number for certain cell types. RT-PCR analyses revealed that the transcript was absent in the homozygous mutant mice.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

Flourescence-Activated Cell-Sorting (FACS) Analysis/Tissue Specific FACS Analysis Procedure: FACS analysis of immune cell composition from peripheral blood was performed including analysis of CD4, CD8 and T cell receptors to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results: Tissue specific FACS analysis gave the following results: The (−/−) mice exhibited a 2½ fold increase percentage of immature B cells in bone marrow when compared with their (+/+) littermates and the historical mean. Lymph node FACS analysis showed increased cell number for certain cell types (TcR+ cells; CD19+ cells; and GR1-cells).

In summary, tissue specific FACS analysis indicate that knockout mice deficient in the gene encoding PRO233 polypeptides exhibit immunological abnormalities when compared with their wild-type littermates. The mutant mice exhibited an abnormal immune cell composition and tissue specific FACS analysis, suggesting that inhibitors or antagonists to PRO233 polypeptides would stimulate the immune system (such as T cell proliferation) and would find utility in the cases wherein this effect would be beneficial to the individual such as in the case of leukemia, and other types of cancer, and in immunocompromised patients, such as AIDS sufferers. Accordingly, PRO233 polypeptides or agonists thereof would inhibit the immune response and would be useful candidates for suppressing harmful immune responses, e.g. in the case of graft rejection or graft-versus-host diseases.

C. Generation and Analysis of Mice Comprising DNA35600-1162 (UNQ212) Gene Disruptions In these knockout experiments, the gene encoding PRO238 polypeptides (designated as DNA35600-1162 (UNQ212) was disrupted. The gene specific information for these studies is as follows: the mutated mouse gene corresponds to nucleotide reference: NM_145428: or *Mus musculus* similar to DKFZP566O084 protein (LOC216820); protein reference: NP_663403 or *Mus musculus* similar to DKFZP566O084 protein; the human gene sequence reference: NM_015510 or DKFZP566O084 protein gene; the human protein sequence corresponds to reference: NP_056325 or *Homo sapiens* DKFZP566O084 protein. Mutation Specific Information corresponds to retroviral insertion (OST). Retroviral insertion disrupted the gene prior to the exon encoding amino acid 18 in a protein of 323 amino acids (NCBI accession number NP_663403).

The gene of interest is represented by NCBI accession NM_145428, ortholog of human DKFZP566O084 protein. Aliases include cDNA sequence BC003479, LOC216820, CGI-93 and MGC8916.

DKFZp566O084 is a hypothetical protein containing a short chain dehydrogenase domain (Pfam PF00106). Typically, such proteins are NAD- or NADP-dependent oxidoreductases. A signal peptide is predicted at the N-terminus, and ProtComp (Softberry, Inc. Mount Kisco, N.Y.) software analysis indicates the protein may be targeted to the mitochondrion.

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice.

|  | wt | het | hom | Total |
|---|---|---|---|---|
| Observed | 26 | 58 | 16 | 100 |
| Expected | 25 | 50 | 25 | 100 |

Chi-Sq. = 4.56 Significance = 0.10228 (hom/n) = 0.16 Avg. Litter size = 0

In the wild-type animals, expression of the target gene was detected in embryonic stem (ES) cells and in all 19 adult tissue samples tested by RT-PCR, except asthmatic lung, skeletal muscle, and adipose tissue. Genetic data indicate that this retroviral insertion resulted in lethality of the homozygous mutants. Due to lethality, transcript expression analysis was not performed. It is not clear when lethality occurs but by three weeks of age all of the (−/−) mutant mice were dead.

Discussion Related to Embryonic Developmental Abnormality of Lethality:

Embryonic lethality in knockout mice usually results from various serious developmental problems including but not limited to neurodegenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs. In the instant example, PRO238 mutant mice showed serious and multiple physiological abnormalities involving the gastrointestinal tract (GI), hematopoietic, respiratory, neuromuscular, and reproductive systems.

1. Overall Phenotypic Analysis (for Disrupted Gene: DNA35600-1162 (UNQ212)

(a) Overall Phenotypic Summary:

Multiple histological defects were observed in KO mice involving GI, hematopoietic, respiratory, neuromuscular, and reproductive systems. Necropsy revealed that the 13 day-old homozygous mutants exhibited numerous lesions, including megaesophagus and hypoplasia of the glandular stomach. Three fourths of the (−/−) mice exhibited thymic atrophy, lymphoid depletion, and muscle degeneration. Exophthalmus was present in most homozygotes. Homozygous mutant mice resulted in embryonic lethality by three weeks of age. Thus, PRO238 polypeptides or the gene encoding PRO238 must be essential for embryonic development.

(b) Pathology Analysis

Multiple histological defects were observed in KO mice involving GI, hematopoietic, respiratory, neuromuscular, and reproductive systems. Necropsy revealed that the 13 day-old homozygous mutants exhibited numerous lesions, including megaesophagus and hypoplasia of the glandular stomach. Three fourths of the (−/−) mice exhibited thymic atrophy, lymphoid depletion, and muscle degeneration. Exophthalmus was present in most homozygotes. In the GI tract, esophageal dilatation with multifocal hyperkeratosis, as well as gastric hypoplasia was observed with significantly reduced parietal cells and chief cells. These KO mice appeared to be stressed with thymic atrophy/necrosis and/or splenic lymphoid depletion. Increased hematopoiesis was also noted in bone marrow, liver, spleen and thymus. Aspiration pneumonia was found in several mice, which may be related to esophageal dysfunction. Other findings included seminiferous tubule necrosis, multifocal vacuolation in brain, focal muscular degeneration, and diffuse degeneration in the Harderia gland. All the (−/−) mice died by three weeks of age.

As summarized above, embryonic lethality in knockout mice usually results from various serious developmental problems including but not limited to neurodegenerative diseases, angiogenic disorders, inflammatory diseases, or where the gene/protein has an important role in basic cell signaling processes in many cell types. In addition, embryonic lethals are useful as potential cancer models. In the instant example, it is likely that antagonists to PRO238 or its encoding gene results in serious disorders of the gastrointestinal tract and could lead to such disorders as stomach or esophageal cancer. Likewise, PRO238 or agonists would be useful in the treatment of gastrointestinal disorders including cancer.

D. Generation and Analysis of Mice Comprising DNA66658-1584 (UNQ688) Gene Disruptions In these knockout experiments, the gene encoding PRO1328 polypeptides (designated as DNA66658-1584 (UNQ688) was disrupted. The gene specific information for these studies is as follows: the mutated mouse gene corresponds to nucleotide reference: NM_026674 or *Mus musculus* RIKEN cDNA 0610008A10 gene (0610008A10Rik); protein reference: BAB22004; the human gene sequence reference: NM_031301 or *Homo sapiens* which is likely the ortholog of *C. elegans* anterior pharynx defective 1B (APH-1B); protein reference: AAH20905 or hypothetical protein DKFZp564D0372 [*Homo sapiens*]. Mutation Specific Information corresponds to homologous recombination (conditional) (codon 2 was targeted).

The mouse gene targeted is represented by RIKEN cDNA 0610008A10, which is orthologous to human anterior pharynx defective 1B-like (PSFL). Aliases include presenilin stabilization factor-like and APH-1B. PSFL consists of a signal peptide sequence and six or seven transmembrane spanning segments. The protein is predicted to be located at the plasma membrane, as determined by ProtComp analysis (Softberry, Inc., Mount Kisco, N.Y., 2003).

PSFL interacts with presenilin enhancer 2, nicastrin, and presenilin. PSFL is required for the activity and accumulation of gamma-secretase, which is involved in Notch and beta-amyloid precursor protein signaling. Notch is involved in developmental cell fate, and beta-amyloid precursor protein is involved in gene expression and Alzheimer's disease.

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice.

|  | wt | het | hom | Total |
|---|---|---|---|---|
| Observed | 12 | 29 | 16 | 57 |
| Expected | 14.25 | 28.5 | 14.25 | 57 |

Chi-Sq. = 0.58 Significance = 0.74866 (hom/n) = 0.28 Avg. Liter Size = 0

Level I phenotypic analysis was performed on mice from this generation as described below.

Wild-type expression of the target gene was detected in embryonic stem (ES) cells and in all 13 adult tissue samples tested by RT-PCR, except tail. Disruption of the target gene was confirmed by Southern hybridization analysis.

1. Phenotypic Analysis (for Disrupted Gene: DNA66658-1584 (UNQ688)

(a) Overall Phenotypic Summary

The male and female (−/−) mice exhibited increased mean serum cholesterol levels when compared with their gender-matched (+/+) littermates and the historical means. In addition, abnormalities in the urinalysis was observed in the homozygous mice.

(b) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), cancer and/or obesity.

The phenotypic tests included the measurement of serum cholesterol and triglycerides.

Blood Lipids

Procedure:

A cohort of 4 wild type, 4 heterozygotes and 8 homozygotes were tested in this assay. High cholesterol levels are recognized risk factors in the development of cardiovascular disease. Measuring blood lipids allowed finding of the biological switches that regulate blood lipid levels and that upon inhibition would lead to a reduction in the risk for cardiovascular disease. Cholesterol measurements were recorded. The COBAS Integra 400 (mfr: Roche) was used for running blood chemistry tests on mice.

Results:

As summarized above, the (−/−) mice exhibited an increased mean serum cholesterol level (compared to normal levels) when compared with their gender-matched (+/+) littermates and the historical mean. No change in triglycerides was observed. (Analyzed Wt/Het/Hom: 4/4/8)

Thus, mutant mice deficient in the PRO1328 can serve as a model for cardiovascular disease. PRO1328 or its encoding gene would be useful for regulating blood lipids and in particular maintaining normal cholesterol and triglyceride levels. Thus, PRO1328 polypeptides would be useful in the treatment of such cardiovascular diseases as: hypertension, atherosclerosis, heart failure, stroke, various coronary artery diseases, and/or obesity or diabetes.

Urinalysis:

Test Description:

The routine urinalysis is a screening test done to provide a general evaluation of the renal/urinary system. The characteristics for which urine is routinely examined includes tests for protein, glucose, ketones, blood, bilirubin, urobilinogen, nitrate and leukocyte esterase, as well as pH and specific gravity. The histograms show 9 measurements grouped by genotype: Leukocyte, nitrate, protein, glucose, osmolality, ketone, urobilinogen, bilirubin, blood.

Results:

The (−/−) mutant mice showed abnormalities in the urinalysis as described above. Elevated levels of urobilinogen, ketones and blood were observed. The presence of ketones in the urine is indicative of an abnormal lipid metabolism or dyslipidemia which may be an early sign of the onset of diabetes.

E. Generation and Analysis of Mice Comprising DNA96787-2534-1 (UNQ1896) Gene Disruptions In these knockout experiments, the gene encoding PRO4342 polypeptides (designated as DNA96787-2534-1 (UNQ1896) was disrupted. The gene specific information for these studies is as follows: the mutated mouse gene corresponds to nucleotide reference: NM_019451 or *Mus musculus* interleukin 1 family, member 5 (delta) (Il1f5); protein reference: NP_062324 or interleukin 1 family, member 5; interleukin 1 receptor antagonist homolog 1 [*Mus musculus*]; the human gene sequence reference: NM_012275 or *Homo sapiens* interleukin 1 family, member 5 (delta) (IL1F5), transcript variant 1; protein reference: NP_036407 or interleukin 1 family, member 5; interleukin-1 receptor antagonist homolog 1; interleukin 1, delta; interleukin-1-like protein 1; family of interleukin 1-delta; interleukin-1 HY1; IL-1ra homolog; IL-1 related protein 3 [*Homo sapiens*]. Mutation Specific Information corresponds to homologous recombination (standard) (exons 3, 4 and 5 were targeted—AK014576).

The disrupted mouse gene is an interleukin 1 family, member 5 (delta) (Il1f5), ortholog of human interleukin 1 family, member 5 (delta) (IL1F5). Aliases include IL-1H3, IL1HY1, FIL1delta, interleukin 1 receptor antagonist homolog 1, FIL1, FIL1D, IL1L1, IL1RP3, MGC29840, IL-1ra homolog, interleukin-1 HY1, IL-1 related protein 3, interleukin-1-like protein 1, family of interleukin 1-delta, and interleukin-1 receptor antagonist homolog 1.

IL1F5, a member of the interleukin 1 cytokine family, specifically inhibits activation of nuclear factor-kappaB by IL1F6 (interleukin 1 family, member 6 [epsilon]); (Debets et al., *J. Immunol.* 167(3):1440-6 (2001)). However, IL1F5 does not have antagonist activities associated with its close paralog, IL1RN (interleukin 1 receptor antagonist; (Barton et al., *Eur J Immunol* 30(11):3299-308 (2000)). Allelic variation in IL1F5 has been suggested as a predisposing factor in some forms of severe alopecia areata (Tazi-Ahnini et al., *Eur J Immunogenet* 29(1):25-30 (2002)). By similarity with other members of the interleukin 1 family, an extracellular location is inferred.

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis was performed on mice from this generation as described below.

|  | wt | het | hom | Total |
|---|---|---|---|---|
| Observed | 25 | 46 | 29 | 100 |
| Expected | 25 | 50 | 25 | 100 |

Chi-Sq. = 0.96 Significance = 0.61878 (hom/n) = 0.29 Avg. Litter Size = 0

Wild-type expression of the target gene was detected in embryonic stem (ES) cells and in all 13 adult samples tested by RT-PCR, except lung, liver, skeletal muscle, bone, and heart. Disruption of the target gene was confirmed by Southern hybridization analysis.

1. Phenotypic Analysis (for disrupted gene: DNA96787-2534-1 (UNQ1896)
   (a) Overall Phenotypic Summary
   The female (−/−) mice exhibited increased activity during home-cage activity testing when compared with their wild-type littermates and the historical means. Whiskers were absent on most homozygotes, with bald patches on the snouts. There was moderate degeneration of the seminiferous tubules in the male (−/−) mice examined.

(b) Phenotypic Analysis: CNS/Neurology
In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include include but are not limited to: depression, generalized anxiety disorders, attention deficit disorder, sleep disorder, hyperactivity disorder, obsessive compulsive disorder, schizophrenia, cognitive disorders, hyperalgesia and sensory disorders, mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:
Behavioral screens were performed on a cohort of 4 wild type, 4 heterozygous and 8 homozygous mutant mice. All behavioral tests were done between 12 and 16 weeks of age unless reduced viability necessitates earlier testing. These tests included measurements of circadian rhythms as well as a functional observational battery (FOB) to measure anxiety, or activity levels.

Circadian Test Description:
Female mice are individually housed at 4 pm on the first day of testing in 48.2 cm×26.5 cm home cages and administered food and water ad libitum. Animals are exposed to a 12-hour light/dark cycle with lights turning on at 7 am and turning off at 7 pm. The system software records the number of beam interruptions caused by the animal's movements, with beam breaks automatically divided into ambulations. Activity is recorded in 60, one-hour intervals during the three-day test. Data generated are displayed by median activity levels recorded for each hour (circadian rhythm) and median total activity during each light/dark cycle (locomotor activity) over the three-day testing period.

Results:
The female (−/−) mice exhibited increased ambulatory counts during the 12 hour habituation and both dark phases when compared with their gender-matched (+/+) littermates and the historical means. These results are indicative of increased anxiety of the (−/−) mutant mice.

Functional Observational Battery (FOB) Test:
Test Description The FOB is a series of situations applied to the animal to determine gross sensory and motor deficits. A subset of tests from the Irwin neurological screen that evaluates gross neurological function is used. In general, short-duration, tactile, olfactory, and visual stimuli are applied to the animal to determine their ability to detect and respond normally. These simple tests take approximately 10 minutes and the mouse is returned to its home cage at the end of testing.

Results:

Whiskers were absent on most homozygotes with bald patches on the snout. This finding is indicative of an increased anxiety level of the mutant (−/−) mice. In addition, the negative phenotype of alopecia (baldness) was observed. Thus, antagonists to PRO4342 would be a causative factor for alopecia (baldness). In this regard, PRO4342 or agonists would be useful in the treatment of balding or premature hair loss.

In summary, both the circadian rhythm testing and functional observational battery tests indicated an increased anxiety behavior pattern for the (−/−) mice. Thus, knockout mice demonstrated a phenotype consistent with "anxiety disorders" which include but are not limited to: mild to moderate anxiety, generalized anxiety disorder, panic attack, panic disorder with agoraphobia, panic disorder without agoraphobia, obsessive compulsive disorder, agoraphobia, bipolar disorder I or II, or cyclothymic disorder. In view of these findings, PRO4342 or agonists thereof would be useful for treating such neurological anxiety disorders.

(c) Pathology

Microscopic observations on the two male (−/−) mice examined exhibited a moderate degeneration of the seminiferous tubules. This negative phenotype suggests that antagonists to PRO4342 may lead to reproductive disorders. In contrast, PRO4342 or agonists thereof would be useful in the prevention or treatment of such reproductive disorders.

F. Generation and Analysis of Mice Comprising DNA108809 (UNQ2964) Gene Disruptions In these knockout experiments, the gene encoding PRO7423 polypeptides (designated as DNA108809 (UNQ2964) was disrupted. The gene specific information for these studies is as follows: the mutated mouse gene corresponds to nucleotide reference: AJ245857 or *Mus musculus* mRNA for carbonic anhydrase (MN/CA9 gene); protein reference: NP_647466 or carbonic anhydrase 9 [*Mus musculus*]; the human gene sequence reference: BC014950 or *Homo sapiens*, carbonic anhydrase IX, clone MGC:22967 IMAGE:4865275; protein reference: NP_001207 or carbonic anhydrase IX precursor; RCC-associated protein G250; carbonic dehydratase [*Homo sapiens*]. Mutation type corresponds to Homologous Recombination (standard). Coding exons 1 through 6 were targeted (NM_139305).

The disrupted mouse gene is carbonic anhydrase 9 (Car9), ortholog of human carbonic anhydrase 9 (CA9). Aliases include CAIX, MN/CA9, MN, membrane antigen MN, carbonic dehydratase, and RCC-associated protein G250. Carbonic anhydrases (CAs) are a large group of enzymes involved in numerous physiological functions such as respiration, bone resorption, and the formation of saliva, etc. Three major families of CAs are known; alpha, beta, and gamma CA9, an alpha family member, binds zinc and DNA, and has some similarity with transcription factors (Pastorek et al, Oncogene 9(10):2877-88 (1994)).

CA9 expression has been proposed as a marker for certain aggressive tumors (Potter and Harris, *Br J Cancer* 89(1):2-7 (2003), and its expression is induced by hypoxia (Olive et al, *Cancer Res* 61(24):8924-9 (2001)). CA9 is reported to reside in the plasma membrane, cytoplasm or extracellular spaces (Ivanov et al, *Am J Pathol* 158(3):905-19 (2001); Zavada et al., *Br J Cancer* 89(6):1067-71 (2003)).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice.

|  | wt | het | hom | Total |
|---|---|---|---|---|
| Observed | 30 | 43 | 27 | 100 |
| Expected | 25 | 50 | 25 | 100 |

Chi-Sq. = 2.14 Significance = 0.34301 hom/n Avg. Litter Size = 0

In the wild-type animals, expression of the target gene was detected in embryonic stem (ES) cells and in all 13 adult tissues samples tested by RT-PCR, except thymus, liver, testis, bone, heart, adipose, and blood. Disruption of the target gene was confirmed by Southern hybridization analysis.

1. Phenotypic Analysis (for Disrupted Gene: DNA108809 (UNQ2964)

(a) Overall Phenotypic Summary

The homozygous mutant mice exhibited an increased ability to respond to an inflammatory response after a zymosan challenge.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc.

In the area of immunology, targets were identified herein for the treatment of inflammation and inflammatory disorders. Immune related diseases could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Zymosan Challenge Assay—Peritoneal Inflammation:

Procedure: A cohort of 1 wild type and 2 homozygous mutants were used in this assay. Peritoneal leukocyte recruitment assays were used to identify targets that may regulate the inflammatory component of atherosclerosis. These assays detect abnormalities in immune cell recruitment to a site of inflammation. Zymosan (an agent which induces inflammation) was injected into the intraperitoneal cavity and fluid was later removed and measurements were taken of total WBC counts, neutrophil/monocyte ratio and percent granulocytes, monocytes, lymphocytes and eosinophils in the ip fluid.

Results: The (−/−) mice exhibited a notably increased total white blood cell count after zymosan challenge when compared with their (+/+) littermate and the historical range, suggestive of an increased response to an inflammatory stimulus in these mutants.

In summary, the zymosan challenge studies indicate that knockout mice deficient in the gene encoding PRO7423 polypeptides exhibit a proinflammatory response when compared with their wild-type littermates. Thus, antagonists of PRO7423 polypeptides would stimulate the immune system (such as T cell proliferation) and would find utility in the cases wherein this effect would be beneficial to the individual such as in the case of leukemia, and other types of cancer, and in immunocompromised patients, such as AIDS sufferers. Accordingly, PRO7423 polypeptides or agonists thereto would inhibit the immune response and would be useful candidates for suppressing harmful immune responses, e.g. in the case of graft rejection or graft-versus-host diseases.

G. Generation and Analysis of Mice Comprising DNA125185-2806 (UNQ3099) Gene Disruptions In these knockout experiments, the gene encoding PRO10096 polypeptides (designated as DNA125185-2806 (UNQ3099) was disrupted. The gene specific information for these studies is as follows: the mutated mouse gene corresponds to nucleotide reference: NM_016971 or *Mus musculus* interleukin 22 (Il122); protein reference: NP_058667 or interleukin 22; interleukin 10-related T cell-derived inducible factor; the human gene sequence reference: NM_020525 or *Homo sapiens* interleukin 22 (IL22); protein reference: NP_065386 or IL-10-related T-cell-derived inducible factor; interleukin 21 [*Homo sapiens*]. Mutation type corresponds to Homologous Recombination (conditional). Coding exons 1 through 4 were targeted (NM_016971).

The gene of interest is interleukin 22 (IL22), ortholog of human IL22. Aliases include IL-22, ILtif, IL-TIF, interleukin 10-related T cell-derived inducible factor, interleukin 21, IL21, TIFa, IL-21, ILTIF, IL-IL-D110, zcyto18, and TIFIL-23.

IL22, a homolog of IL-10, is a cytokine that binds to and signals through the class II cytokine receptor heterodimer IL-22RA1/CRF2-4 (Xu et al, *Proc Natl Acad Sci USA* 98(17): 9511-6 (2001)). IL22 triggers all three major mitogen-activated protein kinase pathways (Lejeune et al, *J Biol Chem* 277(37):33676-82 (2002)), activating signal transducer and activator of transcription (STAT) 1 STAT3, and STAT5 (Xie et al, *J Biol Chem* 275(40):31335-9 (2000)).

T cells and mast cells produce IL22 to induce acute-phase reactants in other tissues, suggesting IL22 is involved in inflammation (Xu et al, 2001 supra). Moreover, IL22 modulates IL-4 production from Th2T cells (Xie et al, 2000 supra). The cytokine receptor IL22RA2 is a naturally occurring antagonist of IL22 and may be an important regulator of IL22 in the immune response (Xu et al, 2001 supra). The interleukin 10 family of cytokines have been the subject of several reviews (Wolk et al., *J Immunol* 168(11):5397-402 (2002); Kotenko, S. V., *Cytokine Growth Factor Rev* 13(3):223-40 (2003); Conti et al., *Immunol Lett* 88(3):171-4 (2003)) and a crystal structure has been proposed for IL22 (Nagem et al., *Structure (Camb)* 10(8):1051-62 (2002)).

Interpreting the literature is done with caution because two of the aliases encountered for IL22 have been used to refer to other genes; IL-21 is an synonym for interleukin 21 (Locus-Link 50616), and IL-22 is an alias for interleukin 17D (Locus-Link 53342).

Current knowledge of IL-22 suggests it can induce a variety of "acute phase" proteins including serum amyloid A, PAP1, osteopontin, alpha1-antichymotrypsin, and haptoglobin, and S100A8, MMP-3, and mucins.

Targeted or gene trap mutations are generated in strain 129SvEv$^{Brd}$-derived embryonic stem (ES) cells. The chimeric mice are bred to C57BL/6J albino mice to generate F1 heterozygous animals. These progeny are crossed to hybrid 129SvEv$^{Brd}$/C57 Cre homozygous mice to generate mice carrying both the mutant and Cre alleles (compound heterozygous mice). The male compound heterozygous mice are then crossed to hybrid 129SvEv$^{Brd}$/C57 F1 mice, derived from crossing 129SvEv$^{Brd}$ mice to C57BL/6J mice, to generate heterozygous Cre-excised animals. Finally, these progeny are intercrossed to generate wild-type, Cre-excised heterozygous, and Cre-excised homozygous mice. Level I phenotypic analysis is performed on mice from this generation.

|  | wt | het | hom | Total |
|---|---|---|---|---|
| Observed | 14 | 37 | 20 | 71 |
| Expected | 17.75 | 35.5 | 17.75 | 71 |

Chi-Sq. = 1.14 Significance = 0.56529 (hom/n) = 0.28 Avg. Litter Size = 0

1. Phenotypic Analysis (for disrupted gene: DNA125185-2806 (UNQ3099)

(a) Overall Phenotypic Summary:

Mutation of the gene encoding the ortholog of human interleukin 22 (IL22) resulted in anxiety-related phenotypes and an abnormal exploratory response in (−/−) mice. Females showed an increased anxiety response in open field testing. The (−/−) mice also exhibited an increased percentage of CD4 cells and a decreased percentage of B cells in the peripheral blood. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc.

In the area of immunology, targets were identified herein for the treatment of inflammation and inflammatory disorders. Immune related diseases could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

Flourescence-Activated Cell-Sorting (FACS) Analysis

Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 6 wild type and 8 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio. The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:

The homozygous mutant mice exhibited an increased mean percentage of CD4+ cells and a decreased mean percentage of B cells when compared with their wild-type littermates. In summary, FACS analysis of immune cell composition from peripheral blood indicates that knockout mice exhibit immunological differences with respect to CD4 cells when compared with their wild-type littermates. Thus, antagonists of PRO10096 polypeptides or its encoding gene would elicit increased levels of CD4. The co-receptor CD4 molecule cooperates with the T-cell receptor which differentially recognizes MHC class II molecules in the antigen recognition process.

(c) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include include but are not limited to: depression, generalized anxiety disorders, attention deficit disorder, sleep disorder, hyperactivity disorder, obsessive compulsive disorder, schizophrenia, cognitive disorders, hyperalgesia and sensory disorders, mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the serotonin transporter, the dopamine transporter (Giros et al., Nature. 1996 Feb. 15; 379(6566):606-12), and the GABA receptor (Homanics et al., Proc Natl Acad Sci USA. 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value.

Results: A notable difference was observed during open field activity testing. The female (−/−) mice exhibited a decreased median sum time in the center area when compared with their gender-matched (+/+) littermates. This type of behavior is consistent with an increased anxiety like response. Knockout mice demonstrated a phenotype consistent with anxiety related disorders which are associated with mild to moderate anxiety, anxiety due to a general medical condition, and/or bipolar disorders; hyperactivity; sensory disorders; obsessive-compulsive disorders, schizophrenia or a paranoid personality. Thus, PRO10096 polypeptides or agonists thereof would be useful in the treatment of such neurological disorders or the amelioration of the symptoms associated with anxiety disorders.

H. Generation and Analysis of Mice Comprising DNA177313-2982 (UNQ6368) Gene Disruptions In these knockout experiments, the gene encoding PRO21384 polypeptides (designated as DNA177313-2982 (UNQ6368) was disrupted. The gene specific information for these studies is as follows: the mutated mouse gene corresponds to nucleotide reference: NM_139299 or *Mus musculus* gp130-like monocyte receptor (Glmr-pending); protein reference: NP_647460 or gp130-like monocyte receptor; cytokine receptor NR10 [*Mus musculus*]; the human gene sequence reference: NM_139017 or *Homo sapiens* gp130-like monocyte receptor (CRL3); protein reference: NP_620586 or gp130-like monocyte receptor; soluble type I cytokine receptor CRL3 [*Homo sapiens*]. Mutation type corresponds to Homologous Recombination (standard). Coding exon 4 was targeted.

The disrupted mouse gene is Gp130-like monocyte receptor (Glmr), ortholog of human gp130-like monocyte receptor (CRL3). Aliases include NR10, GLM-R, cytokine receptor NR10, GLMR, and soluble type I cytokine receptor CRL3. CRL3 is a novel type I cytokine receptor with homology to interleukin-6 receptor gp130 and granulocyte colony-stimulating factor receptor. CRL3 is expressed on CD14-positive cells, activates STAT3 and STAT5, and may be involved in monocyte maturation and development. Bioinformatic analyses indicate the receptor has a signal peptide sequence, a large extracellular domain, and a cytoplasmic signaling domain.

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis was performed on mice from this generation as shown below.

|  | wt | het | hom | Total |
|---|---|---|---|---|
| Observed | 22 | 54 | 24 | 100 |
| Expected | 25 | 50 | 25 | 100 |

Chi-Sq. = 0.72 Significance = 0.69768 (hom/n) = 0.24 Avg. Litter Size = 0

Wild-type expression of the target gene was detected all 13 adult tissue samples tested by RT-PCR, except liver, testis, small intestine and colon, heart, and tail. Disruption of the target gene was confirmed by Southern hybridization analysis.

1. Phenotypic Analysis (for Disrupted Gene: DNA177313-2982 (UNQ6368)

(a) Overall Phenotypic Summary:

The male homozygous mutant mice exhibited a decreased anxiety-like response during open field activity testing when compared with their gender-matched wild-type littermates and the historical mean. No other notable phenotype was observed for the homozygous mutant mice. Disruption of the target gene was confirmed by Southern hybridization analysis.

(b) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include include but are not limited to: depression, generalized anxiety disorders, attention deficit disorder, sleep disorder, hyperactivity disorder, obsessive compulsive disorder, schizophrenia, cognitive disorders, hyperalgesia and sensory disorders, mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the serotonin transporter, the dopamine transporter (Giros et al., Nature. 1996 Feb. 15; 379(6566):606-12), and the GABA receptor (Homanics et al., Proc Natl Acad Sci USA. 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value.

Results: A notable difference was observed during open field activity testing. The male (−/−) mice exhibited an increased median sum time in the center area when compared with their gender-matched (+/+) littermates, which is indicative of a decreased anxiety-like response in the mutants. Thus, male knockout mice demonstrated a phenotype consistent with depressive disorders, including depression, generalized anxiety disorders, attention deficit disorder, sleep disorder, hypoactivity disorder, obsessive compulsive disorder, schizophrenia, cognitive disorders, hyperalgesia and/or sensory disorders. Thus, PRO21384 polypeptides and agonists thereof would be useful in the treatment or amelioration of the symptoms associated with depressive disorders.

I. Generation and Analysis of Mice Comprising DNA41234-1242-1 (UNQ310) Gene Disruptions In these knockout experiments, the gene encoding PRO353 polypeptides (designated as DNA41234-1242-1 (UNQ310) was disrupted. The gene specific information for these studies is as follows: the mutated mouse gene corresponds to nucleotide reference: NM_019959 or *Mus musculus* putative secreted protein ZSIG37 (Zsig37); protein reference: NP_064343 or putative secreted protein ZSIG37 [*Mus musculus*]; the human gene sequence reference: AF232905 or *Homo sapiens* putative GPCR interacting protein GIP; protein reference: AAG44303 or putative GPCR interacting protein GIP [*Homo sapiens*]. Mutation type corresponds to Homologous Recombination (standard). Coding exon 4 was targeted (NM_019959).

The gene that is mutated in these animals is represented by mouse UniGene cluster Mm.23845, which is the ortholog of human cluster Hs.201398 (C1QTNF1). C1QTNF1 encodes G protein coupled receptor interacting protein [that is] complement-C1q tumor necrosis factor-related. Alternate names include GIP, CTRP1, ZSIG37 and FLJ90694.

C1QTNF1 encodes several distinct domains. The N-terminus contains two overlapping cysteine-rich regions characteristic of the TNFR/NGFR motif Receptors in this family include certain tumor necrosis factor receptors and nerve growth factor receptors. The C-terminus contains a C1q-like domain, a globular domain found in many collagens.

Overall, the protein has similarities to a variety of soluble collagens that are thought to be involved in defense processes, and may be membrane bound or secreted (by similarity).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis was performed on mice from this generation as shown below.

|  | wt | het | hom | Total |
|---|---|---|---|---|
| Observed | 23 | 37 | 9 | 69 |
| Expected | 17.5 | 34.5 | 17.25 | 69 |

Chi-Sq. = 6.04 Significance = 0.04872 (hom/n) = 0.13 Avg. Litter Size = 0

Disruption of the target gene was confirmed by Southern hybridization analysis.

1. Phenotypic Analysis (for Disrupted Gene: DNA41234-1242-1 (UNQ310)

(a) Overall Phenotypic Summary:

Knockout homozygous (−/−) and heterozygous (+/−) mice showed an increased blood glucose level. In addition, both also showed an increased level of ketones and proteins in the urine compared with wild-type littermates and the historical mean.

(b) Phenotypic Analysis: Metabolism—Blood Chemistry & Urinalysis

In the area of metabolism, targets may be identified for the treatment of diabetes.

Blood chemistry phenotypic analysis includes blood glucose measurements as well as urinalysis to determine if protein and/or ketone bodies may be present. Abnormal glucose metabolism may indicate the following disorders or conditions: cachexia, Diabetes Type 1 and Type 2, Syndrome X, and various cardiovascular diseases. The COBAS Integra 400 (mfr: Roche) was used for running blood chemistry tests on the mice. The routine urinalysis is a screening test done to provide a general evaluation of the renal/urinary system. The characteristics for which urine is routinely examined includes tests for protein, glucose, ketones, blood, bilirubin, urobilinogen, nitrate and leukocyte esterase, as well as pH and specific gravity.

Results: Blood chemistry and urinalysis tests results indicated increased levels of glucose in the blood as well as the presence of both protein and ketones in the urine for homozygous (−/−) mutant mice and heterozygous (+/−) mice compared with wild-type littermates and the historical mean. These results suggest a phenotype associated with diabetes. As such, PRO353 polypeptides and/or its encoding gene would be useful in maintaining normal glucose metabolism.

J. Generation and Analysis of Mice Comprising DNA79302-2521 (UNQ868) Gene Disruptions In these knockout experiments, the gene encoding PRO1885 polypeptides (designated as DNA79302-2521 (UNQ868) was disrupted. The gene specific information for these studies is as follows: the mutated mouse gene corresponds to nucleotide reference: AB053181 or *Mus musculus* ACE2 mRNA for angiotensin-converting enzyme-related carboxypeptidase; protein reference: BAB40431 or angiotensin-converting enzyme-related carboxypeptidase [*Mus musculus*]; the human gene sequence reference: NM_021804 or *Homo sapiens* angiotensin I converting enzyme (peptidyl-dipeptidase A) 2 (ACE2); protein reference: BAB40370 or ACE2. Mutation type corresponds to Homologous Recombination (standard). Coding exon 1 was targeted. Mutation appears to be X-linked.

The gene that is mutated in these animals is represented by mouse UniGene cluster Mm.13451, which is the ortholog of human UniGene cluster Hs.178098 (ACE2). ACE2 encodes angiotensin I converting enzyme (peptidyl-dipeptidase A) 2, also known as angiotensin-converting enzyme-related carboxypeptidase and ACEH (OMIM 300335). The physiological substrate for ACE2 is not precisely known. Unlike ACE, which catalyzes the cleavage of the carboxy-terminal dipeptide of biologically inactive Ang1-10 to the potent vasoconstrictor Ang1-8, ACE2 catalyzes the cleavage of the carboxy-terminal residue of Ang1-10 to form Ang1-9, and the carboxy-terminal residue of Ang1-8 to form Ang1-7. Moreover, Ang1-8 is a 400-fold better substrate than Ang1-10. ACE2 is not inhibited by the ACE inhibitors linesopril or captopril.

Male ACE2 knockout mice at 6 months (but not 3 months) display decreased cardiac contractility and decreased blood pressure, which is a consequence of decreased cardiac function. Apparently, lack of ACE2 activity in ace2 null mice locally elevates Ang1-8 and causes vasoconstriction of coronary arteries and hypoxia in cardiomyocytes, which damages cardiac tissue and culminates in heart dysfunction.

Targeted or gene trap mutations are generated in strain 129SvEv$^{Brd}$-derived embryonic stem (ES) cells. The chimeric mice are bred to C57BL/6J albino mice to generate F1 female heterozygous animals. These progeny are crossed to hybrid 129SvEv$^{Brd}$/C57 F1 mice, derived from crossing 129SvEv$^{Brd}$ mice to C57BL/6J mice, to generate F1A wild-type, female heterozygous, and male hemizygous mice. Level I phenotypic analysis is performed on mice from this generation.

Summary of X-linked Gene Distributions for Sex by Genotype:

| Progeny | Agouti F1 (M chimera × wt) | | Progeny | F1a (F het × wt) | | |
|---|---|---|---|---|---|---|
| Sex | wt | het | Sex | wt | het | hemi |
| M | 26 | 0 | M | 25 | N/A | 24 |
| F | 0 | 17 | F | 26 | 23 | N/A |

Disruption of the target gene was confirmed by Southern hybridization analysis.

1. Phenotypic Analysis (for Disrupted Gene: DNA79302-2521 (UNQ868)

(a) Overall Phenotypic Summary:

This retroviral insertion is in an X-linked gene. Only male hemizygous (0/−) and female heterozygous (+/−) mice were analyzed, whereas the wild-type mice analyzed were both male and female. General Observations: The female (+/−) and male (0/−) albino mice had yellow-tinted coats when compared with their (+/+) albino littermates. [Analyzed wt/het/hom: 35/16/18]

Male hemizygous (0/−) mice (M-105 and M-112) exhibited heterogeneous retinal backgrounds with mild depigmentation spots, which indicates early signs of retinal degeneration. [Analyzed wt/het/hemi: 4/4/8]

(b Cardiovascular Phenotypic Analysis:

In the area of cardiovascular biology, phenotypic testing was performed to identify potential targets for the treatment of cardiovascular, endothelial or angiogenic disorders. One such phenotypic test included optic fundus photography and angiography to determine the retinal arteriovenous ratio (A/V ratio) in order to flag various eye abnormalities. An abnormal A/V ratio signals such systemic diseases or disorders that may be related to the vascular disease of hypertension (and any disease that causes hypertension, e.g. atherosclerosis), diabetes or other ocular diseases corresponding to ophthalmological disorders. Such eye abnormalities may include but are not limited to the following: retinal abnormality is retinal dysplasia, various retinopathies, restenosis, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

Procedure: Optic fundus photography was performed on conscious animals using a Kowa Genesis small animal fundus camera modified according to Hawes and coauthors (Hawes et al., 1999 Molecular Vision 1999; 5:22). Intra-peritoneal injection of fluorescein permitted the acquisition of direct light fundus images and fluorescent angiograms for each examination. In addition to direct ophthalmological changes, this test can detect retinal changes associated with systemic diseases such as diabetes and atherosclerosis or other retinal abnormalities. Pictures were provided of the optic fundus under normal light. The angiographic pictures allowed examination of the arteries and veins of the eye. In addition an artery to vein (A/V) ratio was determined for the eye.

Ophthalmology analysis was performed on generated F2 wild type, heterozygous, and hemizygous mutant progeny using the protocol described above. Specifically, the A/V ratio was measured and calculated according to the fundus images with Kowa COMIT+ software. This test takes color photographs through a dilated pupil: the images help in detecting and classifying many diseases. The artery to vein ratio (A/V) is the ratio of the artery diameter to the vein diameter (measured before the bifurcation of the vessels). Many diseases will influence the ratio, i.e., diabetes, cardiovascular disorders, papilledema, optic atrophy or other eye abnormalities such as retinal degeneration (known as retinitis pigmentosa) or retinal dysplasia, vision problems or blindness. Thus, phenotypic observations which result in an increased artery-to-vein ratio in homozygous (−/−) and heterozygous (+/−) mutant progeny compared to wildtype (+/+) littermates would be indicative of such pathological conditions.

Results: In this study, male hemizygous (0/−) mice (M-105 and M-112) exhibited heterogeneous retinal backgrounds with mild depigmentation spots, which indicates early signs of retinal degeneration. In addition, the hemizygous mice exhibited an increased mean artery-to-vein (A/V) ratio when compared with their (+/+) littermates indicative of retinal degeneration. In summary, by knocking out the gene identified as DNA79302-2521 encoding PRO1885 polypeptides, hemizygous mutant progeny exhibit phenotypes which are associated with retinal degeneration. Such detected retinal changes are most commonly associated with cardiovascular systemic diseases or disorders that are related to the vascular disease of hypertension (and/or any disease that causes hypertension, e.g. atherosclerosis), diabetes or other ocular diseases corresponding to ophthalmological disorders such as retinal degeneration. Thus, antagonists of PRO1885 encoding genes would lead to similar pathological retinal changes, whereas agonists would be useful as therapeutic agents in the treatment of hypertension, atherosclerosis or other opthamological disorders including retinal degeneration and diseases associated with this condition (as indicated above).

Example 14

Use of PRO227, PRO233, PRO238, PRO1328, PRO4342, PRO7423, PRO10096, PRO21384, PRO353 or PRO1885 as a Hybridization Probe The following method describes use of a nucleotide sequence encoding a PRO227, PRO233, PRO238, PRO1328, PRO4342, PRO7423, PRO10096, PRO21384, PRO353 or PRO1885 polypeptide as a hybridization probe.

DNA comprising the coding sequence of full-length or mature PRO227, PRO233, PRO238, PRO1328, PRO4342, PRO7423, PRO10096, PRO21384, PRO353 or PRO1885 polypeptides as disclosed herein is employed as a probe to screen for homologous DNAs (such as those encoding naturally-occurring variants of PRO227, PRO233, PRO238, PRO1328, PRO4342, PRO7423, PRO10096, PRO21384, PRO353 or PRO1885 polypeptides) in human tissue cDNA libraries or human tissue genomic libraries.

Hybridization and washing of filters containing either library DNAs is performed under the following high stringency conditions. Hybridization of radiolabeled PRO227-, PRO233-, PRO238-, PRO1328-, PRO4342-, PRO7423-, PRO10096-, PRO21384-, PRO353- or PRO1885-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO227, PRO233, PRO238, PRO1328, PRO4342, PRO7423, PRO10096, PRO21384, PRO353 or PRO1885 polypeptides can then be identified using standard techniques known in the art.

Example 15

Expression of PRO227, PRO233, PRO238, PRO1328, PRO4342, PRO7423, PRO10096, PRO21384, PRO353 or PRO1885 in *E. coli*

This example illustrates preparation of an unglycosylated form of PRO227, PRO233, PRO238, PRO1328, PRO4342, PRO7423, PRO10096, PRO21384, PRO353 or PRO1885 polypeptides by recombinant expression in *E. coli*.

The DNA sequence encoding a PRO227, PRO233, PRO238, PRO1328, PRO4342, PRO7423, PRO10096, PRO21384, PRO353 or PRO1885 polypeptide is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO227, PRO233, PRO238, PRO1328, PRO4342, PRO7423, PRO10096, PRO21384, PRO353 or PRO1885 coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO227, PRO233, PRO238, PRO1328, PRO4342, PRO7423, PRO10096, PRO21384, PRO353 or PRO1885 protein can then be purified using a metal chelating column under conditions that allow tight binding of the protein.

PRO227, PRO233, PRO238, PRO1328, PRO4342, PRO7423, PRO10096, PRO21384, PRO353 or PRO1885 may be expressed in *E. coli* in a poly-His tagged form, using the following procedure. The DNA encoding PRO227, PRO233, PRO238, PRO1328, PRO4342, PRO7423, PRO10096, PRO21384, PRO353 or PRO1885 is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA (tonA) lon galE rpoHts (htpRts) clpP (lacIq). Transformants are first grown in LB containing 50 mg/ml carbenicillin at 30° C. with shaking until an O.D. 600 of 3-5 is reached. Cultures are then diluted 50-100 fold into CRAP media (prepared by mixing 3.57 g $(NH_4)_2SO_4$, 0.71 g sodium citrate.2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO227, PRO233, PRO238, PRO1328, PRO4342, PRO7423, PRO10096, PRO21384, PRO353 or PRO1885 polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Example 16

Expression of PRO227, PRO233, PRO238, PRO1328, PRO4342, PRO7423, PRO10096, PRO21384, PRO353 or PRO1885 in Mammalian Cells This example illustrates preparation of a potentially glycosylated form of a PRO227, PRO233, PRO238, PRO1328, PRO4342, PRO7423, PRO10096, PRO21384, PRO353 or PRO1885 polypeptide by recombinant expression in mammalian cells.

The vector, pRK5 (see EP 307,247, published Mar. 15, 1989), is employed as the expression vector. Optionally, the PRO227, PRO233, PRO238, PRO1328, PRO4342, PRO7423, PRO10096, PRO21384, PRO353 or PRO1885 DNA is ligated into pRK5 with selected restriction enzymes to allow insertion of the PRO227, PRO233, PRO238, PRO1328, PRO4342, PRO7423, PRO10096, PRO21384, PRO353 or PRO1885 DNA using ligation methods such as described in Sambrook et al., supra. The resulting vector is called pRK5-PRO227, pRK5-pRK5-PRO233, pRK5-PRO238, pRK5-PRO1328, pRK5-PRO4342, pRK5-PRO7423; pRK5-PRO10096; pRK5-PRO21384; pRK5-PRO353 or pRK5-PRO1885.

The selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg pRK5-PRO227, pRK5-pRK5-PRO233, pRK5-PRO238, pRK5-PRO1328, pRK5-PRO4342, pRK5-PRO7423; pRK5-PRO10096; pRK5-PRO21384; pRK5-PRO353 or pRK5-PRO1885 DNA is mixed with about 1 µg DNA encoding the VA RNA gene [Thimmappaya et al., *Cell*, 31:543 (1982)] and dissolved in 500 µl of 1 mM Tris-HCl, 0.1 mM EDTA, 0.227 M $CaCl_2$. To this mixture is added, dropwise, 500 µl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}$S-cysteine and 200 µCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO227, PRO233, PRO238, PRO1328, PRO4342, PRO7423, PRO10096, PRO21384, PRO353 or PRO1885 polypeptides. The cultures containing transfected cells may undergo further incubation (in serum free medium) and the medium is tested in selected bioassays.

In an alternative technique, PRO227, PRO233, PRO238, PRO1328, PRO4342, PRO7423, PRO10096, PRO21384, PRO353 or PRO1885 may be introduced into 293 cells transiently using the dextran sulfate method described by Somparyrac et al., *Proc. Natl. Acad. Sci.*, 12:7575 (1981). 293 cells are grown to maximal density in a spinner flask and 700 μg pRK5-PRO227, pRK5-pRK5-PRO233, pRK5-PRO238, pRK5-PRO1328, pRK5-PRO4342, pRK5-PRO7423; pRK5-PRO10096; pRK5-PRO21384; pRK5-PRO353 or pRK5-PRO1885 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed PRO227, PRO233, PRO238, PRO1328, PRO4342, PRO7423, PRO10096, PRO21384, PRO353 or PRO1885 can then be concentrated and purified by any selected method, such as dialysis and/or column chromatography.

PRO227, PRO233, PRO238, PRO1328, PRO4342, PRO7423, PRO10096, PRO21384, PRO353 or PRO1885 can be expressed in CHO cells. The pRK5-PRO227, pRK5-pRK5-PRO233, pRK5-PRO238, pRK5-PRO1328, pRK5-PRO4342, pRK5-PRO7423; pRK5-PRO10096; pRK5-PRO21384; pRK5-PRO353 or pRK5-PRO1885 can be transfected into CHO cells using known reagents such as $CaPO_4$ or DEAE-dextran. As described above, the cell cultures can be incubated, and the medium replaced with culture medium (alone) or medium containing a radiolabel such as $^{35}S$-methionine. After determining the presence of PRO227, PRO233, PRO238, PRO1328, PRO4342, PRO7423, PRO10096, PRO21384, PRO353 or PRO1885 polypeptide, the culture medium may be replaced with serum free medium. Preferably, the cultures are incubated for about 6 days, and then the conditioned medium is harvested. The medium containing the expressed PRO227, PRO233, PRO238, PRO1328, PRO4342, PRO7423, PRO10096, PRO21384, PRO353 or PRO1885 can then be concentrated and purified by any selected method.

Epitope-tagged PRO227, PRO233, PRO238, PRO1328, PRO4342, PRO7423, PRO10096, PRO21384, PRO353 or PRO1885 may also be expressed in host CHO cells. The PRO227, PRO233, PRO238, PRO1328, PRO4342, PRO7423, PRO10096, PRO21384, PRO353 or PRO1885 may be subcloned out of the pRK5 vector. The subclone insert can undergo PCR to fuse in frame with a selected epitope tag such as a poly-his tag into a Baculovirus expression vector. The poly-his tagged PRO227, PRO233, PRO238, PRO1328, PRO4342, PRO7423, PRO10096, PRO21384, PRO353 or PRO1885 insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO227, PRO233, PRO238, PRO1328, PRO4342, PRO7423, PRO10096, PRO21384, PRO353 or PRO1885 can then be concentrated and purified by any selected method, such as by $Ni^{2+}$-chelate affinity chromatography.

PRO227, PRO233, PRO238, PRO1328, PRO4342, PRO7423, PRO10096, PRO21384, PRO353 or PRO1885 may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Qiagen), Dosper® or Fugene® (Boehringer Mannheim). The cells are grown as described in Lucas et al., supra. Approximately $3 \times 10^7$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3L production spinner is seeded at $1.2 \times 10^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 μm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 µL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Example 17

Expression of PRO227, PRO233, PRO238, PRO1328, PRO4342, PRO7423, PRO10096, PRO21384, PRO353 or PRO1885 in Yeast The following method describes recombinant expression of PRO227, PRO233, PRO238, PRO1328, PRO4342, PRO7423, PRO10096, PRO21384, PRO353 or PRO1885 in yeast.

First, yeast expression vectors are constructed for intracellular production or secretion of PRO227, PRO233, PRO238, PRO1328, PRO4342, PRO7423, PRO10096, PRO21384, PRO353 or PRO1885 from the ADH2/GAPDH promoter. DNA encoding PRO227, PRO233, PRO238, PRO1328, PRO4342, PRO7423, PRO10096, PRO21384, PRO353 or PRO1885 and the promoter is inserted into suitable restriction enzyme sites in the selected plasmid to direct intracellular expression of PRO227, PRO233, PRO238, PRO1328, PRO4342, PRO7423, PRO10096, PRO21384, PRO353 or PRO1885. For secretion, DNA encoding PRO227, PRO233, PRO238, PRO1328, PRO4342, PRO7423, PRO10096, PRO21384, PRO353 or PRO1885 can be cloned into the selected plasmid, together with DNA encoding the ADH2/GAPDH promoter, a native PRO227, PRO233, PRO238, PRO1328, PRO4342, PRO7423, PRO10096, PRO21384, PRO353 or PRO1885 signal peptide or other mammalian signal peptide, or, for example, a yeast alpha-factor or invertase secretory signal/leader sequence, and linker sequences (if needed) for expression of PRO227, PRO233, PRO238, PRO1328, PRO4342, PRO7423, PRO10096, PRO21384, PRO353 or PRO1885.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO227, PRO233, PRO238, PRO1328, PRO4342, PRO7423, PRO10096, PRO21384, PRO353 or PRO1885 can subsequently be isolated and purified by removing the yeast cells from the fermentation medium by centrifugation and then concentrating the medium using selected cartridge filters. The concentrate containing PRO227, PRO233, PRO238, PRO1328, PRO4342, PRO7423, PRO10096, PRO21384, PRO353 or PRO1885 may further be purified using selected column chromatography resins.

Example 18

Expression of PRO227, PRO233, PRO238, PRO1328, PRO4342, PRO7423, PRO10096, PRO21384, PRO353 or PRO1885 in Baculovirus-Infected Insect Cells The following method describes recombinant expression of PRO227, PRO233, PRO238, PRO1328, PRO4342, PRO7423, PRO10096, PRO21384, PRO353 or PRO1885 in Baculovirus-infected insect cells.

The sequence coding for PRO227, PRO233, PRO238, PRO1328, PRO4342, PRO7423, PRO10096, PRO21384, PRO353 or PRO1885 is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding PRO227, PRO233, PRO238, PRO1328, PRO4342, PRO7423, PRO10096, PRO21384, PRO353 or PRO1885 or the desired portion of the coding sequence of PRO227, PRO233, PRO238, PRO1328, PRO4342, PRO7423, PRO10096, PRO21384, PRO353 or PRO1885 such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged PRO227, PRO233, PRO238, PRO1328, PRO4342, PRO7423, PRO10096, PRO21384, PRO353 or PRO1885 can then be purified, for example, by $Ni^{2+}$-chelate affinity chromatography as follows. Extracts are prepared from recombinant virus-infected Sf9 cells as described by Rupert et al., *Nature,* 362:175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 µm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged PRO227, PRO233, PRO238, PRO1328, PRO4342, PRO7423, PRO10096, PRO21384, PRO353 or PRO1885 are pooled and dialyzed against loading buffer.

Alternatively, purification of the IgG tagged (or Fc tagged) PRO227, PRO233, PRO238, PRO1328, PRO4342, PRO7423, PRO10096, PRO21384, PRO353 or PRO1885 can be performed using known chromatography techniques, including for instance, Protein A or protein G column chromatography.

Example 19

Preparation of Antibodies that Bind PRO227, PRO233, PRO238, PRO1328, PRO4342, PRO7423, PRO10096, PRO21384, PRO353 or PRO1885

This example illustrates preparation of monoclonal antibodies which can specifically bind PRO227, PRO233, PRO238, PRO1328, PRO4342, PRO7423, PRO10096, PRO21384, PRO353 or PRO1885.

Techniques for producing the monoclonal antibodies are known in the art and are described, for instance, in Goding, supra. Immunogens that may be employed include purified PRO227, PRO233, PRO238, PRO1328, PRO4342, PRO7423, PRO10096, PRO21384, PRO353 or PRO1885 polypeptides, fusion proteins containing PRO227, PRO233, PRO238, PRO1328, PRO4342, PRO7423, PRO10096, PRO21384, PRO353 or PRO1885 polypeptides, and cells expressing recombinant PRO227, PRO233, PRO238, PRO1328, PRO4342, PRO7423, PRO10096, PRO21384, PRO353 or PRO1885 polypeptides on the cell surface. Selection of the immunogen can be made by the skilled artisan without undue experimentation.

Mice, such as Balb/c, are immunized with the PRO227, PRO233, PRO238, PRO1328, PRO4342, PRO7423, PRO10096, PRO21384, PRO353 or PRO1885 immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO227, anti-PRO233, anti-PRO238, anti-PRO1328, anti-PRO4342, anti-PRO7423, anti-PRO10096, anti-PRO21384, anti-PRO353 or anti-PRO1885 antibodies.

After a suitable antibody titer has been detected, the animals "positive" for antibodies can be injected with a final intravenous injection of PRO227, PRO233, PRO238, PRO1328, PRO4342, PRO7423, PRO10096, PRO21384, PRO353 or PRO1885. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO227, PRO233, PRO238, PRO1328, PRO4342, PRO7423, PRO10096, PRO21384, PRO353 or PRO1885. Determination of "positive" hybridoma cells secreting the desired monoclonal antibodies against PRO227, PRO233, PRO238, PRO1328, PRO4342, PRO7423, PRO10096, PRO21384, PRO353 or PRO1885 is within the skill in the art.

The positive hybridoma cells can be injected intraperitoneally into syngeneic Balb/c mice to produce ascites containing the anti-PRO227, anti-PRO233, anti-PRO238, anti-PRO1328, anti-PRO4342, anti-PRO7423, anti-PRO10096, anti-PRO21384, anti-PRO353 or anti-PRO1885 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 20

Purification of PRO227, PRO233, PRO238, PRO1328, PRO4342, PRO7423 PRO10096 PRO21384 PRO353 or PRO1885 Polypeptides Using Specific Antibodies Native or recombinant PRO227, PRO233, PRO238, PRO1328, PRO4342, PRO7423, PRO10096, PRO21384, PRO353 or PRO1885 polypeptides may be purified by a variety of standard techniques in the art of protein purification. For example, pro-PRO227, pro-PRO233, pro-PRO238, pro-PRO1328, pro-PRO4342, pro-PRO7423; pro-PRO10096; pro-PRO21384; pro-PRO353 or pro-PRO1885 polypeptide, mature PRO227, PRO233, PRO238, PRO1328, PRO4342, PRO7423, PRO10096, PRO21384, PRO353 or PRO1885 polypeptide, or pre-PRO227, pre-PRO233, pre-PRO238, pre-PRO1328, pre-PRO4342, pre-PRO7423; pre-PRO10096; pre-PRO21384; pre-PRO353 or pre-PRO1885 polypeptide is purified by immunoaffinity chromatography using antibodies specific for the PRO227, PRO233, PRO238, PRO1328, PRO4342, PRO7423, PRO10096, PRO21384, PRO353 or PRO1885 polypeptide of interest. In general, an immunoaffinity column is constructed by covalently coupling the anti-PRO227, anti-PRO233, anti-PRO238, anti-PRO1328, anti-PRO4342, anti-PRO7423, anti-PRO10096, anti-PRO21384, anti-PRO353 or anti-PRO1885 polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of PRO227, PRO233, PRO238, PRO1328, PRO4342, PRO7423, PRO10096, PRO21384, PRO353 or PRO1885 polypeptide by preparing a fraction from cells containing PRO227, PRO233, PRO238, PRO1328, PRO4342, PRO7423, PRO10096, PRO21384, PRO353 or PRO1885 polypeptide in a soluble form. This preparation is derived by solubilization of the whole cell or of a subcellular fraction obtained via differential centrifugation by the addition of detergent or by other methods well known in the art. Alternatively, soluble polypeptide containing a signal sequence may be secreted in useful quantity into the medium in which the cells are grown.

A soluble PRO227, PRO233, PRO238, PRO1328, PRO4342, PRO7423, PRO10096, PRO21384, PRO353 or PRO1885 polypeptide-containing preparation is passed over the immunoaffinity column, and the column is washed under conditions that allow the preferential absorbance of PRO227, PRO233, PRO238, PRO1328, PRO4342, PRO7423, PRO10096, PRO21384, PRO353 or PRO1885 polypeptide (e.g., high ionic strength buffers in the presence of detergent). Then, the column is eluted under conditions that disrupt antibody/PRO227, antibody/PRO233, antibody/PRO238, antibody/PRO1328, antibody/PRO4342, antibody/PRO7423; antibody/PRO10096; antibody/PRO21384; antibody/PRO353 or antibody/PRO1885 polypeptide binding (e.g., a low pH buffer such as approximately pH 2-3, or a high concentration of a chaotrope such as urea or thiocyanate ion), and PRO227, PRO233, PRO238, PRO1328, PRO4342, PRO7423, PRO10096, PRO21384, PRO353 or PRO1885 polypeptide is collected.

Example 21

Drug Screening

This invention is particularly useful for screening compounds by using PRO227, PRO233, PRO238, PRO1328, PRO4342, PRO7423, PRO10096, PRO21384, PRO353 or PRO1885 polypeptides or binding fragment thereof in any of a variety of drug screening techniques. The PRO227, PRO233, PRO238, PRO1328, PRO4342, PRO7423, PRO10096, PRO21384, PRO353 or PRO1885 polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO227, PRO233, PRO238, PRO1328, PRO4342, PRO7423, PRO10096, PRO21384, PRO353 or PRO1885 polypeptide or fragment. Drugs are screened against such transformed cells in competitive binding assays. Such cells, either in viable or fixed form, can be used for standard binding assays. One may measure, for example, the formation of complexes between PRO227, PRO233, PRO238, PRO1328, PRO4342, PRO7423, PRO10096, PRO21384, PRO353 or PRO1885 polypeptide or a fragment and the agent being tested. Alternatively, one can examine the diminution in complex formation between the PRO227, PRO233, PRO238, PRO1328, PRO4342, PRO7423, PRO10096, PRO21384, PRO353 or PRO1885 polypeptide and its target cell or target receptors caused by the agent being tested.

Thus, the present invention provides methods of screening for drugs or any other agents which can affect a PRO227, PRO233, PRO238, PRO1328, PRO4342, PRO7423, PRO10096, PRO21384, PRO353 or PRO1885 polypeptide-associated disease or disorder. These methods comprise contacting such an agent with an PRO227, PRO233, PRO238, PRO1328, PRO4342, PRO7423, PRO10096, PRO21384, PRO353 or PRO1885 polypeptide or fragment thereof and assaying (I) for the presence of a complex between the agent and the PRO227, PRO233, PRO238, PRO1328, PRO4342, PRO7423, PRO10096, PRO21384, PRO353 or PRO1885 polypeptide or fragment, or (ii) for the presence of a complex between the PRO227, PRO233, PRO238, PRO1328, PRO4342, PRO7423, PRO10096, PRO21384, PRO353 or PRO1885 polypeptide or fragment and the cell, by methods well known in the art. In such competitive binding assays, the PRO227, PRO233, PRO238, PRO1328, PRO4342, PRO7423, PRO10096, PRO21384, PRO353 or PRO1885 polypeptide or fragment is typically labeled. After suitable incubation, free PRO227, PRO233, PRO238, PRO1328, PRO4342, PRO7423, PRO10096, PRO21384, PRO353 or PRO1885 polypeptide or fragment is separated from that present in bound form, and the amount of free or uncomplexed label is a measure of the ability of the particular agent to bind to PRO227, PRO233, PRO238, PRO1328, PRO4342, PRO7423, PRO10096, PRO21384, PRO353 or PRO1885 polypeptide or to interfere with the PRO227, PRO233, PRO238, PRO1328, PRO4342, PRO7423, PRO10096, PRO21384, PRO353 or PRO1885 polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a PRO227, PRO233, PRO238, PRO1328, PRO4342, PRO7423, PRO10096, PRO21384, PRO353 or PRO1885 polypeptide, the peptide test compounds are reacted with PRO227, PRO233, PRO238, PRO1328, PRO4342, PRO7423, PRO10096, PRO21384, PRO353 or PRO1885 polypeptide and washed. Bound PRO227, PRO233, PRO238, PRO1328, PRO4342, PRO7423, PRO10096, PRO21384, PRO353 or PRO1885 polypeptide is detected by methods well known in the art. Purified PRO227, PRO233, PRO238, PRO1328, PRO4342, PRO7423, PRO10096, PRO21384, PRO353 or PRO1885 polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PRO227, PRO233, PRO238, PRO1328, PRO4342, PRO7423, PRO10096, PRO21384, PRO353 or PRO1885 polypeptide specifically compete with a test compound for binding to PRO227, PRO233, PRO238, PRO1328, PRO4342, PRO7423, PRO10096, PRO21384, PRO353 or PRO1885 polypeptide or fragments thereof. In this manner, the antibodies can be used to detect the presence of any peptide which shares one or more antigenic determinants with PRO227, PRO233, PRO238, PRO1328, PRO4342, PRO7423, PRO10096, PRO21384, PRO353 or PRO1885 polypeptide.

Example 22

Rational Drug Design

The goal of rational drug design is to produce structural analogs of biologically active polypeptide of interest (i.e., a PRO227, PRO233, PRO238, PRO1328, PRO4342, PRO7423, PRO10096, PRO21384, PRO353 or PRO1885 polypeptide) or of small molecules with which they interact, e.g., agonists, antagonists, or inhibitors. Any of these examples can be used to fashion drugs which are more active or stable forms of the PRO227, PRO233, PRO238, PRO1328, PRO4342, PRO7423, PRO10096, PRO21384, PRO353 or PRO1885 polypeptide or which enhance or interfere with the function of the PRO227, PRO233, PRO238, PRO1328, PRO4342, PRO7423, PRO10096, PRO21384, PRO353 or PRO1885 polypeptide in vivo (c.f., Hodgson, *Bio/Technology,* 9: 19-21 (1991)).

In one approach, the three-dimensional structure of the PRO227, PRO233, PRO238, PRO1328, PRO4342, PRO7423, PRO10096, PRO21384, PRO353 or PRO1885 polypeptide, or of a PRO227, PRO233, PRO238, PRO1328, PRO4342, PRO7423, PRO10096, PRO21384, PRO353 or PRO1885 polypeptide-inhibitor complex, is determined by x-ray crystallography, by computer modeling or, most typically, by a combination of the two approaches. Both the shape and charges of the PRO227, PRO233, PRO238, PRO1328, PRO4342, PRO7423, PRO10096, PRO21384, PRO353 or PRO1885 polypeptide must be ascertained to elucidate the structure and to determine active site(s) of the molecule. Less often, useful information regarding the structure of the PRO227, PRO233, PRO238, PRO1328, PRO4342, PRO7423, PRO10096, PRO21384, PRO353 or PRO1885 polypeptide may be gained by modeling based on the structure of homologous proteins. In both cases, relevant structural information is used to design analogous PRO227, PRO233, PRO238, PRO1328, PRO4342, PRO7423, PRO10096, PRO21384, PRO353 or PRO1885 polypeptide-like molecules or to identify efficient inhibitors. Useful examples of rational drug design may include molecules which have improved activity or stability as shown by Braxton and Wells, *Biochemistry,* 31:7796-7801 (1992) or which act as inhibitors, agonists, or antagonists of native peptides as shown by Athauda et al., *J. Biochem.,* 113:742-746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO227, PRO233, PRO238, PRO1328, PRO4342, PRO7423, PRO10096, PRO21384, PRO353 or PRO1885 polypeptide may be made available to perform such analytical studies as X-ray crystallography. In addition, knowledge of the PRO227, PRO233, PRO238, PRO1328, PRO4342, PRO7423, PRO10096, PRO21384, PRO353 or PRO1885 polypeptide amino acid sequence provided herein will provide guidance to those employing computer modeling techniques in place of or in addition to x-ray crystallography.

What is claimed is:

1. A method of identifying an agent that modulates serum cholesterol levels, the method comprising:

(a) providing a transgenic mouse whose genome comprises a homozygous disruption of the gene which encodes for the PRO1328 polypeptide; (b) measuring the serum cholesterol levels of the transgenic mouse of (a);

(c) comparing the measured serum cholesterol levels of (b) with that of a gender matched wild-type mouse, wherein the serum cholesterol levels of the transgenic mouse that differs from the serum cholesterol levels of the wild-type mouse is identified as a phenotype resulting from the gene disruption in the transgenic mouse;

(d) administering a test agent to the transgenic mouse of (a); and (e) determining whether the test agent modulates serum cholesterol levels in the transgenic mouse.

2. The method of claim 1, wherein the transgenic mouse exhibits at least one of the following physiological characteristics compared with gender matched wild-type littermates: an increased mean serum cholesterol level and increased levels of one or more of urobilinogen, ketones, and blood in the urine.

3. The method of claim 1, wherein the transgenic mouse exhibits increased mean serum cholesterol level compared with gender matched wild-type littermates.

* * * * *